US010556900B2

(12) United States Patent
Stump et al.

(10) Patent No.: US 10,556,900 B2
(45) Date of Patent: *Feb. 11, 2020

(54) TRKA KINASE INHIBITORS, COMPOSITIONS AND METHODS THEREOF

(71) Applicant: Merck Sharp & Dohme Corp., Rahway, NJ (US)

(72) Inventors: Craig A. Stump, Pottstown, PA (US); Yi Heng Chen, Whippany, NJ (US); Ping Liu, Westfield, NJ (US); Dongfang Meng, Morganville, NJ (US); Jane Yang Wu, Marlboro, NJ (US); Chun Sing Li, Shanghai (CN); Zhiqi Qi, Shanghai (CN)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/562,617

(22) PCT Filed: Apr. 4, 2016

(86) PCT No.: PCT/US2016/025810
§ 371 (c)(1),
(2) Date: Sep. 28, 2017

(87) PCT Pub. No.: WO2016/164286
PCT Pub. Date: Oct. 13, 2016

(65) Prior Publication Data
US 2018/0105518 A1  Apr. 19, 2018

(30) Foreign Application Priority Data
Apr. 8, 2015  (CN) .................. PCT/CN2015/076042

(51) Int. Cl.
| | |
|---|---|
| *C07D 471/04* | (2006.01) |
| *C07D 487/04* | (2006.01) |
| *C07D 403/12* | (2006.01) |
| *C07D 417/12* | (2006.01) |
| *A61P 7/02* | (2006.01) |
| *A61P 17/06* | (2006.01) |
| *A61P 9/10* | (2006.01) |
| *A61P 25/00* | (2006.01) |
| *A61P 35/00* | (2006.01) |

(52) U.S. Cl.
CPC .............. *C07D 471/04* (2013.01); *A61P 7/02* (2018.01); *A61P 9/10* (2018.01); *A61P 17/06* (2018.01); *A61P 25/00* (2018.01); *A61P 35/00* (2018.01); *C07D 403/12* (2013.01); *C07D 417/12* (2013.01); *C07D 487/04* (2013.01)

(58) Field of Classification Search
None
See application file for complete search history.

(56) References Cited

U.S. PATENT DOCUMENTS

| | | | |
|---|---|---|---|
| 7,220,771 B2 | 5/2007 | Bhagwat et al. | |
| 2005/0143384 A1 | 6/2005 | Sartori et al. | |
| 2010/0029619 A1 | 2/2010 | Uchikawa et al. | |
| 2010/0120862 A1 | 5/2010 | Tafesse | |
| 2011/0319416 A1* | 12/2011 | Traynelis ............. | C07D 209/08 514/237.5 |

FOREIGN PATENT DOCUMENTS

| | | | |
|---|---|---|---|
| EP | 1181318 | 5/2000 | |
| EP | 1388341 | 8/2002 | |
| WO | WO-9634866 A1 * | 11/1996 | ........... C07D 407/04 |
| WO | WO200178698 A2 | 10/2001 | |
| WO | WO2004058184 | 7/2004 | |
| WO | WO2004096122 | 11/2004 | |
| WO | WO2004098518 A2 | 11/2004 | |
| WO | WO2005019266 | 3/2005 | |
| WO | WO2005030128 | 4/2005 | |
| WO | WO2005061540 | 7/2005 | |
| WO | WO2005110994 | 11/2005 | |
| WO | WO200210137 | 5/2006 | |
| WO | WO2006137106 | 6/2006 | |
| WO | WO2007013673 | 7/2006 | |
| WO | WO2006087538 | 8/2006 | |
| WO | WO2006115452 | 11/2006 | |
| WO | WO2006123113 | 11/2006 | |
| WO | WO2006131952 | 12/2006 | |
| WO | WO2007025540 A2 | 3/2007 | |
| WO | WO2007042321 | 4/2007 | |

(Continued)

OTHER PUBLICATIONS

Assumi et al., Expression of Neurotrophins and Their Receptors (TRK) During Fracture Healing, Bone, 2000, pp. 625-633, 26.
Bardelli et al., Mutational Analysis of the Tryosine Kinome in Colorectal Cancers, Science, May 9, 2003, pp. 949, 300.
Brodeur et al., Neuroblastoma: Biological Insights into A Clincal Enigma, Nat. Rev Cancer, 2003, pp. 203-216, 3.
Dang et al., Expression of Nerve Growth Factor Receptors is Correlated with Progression and Prognosis of Human Pancreatic Cancer, J. of Gastroenterology and Hepatology, 2006, pp. 850-858, 21 (5).
Delafoy et al., Role of Nerve Growth Factor in the Trinitrobenzene Sulfonic Acid-Induced Colonic Hypersensitivity, Pain, 2003, pp. 489-497, 105.

(Continued)

*Primary Examiner* — Emily A Bernhardt
*Assistant Examiner* — Laura M Daniel
(74) *Attorney, Agent, or Firm* — Dianne Pecoraro; John C. Todaro

(57) ABSTRACT

The present invention is directed to bicyclic heteroaryl benzamide compounds of formulas (I): which are tropomyos-in-related kinase (Trk) family protein kinase inhibitors, and hence are useful in the treatment of pain, inflammation, cancer, restenosis, atherosclerosis, psoriasis, thrombosis, a disease, disorder, injury, or malfunction relating to dysmyelination or demyelination or a disease or disorder associated with abnormal activities of nerve growth factor (NGF) receptor TrkA.

11 Claims, No Drawings

(56) References Cited

FOREIGN PATENT DOCUMENTS

| WO | WO2007069773 A1 | 6/2007 | | |
|---|---|---|---|---|
| WO | 2008003770 A1 | 1/2008 | | |
| WO | WO2008052734 | 5/2008 | | |
| WO | WO2008124610 A1 | 10/2008 | | |
| WO | WO2009003999 A2 | 1/2009 | | |
| WO | WO2009046802 A1 | 4/2009 | | |
| WO | WO2009003998 | 8/2009 | | |
| WO | WO2010033941 | 3/2010 | | |
| WO | WO2010077680 A2 | 7/2010 | | |
| WO | WO2010111653 | 9/2010 | | |
| WO | WO2006052936 | 8/2011 | | |
| WO | WO2011099832 | 8/2011 | | |
| WO | WO2012003387 A1 | 1/2012 | | |
| WO | WO2012028579 A1 | 3/2012 | | |
| WO | WO2012100223 A1 | 7/2012 | | |
| WO | WO2012105594 | 8/2012 | | |
| WO | WO2012107434 A1 | 8/2012 | | |
| WO | WO2012158413 | 11/2012 | | |
| WO | WO2012159565 A1 | 11/2012 | | |
| WO | WO2012161879 A1 | 11/2012 | | |
| WO | WO-2013102142 A1 * | 7/2013 | ........... | C07D 215/14 |
| WO | WO2014016434 | 1/2014 | | |
| WO | WO2014209841 | 12/2014 | | |

OTHER PUBLICATIONS

Di Mola, Nerve Growth Factor and Trk Hihg Affinity Receptor (TRkA) Gene Expression in Inflammatory Bowel Disease, Gut, 2000, pp. 670-678, 46(5).

Dionne et al., Cell cycle-independent death of prostate adenocarcinoma is Induced by the trk Tyrosine Kinase Inhibitor CEP-751 (KT6587), Clinical Cancer Research, 1998, pp. 1887-1898, 4(8).

Dou et al., Increased nerve growth factor and its receptors in atopic dermatitis:, Archives of Dermatological Research, 2006, pp. 31-37 (1), 298.

Freund-Michel et al., The Nerve Growth Factor and Its Receptors in Airway Inflammatory Diseases, Pharmacology & Thereapeutics, 2008, pp. 52-76, 117 (1).

Hu et al., Decrease in Bladder Overactivity With REN1820 in Rats, J. of Urology, 2005, pp. 1016-1021, 173 (3).

Iannone, Increased Expression of Nerve Growth Factoer (NGF) and high Affinity NGF Receptor (p140 TrkA) in Human Osteoarthritic Chondrocytes, Rheumatology, 2002, pp. 1413-1418, 4.

Jaggar et al., Inflammation of the Rat Urinary Bladder is associated with a Referred Thermal Hyperalgesia Which is Nerve Growth Factor Dependent, Br. J. Anaesth., 1999, pp. 442-448, 83.

Kruettgen et al., The Dark Side of the NGF Family: Neurotrophin in Neoplasia, Brain Pathology, 2006, pp. 304-310, 16.

Lamb et al., Nerve Growth Factor and Gastric Hyperalgesia in the Rat, Neurogastroenterol Motil., 2003, pp. 355-361, 15.

Ma et al., The Progressive Tactile Hyperalgesia Induced by Peripheral Inflammation is Nerve Growth Factor Dependent, Neuroreport, 1997, pp. 807-810, 8.

Marchetti et al., Frequent Mutations in the Neuroptrophic Trrosine Receptor Kinase Gene Family in Large Cell Neuroendocrine Carcinioma of the Lung, Rapid Communication, 2008, pp. 609-616, 29 (5).

McMahon et al., The Biological Effects of Endogenous Nerve Growth Factor on Adult Sensory Neurons Revealed by a trkA-IgG Fusion Molecule, Nature Medicine, 1995, pp. 774-780, 1.

Pubchem SID228838556, Feb. 2, 2012.

PubChem, Compound Summary for SID 189306562, Create Date: Jul. 12, 2014 [retrieved on 05<URL:https://pubchem.ncbi.nlm.nih.gov/substances/189306562>.

Raychaudhuri et al., K252a, a High-Affinity Nerve Growth Factor Receptor Blocker,, J. of Investigative Dermatology, 2004, pp. 812-819, 122 (3).

Shelton et al., Nerve growth factor mediates hyperalgesia and cachexia, Pain, 2005, pp. 8-16, 116.

Sohrabji et al., Estrogen—BDNF interactions: Implications, Frontiers in Neuroendocrinology, 2006, pp. 404-414, 27(4).

Tripathy et al., TrkA kinase inhibitors from a library of modified and isosteric, Bioganic & Medicinal Chemistry Letters, 2008, pp. 3551-3555, 18.

Undevia et al., Phase I Clinical Trial of CEP-2563 Dihydrochloride, A Receptor Tyrosine Kinase Inhibitor, in Patients with Refractory Solid Tumors, Investigational New Drugs, 2004, pp. 449-458, 22.

Wang et al., Trk Kinase Inhibitors as New Treatments for Cancer and Pain, Expert Opinion, 2009, pp. 305-319, 19(3).

Woolf, Nerve Growth Factor Contributes to the Generation of Inflammatory Sensory Hypersenstivity, Neuroscience, 1994, pp. 327-331, 62.

Zhu et al., Nerve Growth Factor Expression Correlation with Perineural Invasion and Pain in Human Pancreatic Cancer, J. of Clinicl Oncology, 1999, pp. 2419-2428, 17.

\* cited by examiner

TRKA KINASE INHIBITORS, COMPOSITIONS AND METHODS THEREOF

CROSS REFERENCE TO RELATED APPLICATIONS

This application is the National Stage of International Application No. PCT/US2016/025810 filed on Apr. 4, 2016, which claims the benefit under International Application No. PCT/CN2015/076042, filed Apr. 8, 2015.

FIELD OF THE INVENTION

The invention is directed to a class of substituted six membered aryl or heteroaryl benzamide compounds, their salts, pharmaceutical compositions comprising them and their use in therapy of the human body. In particular, the invention is directed to a class of substituted heteroaryl benzamide compounds, which are tropomyosin-related kinase (Trk) family protein kinase inhibitors, and hence are useful in the treatment of pain, inflammation, cancer, restenosis, atherosclerosis, psoriasis, thrombosis, a disease, disorder, injury, or malfunction relating to dysmyelination or demyelination or a disease or disorder associated with abnormal activities of nerve growth factor (NGF) receptor TrkA.

BACKGROUND OF THE INVENTION

Trk receptors are high affinity binding protein kinase receptors that are activated by Neurotrophins (NT), a group of soluble growth factors including Nerve Growth Factor (NGF), Brain-Derived Neurotrophic Factor (BDNF) and Neurotrophin 3-5 (NT 3-5). The Trk receptors consist of three family members TrkA, TrkB and TrkC that bind to and mediate the signal transduction derived from the Neurotrophins. NGF activates TrkA, BDNF and NT-4/5 activate TrkB and NT3 activates TrkC.

Inhibitors of the Trk/neutrophin pathway have been demonstrated to be highly effective in numerous pre-clinical animal models of pain. Antagonistic NGF and TrkA antibodies have been shown to be efficacious in inflammatory and neuropathic pain animal models and in human clinical trials. See Woolf, C. J. et al. (1994) Neuroscience 62, 327-331; Zahn, P. K. et al. (2004) J. Pain 5, 157-163; McMahon, S. B. et al., (1995) Nat. Med. 1, 774-780; Ma, Q. P. and Woolf, C. J. (1997) Neuroreport 8, 807-810; Shelton, D. L. et al. (2005) Pain 116, 8-16; Delafoy, L. et al. (2003) Pain 105, 489-497; Lamb, K. et al. (2003) Neurogastroenterol. Motil. 15, 355-361; and Jaggar, S. I. et al. (199) Br. J. Anaesth. 83, 442-448. Through gene disruption studies in mice the TrkA-NGF interaction was found to be required for the survival of certain peripheral neuron populations involved in mediating pain signaling in the case of pancreatic cancer—an increase in the expression of TrkA was shown to correlate with an increase level of pain signaling (Zhu et al., Journal of Clinical oncology, 17:2419-2428 (1999)). Increased expression of NGF and TrkA was also observed in human osteoarthritis chondrocytes (Iannone et al, Rheumatology 41:1413-1418 (2002)). In particular, anti-TrkA antibodies and anti-NGF antibodies have been demonstrated to be effective analgesics in in vivo models of inflammatory and neuropathic pain. See WO2006/131952, WO2005/061540, EP1181318 and WO01/78698, WO2004/058184 and WO2005/019266, respectively. See also WO2004/096122 and WO2006/137106 which describe the use of an anti-TrkA antibody in combination with an opioid analgesic for the treatment or prevention of pain.

Trk inhibitors that can induce apoptosis of proliferating osteoblasts may be useful in treating diseases related to an imbalance of the regulation of bone remodeling, such as osteoporosis, rheumatoid arthritis and bone metastases. The expression of TrkA and TrkC receptors in the bone forming area in mouse models of bone fracture and localization of NGF in almost all bone forming cells have been observed (K. Asaumi, et al., Bone (2000) 26(6) 625-633). See also Expert Opin. Ther. Patents (2009) 19(3)), WO2006/115452 and WO2006/087538, WO6123113, WO10033941, WO10077680, WO2005110994, Investigational New Drugs (2004), 22, 449-458 and R. Tripathy, et al., Bioorg. Med. Chem. Lett., 2008, 18, 3551-3555. The association between overexpression, activation, amplification and/or mutation of Trk receptors and several cancers as seen with studies conduct on neuroblastoma (Brodeur, G. M., Nat. Rev. Cancer 2003, 3, 203-216), ovarian cancer (Kruettgen et al., Brain Pathology 2006, 16: 304-310), prostate cancer (Dionne et al., Clin. Cancer Res. 1998, 4(8): 1887-1898), pancreatic cancer (Dang et al., J of Gastroenterology and Hepatology 2006, 21(5): 850-858), large cell neuroendocrine tumors (Marchetti et al., Human Mutation 2008, 29(5), 609-616, and colorectal cancer (Bardelli, A., Science 2003, 300, 949) support the reasoning that therapeutic implications of an effective Trk inhibitor may extend far beyond pain therapy. See also WO2005/030128, WO2012158413, WO07013673, WO07025540, WO8052734, WO2012028579, WO2012159565, WO2012107434, WO2012003387, WO2010111653, WO2008124610, WO2004098518, EP1388341, WO2012028579, WO2008003770, WO2012161879, WO2012100223, WO2009046802, WO2009003999, WO2007042321, US2005143384, WO2009003998, WO2007069773, WO2005/030128, and US2010120862.

Also promising is the utility of Trk inhibitors in the treatment of inflammatory lung diseases such as asthma (Freund-Michel, V; et al., Pharmacology & Therapeutics (2008), 117(1), 52-76), interstitial cystitis (Hu Vivian Y; et. al., J of Urology (2005, 173(3), 1016-21), inflammatory bowel disease including ulcerative colitis and Crohn's disease (Di Mola, F. F., et al., Gut (2000), 46(5), 670-678 and inflammatory skin diseases such as atopic dermatitis (Dou, Y. C., et. Al., Archives of Dermatological Research (2006), 298(1), 31-37, eczema and psoriasis (Raychaudhuri, S. P. et. al., J of Investigative Dermatology (2004), 122(3), 812-819).

Modulation of the neutrophin/Trk pathway also has been shown to have an effect in the etiology of neurodegenerative diseases including multiple sclerosis, Parkinson's disease and Alzheimer's disease (Sohrabji, et. al., Neuroendocrinology (2006), 27(4), 404-414).

Thus, the compounds of the invention, which are Trk inhibitors, are believed to be useful in the treatment of multiple types of acute and chronic pain including but not limited to inflammatory pain, neuropathic pain, and pain associated with cancer, surgery and bone fracture. The compounds may also be useful in the treatment of cancer, inflammation, neurodegenerative diseases and certain infectious diseases.

SUMMARY OF THE INVENTION

The present invention is directed to compounds of the generic formulas (I and II) below or pharmaceutically acceptable salts thereof that are useful as a Trk kinase mediator of NGF driven biological responses, an inhibitor of TrkA as well as other Trk kinases.

The invention is further directed to methods of treating a patient (preferably a human) for diseases or disorders in which the NGF receptor Trk kinases are involved, in particular TrkA. The invention further involves use of the compounds as NGF receptor TrkA inhibitor and/or antagonist for the preparation of a medicament for the treatment and/or prevention of diseases associated with inhibiting TrkA, which includes pain, cancer, restenosis, atherosclerosis, psoriasis, thrombosis, or a disease, disorder, or injury relating to dysmyelination or demyelination. The invention is also directed to pharmaceutical compositions which include an effective amount of a compound of formula (I), or a pharmaceutically acceptable salt thereof, and a pharmaceutically acceptable carrier, and the use of the compounds and pharmaceutical compositions of the invention in the treatment of such diseases.

DETAILED DESCRIPTION OF THE INVENTION

In one embodiment, the invention is directed to compounds of general formula (I):

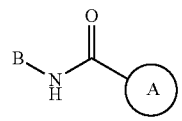

I or a pharmaceutically acceptable salt thereof, wherein:
A is phenyl or thiophenyl, said groups optionally substituted with 1 to 3 groups of $R^a$;
B is represented by structural formula:

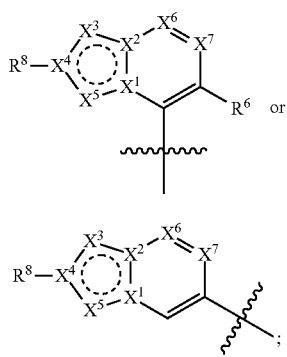

----- represents a double bond between $X^1$-$X^2$, $X^2$-$X^3$, $X^3$-$X^4$, and/or $X^4$-$X^5$, wherein no more than two double bonds are present at $X^1$-$X^2$, $X^2$-$X^3$, $X^3$-$X^4$, and/ $X^4$-$X^5$ at the same time;
$X^1$, $X^2$, $X^3$, $X^4$ and $X^5$ are represented as follows:
$X^1$=N, $X^2$=C, $X^3$=NH, $X^4$=C, and $X^5$=CH;
$X^1$=C, $X^2$=N, $X^3$=$CR^c$, $X^4$=C, and $X^5$=N;
$X^1$=C, $X^2$=C, $X^3$=N, $X^4$=C, and $X^5$=S;
$X^1$=C, $X^2$=C, $X^3$=S, $X^4$=C, and $X^5$=N;
$X^1$=C, $X^2$=N, $X^3$=$CR^c$, $X^4$=N, and $X^5$=N;
$X^1$=N, $X^2$=C, $X^3$=$CR^c$, $X^4$=C, and $X^5$=N;
$X^1$=C, $X^2$=C, $X^3$=$CR^c$, $X^4$=C, and $X^5$=NH;
$X^1$=C, $X^2$=C, $X^3$=$CR^c$, $X^4$=N, and $X^5$=NH;

$X^1$=N, $X^2$=C, $X^3$=$CR^c$, $X^4$=N, and $X^5$=$CR^c$;
$X^6$ is selected from the group consisting of CH and N;
$X^7$ is selected from the group consisting of CH, $CR^7$ and N;
$R^6$ and $R^7$ are independently selected from the group consisting of hydrogen, OH, $C_{1-6}$alkyl, $C_{6-10}$aryl, and halogen, said alkyl and aryl optionally substituted with 1 to 3 groups of $R^a$;
$R^8$ is selected from the group consisting of hydrogen and $C_{1-6}$alkyl, said alkyl optionally substituted with 1 to 3 groups of $R^a$;
R is selected from the group consisting of hydrogen, OH, or —$C_{1-6}$alkyl;
$R^a$ is selected from the group consisting of —CN, $NO_2$, —O—$C_{1-6}$alkyl, —OH, —$C_{1-4}$haloalkyl, —$OC_{1-4}$haloalkyl, —$C_{1-6}$alkyl, —$C_{1-6}$alkenyl, —$C_{1-6}$alkynyl, —(CHR)$_n$$C_{6-10}$ aryl, —(CHR)$_n$$C_{4-10}$ heterocycle, $C_{3-6}$cycloalkyl, —O—, —$(CH_2)_n$$N(R)_2$, —$C(O)CF_3$, COR, C(O)OR, —$(CH_2)_n$halo, —$(CH_2)_n$NHC(O)R—(CHR)$_n$C(O)N(R)$_2$, said alkyl, cycloalkyl, aryl and heterocycle optionally substituted with 1 to 3 groups of $R^b$,
$R^b$ is selected from the group consisting of —$C_{1-6}$alkyl, —$C_{1-6}$alkylOR, —$C_{1-4}$haloalkyl, —$(CH_2)_n$$N(R)_2$, —$(CH_2)_n$OR, —O—, halogen, —CN, —$(CH_2)_n$$C_{6-10}$ aryl, —$(CH_2)_n$$C_{4-10}$ heterocycle, —$(CH_2)_n$C(O)N(R)$_2$, —$(CH_2)_n$NHC(O)R,
$R^c$ is selected from the group consisting of hydrogen, —$C_{1-6}$alkyl, —$C_{1-6}$alkylOR, —$C_{1-4}$haloalkyl, C(O)R, C(O)OR, —$(CH_2)_n$C(O)N(R)$_2$, and —$(CH_2)_n$N(R)$_2$, said alkyl optionally substituted with 1 to 3 groups of OH, $CH_3$, and halogen, and
n represents 0-4.

An embodiment of the invention of formula I is realized when A is an optionally substituted phenyl. A subembodiment of this aspect of the invention of formula I is realized when A is substituted phenyl represented by structural formula (i):

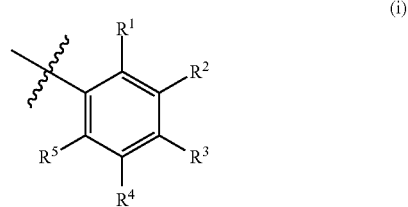

(i)

wherein:
$R^1$ and $R^5$ are independently selected from the group consisting of hydrogen, CN, OH, $C_{1-6}$alkyl, and halogen;
$R^2$ and $R^4$ are independently selected from the group consisting of hydrogen, halogen, $C_{1-4}$ haloalkyl, $C_{1-6}$ alkyl, (CHR)$_n$$C_{6-10}$ aryl and (CHR)$_n$$C_{5-10}$ heterocycle, said alkyl, aryl, and heterocycle optionally substituted with 1 to 3 groups of $R^a$, and
$R^3$ is selected from the group consisting of hydrogen, $C_{1-6}$ alkyl, $C_{1-4}$ haloalkyl, —$OC_{1-4}$ haloalkyl, and halogen, wherein at least one of $R^1$-$R^5$ is other than hydrogen.

Another embodiment of the invention of formula I is realized when A is optionally substituted thiophenyl. A subembodiment of this aspect of the invention of formula I is realized when A is substituted thiophenyl represented by structural formula (ii):

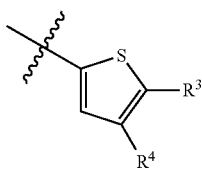
(ii)

wherein $R^3$ and $R^4$ are as originally described.

It is understood that to complete valency of a nitrogen atom present in ring B a double bond is present on the nitrogen atom and when $X^4$ is a nitrogen atom $R^8$ is not present.

An embodiment of the invention of formula I is realized when B is selected from the group consisting of indolyl, indazolyl, pyrazolopyridinyl, triazolopyrimindyl, imidazopyridinyl, benzthiazolyl, imidazopyrimidinyl, imidazopyridazinyl, and imidazothiadiazolyl.

Another embodiment of the invention of formula I is realized when B is indolyl.

Another embodiment of the invention of formula I is realized when B is indazolyl.

Another embodiment of the invention of formula I B is pyrazolopyridinyl.

Another embodiment of the invention of formula I B is triazolopyrimindyl.

Another embodiment of the invention of formula I B is imidazopyridinyl.

Another embodiment of the invention of formula I B is benzothiazolyl.

Another embodiment of the invention of formula I B is imidazopyrimidinyl.

Another embodiment of the invention of formula I B is imidazopyridazinyl.

Another embodiment of the invention of formula I B is imidazothiadiazolyl.

Still another embodiment of the invention of formula I is realized when B is B1.

Another embodiment of the invention of formula I is realized when B is B2.

Another embodiment of the invention of formula I is realized when $X^6$ is CH.

Still another embodiment of the invention of formula I is realized when $X^6$ is and N.

Still another embodiment of the invention of formula I is realized when $X^7$ is CH.

Still another embodiment of the invention of formula I is realized when $X^7$ is $CR^7$.

Still another embodiment of the invention of formula I is realized when $X^7$ is N.

Another embodiment of the invention of formula I is realized when $R^a$ is selected from —O—$C_{1-6}$alkyl, —OH, —$C_{1-4}$haloalkyl, —$OC_{1-4}$haloalkyl, —$C_{1-6}$alkyl, —$(CHR)_n$$C_{6-10}$ aryl, —$(CHR)_n$$C_{4-10}$ heterocycle, $C_{3-6}$cycloalkyl, —O—, —$(CH_2)_n$$N(R)_2$, —$C(O)CF_3$, COR, C(O)OR, and —$(CH_2)_n$halo, said alkyl, cycloalkyl, aryl and heterocycle optionally substituted with 1 to 3 groups of $R^b$. A subembodiment of this aspect of the invention is realized when $R^a$ is selected from —$C_{1-4}$haloalkyl, —$C_{1-6}$alkyl, —$(CHR)_n$$C_{6-10}$ aryl, —$(CHR)_n$$C_{5-10}$ heterocycle, halogen, and —OR said alkyl, aryl, and heterocycle optionally substituted with 1 to 3 groups of $R^b$.

Another embodiment of the invention of formula I is realized when $R^b$ is selected from —$C_{1-6}$alkyl, $OR^c$, and halogen.

Still another embodiment of the invention of formula I is realized when A is phenyl represented by structural formula (i). An aspect of this embodiment of the invention is realized when A is phenyl represented by structural formula (i) and $R^1$ and $R^5$ are both hydrogen. Another embodiment of the invention of formula I is realized when A is phenyl represented by structural formula (i) and one of $R^1$ and $R^5$ is hydrogen and the other is halogen. Another embodiment of the invention of formula I is realized when A is phenyl represented by structural formula (i) and one of $R^1$ and $R^5$ is hydrogen and the other is CN, OH, or $C_{1-6}$alkyl Yet another embodiment of the invention of formula I is realized when A is phenyl represented by structural formula (i) and one of $R^1$ and $R^5$ hydrogen and the other is —$C_{1-6}$alkyl. Yet another embodiment of the invention of formula I is realized when A is phenyl represented by structural formula (i) and one of $R^1$ and $R^5$ hydrogen and the other is OH.

Another embodiment of the invention of formula I is realized when A is phenyl represented by structural formula (i) and at least one of $R^2$ and $R^4$ is $(CHR)_n$$C_{5-10}$ heterocycle optionally substituted with 1 to 3 groups of $R^a$.

Another embodiment of the invention of formula I is realized when A is phenyl represented by structural formula (i) and one of $R^2$ and $R^4$ is hydrogen and the other is $(CHR)_n$$C_{5-10}$ heterocycle, said heterocycle optionally substituted with 1 to 3 groups of $R^a$. A subembodiment of this aspect of the invention is realized when the n in $(CHR)_n$$C_{5-10}$ heterocycle of $R^2$ and $R^4$ is zero. Another subembodiment of this aspect of the invention is realized when the optionally substituted heterocycle of $R^2$ and $R^4$ is a five or six membered ring containing one or more heteroatoms at least one of which is nitrogen. Still another subembodiment of this aspect of the invention is realized when the optionally substituted heterocycle of $R^2$ and $R^4$ is a five membered ring containing one or more heteroatoms at least one of which is nitrogen. Still another subembodiment of this aspect of the invention is realized when the optionally substituted heterocycle of $R^2$ and $R^4$ is a six membered ring containing one or more heteroatoms at least one of which is nitrogen. Another subembodiment of this aspect of the invention is realized when the heterocycle of $R^2$ and $R^4$ is selected from the group consisting of pyrazolyl, pyridyl, thiazolyl, oxazolyl, pyrimidinyl, pyridazinyl, pyrazinyl, thiadiazolyl, oxadiazolyl, and triazolyl, said groups optionally substituted. Another subembodiment of this aspect of the invention is realized when the heterocycle of $R^2$ and $R^4$ is optionally substituted pyrazolyl. Another subembodiment of this aspect of the invention is realized when the heterocycle of $R^2$ and $R^4$ is substituted pyrazolyl. Yet another subembodiment of this aspect of the invention is realized when the heterocycle of $R^2$ and $R^4$ is optionally substituted pyridyl. Yet another subembodiment of this aspect of the invention is realized when the heterocycle of $R^2$ and $R^4$ is optionally substituted pyrimidinyl. Still another subembodiment of this aspect of the invention is realized when the heterocycle of $R^2$ and $R^4$ is optionally substituted with 1 to 3 groups of $R^a$ selected from —O—$C_{1-6}$alkyl, —OH, —$C_{1-4}$haloalkyl, —$OC_{1-4}$haloalkyl, —$C_{1-6}$alkyl, —$(CHR)_n$$C_{6-10}$ aryl, —$(CHR)_n$$C_{4-10}$ heterocycle, $C_{3-6}$cycloalkyl, —O—, —$(CH_2)_n$$N(R)_2$, —$C(O)CF_3$, COR, C(O)OR, and —$(CH_2)_n$halo, said alkyl, cycloalkyl, aryl and heterocycle optionally substituted with 1 to 3 groups of $R^b$.

Another embodiment of the invention of formula I is realized when A is phenyl represented by structural formula (i) and $R^2$ and $R^4$ both are hydrogen. Another embodiment of the invention of formula I is realized when A is phenyl represented by structural formula (i) and one of $R^2$ and $R^4$ is hydrogen and the other is $CF_3$ or halogen.

Another embodiment of the invention of formula I is realized when A is phenyl represented by structural formula (i) and $R^3$ is selected from the group consisting of hydrogen, $CF_3$, $OCF_3$, $CH_3$, $CF_2CH_2F$, chlorine, and fluorine. A subembodiment of this aspect of the invention is realized when $R^3$ is $CF_3$. Still another subembodiment of this aspect of the invention is realized when $R^3$ is $OCF_3$. Still another subembodiment of this aspect of the invention is realized when $R^3$ is $CF_2CH_2F$. Yet another subembodiment of this aspect of the invention is realized when $R^3$ is chlorine or fluorine.

Another embodiment of the invention of formula I is realized when $R^c$ is selected from hydrogen, $-C_{1-6}$alkyl, $C(O)NH_2$, $-C_{1-6}$alkylOR, $C(O)R$, and $-(CH_2)_nN(R)_2$.

Another embodiment of the invention of formula I is realized when $R^6$ is halogen. Still another embodiment of the invention of formula I is realized when $R^6$ is optionally substituted $C_{1-6}$alkyl. A further aspect of this embodiment is realized when the alkyl of $R^6$ is methyl or $CH_2OH$. Still another embodiment of the invention of formula I is realized when $R^6$ is optionally substituted $C_{6-10}$aryl. A further aspect of this embodiment is realized when the aryl of $R^6$ is phenyl. A further aspect of this embodiment is realized when the aryl of $R^6$ is substituted phenyl.

Another embodiment of the invention of formula I is realized when $R^7$ is hydrogen. Another embodiment of the invention of formula I is realized when $R^7$ is optionally substituted $C_{6-10}$aryl. A further aspect of this embodiment is realized when the aryl of $R^6$ is phenyl. A further aspect of this embodiment is realized when the aryl of $R^6$ is substituted phenyl.

Another embodiment of the invention of formula I is realized when $R^8$ is hydrogen. Another embodiment of the invention of formula I is realized when $R^8$ is $C_{1-6}$alkyl, said alkyl optionally substituted with 1 to 3 groups of $R^a$. A subembodiment of this aspect of the invention is realized when the $C_{1-6}$alkyl is selected from the group consisting of $C(CH_3)_2OH$, $CH(CH_3)OH$, methyl, ethyl and propyl.

Another embodiment of the invention of formula I is realized when B is imidazopyridinyl. An aspect of this embodiment of the invention is realized when B is imidazopyridinyl represented by structural formulas (a), (b) and (c):

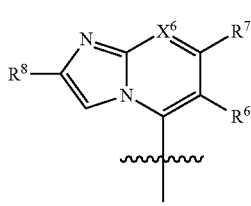

(a)

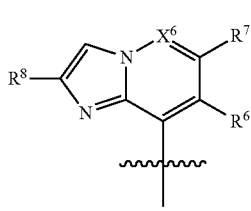

(b)

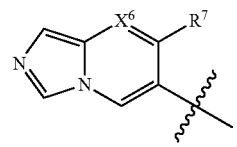

(c)

wherein $X^6$ is CH and $R^6$, $R^7$, and $R^8$ are as originally described. An aspect of this subembodiment of the invention of formula I is realized when $R^6$ of imidazopyridinyl structural formulas (a) and (b) is halogen. Still another embodiment of the invention of formula I is realized when $R^6$ of imidazopyridinyl structural formulas (a) and (b) is optionally substituted $C_{1-6}$alkyl. A further aspect of this embodiment is realized when the alkyl of $R^6$ of structural formulas (a) and (b) is methyl or $CH_2OH$. Still another embodiment of the invention of formula I is realized when $R^6$ imidazopyridinyl of structural formulas (a) and (b) is optionally substituted $C_{6-10}$aryl. A further aspect of this embodiment is realized when the aryl of $R^6$ is phenyl. A further aspect of this embodiment is realized when the aryl of $R^6$ of structural formulas (a) and (b) is substituted phenyl.

Another subembodiment of the invention of formula I is realized when $X^6$ is CH or N and $R^7$ of structural formulas (a), (b) and (c) of B is hydrogen. Another subembodiment of the invention of formula I is realized when $R^7$ of structural formulas (a), (b) and (c) of B is optionally substituted $C_{6-10}$aryl. A further aspect of this embodiment is realized when the aryl of $R^7$ is phenyl.

Another embodiment of the invention of formula I is realized when $X^6$ is CH or N and $R^8$ of structural formulas (a) and (b) of B is hydrogen.

Another embodiment of the invention of formula I is realized when $X^6$ is CH or N and $R^8$ of structural formulas (a) and (b) of B is $C_{1-6}$alkyl, said alkyl optionally substituted with 1 to 3 groups of $R^a$. A subembodiment of this aspect of the invention is realized when $C_{1-6}$alkyl is selected from the group consisting of $C(CH_3)_2OH$, $CH(CH_3)OH$, methyl, ethyl and propyl.

Another embodiment of the invention of formula I is realized when B is imidazopyridinyl represented by structural formulas (a), (b) and (c):

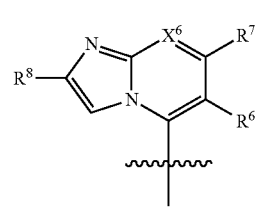

(a)

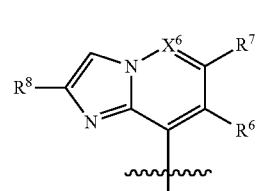

(b)

-continued (c)

wherein $X^6$ of structural formulas (a), (b) and (c) is CH, $R^6$ is $C_{6-10}$aryl, $R^7$ is hydrogen or optionally substituted $C_{6-10}$aryl, and $R^8$ of structural formulas (a) and (b) is hydrogen or optionally substituted $C_{1-6}$alkyl. A subembodiment of this aspect of the invention is realized when the B imidazolpyridinyl of structural formulas (a), (b) and (c) is linked to —NHC(O)-A wherein A is phenyl substituted with 1 to 3 groups of $R^a$. Another subembodiment of this aspect of the invention is realized when the B imidazolpyridinyl of structural formulas (a), (b) and (c) is linked to the —NHC(O)-A wherein A is thiophenyl substituted with 1 to 3 groups of $R^a$.

Still another embodiment of the invention of formula I is realized by structural formulas (A'), (B'), and (C'):

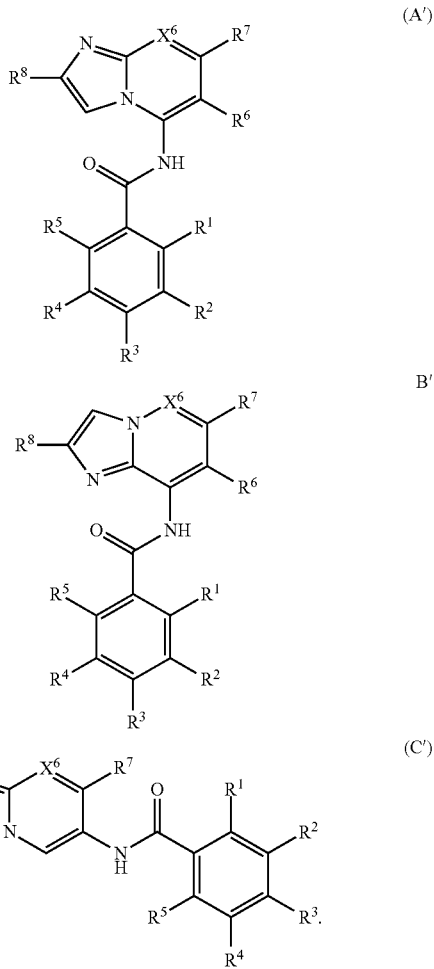

A subembodiment of the invention of formula I represented by structural formulas (A'), (B'), and (C') is realized when $X^6$ is CH, or N, $R^6$ is $C_{6-10}$aryl, $R^7$ is hydrogen or optionally substituted $C_{6-10}$aryl, $R^8$ is hydrogen or optionally substituted $C_{1-6}$alkyl, $R^1$ and $R^5$ are both hydrogen, or one of $R^1$ and $R^5$ is hydrogen and the other is halogen, one of $R^2$ and $R^4$ is hydrogen and the other is $(CHR)_nC_{5-10}$ heterocycle, the n in the heterocycle of $R^2$ and $R^4$ is zero, the heterocycle of $R^2$ and $R^4$ is selected from optionally substituted pyrazolyl, pyridyl, thiazolyl, oxazolyl, pyrimidinyl, pyridazinyl, pyrazinyl, thiadiazolyl, oxadiazolyl, and triazolyl, and $R^3$ is selected from the group consisting of hydrogen, $CF_3$, $OCF_3$, $CH_3$, $CF_2CH_2F$, chlorine, and fluorine. A subembodiment of this aspect of the invention is realized when the invention of formula I is represented by structural formula (A'). Another subembodiment of this aspect of the invention is realized when the invention of formula I is represented by structural formula (B'). Still another subembodiment of this aspect of the invention is realized when the invention of formula I is represented by structural formula (C').

Another embodiment of the invention of formula I is realized when B is optionally substituted indolyl and $R^6$ is selected from halogen, methyl, $CH_2OH$, and phenyl. An aspect of this embodiment of the invention is realized when $R^7$ is hydrogen or optionally substituted $C_{6-10}$aryl and $R^8$ is hydrogen or optionally substituted $C_{1-6}$alkyl.

Another embodiment of the invention of formula I is realized when B is indazolyl and $R^6$ of is selected from halogen, methyl, $CH_2OH$, and phenyl. An aspect of this embodiment of the invention is realized when $R^7$ is hydrogen or optionally substituted $C_{6-10}$aryl and $R^8$ is hydrogen or optionally substituted $C_{1-6}$alkyl.

Another embodiment of the invention of formula I is realized when B is pyrazolopyridinyl and $R^6$ is selected from halogen, methyl, $CH_2OH$, and phenyl. An aspect of this embodiment of the invention is realized when $R^7$ is hydrogen or optionally substituted $C_{6-10}$aryl and $R^8$ is hydrogen or optionally substituted $C_{1-6}$alkyl.

Another embodiment of the invention of formula I is realized when B is triazolopyrimindyl and $R^6$ is selected from halogen, methyl, $CH_2OH$, and phenyl. An aspect of this embodiment of the invention is realized when $R^7$ is hydrogen or optionally substituted $C_{6-10}$aryl and $R^8$ is hydrogen or optionally substituted $C_{1-6}$alkyl.

Another embodiment of the invention of formula I is realized when B is benzothiazolyl and $R^6$ is selected from halogen, methyl, $CH_2OH$, and phenyl. An aspect of this embodiment of the invention is realized when $R^7$ is hydrogen or optionally substituted $C_{6-10}$aryl and $R^8$ is hydrogen or optionally substituted $C_{1-6}$alkyl.

Another embodiment of the invention of formula I is realized B is imidazopyrimidinyl and $R^6$ is selected from halogen, methyl, $CH_2OH$, and phenyl. An aspect of this embodiment of the invention is realized when $R^7$ is hydrogen or optionally substituted $C_{6-10}$aryl and $R^8$ is hydrogen or optionally substituted $C_{1-6}$alkyl.

Another embodiment of the invention of formula I is realized B is imidazopyridazinyl and $R^6$ of is selected from halogen, methyl, $CH_2OH$, and phenyl. An aspect of this embodiment of the invention is realized when $R^7$ is hydrogen or optionally substituted $C_{6-10}$aryl and $R^8$ is hydrogen or optionally substituted $C_{1-6}$alkyl.

Another embodiment of the invention of formula I is realized when B is imidazothiadiazolyl and $R^6$ is selected from halogen, methyl, $CH_2OH$, and phenyl. An aspect of this embodiment of the invention is realized when $R^7$ is hydrogen or optionally substituted $C_{6-10}$aryl and $R^8$ is hydrogen or optionally substituted $C_{1-6}$alkyl.

The invention is also directed to methods of treating a patient (preferably a human) for diseases or disorders in which the TrkA receptor is involved, such as pain, inflammation, cancer, restenosis, atherosclerosis, psoriasis, thrombosis, a disease, disorder, injury, or malfunction relating to dysmyelination or demyelination or a disease or disorder associated with abnormal activities of nerve growth factor (NGF) receptor TrkA, by administering to the patient a therapeutically effective amount of a compound of the invention, or a pharmaceutically acceptable salt thereof.

The invention is also directed to the use of a compound of the invention for treating a disease or disorder in which the TrkA receptor is involved, such as pain, inflammation, cancer, restenosis, atherosclerosis, psoriasis, thrombosis, a disease, disorder, injury, or malfunction relating to dysmyelination or demyelination or a disease or disorder associated with abnormal activities of nerve growth factor (NGF) receptor TrkA, by administering to the patient a compound of the invention, or a pharmaceutically acceptable salt thereof.

The invention is also directed to medicaments or pharmaceutical compositions for the treatment of diseases or disorders in a patient (preferably a human) in which the TrkA receptor is involved, such as pain, inflammation, cancer, restenosis, atherosclerosis, psoriasis, thrombosis, a disease, disorder, injury, or malfunction relating to dysmyelination or demyelination or a disease or disorder associated with abnormal activities of nerve growth factor (NGF) receptor TrkA, which comprise a compound of the invention, or a pharmaceutically acceptable salt thereof, and a pharmaceutically acceptable carrier.

The invention is also directed to a method for the manufacture of a medicament or a pharmaceutical composition for treating diseases in which TrkA receptor is involved, such as pain, inflammation, cancer, restenosis, atherosclerosis, psoriasis, thrombosis, a disease, disorder, injury, or malfunction relating to dysmyelination or demyelination or a disease or disorder associated with abnormal activities of nerve growth factor (NGF) receptor TrkA comprising combining a compound of the invention or a pharmaceutically acceptable salt thereof, with a pharmaceutically acceptable carrier.

Where a variable occurs more than once in any formula of the invention, or in a substituent thereof, the individual occurrences of that variable are independent of each other, unless otherwise specified. Also, combinations of substituents/or variables are permissible only if such combinations result in stable compounds.

As used herein, the term "alkyl," by itself or as part of another substituent, means a saturated straight or branched chain hydrocarbon radical having the number of carbon atoms designated (e.g., $C_{1-10}$ alkyl means an alkyl group having from one to ten carbon atoms).

Preferred alkyl groups for use in the invention are $C_{1-6}$ alkyl groups, having from one to six atoms. Exemplary alkyl groups include methyl, ethyl, n-propyl, isopropyl, n-butyl, isobutyl, tert-butyl, pentyl, hexyl, and the like. $C_0$ alkyl means a bond.

As used herein, the term "alkenyl," by itself or as part of another substituent, means a straight or branched chain hydrocarbon radical having a single carbon-carbon double bond and the number of carbon atoms designated (e.g., $C_{2-10}$ alkenyl means an alkenyl group having from two to ten carbon atoms). Preferred alkenyl groups for use in the invention are $C_{2-6}$ alkenyl groups, having from two to six carbon atoms. Exemplary alkenyl groups include ethenyl and propenyl.

As used herein, the term "cycloalkyl," by itself or as part of another substituent, means a saturated cyclic hydrocarbon radical having the number of carbon atoms designated (e.g., $C_{3-12}$ cycloalkyl means a cycloalkyl group having from three to twelve carbon atoms). The term cycloalkyl as used herein includes mono-, bi- and tricyclic saturated carbocycles, spirocycles, and bridged and fused ring carbocycles as well as oxo substituted cycloalkyl groups.

Preferred cycloalkyl groups for use in the invention are monocyclic $C_{3-8}$ cycloalkyl groups, having from three to eight carbon atoms. Exemplary monocyclic cycloalkyl groups include cyclopropyl, cyclobutyl, cyclopentyl, cyclohexyl and the like. Exemplary bridged cycloalkyl groups include adamantyl and norbornyl. Exemplary fused cycloalkyl groups include decahydronaphthalene.

The term "heteroatom" means O, S or N, selected on an independent basis.

As used herein, the term "aryl," by itself or as part of another substituent, means an aromatic cyclic hydrocarbon radical. Preferred aryl groups have from six to ten carbon atoms. The term "aryl" includes multiple ring systems as well as single ring systems. Preferred aryl groups for use in the invention include phenyl and naphthyl.

The term "aryl" also includes fused cyclic hydrocarbon rings which are partially aromatic (i.e., one of the fused rings is aromatic and the other is non-aromatic). An exemplary aryl group which is partially aromatic is indanyl.

The term heterocyclyl, heterocycle or heterocyclic, as used herein, represents a stable 5- to 7-membered monocyclic or stable 8- to 11-membered bicyclic heterocyclic ring which is either saturated or unsaturated, and which consists of 3 or more carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. The term heterocyclyl, heterocycle or heterocyclic includes heteroaryl moieties. Examples of such heterocyclic elements include, but are not limited to, azepinyl, benzodioxolyl, benzimidazolyl, benzisoxazolyl, benzofurazanyl, benzopyranyl, benzothiopyranyl, benzofuryl, benzothiazolyl, benzothienyl, benzotriazolyl, benzoxazolyl, chromanyl, cinnolinyl, dihydrobenzofuryl, dihydrobenzothienyl, dihydrobenzothiopyranyl, dihydrobenzothiopyranyl sulfone, 1,3-dioxolanyl, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, oxazolyl, 2-oxopiperazinyl, 2-oxopiperdinyl, 2-oxopyrrolidinyl, piperidyl, piperazinyl, pyridyl, pyrazinyl, pyrazolidinyl, pyrazolyl, pyrazolopyridinyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, thienyl, triazolyl, N-oxides and —C=O derivatives thereof.

The term "heteroaryl", as used herein except where noted, represents a stable 5- to 7-membered monocyclic- or stable 9- to 10-membered fused bicyclic heterocyclic ring system which contains an aromatic ring, any ring of which may be saturated, such as piperidinyl, partially saturated, or unsaturated, such as pyridinyl, and which consists of carbon atoms and from one to four heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure. Examples of such heteroaryl groups include, but are not limited to, benzimidazole, benzisothiazole, benzisoxazole, benzofuran, benzothiazole, benzothiophene, benzotriazole, benzoxazole, carboline, cinnoline, furan, furazan, imidazole, indazole, indole, indolizine, isoquinoline, isothiazole, isoxazole, naphthyridine, oxadiazole, oxazole, phthalazine, pteridine, purine, pyran, pyrazine, pyrazole, pyridazine, pyridine, pyrimidine, pyrrole, quinazoline, quinoline, quinoxaline, tetrazole, thiadiazole, thiazole, thiophene, triazine, triazole, N-oxides thereof and —C═O derivatives thereof. Suitable heteroaryl groups are imidazopyridinyl, indazolyl, imidazothiazolyl, imidazopyrimidinyl, imidazopyridazinyl, imidazothiadiazolyl, quinoxalinyl, and imidazopyrrolyl.

When a heterocyclyl group as defined herein is substituted, the substituent may be bonded to a ring carbon atom of the heteroaryl group, or on a ring heteroatom (i.e., a nitrogen, oxygen or sulfur), which has a valence which permits substitution. Preferably, the substituent is bonded to a ring carbon atom. Similarly, when a heteroaryl group is defined as a substituent herein, the point of attachment may be at a ring carbon atom of the heteroaryl group, or on a ring heteroatom (i.e., a nitrogen, oxygen or sulfur), which has a valence which permits attachment. Preferably, the attachment is at a ring carbon atom.

As used herein, the term "halo" or "halogen" includes fluoro, chloro, bromo and iodo.

As used herein —O— includes oxo (e.g., an annular —CH— substituted with oxo is —C(O) or carbonyl.

The compounds of the invention may have one or more asymmetric centers. Compounds with asymmetric centers give rise to enantiomers (optical isomers), diastereomers (configurational isomers) or both, and it is intended that all of the possible enantiomers and diastereomers in mixtures and as pure or partially purified compounds are included within the scope of this invention. The present invention is meant to encompass all such isomeric forms of the compounds of the invention. The present invention includes all stereoisomers of formulae (I) and pharmaceutically acceptable salts thereof.

The independent syntheses of the enantiomerically or diastereomerically enriched compounds, or their chromatographic separations, may be achieved as known in the art by appropriate modification of the methodology disclosed herein. Their absolute stereochemistry may be determined by the x-ray crystallography of crystalline products or crystalline intermediates that are derivatized, if necessary, with a reagent containing an asymmetric center of known absolute configuration.

If desired, racemic mixtures of the compounds may be separated so that the individual enantiomers or diastereomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods using chiral stationary phases, which methods are well known in the art.

Alternatively, any enantiomer or diastereomer of a compound may be obtained by stereoselective synthesis using optically pure starting materials or reagents of known configuration by methods well known in the art.

In the compounds of the invention the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic formulae (I). For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic formulae (I) can be prepared without undue experimentation by conventional techniques well known to those skilled in the art or by processes analogous to those described in the Schemes and Examples herein using appropriate isotopically-enriched reagents and/or intermediates.

The term "substantially pure" means that the isolated material is at least 90% pure, and preferably 95% pure, and even more preferably 99% pure as assayed by analytical techniques known in the art.

As used herein, the term TrkA refers to one of Trk high affinity binding protein kinase receptors that are activated by Neurotrophins (NT), a group of soluble growth factors Nerve Growth Factor (NGF), Brain-Derived Neurotrophic Factor (BDNF) and Neurotrophin 3-5 (NT 3-5). The Trk receptors are made up of three family members, TrkA, TrkB and TrkC, that bind to and mediate the signal transduction derived from the Neurotrophins. Inhibitors of the Trk/neutrophin pathway have been demonstrated to be highly effective in numerous pre-clinical animal models of pain. The compounds of the invention are modulators of the Trk receptors, particularly TrkA.

The term "pharmaceutically acceptable salts" refers to salts prepared from pharmaceutically acceptable non-toxic bases or acids including inorganic or organic bases and inorganic or organic acids. The compounds of the invention may be mono, di or tri salts, depending on the number of acid functionalities present in the free base form of the compound. Free bases and salts derived from inorganic bases include aluminum, ammonium, calcium, copper, ferric, ferrous, lithium, magnesium, manganic salts, manganous, potassium, sodium, zinc, and the like.

Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, trifluoroacetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, para-toluenesulfonic acid, and the like.

The present invention is directed to the use of the compounds of formulae (I) disclosed herein as TrkA inhibitors in a patient or subject such as a mammal in need of such activity, comprising the administration of an effective amount of the compound. In addition to humans, a variety of other mammals can be treated according to the method of the present invention.

The compounds of the present invention have utility in treating or ameliorating pain disorders (including pain associated with cancer, surgery, and bone fracture, acute pain, inflammatory pain and neuropathic pain). The compounds of formula I are also useful for treating cancers including neuroblastoma, ovarian, pancreatic and colorectal cancer. Other conditions that may be treated by the compounds of the invention include inflammation and certain infectious diseases, interstitial cystitis, painful bladder syndrome, urinary incontinence, asthma, anorexia, atopic dermatitis, and psoriasis. Treatment of demyelination and dysmyelination, by promoting myelination, neuronal survival, and oligodendrocyte differentiation via blocking Sp35-TrkA interaction may also be possible with the compounds of the present invention.

The compounds of formula I may also be useful in the treatment of bone-related diseases (e.g., those involved in bone resorption). Examples of bone-related diseases include metastatic bone disease, treatment-induce bone loss, osteoporosis, rheumatoid arthritis, ankylosing spondylitis, Paget's disease, and periodontal disease. Another bone disorder or disease that can be treated with the compounds of the claimed invention is metastatic tumor-induced osteolysis. Cancers known to cause tumor induced osteolysis are hematological malignancies such as myeloma and lymphoma and solid tumors such as breast, prostate, lung, renal and thyroid.

Pain disorders for which the compounds of the invention may be useful include neuropathic pain (such as postherpetic neuralgia, nerve injury, the "dynias", e.g., vulvodynia, phantom limb pain, root avulsions, painful diabetic neuropathy, painful traumatic mononeuropathy, painful polyneuropathy); central pain syndromes (potentially caused by virtually any lesion at any level of the nervous system); postsurgical pain syndromes (e.g., postmastectomy syndrome, postthoracotomy syndrome, stump pain); bone and joint pain (osteoarthritis), repetitive motion pain, dental pain, cancer pain, myofascial pain (muscular injury, fibromyalgia); perioperative pain (general surgery, gynecological), chronic pain, dysmennorhea, as well as pain associated with angina, and inflammatory pain of varied origins (e.g. osteoarthritis, rheumatoid arthritis, rheumatic disease, teno-synovitis and gout), headache, migraine and cluster headache, headache, primary hyperalgesia, secondary hyperalgesia, primary allodynia, secondary allodynia, or other pain caused by central sensitization.

Compounds of the invention may also be used to treat or prevent dyskinesias. Furthermore, compounds of the invention may be used to decrease tolerance and/or dependence to opioid treatment of pain, and for treatment of withdrawal syndrome of e.g., alcohol, opioids, and cocaine.

The subject or patient to whom the compounds of the present invention is administered is generally mammals such a human being, male or female, in whom TrkA and/or TrkB modulation is desired. Thus, an aspect of the present invention is a method of treating diseases with an inhibitor of TrkA and/or TrkB comprising administering to said mammal one or more compounds of formula I or a pharmaceutically acceptable salt thereof in an amount effective to treat or prevent said disorder. A particular aspect of the invention is directed to a method of treating pain, cancer, inflammation, neurodegenerative disease or *Typanosoma cruzi* infection by administering to said mammal a therapeutically effective amount of a compound of formula I or a pharmaceutically acceptable salt thereof. Still another aspect of the present invention is directed to a method of treating osteolytic disease in a mammal by administering a therapeutically effective amount of a compound of formula I or a pharmaceutically acceptable salt thereof. For purposes of this invention mammals include dogs, cats, mice, rats, cattle, horses, sheep, rabbits, monkeys, chimpanzees or other apes or primates, for which treatment of the above noted disorders is desired.

The compounds of the present invention may be used in combination with one or more other drugs in the treatment of diseases or conditions for which the compounds of the present invention have utility, where the combination of the drugs together are safer or more effective than either drug alone. Additionally, the compounds of the present invention may be used in combination with one or more other drugs that treat, prevent, control, ameliorate, or reduce the risk of side effects or toxicity of the compounds of the present invention. Such other drugs may be administered, by a route and in an amount commonly used therefor, contemporaneously or sequentially with the compounds of the present invention. Accordingly, the pharmaceutical compositions of the present invention include those that contain one or more other active ingredients, in addition to the compounds of the present invention. The combinations may be administered as part of a unit dosage form combination product, or as a kit or treatment protocol wherein one or more additional drugs are administered in separate dosage forms as part of a treatment regimen.

Examples of combinations of the compounds include combinations with agents for the treatment of pain, for example steroids such as dexamethasone, cortisone, and fluticasone, non-steroidal anti-inflammatory agents, such as aspirin, diclofenac, duflunisal, fenoprofen, flurbiprofen, ibuprofen, indomethacin, ketoprofen, ketorolac, naproxen, oxaprozin, piroxicam, sulindac and tolmetin; COX-2 inhibitors, such as celecoxib, rofecoxib and valdecoxib; CB-2 agonists; VR-1 antagonists; bradykinin B 1 receptor antagonists; sodium channel blockers and antagonists; nitric oxide synthase (NOS) inhibitors (including iNOS and nNOS inhibitors); glycine site antagonists, including lacosamide; neuronal nicotinic agonists; NMDA antagonists; potassium channel openers; AMPA/kainate receptor antagonists; calcium channel blockers, such as ziconotide; GABA-A receptor IO modulators (e.g., a GABA-A receptor agonist); matrix metalloprotease (MMP) inhibitors; thrombolytic agents; chemotherapeutic agents, opioid analgesics such as codeine, fentanyl, hydromorphone, levorphanol, meperidine, methadone, morphine, oxycodone, oxymorphone, pentazocine, propoxyphene; neutrophil inhibitory factor (NIF); pramipexole, ropinirole; anticholinergics; amantadine; monoamine oxidase Bl5 ("MAO-B") inhibitors; 5HT receptor agonists or antagonists; mGlu5 antagonists; alpha agonists; neuronal nicotinic agonists; NMDA receptor agonists or antagonists; NK1 antagonists; selective serotonin reuptake inhibitors ("SSRI") and/or selective serotonin and norepinephrine reuptake inhibitors ("SSNRI"), such as duloxetine; tricyclic antidepressant drugs, norepinephrine modulators; lithium; valproate; gabapentin; pregabalin; rizatriptan; zolmitriptan; naratriptan and sumatriptan.

Another aspect of the present invention is directed to a pharmaceutical composition comprising a compound of formula I or a pharmaceutically acceptable salt thereof and a pharmaceutically acceptable diluent or carrier. Still another aspect of the present invention is directed to a compound of formula I or a pharmaceutically acceptable salt thereof, for use in the treatment of a condition treatable with an inhibitor of TrkA and/or TrkB, such as the disorders, conditions and/or diseases described herein. Still another aspect is directed to use of a compound of formula I or a pharmaceutically acceptable salt thereof in the treatment of pain, cancer, inflammation, neurodegenerative disease or *typanosoma cruzi* infection.

The term "composition" as used herein is intended to encompass a product comprising specified ingredients in predetermined amounts or proportions, as well as any product which results, directly or indirectly, from combination of the specified ingredients in the specified amounts. This term in relation to pharmaceutical compositions is intended to encompass a product comprising one or more active ingredients, and an optional carrier comprising inert ingredients, as well as any product which results, directly or indirectly, from combination, complexation or aggregation of any two or more of the ingredients, or from dissociation of one or more of the ingredients, or from other types of reactions or interactions of one or more of the ingredients.

In general, pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active compound, which is a compound of formulae (I), is included in an amount sufficient to produce the desired effect upon the process or condition of diseases. Accordingly, the pharmaceutical compositions of the present invention encompass any composition made by admixing a compound of the present invention and a pharmaceutically acceptable carrier.

The carrier may take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, or pharmaceutically acceptable salts thereof, may also be administered by controlled release means and/or delivery devices.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period.

A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.1 mg to about 500 mg of the active ingredient and each cachet or capsule preferably containing from about 0.1 mg to about 500 mg of the active ingredient.

Compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Other pharmaceutical compositions include aqueous suspensions, which contain the active materials in admixture with excipients suitable for the manufacture of aqueous suspensions. In addition, oily suspensions may be formulated by suspending the active ingredient in a vegetable oil, for example *arachis* oil, olive oil, sesame oil or coconut oil, or in a mineral oil such as liquid paraffin. Oily suspensions may also contain various excipients. The pharmaceutical compositions of the invention may also be in the form of oil-in-water emulsions, which may also contain excipients such as sweetening and flavoring agents.

The pharmaceutical compositions may be in the form of a sterile injectable aqueous or oleaginous suspension, or in the form of sterile powders for the extemporaneous preparation of such sterile injectable solutions or dispersions. In all cases, the final injectable form must be sterile and must be effectively fluid for easy syringeability. The pharmaceutical compositions must be stable under the conditions of manufacture and storage; thus, preferably should be preserved against the contaminating action of microorganisms such as bacteria and fungi.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can also be in a form suitable for rectal administration wherein the carrier is a solid. It is preferable that the mixture forms unit dose suppositories. Suitable carriers include cocoa butter and other materials commonly used in the art.

By "pharmaceutically acceptable" it is meant the carrier, diluent or excipient must be compatible with the other ingredients of the formulation and not deleterious to the recipient thereof.

The terms "administration of" or "administering a" compound should be understood to mean providing a compound of the invention to the individual in need of treatment in a form that can be introduced into that individual's body in a therapeutically useful form and therapeutically useful amount, including, but not limited to: oral dosage forms, such as tablets, capsules, syrups, suspensions, and the like; injectable dosage forms, such as IV, IM, or IP, and the like; transdermal dosage forms, including creams, jellies, powders, or patches; buccal dosage forms; inhalation powders, sprays, suspensions, and the like; and rectal suppositories.

The terms "effective amount" or "therapeutically effective amount" means the amount of the subject compound that will elicit the biological or medical response of a tissue, system, animal or human that is being sought by the researcher, veterinarian, medical doctor or other clinician.

As used herein, the term "treatment" or "treating" means any administration of a compound of the present invention and includes (1) inhibiting the disease in an animal that is experiencing or displaying the pathology or symptomotology of the disease (i.e., arresting further development of the pathology and/or symptomotology), or (2) ameliorating the disease in an animal that is experiencing or displaying the pathology or symptomotology of the disease (i.e., reversing the pathology and/or symptomotology).

The compositions containing compounds of the present invention may conveniently be presented in unit dosage form and may be prepared by any of the methods well known in the art of pharmacy. The term "unit dosage form" is taken to mean a single dose wherein all active and inactive ingredients are combined in a suitable system, such that the patient or person administering the drug to the patient can open a single container or package with the entire dose contained therein, and does not have to mix any components together from two or more containers or packages. Typical examples of unit dosage forms are tablets or capsules for oral administration, single dose vials for injection, or suppositories for rectal administration. This list of unit dosage forms is not intended to be limiting in any way, but merely to represent typical examples of unit dosage forms.

The compositions containing compounds of the present invention may conveniently be presented as a kit, whereby two or more components, which may be active or inactive ingredients, carriers, diluents, and the like, are provided with instructions for preparation of the actual dosage form by the patient or person administering the drug to the patient. Such kits may be provided with all necessary materials and ingredients contained therein, or they may contain instructions for using or making materials or components that must be obtained independently by the patient or person administering the drug to the patient.

When treating or ameliorating a disorder or disease for which compounds of the present invention are indicated, generally satisfactory results are obtained when the compounds of the present invention are administered at a daily dosage of from about 0.1 mg to about 100 mg per kg of animal body weight, preferably given as a single daily dose or in divided doses two to six times a day, or in sustained release form. The total daily dosage is from about 1.0 mg to about 2000 mg, preferably from about 0.1 mg to about 20 mg per kg of body weight. In the case of a 70 kg adult human, the total daily dose will generally be from about 7 mg to about 1,400 mg. This dosage regimen may be adjusted to provide the optimal therapeutic response. The compounds may be administered on a regimen of 1 to 4 times per day, preferably once or twice per day.

The amount of active ingredient that may be combined with the carrier materials to produce a single dosage form will vary depending upon the host treated and the particular mode of administration. For example, a formulation intended for the oral administration to humans may conveniently contain from about 0.005 mg to about 2.5 g of active agent, compounded with an appropriate and convenient amount of carrier material. Unit dosage forms will generally contain between from about 0.005 mg to about 1000 mg of the active ingredient, typically 0.005, 0.01 mg, 0.05 mg, 0.25 mg, 1 mg, 5 mg, 25 mg, 50 mg, 100 mg, 200 mg, 300 mg, 400 mg, 500 mg, 600 mg, 800 mg or 1000 mg, administered once, twice or three times a day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Several methods for preparing the compounds of this invention are illustrated in the following Schemes and Examples. Starting materials and the requisite intermediates are in some cases commercially available, or can be prepared according to literature procedures or as illustrated herein.

The compounds of this invention may be prepared by employing reactions as shown in the following schemes, in addition to other standard manipulations that are known in the literature or exemplified in the experimental procedures. Substituent numbering as shown in the schemes does not necessarily correlate to that used in the claims and often, for clarity, a single substituent is shown attached to the compound where multiple substituents are allowed under the definitions hereinabove. Reactions used to generate the compounds of this invention are prepared by employing reactions as shown in the schemes and examples herein, in addition to other standard manipulations such as ester hydrolysis, cleavage of protecting groups, etc., as may be known in the literature or exemplified in the experimental procedures.

During any of the synthetic sequences it may be necessary or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973, and T. W. Greene & P/G. M. Wuts, *Protective Groups in Organic Synthesis*, John Wiley & Sons, 1999. The protecting groups may be removed at a convenient sequent stage using methods known from the art.

In some cases the final product may be further modified, for example, by manipulation of substituents. These manipulations may include, but are not limited to, reduction, oxidation, alkylation, acylation, and hydrolysis reactions which are commonly known to those skilled in the art. In some cases the order of carrying out the foregoing reaction schemes may be varied to facilitate the reaction or to avoid unwanted reaction products. The following examples are provided so that the invention might be more fully understood. These examples are illustrative only and should not be construed as limiting the invention in any way.

The following abbreviations are used throughout the text:
Me: methyl
Et: ethyl
Bu: butyl
t-Bu: tert-butyl
Ar: aryl
Ph: phenyl
Bn: benzyl
Ac: acetyl
DMF.DMA: N,N-dimethylformamide dimethyl acetal
DMSO: dimethylsulfoxide
DMF: N,N-dimethylformamide
THF: tetrahydrofuran
TEA: triethylamine
aq: aqueous
HPLC: high performance liquid chromatography
MS: mass spectrometry
CDI: 1,1'-carbonyldiimidazole
DCE: 1,2-dichloroethane
HCl: hydrochloric acid
° C.: degrees Celsius
BINAP: 2,2'-bis(diphenylphosphino)-1,1'-binaphthalene
ATP: adenosine triphosphate
i-Pr: isopropyl
Py: pyridyl
OAc: acetate
TFA: trifluoroacetic acid
TFAA: trifluoroacetic anhydride
Boc: tert-butoxycarbonyl
$Boc_2O$: di-tert-butyl dicarbonate
BOP: (benzotriazol-1-yloxy)tris(dimethylamino)phosphonium hexafluorophosphate
DEA: diethylamine
DIEA: N,N-diisopropylethylamine
DIPEA: N,N-diisopropylethylamine
HOBT: 1-hydroxybenzotriazole
EDC: N-(3-dimethylaminopropyl)-N'-ethylcarbodiimide hydrochloride
EDCI: N-(3-dimethylaminopropyl)-N'-ethylcarbodiimide hydrochloride
PyCLU: chlorodipyrrolidinocarbenium
n-BuLi: n-butyllithium
HATU: O-(7-azabenzotriazol-1-yl)-N,N,N'N'-tetramethyluronium hexafluorophosphate
EDTA: ethylenediaminetetraacetic acid
HMDS: hexamethyldisilazane
min: minutes
h: hours
HPLC: high performance liquid chromatography
LCMS: liquid chromatography-mass spectrometry
SFC: supercritical fluid chromatography
TLC: thin layer chromatography
NMP: 1-methyl-2-pyrrolidinone
MTBE: methyl tert-butyl ether
DMA: N,N-dimethylacetamide
NBS: N-bromosuccinimide
CAN: ammonium cerium(IV) nitrate
dppf: 1,1'-bis(diphenylphosphino)ferrocene
dtbpf: 1,1'-bis(di-tert-butylphosphino)ferrocene
dba: dibenzylideneacetone
DMAP: 4-(dimethylamino)pyridine
PMBCl: 4-methoxybenzyl chloride
DIBAL: diisobutylaluminum hydride
DAST: (diethylamino)sulfur trifluoride
DBU: 1,8-diazabicyclo[5.4.0]undec-7-ene
AIBN: 2-2'-azobisisobutyronitrile
m-CPBA: 3-chloroperbenzoic acid
DABCO: diazabicyclo[2.2.2]octane
LDA: lithium diisopropylamide
HOAt: 1-hydroxy-7-azabenzotriazole
LAH: lithium aluminum hydride
AOP: 7-(azabenzotriazol-1-yloxy)tris(dimethylamino)phosphonium hexafluorophosphate
PyAOP: 7-(azabenzotriazol-1-yloxy)tripyrrolidinophosphonium hexafluorophosphate
DCM: dichloromethane
PE: petroleum ether
TMS: trimethylsilyl
Conc: concentrated
TIPS: triisopropylsilyl
OTf: trifluoromethanesulfonate
bis-pin: 4,4,4',4',5,5,5',5'-octamethyl-2,2'-bi(1,3,2-dioxaborolane)
NCS: N-chlorosuccinimide
DPPA: diphenylphosphoryl azide
PCC: pyridinium chlorochromate
DME: 1,2-dimethoxyethane
PMB: 4-methoxybenzyl
NMO: 4-methylmorpholine N-oxide
PyBop: benzotriazol-1-yl-oxytripyrrolidinophosphonium hexafluorophosphate
PS: polystyrene Reaction Schemes The compounds of the present invention can be prepared readily according to the following Schemes and specific examples, or modifications thereof, using readily available starting materials, reagents and conventional synthetic procedures. In these reactions, it is also possible to make use of variants which are themselves known to those of ordinary skill in this art but are not mentioned in greater detail. The general procedures for making the compounds claimed in this invention can be readily understood and appreciated by one skilled in the art from viewing the following Schemes.

Scheme 1 illustrates the general strategy for preparing the compounds of the present invention in which an carboxylic acid intermediate (1.1) may be activated (for example, via treatment with $POCl_3$, $(COCl)_2$, or $SOCl_2$ to generate the acid chloride) followed by coupling to an amine (1.2) to give the desired product amide 1.3. Various carboxylic acid intermediates, such as those described herein (vide infra), may be coupled to a variety of amines to give the compounds of the present invention. There are many known strategies for effecting such coupling chemistry, including use of coupling reagents, such as EDC with HOBT, PyBOP, HATU, AOP, PyAOP, CDI and the like.

SCHEME 1

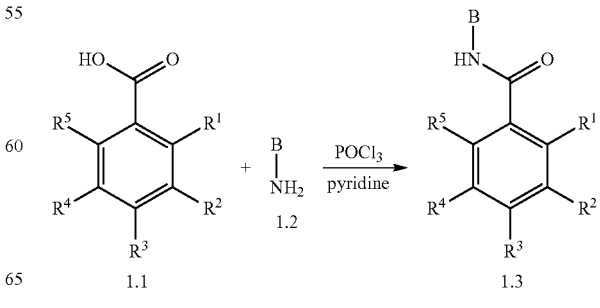

In some cases, various protecting group strategies familiar to one skilled in the art of organic synthesis may be employed to allow preparation of a particular compound of the present invention. This general approach may be successful for the preparation of a range of amide moieties, utilizing a variety of acids and amine intermediates.

Scheme 2 illustrates one of many possible methods that a benzamide intermediate may be modified to prepare alcohols of the type 2.2. Treatment of ester 2.1 with a reducing agent such as lithium aluminum hydride can afford alcohol 2.2.

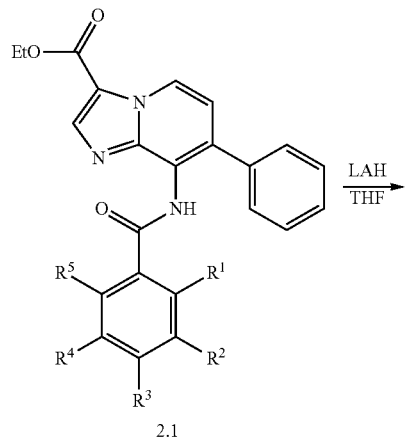

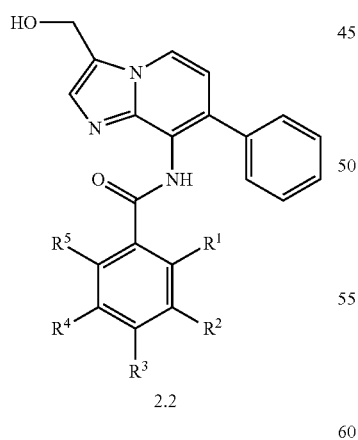

In Scheme 3, the synthesis of secondary alcohol 3.4 is illustrated. Oxidation of primary alcohol 3.1 with manganese dioxide can afford aldehyde 3.2. Treatment of the aldehyde with a Grignard reagent (e.g., 3.3) gives secondary alcohol 3.4. The racemic alcohol can be further resolved by a chiral HPLC or SFC to provide the individual enantiomers.

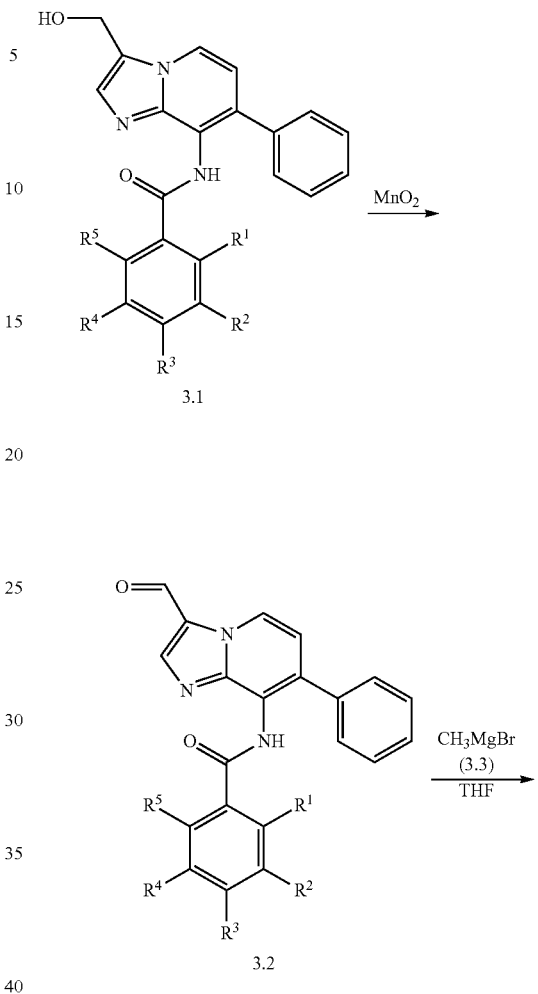

Scheme 4 describes a method in which a Grignard reagent (e.g., 4.2) may be added to ester 4.1 to generate tertiary alcohol 4.3.

SCHEME 4

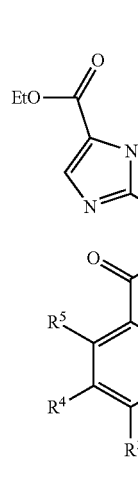
4.1

CH₃MgBr
(4.2)
—————→
THF

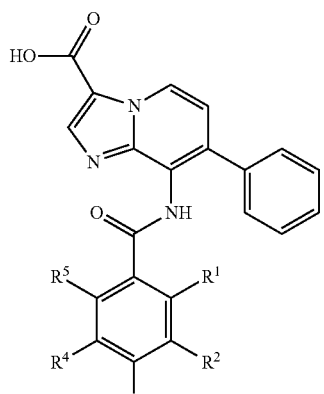
5.2

NH₄Cl, HATU
——————→
Et₃N, DCM

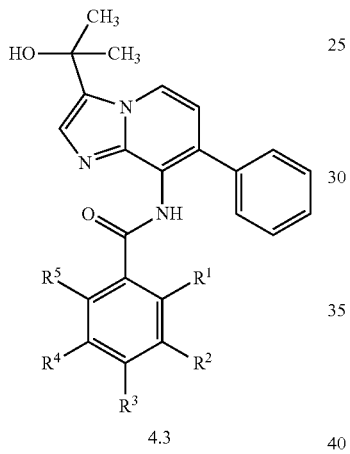
4.3

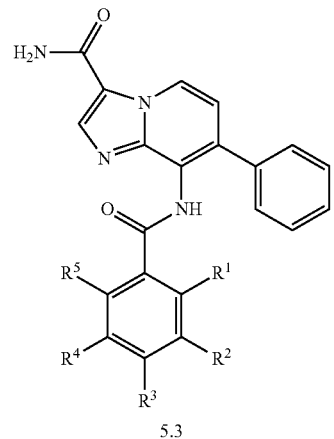
5.3

Scheme 5 shows the synthesis of primary amide 5.3. Ester 5.1 is hydrolized to acid 5.2 which can be coupled with ammonium chloride using HATU, for example, and a base, such as trimethylamine, to afford amide 5.3.

Scheme 6 illustrates the synthesis of a deuterated primary alcohol. Treatment of ester 6.1 with a reducing agent such as deuterated lithium aluminumhydride can afford deuterated alcohol 6.2.

SCHEME 5

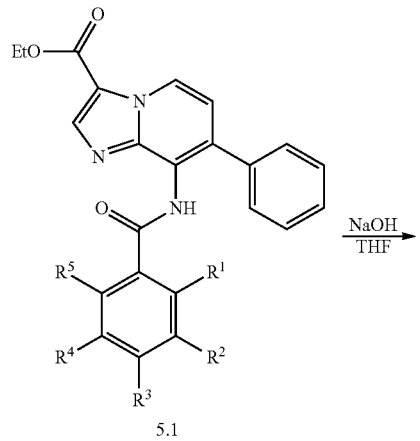
5.1

NaOH
——→
THF

SCHEME 6

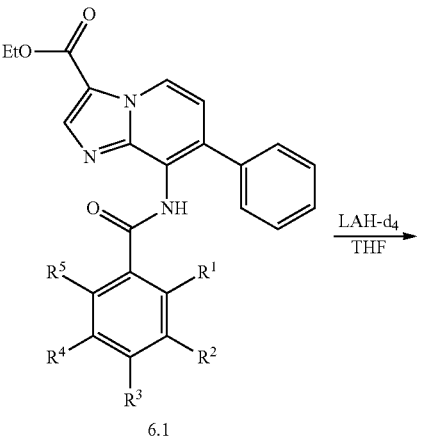
6.1

LAH-d₄
——→
THF

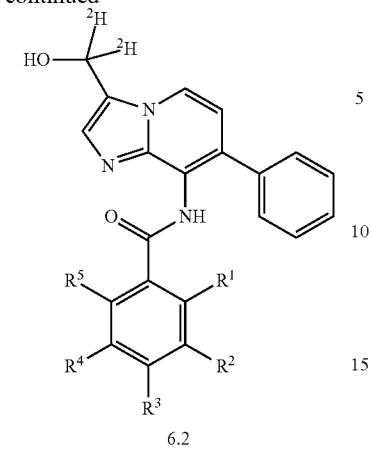

6.2

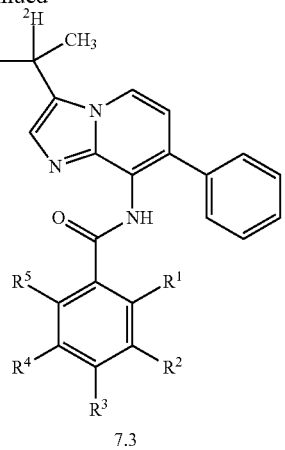

7.3

In Scheme 7, the synthesis of a deuterated secondary alcohol 7.3 is illustrated. Oxidation of secondary alcohol 7.1 with manganese dioxide can afford methyl ketone 7.2. Treatment of the ketone with a reducing agent such as deuterated lithium aluminumhydride can afford deuterated alcohol 7.2. The racemic alcohol can be further resolved by a chiral HPLC or SFC to provide the individual enantiomers.

Alternative modifications are known to those skilled in the art and may include, but are not limited to, reductive amination, ether formation, and heterocycle formation.

In Scheme 8, intermediate amine 8.3 is synthesized by a Suzuki cross-coupling reaction between commercially available aryl chloride 8.1 and phenyl boronic acid 8.2 in the presence of bis(tri-t-butylphosphine)palladium (0) and cesium carbonate.

SCHEME 7

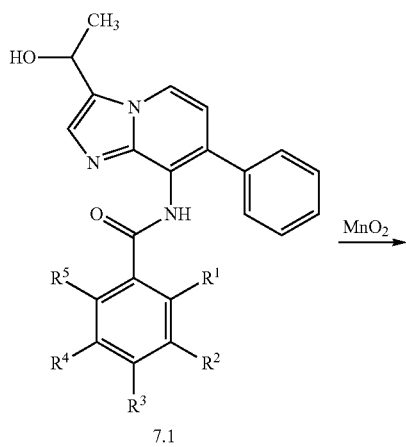

SCHEME 8

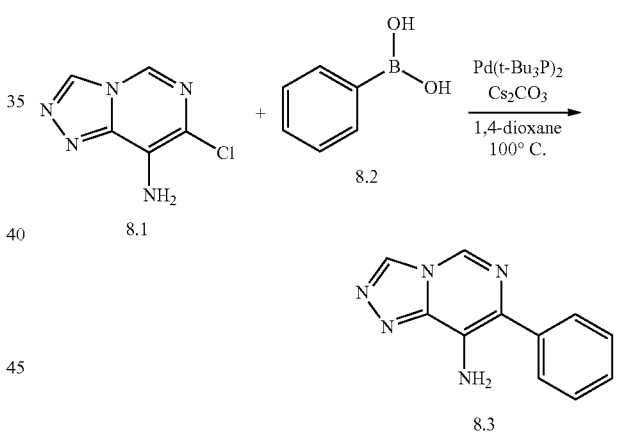

Scheme 9 illustrates the preparation of the intermediate amines of the type 9.5. Cross-coupling between aryl chloride 9.1 and phenyl boronic acid gives biaryl compound 9.2, which upon cyclization with chloroaldehyde 9.3 affords imidazopyridine 9.4. Finally, hydrogenation of the nitro group over palladium on carbon completes the synthesis of intermediate amine 9.5.

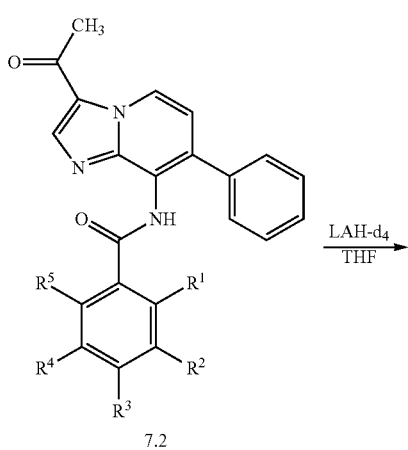

7.2

SCHEME 9

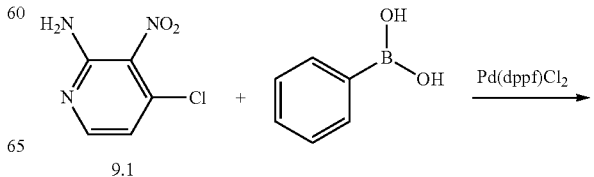

9.1

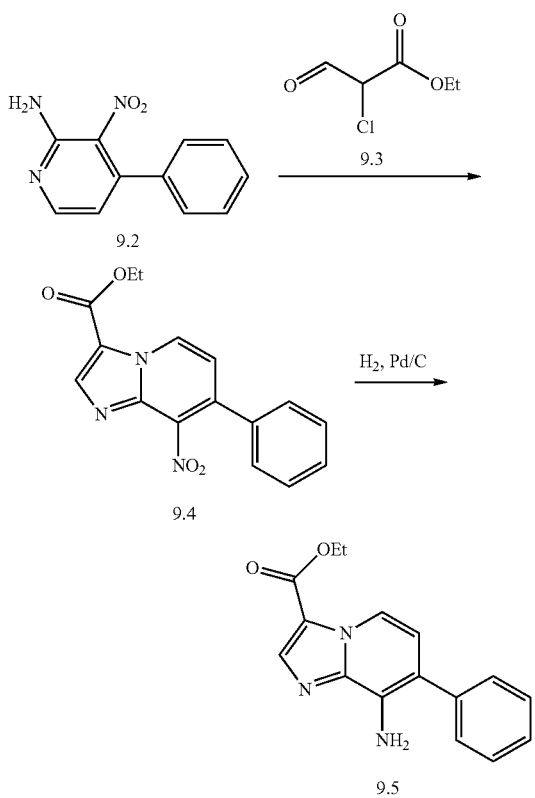

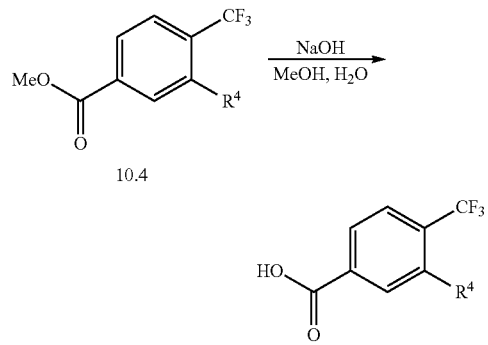

Reaction Scheme 10 illustrates the preparation of the intermediate acids of the type 10.5 which are used to prepare compounds of the invention. Bromide 10.1 is converted to the boronate ester with 4,4,4',4',5,5,5',5'-octamethyl-2,2'-bi(1,3,2-dioxaborolane) in the presence of a suitable catalyst and base system to afford 10.2. Cross-coupling of the ester 10.2 with a suitable aryl or heteroaryl bromide (10.3) is mediated by heating in an aqueous solvent system in the presence of a suitable catalyst and base (e.g., Pd(dppf)Cl$_2$ and Na$_2$CO$_3$ in aqueous DMF) to furnish ester 10.4. Hydrolysis of the ester under basic conditions then affords acid 10.5.

Scheme 10 illustrates the preparation of the intermediate acids of the type 10.5. Bromide 10.1 is converted to the boronate ester with 4,4,4',4',5,5,5',5'-octamethyl-2,2'-bi(1,3,2-dioxaborolane) in the presence of a suitable catalyst and base system to afford 10.2. Palladium-catalyzed cross-coupling of the ester 10.2 with an aryl or heteroaryl bromide (10.3) furnishes ester 10.4. Saponification of the ester then affords acid 10.5.

SCHEME 10

SCHEME 11

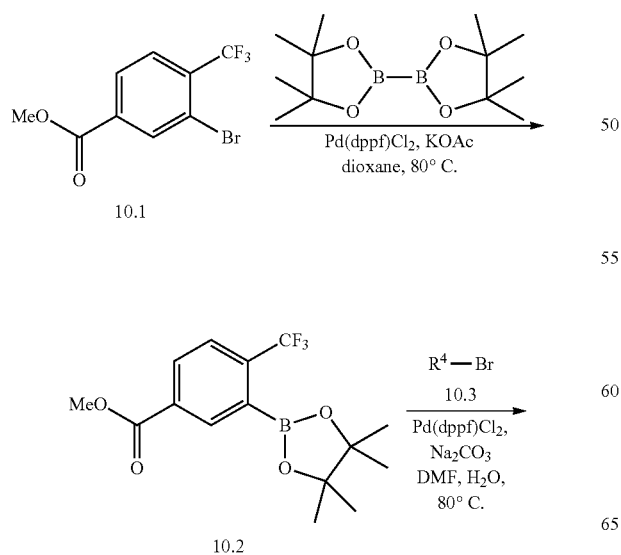

-continued

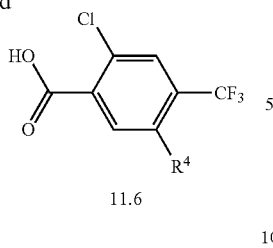

11.6

Reaction Scheme 11 illustrates the preparation of the intermediate acids of the type 11.6 which are used to prepare compounds of the invention. Amine 11.1 is treated with NCS to afford chloride 11.2, which is then converted to bromide 11.3 by exposure to t-butylnitrite and copper bromide. Cross-coupling of bromide 11.3 with an aryl or heteroarylboronic ester 11.4 (or other suitable intermediate) is mediated by heating in an aqueous solvent system in the presence of a suitable catalyst and base (e.g., Pd(dppf)Cl$_2$ and Na$_2$CO$_3$ in aqueous DMF) to furnish ester 11.5. Hydrolysis of the ester under basic conditions then affords acid 11.6.

SCHEME 12

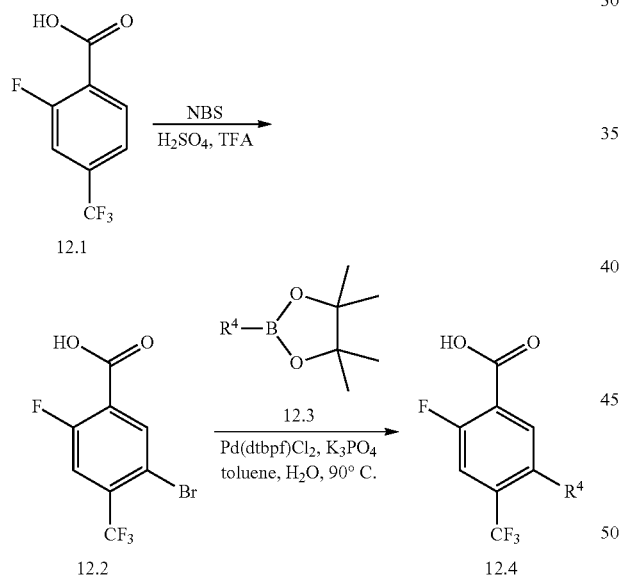

Reaction Scheme 8 depicts the synthesis of intermediates acids of the type 12.4. Bromination of 12.1 followed by cross-coupling of 12.2 and with an aryl or heteroarylboronic ester 12.3 (or other suitable intermediate) is mediated by heating in an aqueous solvent system in the presence of a suitable catalyst and base (e.g., Pd(dtbpf)Cl$_2$ and K$_3$PO$_4$ in aqueous toluene) to furnish 12.4.

Specific embodiments of the compounds of the invention, and methods of making them, are described in the Intermediates and Examples herein. Intermediate amines and acids used in Scheme 1 may be obtained from commercial sources or synthesized using known methods. The following are examples for illustration only.

Reaction Scheme for Intermediate A1

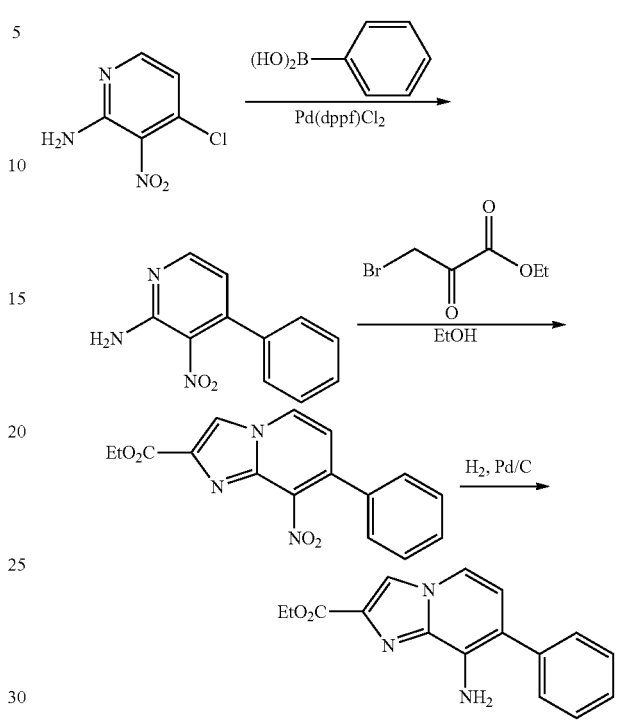

Intermediate A1

Ethyl 8-amino-7-phenylimidazo[1,2-a]pyridine-2-carboxylate

Step A: 3-Nitro-4-phenylpyridin-2-amine

To a deoxygenated mixture of 4-chloro-3-nitropyridin-2-amine (10 g, 57.6 mmol), phenylboronic acid (7.03 g, 57.6 mmol) and potassium carbonate (15.93 g, 115 mmol) in dioxane (100 mL) and water (20 mL) was added PdCl$_2$(dppf) (4.22 g, 5.76 mmol), and the resulting mixture was heated at 120° C. for 5 h. The mixture was cooled and filtered. The filtrate was concentrated and the residue was partitioned between water (50 mL) and EtOAc (100 mL×3). The combined organic layers were dried over Na$_2$SO$_4$ and concentrated. The residue was purified by silica gel column chromatography (PE/EtOAc=5/1) to give the title compound. MS: m/z=216.1 (M+1). $^1$H NMR (400 MHz, CD$_3$OD) δ 8.24 (d, J=5.0 Hz, 1H), 7.41-7.47 (m, 3H), 7.28-7.34 (m, 2H), 6.68 (d, J=5.0 Hz, 1H).

Step B: Ethyl 8-nitro-7-phenylimidazo[1,2-a]pyridine-2-carboxylate

To a solution of 3-nitro-4-phenylpyridin-2-amine (5.00 g, 23.2 mmol) in ethanol (50 mL) was added ethyl 3-bromo-2-oxopropanoate (4.53 g, 23.2 mmol) at 20° C., and the resulting mixture was heated at 100° C. for 15 h. The mixture was concentrated and the residue was purified by silica gel column chromatography (PE:EtOAc=5:1) to give the title compound. MS: m/z=312.2 (M+1). $^1$H NMR (400 MHz, CD$_3$OD) δ 8.69 (d, J=7.0 Hz, 1H), 8.61 (s, 1H), 7.46-7.51 (m, 5H), 7.17 (d, J=7.0 Hz, 1H), 4.41 (q, J=7.3 Hz, 2H), 1.35-1.43 (m, 3H).

Step C: Ethyl 8-amino-7-phenylimidazo[1,2-a]pyridine-2-carboxylate

To a deoxygenated solution of ethyl 8-nitro-7-phenylimidazo[1,2-a]pyridine-2-carboxylate (2.80 g, 8.99 mmol) in methanol (50 mL) was added 10% Pd/C (200 mg, 1.88 mmol) and the resulting mixture was stirred at 20° C. for 3 h under hydrogen (50 psi). The mixture was filtered and the filtrate was concentrated. The residue was purified by silica gel column chromatography (PE/EtOAc=10/1) to give ethyl 8-amino-7-phenylimidazo[1,2-a]pyridine-2-carboxylate. MS: m/z=282.2 (M+1). $^1$H NMR (400 MHz, CD$_3$OD) δ 8.33 (s, 1H), 7.88 (d, J=7.0 Hz, 1H), 7.45-7.55 (m, 4H), 7.36 (t, J=7.0 Hz, 1H), 6.83 (d, J=7.0 Hz, 1H), 4.36-4.44 (m, 2H), 1.41 (t, J=7.2 Hz, 3H).

Reaction Scheme for Intermediate A2

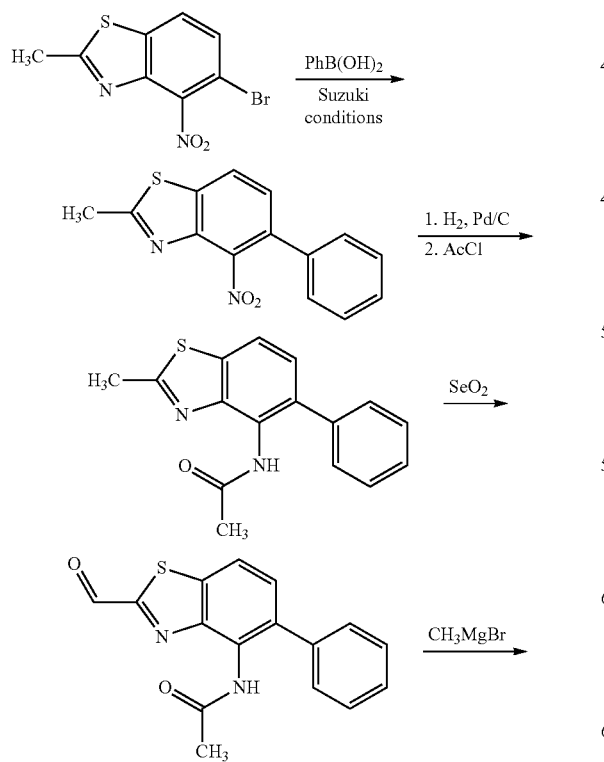

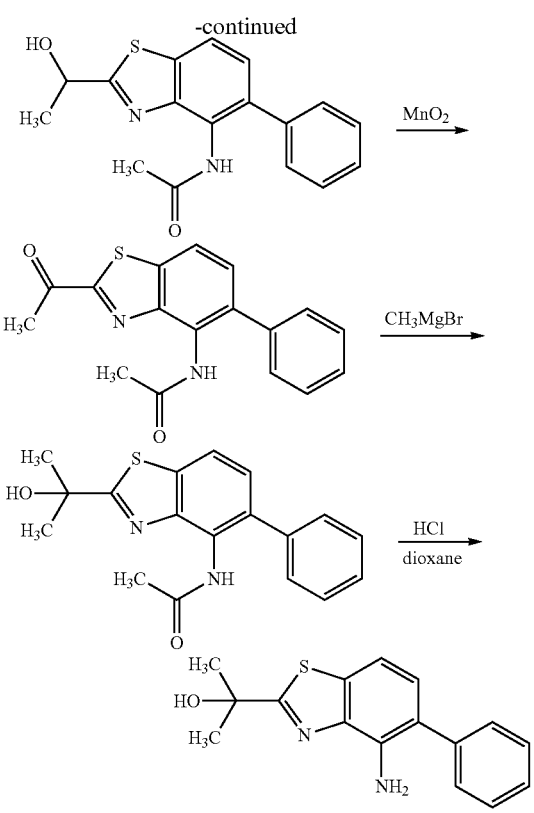

Intermediate A2

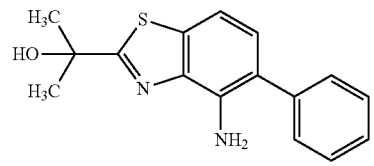 [SMILES: CC(C)(O)c1nc2c(N)c(-c3ccccc3)ccc2s1]

2-(4-Amino-5-phenylbenzo[d]thiazol-2-yl)propan-2-ol

Step A: 2-Methyl-4-nitro-5-phenylbenzo[d]thiazole

The title compound was prepared through a Suzuki cross-coupling reaction using similar procedure to that described in Step A for Intermediate A1. MS: m/z=271.1 (M+1).

Step B: N-(2-Methyl-5-phenylbenzo[d]thiazol-4-yl)acetamide

To a deoxygenated solution of 2-methyl-4-nitro-5-phenylbenzo[d]thiazole (1.50 g, 5.55 mmol) in methanol (100 mL) was added 10% Pd/C (0.12 g, 1.1 mmol), and the resulting mixture was stirred at 20° C. for 5 h under hydrogen (50 psi). The reaction mixture was filtered and the filtrate was concentrated. The residue was purified by preparative TLC (PE/EtOAc=5/1) to give 2-methyl-5-phenylbenzo[d]thiazol-4-amine. To a solution of 2-methyl-5-phenylbenzo[d]thiazol-4-amine (1.2 g, 5.0 mmol) in dichloromethane (10 mL) at 0° C. was added acetyl chloride (0.39 g, 5.0 mmol). The mixture was stirred at 20° C. for 30 min. The reaction mixture was partitioned between water (10 mL) and EtOAc (20 mL×2). The combined organic layers were dried over Na$_2$SO$_4$ and concentrated. The residue was purified by preparative TLC (PE/EtOAc=2/1) to give the title compound. MS: m/z=282.8 (M+1). $^1$H NMR (400 MHz, CD$_3$OD) δ 7.91 (d, J=8.2 Hz, 1H), 7.33-7.46 (m, 6H), 2.84 (s, 3H), 2.02 (s, 3H).

Step C: N-(2-Formyl-5-phenylbenzo[d]thiazol-4-yl) acetamide

To a solution of N-(2-methyl-5-phenylbenzo[d]thiazol-4-yl) acetamide (1.00 g, 3.54 mmol) in dioxane (5 mL) was added selenium dioxide (0.79 g, 7.1 mmol), and the resulting mixture was heated at 100° C. for 5 h. The mixture was filtered and the filtrate was concentrated. The residue was purified by preparative TLC (PE/EtOAc=1/1) to give the title compound. $^1$H NMR (400 MHz, CD$_3$OD) δ 9.25 (s, 1H), 8.07 (d, J=8.2 Hz, 1H), 7.50 (d, J=8.2 Hz, 1H), 7.36-7.46 (m, 5H), 2.04 (s, 3H).

Step D: N-(2-(1-Hydroxyethyl)-5-phenylbenzo[d]thiazol-4-yl)acetamide

To a solution of N-(2-formyl-5-phenylbenzo[d]thiazol-4-yl)acetamide (500 mg, 1.69 mmol) in tetrahydrofuran (10 mL) at 0° C. was added dropwise methylmagnesium bromide (1.68 mL, 5.06 mmol, 3M) under nitrogen atmosphere. The mixture was stirred at 20° C. for 10 min. The reaction mixture was partitioned between water (10 mL) and EtOAc (10 mL×3). The combined organic layers were dried over Na$_2$SO$_4$ and concentrated. The residue was purified by preparative TLC (PE/EtOAc=1/1) to give the title compound. MS: m/z=313.2 (M+1). $^1$H NMR (400 MHz, CD$_3$OD) δ 7.97 (d, J=8.2 Hz, 1H), 7.35-7.42 (m, 6H), 5.15 (q, J=6.7 Hz, 1H), 2.02 (d, J=3.5 Hz, 3H), 1.61 (d, J=6.7 Hz, 3H).

Step E: N-(2-Acetyl-5-phenylbenzo[d]thiazol-4-yl) acetamide

To a solution of N-(2-(1-hydroxyethyl)-5-phenylbenzo[d]thiazol-4-yl)acetamide (200 mg, 0.64 mmol) in dioxane (5 mL) was added manganese (IV) oxide (223 mg, 2.56 mmol) and the resulting mixture was heated at 80° C. for 18 h. The mixture was cooled and filtered. The filtrate was concentrated and the residue was purified by preparative TLC (PE/EtOAc=1/1) to give the title compound. MS: m/z=311.0 (M+1). $^1$H NMR (400 MHz, CD$_3$OD) δ 8.08 (d, J=8.6 Hz, 1H), 7.60 (d, J=8.2 Hz, 1H), 7.32-7.49 (m, 5H), 2.76 (s, 3H), 2.06 (s, 3H).

Step F: N-(2-(2-Hydroxypropan-2-yl)-5-phenyl-benzo[d]thiazol-4-yl)acetamide

To a solution of N-(2-acetyl-5-phenylbenzo[d]thiazol-4-yl)acetamide (150 mg, 0.48 mmol) in tetrahydrofuran (5 mL) at 0° C. was added dropwise methylmagnesium bromide (0.48 mL, 1.45 mmol, 3 M in THF) under nitrogen atmosphere. The mixture was stirred at 0° C. for 30 min. The reaction mixture was partitioned between water (20 mL) and EtOAc (20 mL×3). The combined organic layers were dried over Na$_2$SO$_4$ and concentrated. The residue was purified by preparative TLC (PE/EtOAc=1/1) to give the title compound. MS: m/z=327.0 (M+1). $^1$H NMR (400 MHz, CD$_3$OD) δ 8.07 (d, J=8.2 Hz, 1H), 7.94 (d, J=8.2 Hz, 1H), 7.59 (d, J=6.3 Hz, 1H), 7.41-7.47 (m, 4H), 2.00 (s, 3H), 1.67 (s, 6H).

Step G: 2-(4-Amino-5-phenylbenzo[d]thiazol-2-yl) propan-2-ol

To a solution of N-(2-(2-hydroxypropan-2-yl)-5-phenyl-benzo[d]thiazol-4-yl)acetamide (130 mg, 0.40 mmol) in dioxane (10 mL) was added a solution of HCl in dioxane (5 mL, 4 M), and the resulting mixture was heated at 80° C. for 3 h. The mixture was poured into water (20 mL) and basified to pH 10 with saturated aqueous potassium carbonate solution. The aqueous layer was extracted with EtOAc (20 mL×2) and the combined organic layers were dried over Na$_2$SO$_4$ and concentrated. The residue was purified by preparative TLC (PE/EtOAc=1/3) to give 2-(4-Amino-5-phenylbenzo[d]thiazol-2-yl)propan-2-ol. MS: m/z=285.0 (M+1). $^1$H NMR (400 MHz, CD$_3$OD) δ 7.42-7.51 (m, 4H), 7.31-7.36 (m, 1H), 7.24-7.28 (m, 1H), 7.09 (d, J=8.2 Hz, 1H), 1.68 (s, 6H).

Reaction Scheme for Intermediate A3

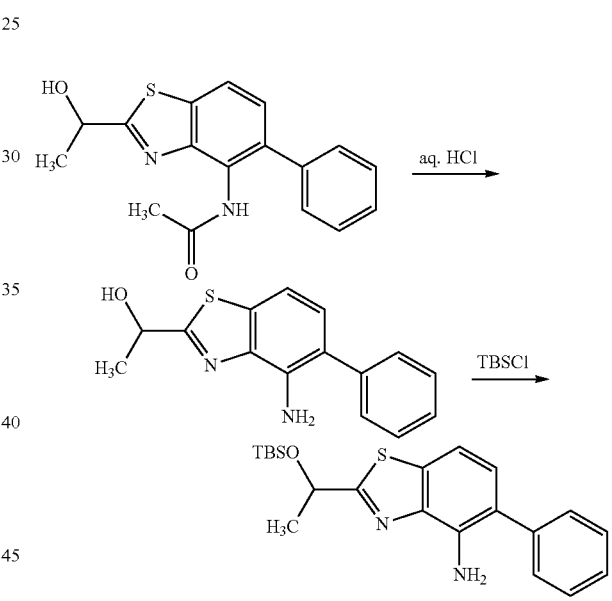

Intermediate A3

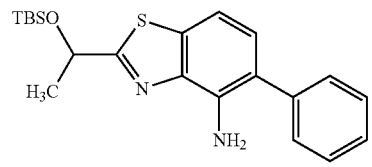 [SMILES: CC(O[Si](C)(C)C(C)(C)C)c1nc2c(N)c(-c3ccccc3)ccc2s1]

Step A: 1-(4-Amino-5-phenylbenzo[d]thiazol-2-yl) ethanol

To a solution of N-(2-(1-hydroxyethyl)-5-phenylbenzo[d]thiazol-4-yl)acetamide (250 mg, 0.80 mmol) in dioxane (5 mL) at 0° C. was added concentrated aqueous hydrogen chloride solution (0.33 mL, 4.0 mmol), and the resulting mixture was heated at 60° C. for 3 h. The mixture was poured into water (10 mL) and basified to pH 10 with saturated aqueous potassium carbonate solution. The aqueous layer was extracted with EtOAc (10 mL×2). The combined organic layers were dried over $Na_2SO_4$ and concentrated. The residue was purified by preparative TLC (PE/EtOAc=1/1) to give the title compound. $^1H$ NMR (400 MHz, $CD_3OD$) δ 7.38-7.48 (m, 4H), 7.28-7.33 (m, 1H), 7.23 (s, 1H), 7.11 (d, J=8.5 Hz, 1H), 5.13 (q, J=6.5 Hz, 1H), 1.63 (d, J=6.5 Hz, 3H).

Step B: 2-(1-((tert-butyldimethylsilyl)oxy)ethyl)-5-phenylbenzo[d]thiazol-4-amine To a solution of 1-(4-amino-5-phenylbenzo[d]thiazol-2-yl)ethanol (150 mg, 0.56 mmol) and DMAP (68 mg, 0.56 mmol) in dioxane (10 mL) was added TBSCl (84 mg, 0.56 mmol), and the resulting mixture was heated at 80° C. for 3 h. The reaction mixture was partitioned between water (20 mL) and EtOAc (20 mL×3). The combined organic layers were dried over $Na_2SO_4$ and concentrated. The residue was purified by preparative TLC (PE/EtOAc=2/1) to give the title compound. MS: m/z=385.2 (M+1). $^1H$ NMR (400 MHz, $CD_3OD$) δ 7.30-7.39 (m, 4H), 7.18-7.25 (m, 1H), 7.14 (d, J=8.2 Hz, 1H), 6.98 (d, J=8.2 Hz, 1H), 5.12 (q, J=6.5 Hz, 1H), 1.48 (d, J=6.7 Hz, 3H), 0.85 (s, 9H), 0.02 (d, J=16.0 Hz, 6H).

Reaction Scheme for Intermediate A4

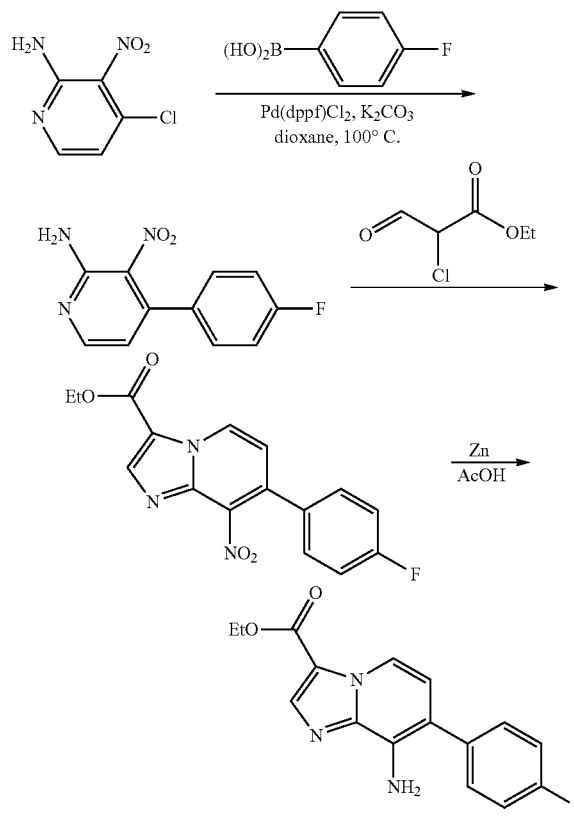

Intermediate A4

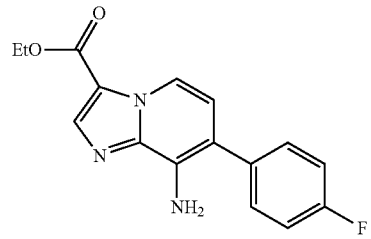 [SMILES: CCOC(=O)c1cnc2c(N)c(-c3ccc(F)cc3)ccn12]

4-(4-Fluorophenyl)-3-nitropyridin-2-amine

Step A: 4-(4-Fluorophenyl)-3-nitropyridin-2-amine

To a deoxygenated mixture of 4-chloro-3-nitropyridin-2-amine (2.00 g, 11.5 mmol) and 4-fluorophenyl boronic acid (1.60 g, 11.5 mmol) in dioxane (30 mL) were added $PdCl_2$(dppf) (0.80 g, 1.2 mmol) and potassium carbonate (3.20 g, 23.1 mmol). The resulting mixture was heated at 100° C. for 18 h, then cooled and filtered. The filtrate was concentrated and the residue was partitioned between water (50 mL) and EtOAc (20 mL×3). The combined organic layers were dried over $Na_2SO_4$ and concentrated. The residue was purified by silica gel column chromatography (PE/EtOAc=10/1) to give the title compound. $^1H$ NMR (400 MHz, $CD_3OD$) δ 8.16 (d, J=4.7 Hz, 1H), 7.34 (dd, $J_1$=8.6 Hz, $J_2$=5.1 Hz, 2H), 7.16 (t, J=8.8 Hz, 2H), 6.65 (d, J 5.1 Hz, 1H).

Step B: Ethyl 7-(4-fluorophenyl)-8-nitroimidazo[1,2-a]pyridine-3-carboxylate

To a solution of ethyl 2-chloro-3-oxopropanoate (3.70 g, 14.6 mmol) in acetonitrile (100 mL) was added concentrated aqueous sulfuric acid solution (0.40 mL, 7.3 mmol) and 4-(4-fluorophenyl)-3-nitropyridin-2-amine (2.0 g, 7.4 mmol). The resulting mixture was heated at 100° C. for 48 h, then cooled and concentrated. The residue was purified by silica gel column chromatography (PE/EtOAc=20/1) to give the title compound. $^1H$ NMR (400 MHz, $CD_3OD$) δ 9.48 (d, J=7.0 Hz, 1H), 8.32 (s, 1H), 7.55 (dd, $J_1$=8.6 Hz, $J_2$=5.1 Hz, 2H), 7.35 (d, J=7.4 Hz, 1H), 7.27 (t, J=8.8 Hz, 2H), 4.45 (q, J=7.0 Hz, 2H), 1.42 (t, J=7.0 Hz, 3H).

Step C: Ethyl 8-amino-7-(4-fluorophenyl)imidazo[1,2-a]pyridine-3-carboxylate

To a solution of ethyl 7-(4-fluorophenyl)-8-nitroimidazo[1,2-a]pyridine-3-carboxylate (2.2 g, 5.9 mmol) in tetrahydrofuran (20 mL) was added zinc powder (2.3 g, 35.3 mmol) and acetic acid (1.0 mL, 17.6 mmol). The resulting mixture was stirred at 26° C. for 5 h. The mixture was filtered and the filtrate was partitioned between water (50 mL) and EtOAc (50 mL×3). The combined organic layers were dried over $Na_2SO_4$ and concentrated. The residue was purified by silica gel column chromatography (PE/EtOAc=10/1) to give the title compound. $^1H$ NMR (400 MHz, $CD_3OD$) δ 8.72 (d, J=7.0 Hz, 1H), 8.15 (s, 1H), 7.56 (dd, $J_1$=8.4 Hz, $J_2$=5.3 Hz, 2H), 7.22 (t, J=8.6 Hz, 2H), 6.95 (d, J=7.0 Hz, 1H), 4.40 (q, J=7.0 Hz, 2H), 1.40 (t, J 7.0 Hz, 3H).

Reaction Scheme for Intermediate A5

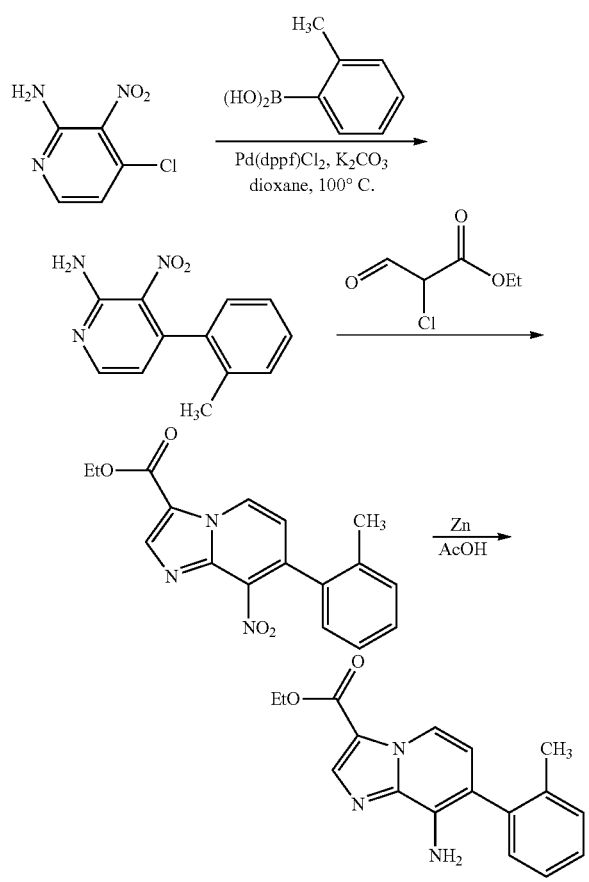

Intermediate A5

Ethyl 8-amino-7-(o-tolyl)imidazo[1,2-a]pyridine-3-carboxylate

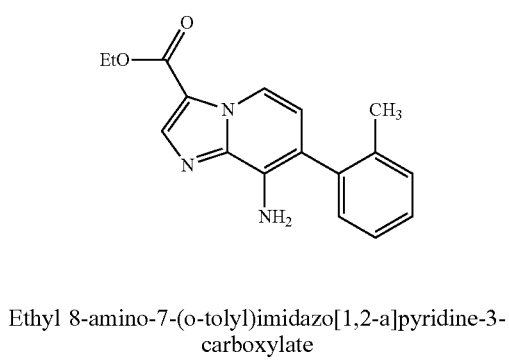

Step A: 3-Nitro-4-(o-tolyl)pyridin-2-amine

To a deoxygenated mixture of 4-chloro-3-nitropyridin-2-amine (2 g, 11.52 mmol) and o-tolylboronic acid (1.57 g, 11.52 mmol) in dioxane (15 mL) was added PdCl$_2$(dppf) (0.84 g, 1.15 mmol) and potassium carbonate (3.19 g, 23.05 mmol). The resulting mixture was heated at 100° C. for 18 h. The mixture was cooled and filtered. The filtrate was concentrated and the residue was partitioned between water (20 mL) and EtOAc (20 mL×3). The combined organic layers were dried over Na$_2$SO$_4$ and concentrated. The residue was purified by silica gel column chromatography (PE/EtOAc=10/1) to the title compound. $^1$H NMR (400 MHz, CD$_3$OD) δ 8.20 (d, J=5.0 Hz, 1H), 7.40-7.46 (m, 2H), 7.36 (s, 1H), 7.24 (d, J=6.5 Hz, 1H), 6.70 (d, J=5.0 Hz, 1H), 3.33 (s, 3H).

Step B: Ethyl 8-nitro-7-(o-tolyl)imidazo[1,2-a]pyridine-3-carboxylate

To a solution of ethyl 2-chloro-3-oxopropanoate (4.51 g, 18.0 mmol) in acetonitrile (100 mL) was added concentrated aqueous sulfuric acid solution (0.720 mL, 13.5 mmol) and 3-nitro-4-(o-tolyl)pyridin-2-amine (2.10 g, 8.98 mmol). The resulting mixture was heated at 100° C. for 40 h, then cooled and concentrated. The residue was purified by silica gel column chromatography (PE/EtOAc=20/1) to give the title compound. $^1$H NMR (400 MHz, CD$_3$OD) δ 9.50 (d, J=7.0 Hz, 1H), 8.35 (s, 1H), 7.35-7.41 (m, 2H), 7.28 (t, J=7.0 Hz, 1H), 7.21 (d, J=7.0 Hz, 2H), 4.47 (q, J=7.3 Hz, 2H), 2.22 (s, 3H), 1.44 (t, J=7.2 Hz, 3H).

Step C: Ethyl 8-amino-7-(o-tolyl)imidazo[1,2-a]pyridine-3-carboxylate

To a solution of ethyl 8-nitro-7-(o-tolyl)imidazo[1,2-a]pyridine-3-carboxylate (2.10 g, 6.33 mmol) in THF (20 mL) was added zinc powder (2.48 g, 38.0 mmol) and acetic acid (1.09 mL, 19.0 mmol), and the resulting mixture was stirred at 26° C. for 5 h. The reaction mixture was partitioned between water (50 mL) and EtOAc (50 mL×3). The combined organic layers were dried over Na$_2$SO$_4$ and concentrated. The residue was purified by silica gel column chromatography (PE/EtOAc=10/1) to give the title compound. $^1$H NMR (400 MHz, CD$_3$OD) δ 8.74 (d, J=7.0 Hz, 1H), 8.17 (s, 1H), 7.28-7.38 (m, 3H), 7.26-7.21 (m, 1H), 6.83 (d, J=7.0 Hz, 1H), 4.39-4.45 (m, 2H), 2.19 (s, 3H), 1.42 (t, J=7.2 Hz, 3H).

Reaction Scheme for Intermediate A6

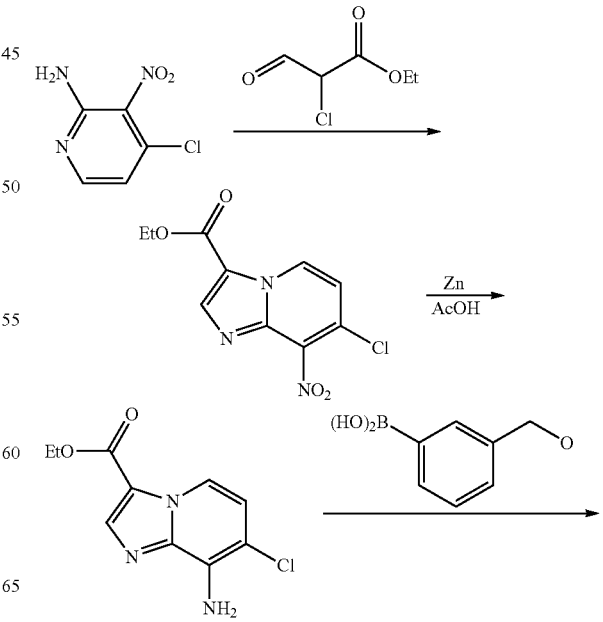

-continued

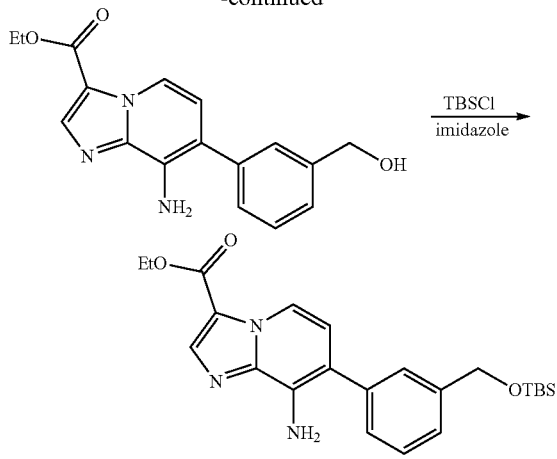

Intermediate A6

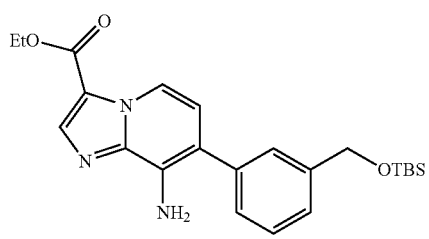 [SMILES: CCOC(=O)c1cnc2c(N)c(-c3cccc(CO[Si](C)(C)C(C)(C)C)c3)ccn12]

Ethyl 8-amino-7-(3-(((tert-butyldimethylsilyl)oxy)methyl)phenyl)imidazo[1,2-a]pyridine-3-carboxylate Step A: Ethyl 7-chloro-8-nitroimidazo[1,2-a]pyridine-3-carboxylate To a solution of ethyl 2-chloro-3-oxopropanoate (13.0 g, 86.3 mmol) in acetonitrile (100 mL) was added concentrated aqueous sulfuric acid solution (2.30 mL, 43.2 mmol) and 4-chloro-3-nitropyridin-2-amine (5.00 g, 28.8 mmol). The resulting mixture was heated at 100° C. for 5 h, then cooled and concentrated. The residue was purified by silica gel column chromatography (PE/EtOAc=5/1) to give the title compound. $^1$H NMR (400 MHz, CD$_3$OD) δ 9.43 (d, J=7.4 Hz, 1H), 7.83 (s, 1H), 7.42 (d, J=7.4 Hz, 1H), 4.45 (q, J=7.2 Hz, 2H), 1.42 (t, J=7.0 Hz, 3H).

Step B: Ethyl 8-amino-7-chloroimidazo[1,2-a]pyridine-3-carboxylate

To a solution of ethyl 7-chloro-8-nitroimidazo[1,2-a]pyridine-3-carboxylate (1.40 g, 5.19 mmol) in THF (20 mL) were added zinc powder (3.39 g, 51.9 mmol) and acetic acid (1.49 mL, 26.0 mmol), and the resulting mixture was stirred at 26° C. for 5 h. The mixture was filtered and the filtrate was partitioned between water (50 mL) and EtOAc (50 mL×3). The combined organic layers were dried over Na$_2$SO$_4$ and concentrated. The residue was purified by silica gel column chromatography (PE/EtOAc=5/1) to give the title compound. $^1$H NMR (400 MHz, CD$_3$OD) δ 8.64 (d, J=7.4 Hz, 1H), 8.14 (s, 1H), 6.91 (d, J=7.0 Hz, 1H), 4.93 (s, 2H), 4.39 (q, J=7.2 Hz, 2H), 1.40 (t, J=7.0 Hz, 3H).

Step C: Ethyl 8-amino-7-(3-(hydroxymethyl)phenyl)imidazo[1,2-a]pyridine-3-carboxylate To a deoxygenated mixture of (3-(hydroxymethyl)phenyl)boronic acid (0.54 g, 3.6 mmol) and ethyl 8-amino-7-chloroimidazo[1,2-a]pyridine-3-carboxylate (1.00 g, 3.55 mmol) in dioxane (30 mL) were added potassium carbonate (0.98 g, 7.1 mmol) and Pd(dppf)Cl$_2$ (0.23 g, 0.36 mmol). The resulting mixture was heated at 100° C. for 48 h, then cooled and filtered. The filtrate was partitioned between water (50 mL) and EtOAc (20 mL×3). The combined organic layers were dried over Na$_2$SO$_4$ and concentrated. The residue was purified by purified by silica gel column chromatography (PE/EtOAc=5/1) to afford the title compound. $^1$H NMR (400 MHz, CD$_3$OD) δ 8.73 (d, J=7.0 Hz, 1H), 8.16 (s, 1H), 7.56 (s, 1H), 7.45-7.52 (m, 2H), 7.39 (d, J=7.0 Hz, 1H), 6.99 (d, J=7.0 Hz, 1H), 4.68 (s, 2H), 4.41 (q, J=7.0 Hz, 2H), 1.41 (t, J=7.0 Hz, 3H).

Step D: Ethyl 8-amino-7-(3-(((tert-butyldimethylsilyl)oxy)methyl)phenyl)imidazo[1,2-a]pyridine-3-carboxylate To a solution of ethyl 8-amino-7-(3-(hydroxymethyl)phenyl)imidazo[1,2-a]pyridine-3-carboxylate (360 mg, 0.93 mmol) in dichloromethane (10 mL) was added 1H-imidazole (94 mg, 1.4 mmol) and TBSCl (167 mg, 1.11 mmol), and the resulting mixture was stirred at 26° C. for 2 h. The mixture was partitioned between water (20 mL) and dichloromethane (20 mL×2). The combined organic layers were dried over Na$_2$SO$_4$ and concentrated. The residue was purified by silica gel column chromatography (PE/EtOAc=30/1) to give ethyl 8-amino-7-(3-(((tert-butyldimethylsilyl)oxy)methyl)phenyl)imidazo[1,2-a]pyridine-3-carboxylate. $^1$H NMR (400 MHz, CD$_3$OD) δ 8.69 (d, J=7.0 Hz, 1H), 8.12 (s, 1H), 7.78 (s, 1H), 7.48 (s, 1H), 7.41 (d, J 7.0 Hz, 1H), 7.32 (d, J=7.4 Hz, 1H), 6.93 (d, J=7.0 Hz, 1H), 4.78 (s, 2H), 4.02-4.08 (m, 2H), 1.37 (t, J=7.2 Hz, 3H), 0.91 (s, 9H), 0.09 (s, 6H).

Reaction Scheme for Intermediates A7 and A8

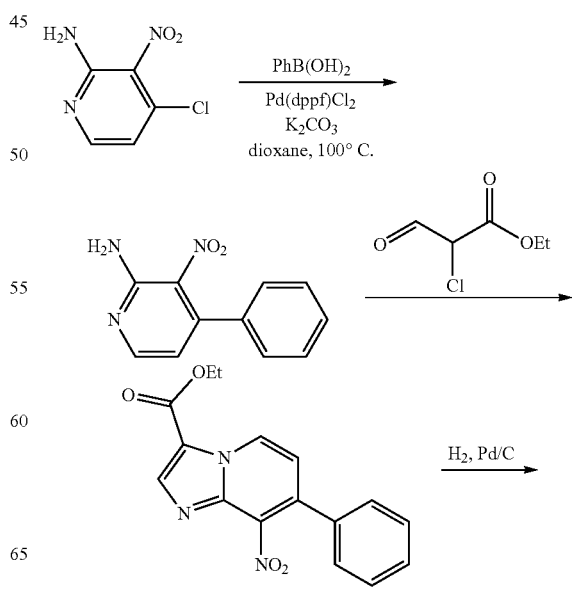

-continued

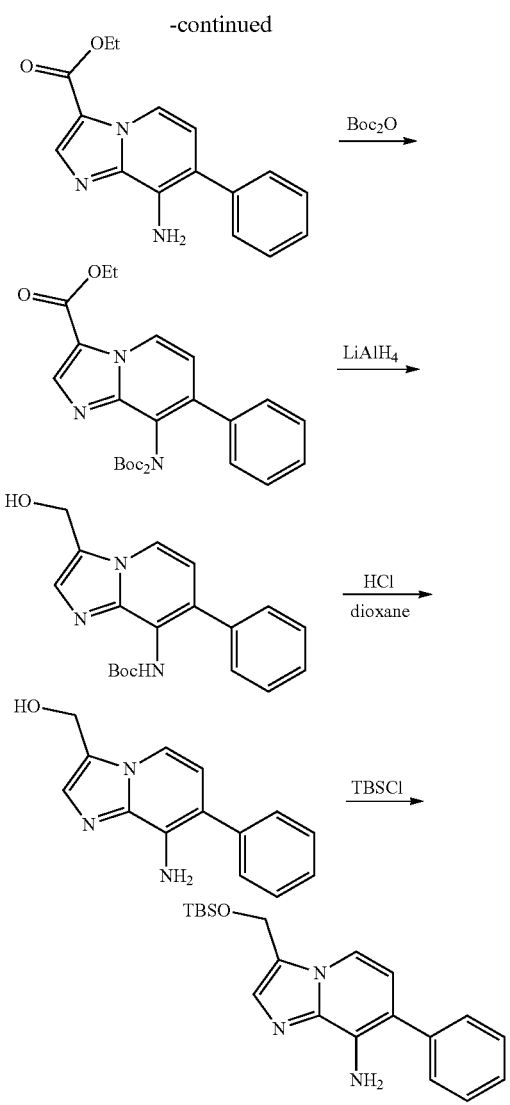

Intermediate A7

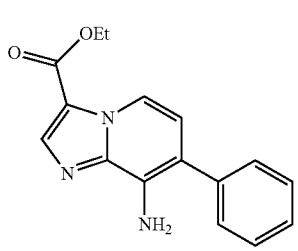 [SMILES: CCOC(=O)c1cnc2c(N)c(-c3ccccc3)ccn12]

Ethyl 8-amino-7-phenylimidazo[1,2-a]pyridine-3-carboxylate

Step A: 3-Nitro-4-phenylpyridin-2-amine

To a deoxygenated mixture of 4-chloro-3-nitropyridin-2-amine (13.8 g, 79.5 mmol), phenylboronic acid (10.7 g, 87.8 mmol) and potassium carbonate (33.0 g, 239 mmol) in dioxane (270 mL) and water (68 mL) was added PdCl$_2$(dppf) (2.00 g, 2.73 mmol). The resulting mixture was heated at 110° C. for 12 h, then cooled and filtered. The filtrate was concentrated. The residue was partitioned between water (100 mL) and EtOAc (50 mL×3). The combined organic layers were washed with brine (50 mL), dried over sodium sulfate, filtered and concentrated. The residue was purified by silica gel column chromatography (PE/EtOAc=3/1) to give the title compound. MS: m/z=216.1 (M+1). $^1$H NMR (400 MHz, CDCl$_3$) δ 8.23 (d, J=4.9 Hz, 1H), 7.38-7.46 (m, 3H), 7.26-7.32 (m, 2H), 6.67 (d, J=4.9 Hz, 1H), 5.93 (br, 2H).

Step B: Ethyl 8-nitro-7-phenylimidazo[1,2-a]pyridine-3-carboxylate

To a solution of 3-nitro-4-phenylpyridin-2-amine (6.00 g, 27.9 mmol) in acetonitrile (200 mL) was added ethyl 2-chloro-3-oxopropanoate (4.20 g, 27.9 mmol), and the resulting mixture was heated at 90° C. for 12 h. The mixture was cooled and concentrated. The residue was purified by silica gel column chromatography (PE/EtOAc=1/1) to give the title compound. MS: m/z=312.1 (M+1). $^1$H NMR (400 MHz, CDCl$_3$): δ 9.50 (d, J=7.5 Hz, 1H), 8.44 (s, 1H), 7.52-7.63 (m, 5H), 7.23 (d, J=7.0 Hz, 1H), 4.53 (q, J=7.4 Hz, 2H), 1.51 (t, J=7.0 Hz, 3H).

Step C: Ethyl 8-amino-7-phenylimidazo[1,2-a]pyridine-3-carboxylate

To a deoxygenated solution of ethyl 8-nitro-7-phenylimidazo[1,2-a]pyridine-3-carboxylate (3.00 g, 9.64 mmol) in dichloromethane (200 mL) and ethanol (50 mL) was added 10% Pd/C (600 mg, 5.64 mmol). The resulting mixture was stirred at 30° C. for 3 h under hydrogen (50 psi). The mixture was filtered and the filtrate was concentrated. The residue was purified by silica gel column chromatography (PE/EtOAc=1/3) to give the title compound. MS: m/z=282.1 (M+1). $^1$H NMR (400 MHz, CDCl$_3$): δ 8.68 (d, J=7.0 Hz, 1H), 8.14 (s, 1H), 7.38-7.54 (m, 4H), 7.28-7.36 (m, 1H), 6.85 (d, J=6.7 Hz, 1H), 4.71 (br, 2H), 4.35 (q, J=7.0 Hz, 2H), 1.36 (t, J=7.0 Hz, 3H).

Intermediate A8

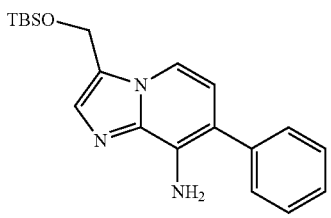 [SMILES: CC(C)(C)[Si](C)(C)OCc1cnc2c(N)c(-c3ccccc3)ccn12]

3-(((tert-Butyl dimethyl silyl)oxy)methyl)-7-phenylimidazo[1,2-a]pyridin-8-amine Step A: Ethyl 8-((di-tert-butoxycarbonyl)amino)-7-phenylimidazo[1,2-a]pyridine-3-carboxylate To a solution of ethyl 8-amino-7-phenylimidazo[1,2-a]pyridine-3-carboxylate (5.00 g, 17.8 mmol) in DCM (50 mL) was added Boc$_2$O (10.6 mL, 45.8 mmol), Et$_3$N (5.51 mL, 39.5 mmol) and DMAP (2.00 g, 16.4 mmol). The resulting mixture was stirred at 20° C. for 1 h, then concentrated. The residue was purified by silica gel column chromatography (PE/EtOAc=5/1) to give the title compound. MS: m/z=482.2 (M+1).

Step B: tert-Butyl (3-(hydroxymethyl)-7-phenylimidazo[1,2-a]pyridin-8-yl)carbamate To a solution of ethyl 8-(bis-(tert-butoxycarbonyl)amino)-7-phenylimidazo[1,2-a]pyridine-3-carboxylate (4.00 g, 8.31 mmol) in THF (40 mL) at 0° C. was added LAH (1.00 g, 26.3 mmol). The resulting mixture was stirred at 20° C. for 1 h. Excess LAH was quenched with H₂O (1 mL), aqueous 15% NaOH solution (1.0 mL) and H₂O (3 mL) successively. After MgSO₄ (2 g) was added, the mixture was filtered and the filtrate was concentrated to give the title compound. MS: m/z=339.9 (M+1).

Step C: (8-Amino-7-phenylimidazo[1,2-a]pyridin-3-yl)methanol

A solution of tert-butyl (3-(hydroxymethyl)-7-phenylimidazo[1,2-a]pyridin-8-yl)carbamate (500 mg, 1.47 mmol) in a solution of HCl in dioxane (10 mL, 4 M) was stirred at 20° C. for 30 min. The mixture was concentrated to give the title compound as HCl salt. MS: m/z=240.0 (M+1).

Step D: 3-(((tert-Butyldimethylsilyl)oxy)methyl)-7-phenylimidazo[1,2-a]pyridin-8-amine To a solution of (8-amino-7-phenylimidazo[1,2-a]pyridin-3-yl)methanol (350 mg, 1.46 mmol) in acetonitrile (10 mL) were added imidazole (300 mg, 4.41 mmol) and TBSCl (350 mg, 2.32 mmol). The resulting mixture was stirred at 20° C. for 2 h, then concentrated. The residue was purified by silica gel column chromatography (PE/EtOAc=5/1, 3/1) to give the title compound. MS: m/z=354.3 (M+1). ¹H NMR (400 MHz, CDCl₃): δ 7.69 (d, J=6.65 Hz, 1H), 7.46-7.52 (m, 2H), 7.42 (t, J=7.43 Hz, 2H), 7.36 (s, 1H), 7.26-7.33 (m, 1H), 6.69 (d, J=7.04 Hz, 1H), 4.91 (s, 2H), 4.65 (br, 2H), 0.82 (s, 9H), 0.00 (s, 6H).

Reaction Scheme for Intermediate A9

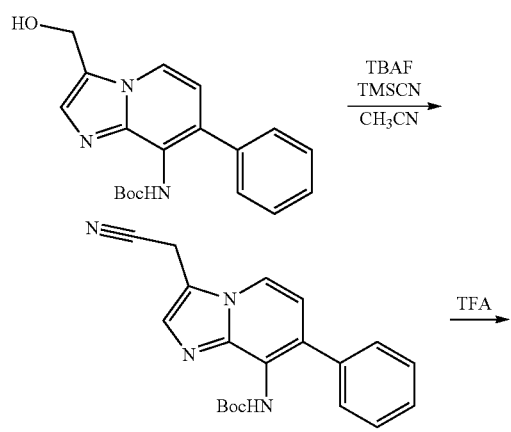

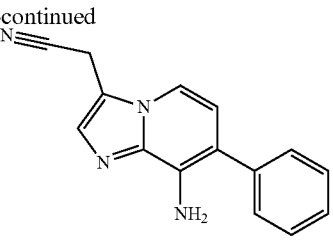

Intermediate A9

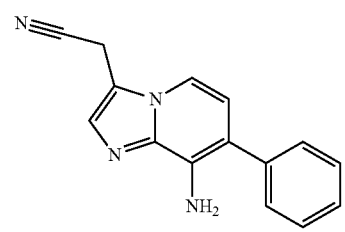 [SMILES: N#CCc1cnc2c(N)c(-c3ccccc3)ccn12]

2-(8-Amino-7-phenylimidazo[1,2-a]pyridin-3-yl)acetonitrile

Step A: tert-Butyl (3-(cyanomethyl)-7-phenylimidazo[1,2-a]pyridin-8-yl)carbamate To a solution of TMSCN (0.200 mL, 1.47 mmol) in acetonitrile (0.5 mL) was added TBAF (1.47 mL, 1.47 mmol). The mixture was stirred at 26° C. for 5 min before tert-butyl (3-(hydroxymethyl)-7-phenylimidazo[1,2-a]pyridin-8-yl)carbamate (100 mg, 0.30 mmol) was added. The resulting mixture was stirred for 6 h, then concentrated. The residue was purified by preparative TLC (100% EtOAc) to afford the title compound. MS: m/z=249.2 (M+1).

Step B: 2-(8-Amino-7-phenylimidazo[1,2-a]pyridin-3-yl)acetonitrile

To a solution of tert-butyl (3-(cyanomethyl)-7-phenylimidazo[1,2-a]pyridin-8-yl)carbamate (13 mg, 0.037 mmol) in DCM (0.5 mL) was added TFA (0.5 mL). The resulting mixture was stirred at 26° C. for 15 h, then basified to pH 9 with saturated aqueous sodium bicarbonate solution and extracted with EtOAc (5 mL×4). The combined organic layers were dried over Na₂SO₄ and concentrated to give the title compound. MS: m/z=248.9 (M+1).

Reaction Scheme for Intermediate A10

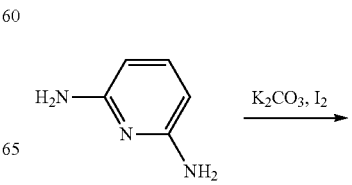

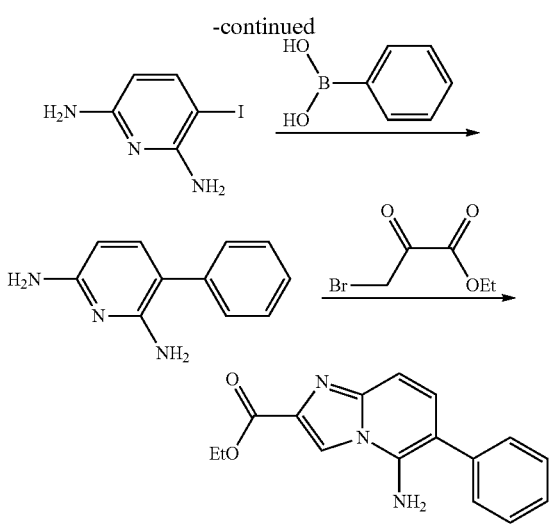

Intermediate A10

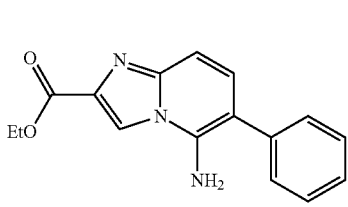 [SMILES: CCOC(=O)c1cn2c(N)c(-c3ccccc3)ccc2n1]

Ethyl 5-(3-(1-methyl-1H-pyrazol-3-yl)-4-(trifluoromethyl)benzamido)-6-phenylimidazo[1,2-a]pyridine-2-carboxylate Step A: 3-Iodopyridine-2,6-diamine To a solution of pyridine-2,6-diamine (20.0 g, 183 mmol) in 2-methyltetrahydrofuran (400 mL) at 20° C. were added potassium carbonate (25.0 g, 181 mmol) and a solution of iodine (46.6 g, 184 mmol) in 2-methyltetrahydrofuran (300 mL). The resulting mixture was stirred at 20° C. for 2 h. The product mixture was filtered and the filtrate was washed with saturated aqueous sodium thiosulfate solution (100 mL) and brine (100 mL). The organic layer was dried over $Na_2SO_4$ and concentrated to give the title compound. MS: m/z=235.9 (M+1). $^1$H NMR (400 MHz, DMSO-$d_6$) δ 7.33 (d, J=7.8 Hz, 1H), 5.63 (s, 2H), 5.54 (d, J=8.2 Hz, 1H), 5.41 (s, 2H).

Step B: 3-Phenylpyridine-2,6-diamine

To a deoxygenated mixture of 3-iodopyridine-2,6-diamine (15.0 g, 63.8 mmol), phenylboronic acid (8.50 g, 69.7 mmol) and potassium carbonate (26.0 g, 188 mmol) in dioxane (300 mL) and water (75 mL) was added $PdCl_2$(dppf) (2.10 g, 2.87 mmol). The resulting mixture was heated at 90° C. for 2 h, then cooled, filtered and concentrated. The residue was partitioned between water (100 mL) and EtOAc (200 mL×3). The combined organic layers were washed with brine (30 mL×2), dried over $Na_2SO_4$ and concentrated. The residue was purified by column chromatography on silica gel (PE/EtOAc=1/1) to give the title compound. MS: m/z=186.1 (M+1). $^1$H NMR (400 MHz, CDCl$_3$) δ 7.39-7.40 (m, 4H), 7.27-7.29 (m, 1H), 7.19 (d, J 8.2 Hz, 1H), 5.98 (d, J=7.8 Hz, 1H), 4.40 (s., 2H), 4.24 (s., 2H).

Step C: Ethyl 5-amino-6-phenylimidazo[1,2-a]pyridine-2-carboxylate

To a solution of 3-phenylpyridine-2,6-diamine (4.50 g, 24.3 mmol) in ethanol (300 mL) was added ethyl 3-bromo-2-oxopropanoate (5.20 g, 26.7 mmol), and the resulting mixture was heated at 90° C. for 12 h. The reaction mixture was cooled and concentrated. The residue was partitioned between saturated aqueous $NaHCO_3$ (50 mL) and EtOAc (100 mL×3). The combined organic layers were washed with brine (30 mL), dried over $Na_2SO_4$ and concentrated. The residue was purified by column chromatography on silica gel (PE/EtOAc=1/3) to give the title compound. MS: m/z=282.0 (M+1). $^1$H NMR (400 MHz, CDCl$_3$) δ 8.10 (s, 1H), 7.35-7.55 (m, 5H), 7.22-7.33 (m, 2H), 4.41-4.55 (m, 4H), 1.44 (t, J=7.2 Hz, 3H).

Reaction Scheme for Intermediate A11

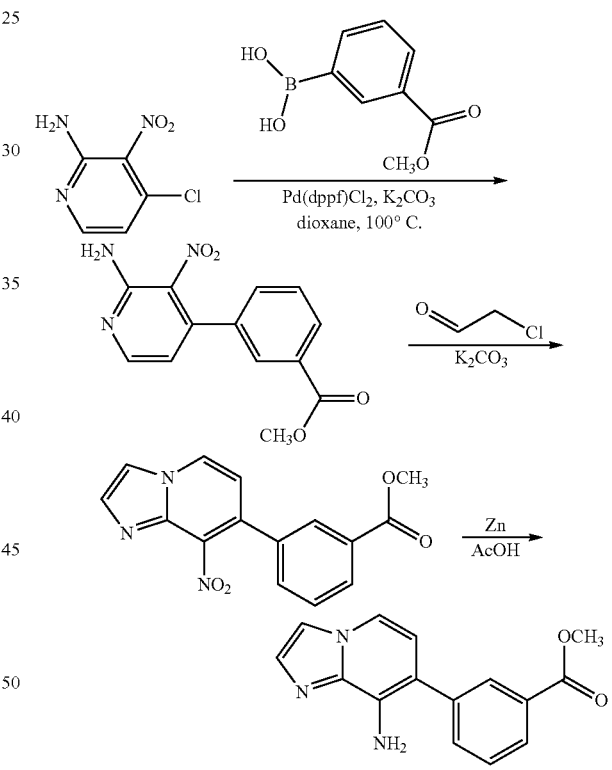

Intermediate A11

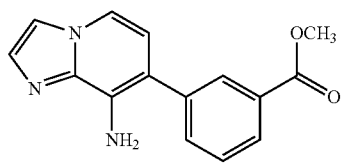 [SMILES: COC(=O)c1cccc(-c2ccn3ccnc3c2N)c1]

Methyl 3-(8-aminoimidazo[1,2-a]pyridin-7-yl)benzoate

Step A: Methyl 3-(2-amino-3-nitropyridin-4-yl)benzoate

A deoxygenated mixture of 4-chloro-3-nitropyridin-2-amine (1.00 g, 5.76 mmol), (3-(methoxycarbonyl)phenyl)boronic acid (1.04 g, 5.76 mmol), potassium carbonate (1.59 g, 11.52 mmol) and PdCl$_2$(dppf) (0.42 g, 0.58 mmol) in dioxane (10 mL) and water (1 mL) was heated at 100° C. for 20 min. The mixture was cooled and filtered. The filtrate was partitioned between water (10 mL) and EtOAc (20 mL×3). The combined organic layers were dried over Na$_2$SO$_4$ and concentrated. The residue was purified by purified by silica gel column chromatography (PE/EtOAc=3/1) to give the title compound. $^1$H NMR (400 MHz, CD$_3$OD) δ 8.21 (d, J=5.1 Hz, 1H), 8.02-8.10 (m, 1H), 7.94 (s, 1H), 7.55 (d, J=4.3 Hz, 2H), 6.66 (d, J=4.7 Hz, 1H), 3.91 (s, 3H)

Step B: Methyl 3-(8-nitroimidazo[1,2-a]pyridin-7-yl)benzoate

To a solution of methyl 3-(2-amino-3-nitropyridin-4-yl)benzoate (1.40 g, 5.12 mmol) in ethanol (15 mL) at 0° C. was added 2-chloroacetaldehyde (1.21 g, 15.4 mmol). The resulting mixture was heated at 100° C. for 10 h. The mixture was cooled and concentrated. The residue was purified by silica gel column chromatography (PE/EtOAc=2/1) to give the title compound. $^1$H NMR (400 MHz, CD$_3$OD) δ 8.70 (d, J=7.0 Hz, 1H), 8.03-8.15 (m, 3H), 7.66-7.75 (m, 2H), 7.58-7.65 (m, 1H), 7.09 (d, J=7.0 Hz, 1H), 3.92 (s, 3H).

Step C: Methyl 3-(8-aminoimidazo[1,2-a]pyridin-7-yl)benzoate

To a solution of methyl 3-(8-nitroimidazo[1,2-a]pyridin-7-yl)benzoate (0.900 g, 3.03 mmol) in THF (5 mL) were added zinc powder (0.20 g, 3.0 mmol) and acetic acid (0.18 g, 3.0 mmol). The resulting mixture was stirred at 26° C. for 5 h, then filtered and concentrated. The residue was purified by silica gel column chromatography (PE/EtOAc=1/1) to give the title compound. $^1$H NMR (400 MHz, CD$_3$OD) δ 8.17 (s, 1H), 8.00 (d, J=7.8 Hz, 1H), 7.88 (d, J 7.0 Hz, 1H), 7.75-7.81 (m, 2H), 7.59 (t, J=7.8 Hz, 1H), 7.51 (s, 1H), 6.74 (d, J=6.7 Hz, 1H), 3.92 (s, 3H).

Reaction Scheme for Intermediate A12

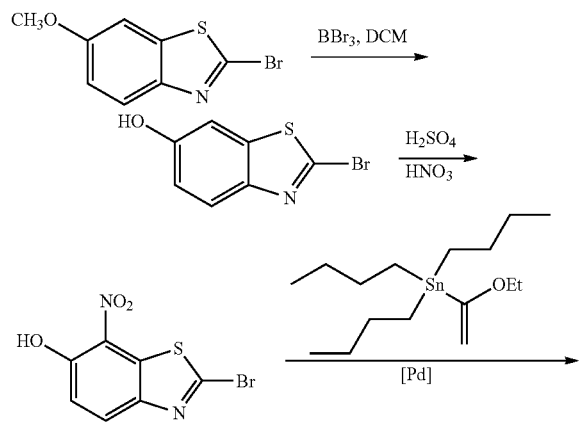

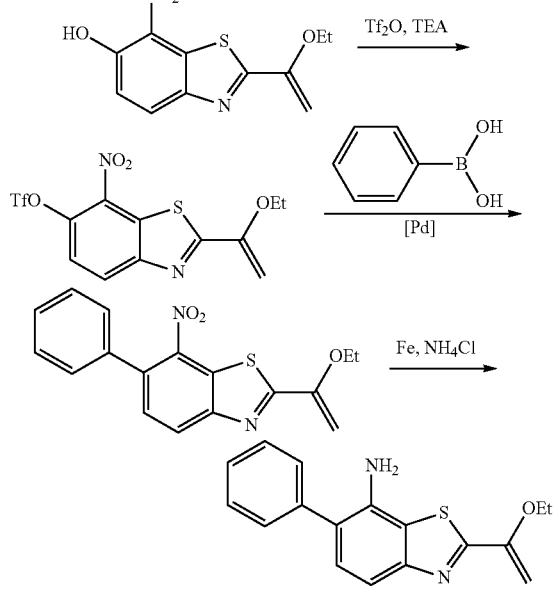

Intermediate A12

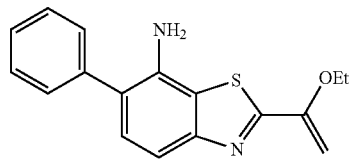 [SMILES: C=C(OCC)c1nc2ccc(-c3ccccc3)c(N)c2s1]

2-(1-Ethoxyvinyl)-6-phenylbenzo[d]thiazol-7-amine

Step A: 2-Bromobenzo[d]thiazol-6-ol

To a stirred solution of 2-bromo-6-methoxybenzo[d]thiazole (8.00 g, 32.8 mmol) in dichloromethane (20 mL) at 15° C. was added tribromoborane (9.1 mL, 98 mmol) dropwise. The resulting mixture was heated at 40° C. for 6 h then poured into ice water. The precipitate was filtered and the filtrate was extracted with dichloromethane (40 mL×3). The precipitate and the organic layers were combined, dried over Na$_2$SO$_4$, and concentrated to give the title compound. MS: m/z=229.9, 231.9 (M+1). $^1$H NMR (400 MHz, CD$_3$OD): δ 7.74 (d, J=8.8 Hz, 1H), 7.28 (d, J=2.4 Hz, 1H), 7.00 (dd, J$_1$=8.8 Hz, J$_2$=2.4 Hz, 1H).

Step B: 2-Bromo-7-nitrobenzo[d]thiazol-6-ol

To a stirred solution of 2-bromobenzo[d]thiazol-6-ol (6.50 g, 28.3 mmol) in concentrated sulfuric acid (70 mL, 28.3 mmol) at 0° C. was added dropwise a solution of fuming nitric acid (10 mL, 28.3 mmol) in water (5 mL). The resulting mixture was stirred at 0° C. for 10 min and poured into ice water (30 mL) carefully. The aqueous layer was extracted with dichloromethane (50 mL×3). The combined organic layers were dried over Na$_2$SO$_4$ and concentrated to give the title compound. H NMR (400 MHz, CD3OD) δ 8.19 (d, J=9.2 Hz, 1H), 7.35 (d, J=9.2 Hz, 1H).

Step C: 2-(1-Ethoxyvinyl)-7-nitrobenzo[d]thiazol-6-ol

To a deoxygenated mixture of 2-bromo-7-nitrobenzo[d]thiazol-6-ol (2.00 g, 7.27 mmol) and tributyl(1-ethoxyvinyl)stannane (3.15 g, 8.72 mmol) in dioxane (30 mL) was added Pd(PPh$_3$)$_2$Cl$_2$ (0.51 g, 0.73 mmol), and the resulting mixture was heated at 100° C. for 16 h. The reaction mixture was concentrated and the residue was purified by column chromatography on silica gel (PE/EtOAc=20/1) to give the title compound. MS: m/z=267.2 (M+1). $^1$H NMR (400 MHz, CDCl$_3$) δ 11.28 (s, 1H), 8.16 (d, J=9.0 Hz, 1H), 7.22 (d, J=9.0 Hz, 1H), 5.40 (d, J=2.7 Hz, 1H), 4.46 (d, J=2.7 Hz, 1H), 3.99 (q, J=6.8 Hz, 2H), 1.43 (t, J=6.8 Hz, 3H).

Step D: 2-(1-Ethoxyvinyl)-7-nitrobenzo[d]thiazol-6-yl trifluoromethanesulfonate To a stirred solution of 2-(1-ethoxyvinyl)-7-nitrobenzo[d]thiazol-6-ol (620 mg, 2.33 mmol) and triethylamine (0.65 mL, 4.7 mmol) in anhydrous dichloromethane (5 mL) at 15° C. was added dropwise trifluoromethanesulfonic anhydride (788 mg, 2.79 mmol), and the resulting mixture was stirred for 1 h. The reaction mixture was partitioned between water (10 mL) and dichloromethane (10 mL×3). The combined organic layers were dried over Na$_2$SO$_4$ and concentrated to give the title compound. MS: m/z=399.0 (M+1). $^1$H NMR (400 MHz, CDCl$_3$) δ 8.26 (d, J=8.6 Hz, 1H), 7.49 (d, J=8.6 Hz, 1H), 5.54 (d, J=2.7 Hz, 1H), 4.57 (d, J=2.7 Hz, 1H), 4.01 (q, J=7.0 Hz, 2H), 1.44 (t, J=7.0 Hz, 3H).

Step E: 2-(1-Ethoxyvinyl)-7-nitro-6-phenylbenzo[d]thiazole

To a deoxygenated mixture of 2-(1-ethoxyvinyl)-7-nitrobenzo[d]thiazol-6-yl trifluoromethanesulfonate (720 mg, 1.81 mmol), phenylboronic acid (264 mg, 2.17 mmol) and potassium carbonate (500 mg, 3.62 mmol) in dioxane (15 mL) and water (2 mL) was added PdCl$_2$(dppf) (130 mg, 0.18 mmol). and the resulting mixture was heated at 100° C. for 4 h. The mixture was cooled and filtered. The filtrate was partitioned between water (10 mL) and EtOAc (20 mL). The organic layer was dried over Na$_2$SO$_4$ and concentrated. The residue was purified by column chromatography on silica gel (PE/EtOAc=50/1) to give the title compound. MS: m/z=327.2 (M+1). $^1$H NMR (400 MHz, CDCl$_3$) δ 8.24 (d, J=8.22 Hz, 1H), 7.53 (d, J=8.61 Hz, 1H), 7.41-7.50 (m, 3H), 7.36 (d, J=5.87 Hz, 2H), 5.57 (d, J=2.74 Hz, 1H), 4.60 (d, J=2.74 Hz, 1H), 4.08 (q, J=7.04 Hz, 2H), 1.51 (t, J=7.04 Hz, 3H).

Step F: 2-(1-Ethoxyvinyl)-6-phenylbenzo[d]thiazol-7-amine

To a mixture of 2-(1-ethoxyvinyl)-7-nitro-6-phenylbenzo[d]thiazole (320 mg, 0.98 mmol) and ammonium chloride (53 mg, 0.98 mmol) in ethanol (5 mL) and water (1 mL) was added iron powder (55 mg, 0.98 mmol). The resulting mixture was heated at 80° C. for 1 h, then cooled and filtered. The filtrate was concentrated and the residue was purified by preparative TLC (PE/EtOAc=5/1) to give the title compound. MS: m/z=297.3 (M+1). $^1$H NMR (400 MHz, CDCl$_3$) δ 7.48-7.59 (m, 1H), 7.38-7.47 (m, 4H), 7.30-7.37 (m, 1H), 7.25 (d, J=8.22 Hz, 1H), 5.44 (d, J=2.74 Hz, 1H), 4.45 (d, J=2.35 Hz, 1H), 4.00 (q, J=7.04 Hz, 2H), 1.41 (t, J=7.04 Hz, 3H).

Reaction Scheme for Intermediate A13

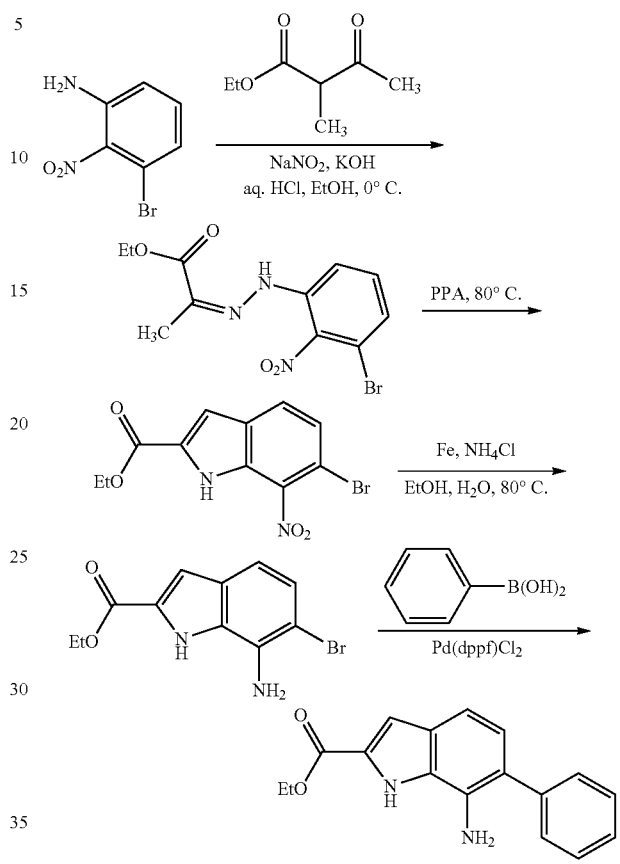

Intermediate A13

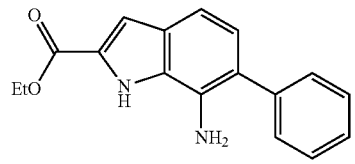 [SMILES: CCOC(=O)c1cc2ccc(-c3ccccc3)c(N)c2[nH]1]

Ethyl 7-amino-6-phenyl-1H-indole-2-carboxylate

Step A: (Z/E)-Ethyl 2-(2-(3-bromo-2-nitrophenyl)hydrazono)propanoate

To a mixture of 3-bromo-2-nitroaniline (20 g, 92 mmol) in water (32 mL) and concentrated aqueous hydrochloric acid solution (38 mL) at 23° C. was added a solution of sodium nitrite (6.68 g, 97 mmol) in water (25 mL) dropwise. In a separate flask, an aqueous solution of 50% (w/w) potassium hydroxide (15.5 g, 276 mmol) was slowly added to a solution of ethyl 2-methyl-3-oxobutanoate (13 g, 92 mmol) in ethanol (95 mL) at 0° C., followed by ice-cold water (190 mL). The resulting mixture was stirred for 10 min before the aforementioned solution of the diazonium salt was added. The resulting mixture was stirred for 10 min. The precipitate was filtered and washed with water until the filtrate was pH 7 by a litmus test. The solid was dissolved in acetonitrile and water and lyophilized to give the title compound. MS: m/z=330.1, 332.1 (M+1). $^1$H NMR (400 MHz, CD$_3$OD) δ 7.27-7.35 (m, 2H), 6.84-6.89 (m, 1H), 4.23 (q, J=6.8 Hz, 2H), 2.07 (s, 3H), 1.33 (t, J=6.8 Hz, 3H).

Step B: Ethyl 6-bromo-7-nitro-1H-indole-2-carboxylate

To a stirred solution of (Z/E)-ethyl 2-((3-bromo-2-nitrophenyl)diazenyl)propanoate (20 g, 61 mmol) in toluene (200 mL) was added PPA (200 mL), and the resulting mixture was stirred at 100° C. for 10 h. The product mixture was poured into water (300 mL) and stirred for 30 min until PPA was hydrolyzed. The aqueous layer was extracted with EtOAc (300 mL×3). The combined organic layers were dried over Na$_2$SO$_4$ and concentrated. The residue was purified by column chromatography on silica gel (PE/EtOAc=10/1, 5/1) to give the title compound. $^1$H NMR (400 MHz, CDCl$_3$) δ 10.15 (s, 1H), 7.76 (d, J=8.4 Hz, 1H), 7.53 (d, J=8.4 Hz, 1H), 7.29 (d, J=2.0 Hz, 1H), 4.44 (q, J=7.2 Hz, 2H), 1.42 (t, J=7.2 Hz, 3H).

Step C: Ethyl 7-amino-6-bromo-1H-indole-2-carboxylate

To a mixture of ethyl 6-bromo-7-nitro-1H-indole-2-carboxylate (500 mg, 1.60 mmol) and ammonium chloride (427 mg, 7.98 mmol) in ethanol (8 mL) and water (2 mL) was added iron powder (446 mg, 7.98 mmol). The resulting mixture was heated at 80° C. for 1 h, then cooled and filtered. The filtrate was concentrated and the residue was purified by preparative TLC (PE/EtOAc=3/1) to give the title compound. MS: m/z=324.1, 326.1 (M+MeCN+1). $^1$H NMR (400 MHz, CD$_3$OD): δ 7.01-7.08 (m, 2H), 6.87 (d, J=8.6 Hz, 1H), 4.36 (q, J=7.0 Hz, 2H), 1.38 (t, J=7.0 Hz, 3H).

Step D: Ethyl 7-amino-6-phenyl-1H-indole-2-carboxylate

To a deoxygenated mixture of ethyl 7-amino-6-bromo-1H-indole-2-carboxylate (200 mg, 0.71 mmol), phenylboronic acid (103 mg, 0.845 mmol) and potassium carbonate (195 mg, 1.41 mmol) in dioxane (4 mL) and water (1 mL) was added PdCl$_2$(dppf) (37 mg, 0.05 mmol), and the resulting mixture was heated at 100° C. for 2 h. The mixture was cooled and partitioned between water (5 mL) and EtOAc (10 mL×3). The combined organic layers were dried over Na$_2$SO$_4$ and concentrated. The residue was purified by preparative TLC (PE/EtOAc=3/1) to give ethyl the title compound. MS: m/z=322.2 (M+MeCN+1). $^1$H NMR (400 MHz, CDCl$_3$): δ 9.05 (s, 1H), 7.65 (d, J=5.9 Hz, 1H), 7.42 (q, J=7.8 Hz, 4H), 7.26-7.33 (m, 1H), 7.16 (d, J=2.0 Hz, 1H), 6.96 (d, J=8.2 Hz, 1H), 4.34 (q, J=7.3 Hz, 2H), 1.36 (t, J=7.2 Hz, 3H).

Reaction Scheme for Intermediate A14

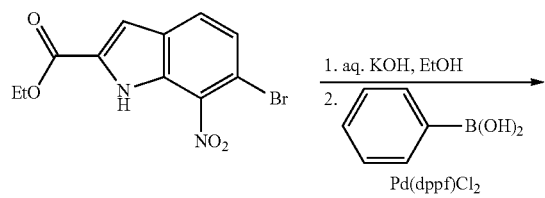

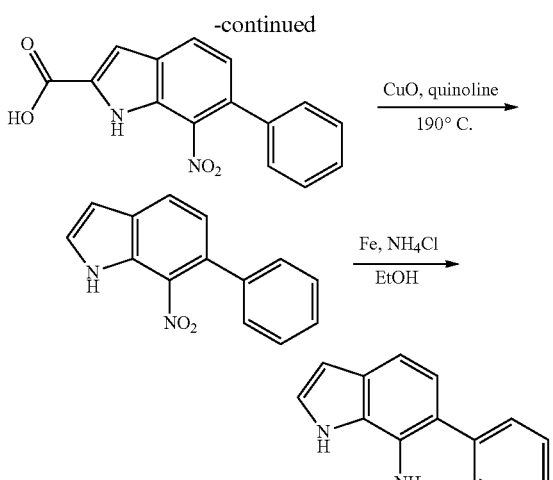

Intermediate A14

6-Phenyl-1H-indol-7-amine

Step A: 6-Bromo-7-nitro-1H-indole-2-carboxylic acid

To a mixture of ethyl 6-bromo-7-nitro-1H-indole-2-carboxylate (9.50 g, 30.3 mmol) in ethanol (75 mL) was added a solution of potassium hydroxide (5.11 g, 91 mmol) in water (20 mL), and the resulting mixture was stirred at 25° C. for 2 h. After evaporation of ethanol, the reaction mixture was acidified to pH 5 with aqueous hydrochloric acid solution (3 M). The aqueous phase was extracted with EtOAc (50 mL×3). The combined organic layer was dried over Na$_2$SO$_4$ and concentrated to give 6-Bromo-7-nitro-1H-indole-2-carboxylic acid. To a deoxygenated mixture of 6-bromo-7-nitro-1H-indole-2-carboxylic acid (6.70 g, 23.5 mmol), phenylboronic acid (3.44 g, 28.2 mmol) and potassium carbonate (9.75 g, 70.5 mmol) in dioxane (50 mL) and water (20 mL) was added PdCl$_2$(dppf) (0.34 g, 0.47 mmol). The resulting mixture was heated at 100° C. for 2 h. The mixture was diluted with EtOAc (70 mL) and water (50 mL) and the precipitate was filtered. The solid was suspended in aqueous HCl solution (50 mL, 3M) and extracted with EtOAc (20 mL×3). The combined organic layers were dried over Na$_2$SO$_4$ and concentrated to give the title compound. $^1$H NMR (400 MHz, CD$_3$OD) δ 7.93 (d, J=8.2 Hz, 1H), 7.28-7.47 (m, 5H), 7.12 (s, 1H), 7.07 (d, J=8.2 Hz, 1H).

Step B: 7-Nitro-6-phenyl-1H-indole

To a mixture of 7-nitro-6-phenyl-1H-indole-2-carboxylic acid (340 mg, 1.21 mmol) in quinoline (4 mL) was added copper powder (77 mg, 1.2 mmol), and the resulting mixture was heated at 190° C. for 30 min. The mixture was cooled and acidified with aqueous hydrochloric acid solution (10 mL, 3M), and extracted with EtOAc (10 mL×3). The combined organic layers were dried over Na₂SO₄ and concentrated. The residue was purified by preparative TLC (PE/EtOAc=3/1) to give the title compound. ¹H NMR (400 MHz, CDCl₃) δ 9.75 (s, 1H), 7.88 (d, J=8.2 Hz, 1H), 7.37-7.46 (m, 4H), 7.34 (d, J=6.7 Hz, 2H), 7.09 (d, J=7.8 Hz, 1H), 6.70 (s, 1H).

Step C: 6-Phenyl-1H-indol-7-amine

To a mixture of 7-nitro-6-phenyl-1H-indole (260 mg, 1.09 mmol) and ammonium chloride (292 mg, 5.46 mmol) in ethanol (2 mL) and water (1 mL) was added iron powder (305 mg, 5.46 mmol), and the resulting mixture was heated at 80° C. for 1 h. The mixture was cooled and filtered. The filtrate was concentrated and the residue was purified by preparative TLC (PE/EtOAc=3/1) to give the title compound. MS: m/z=250.2 (M+CH₃CN+1). ¹H NMR (400 MHz, CDCl₃) δ 8.31 (s, 1H), 7.35-7.49 (m, 3H), 7.24-7.31 (m, 1H), 7.11-7.20 (m, 2H), 6.93 (d, J=8.2 Hz, 1H), 6.49 (s, 1H).

Reaction Scheme for Intermediate A15

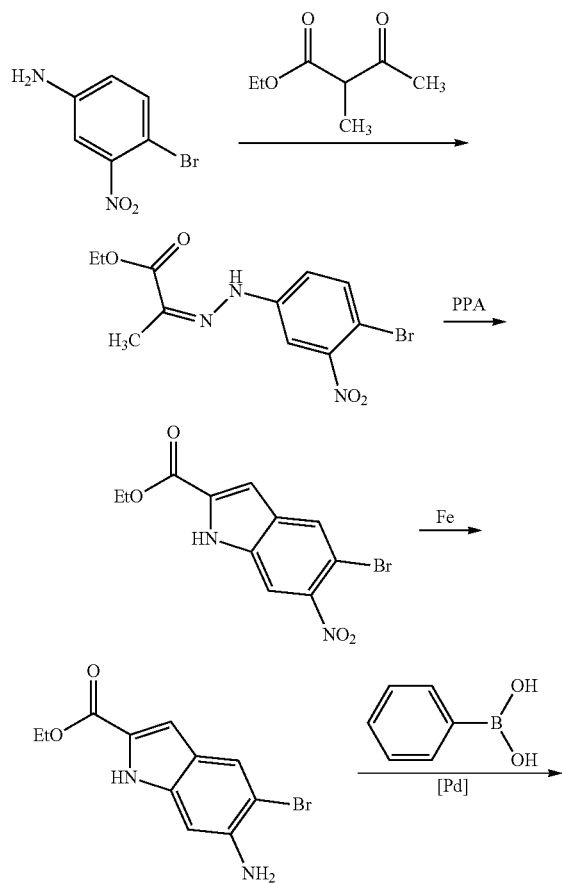

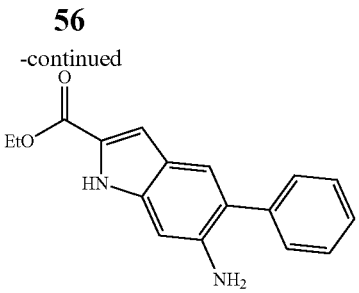

Intermediate A15

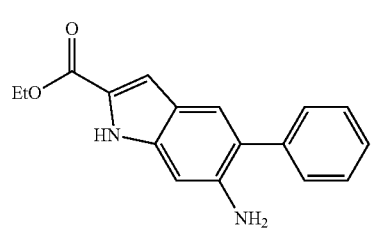 [SMILES: CCOC(=O)c1cc2cc(-c3ccccc3)c(N)cc2[nH]1]

Ethyl 6-amino-5-phenyl-1H-indole-2-carboxylate

Step A: (Z)-Ethyl 2-(2-(4-bromo-3-nitrophenyl)hydrazono)propanoate

To a mixture of 4-bromo-3-nitroaniline (4.00 g, 18.4 mmol) in water (8 mL) and concentrated aqueous hydrochloric acid solution (9.5 mL) at 0° C. was added dropwise a solution of sodium nitrite (1.40 g, 20.3 mmol) in water (6.5 mL). In a separate flask, a solution of aqueous 50% (w/w) potassium hydroxide (3.10 g, 55.3 mmol) was added to a solution of ethyl 2-methyl-3-oxobutanoate (2.70 g, 18.4 mmol) in ethanol (24 mL) at 0° C., followed by cold water (48 mL). The resulting solution was stirred at 0° C. for 10 min before the aforementioned solution of the diazonium salt was added. After 10 min, the precipitate was filtered, washed by water and dried to give the title compound. MS: m/z=329.9, 331.9 (M+1). ¹H NMR (400 MHz, CD₃OD) δ 7.73-7.83 (m, 1H), 7.60-7.69 (m, 1H), 7.37-7.51 (m, 1H), 4.29 (q, J=7.3 Hz, 2H), 2.12 (s, 3H), 1.34 (t, J=7.2 Hz, 3H).

Step B: Ethyl 5-bromo-6-nitro-1H-indole-2-carboxylate

To a mixture of (Z)-ethyl 2-(2-(4-bromo-3-nitrophenyl)hydrazono)propanoate (3.20 g, 9.70 mmol) in toluene (30 mL) was added PPA (30 mL), and the resulting mixture was heated at 90° C. for 1 h. The reaction mixture was poured into water (50 mL) and stirred for 30 min until PPA was hydrolyzed. The aqueous layer was extracted with EtOAc (100 mL×3). The combined organic layers were dried over Na₂SO₄ and concentrated. The residue was purified by column chromatography on silica gel (PE/EtOAc=20/1, 10/1) to give the title compound. ¹H NMR (400 MHz, CDCl₃) δ 8.01-8.09 (m, 1H), 7.56-7.64 (m, 1H), 7.46-7.53 (m, 1H), 4.41-4.50 (m, 2H), 1.44 (dt, J₁ 7.0 Hz, J₂=3.5 Hz, 3H).

Step C: Ethyl 6-amino-5-bromo-1H-indole-2-carboxylate

To a solution of ethyl 5-bromo-6-nitro-1H-indole-2-carboxylate (230 mg, 0.70 mmol) in ethanol (8 mL) and water (2 mL) was added ammonium chloride (196 mg, 3.70 mmol) and iron powder (205 mg, 3.70 mmol). The resulting mixture was sheated at 80° C. for 1 h, then partitioned between water (10 mL) and EtOAc (10 mL×3). The combined organic layers were dried over $Na_2SO_4$ and concentrated. The residue was purified by column chromatography on silica gel (PE/EtOAc=15/1, 10/1) to give the title compound. $^1$H NMR (400 MHz, $CDCl_3$) δ 7.24 (d, J=9.0 Hz, 1H), 7.09 (s, 1H), 6.64-6.70 (m, 1H), 4.33 (q, J=7.0 Hz, 2H), 1.34 (t, J=7.2 Hz, 3H).

Step D: Ethyl 6-amino-5-phenyl-1H-indole-2-carboxylate

To a deoxygenated solution of ethyl 6-amino-5-bromo-1H-indole-2-carboxylate (180 mg, 0.60 mmol) in dioxane (2 mL) and water (0.5 mL) was added phenylboronic acid (93 mg, 0.80 mmol), $PdCl_2$(dppf) (23.30 mg, 0.10 mmol) and potassium carbonate (176 mg, 1.30 mmol). The resulting mixture was stirred at 90° C. for 2 h. The mixture was cooled and filtered. The filtrate was partitioned between water (10 mL) and EtOAc (10 mL×3). The combined organic layers were dried over $Na_2SO_4$ and concentrated. The residue was purified by preparative TLC (PE/EtOAc=3/1) to give the title compound. MS: m/z=281.2 (M+1).

Reaction Scheme for Intermediate A16

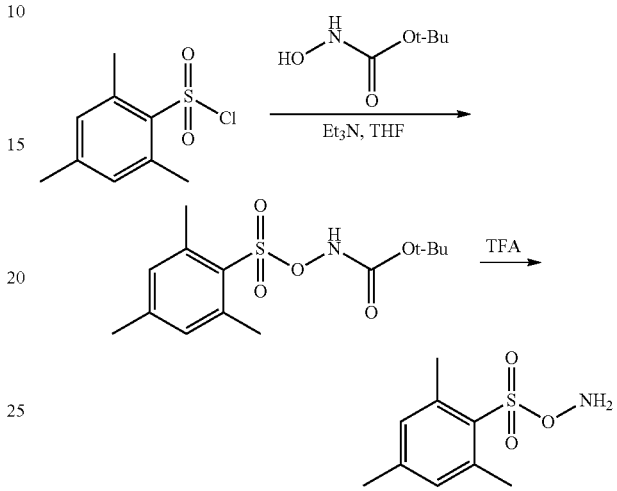

Intermediate A16

7-Phenyl-[1,2,4]triazolo[4,3-c]pyrimidin-8-amine

Bis(tri-tert-butylphosphine)pallatium(0) (30 mg, 0.059 mmol) was added to a degassed mixture of 7-chloro-[1,2,4]triazolo[4,3-c]pyrimidin-8-amine (200 mg, 1.18 mmol), phenylboronic acid (431 mg, 3.54 mmol), and aqueous cesium carbonate solution (2M, 1.18 mL, 2.359 mmol) in dioxane (1 mL). The resulting mixture was heated at 100° C. for 2 h in a microwave reactor. The reaction mixture was diluted with water (3 mL), and the precipitate was filtered, washed with water (3×1 mL) and dried to yield the title compound. MS: m/z=212.1 (M+1).

Reaction Scheme for Intermediate A17

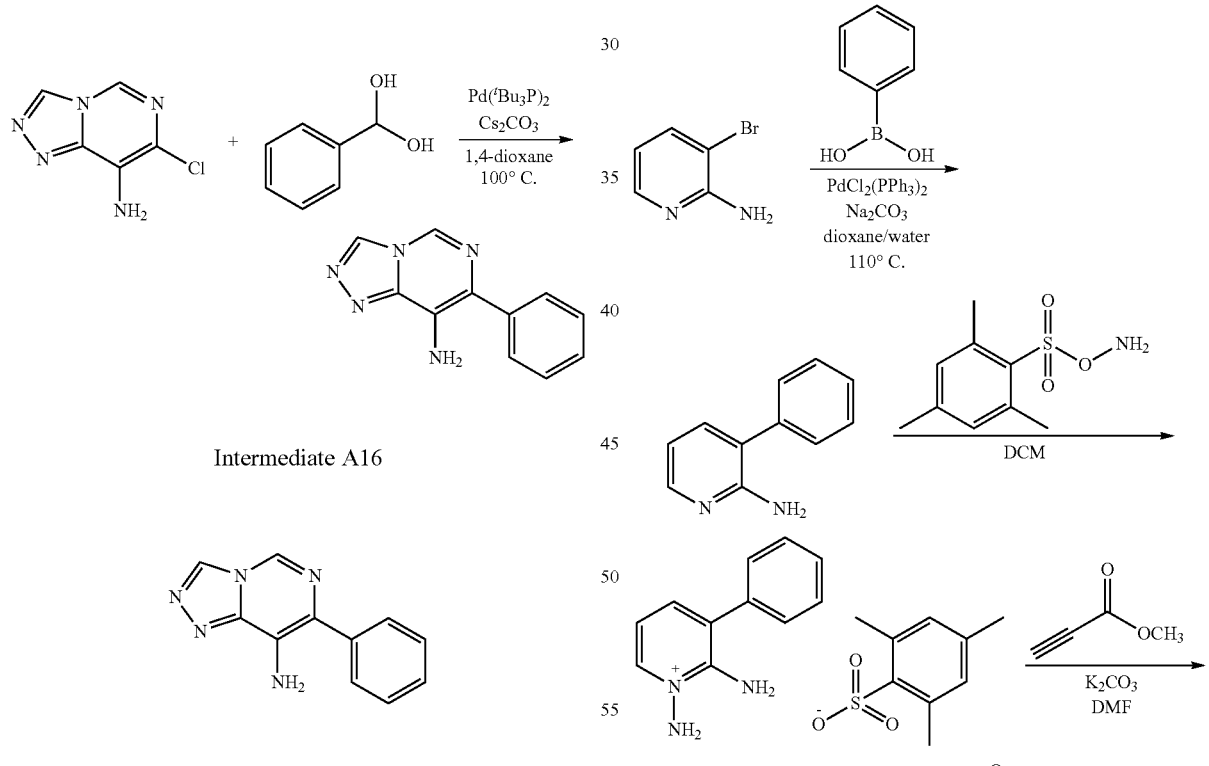

Intermediate A17

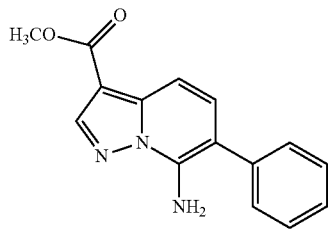 [SMILES: COC(=O)c1cnn2c(N)c(-c3ccccc3)ccc12]

Methyl 7-amino-6-phenylpyrazolo[1,5-a]pyridine-3-carboxylate

Step A: tert-Butyl (mesitylsulfonyl)oxycarbamate

To a solution of 2,4,6-trimethylbenzene-1-sulfonyl chloride (20 g, 91 mmol) in tetrahydrofuran (500 mL) at 0° C. was added tert-butyl hydroxycarbamate (12 g, 91 mmol) under nitrogen atmosphere. The resulting mixture was stirred for 5 min before triethylamine (15.3 mL, 110 mmol) was slowly added over 10 min. The mixture was stirred at 0° C. for 2 h, then concentrated. The residue was dissolved in dichloromethane (250 mL) and the resulting solution was washed with water (100 mL×3) and saturated sodium bicarbonate (100 mL), dried over $Na_2SO_4$ and concentrated to give the title compound. $^1$H NMR (400 MHz, $CDCl_3$) δ 7.56 (s, 1H), 7.00 (s, 2H), 2.69 (s, 6H), 2.33 (s, 3H), 1.33 (s, 9H).

Step B: O-(Mesitylsulfonyl) hydroxylamine tert-Butyl (mesitylsulfonyl) oxycarbamate (6.3 g, 19 mmol) was added slowly to TFA (60 mL) at 0° C. under nitrogen atmosphere. The resulting mixture was stirred at 0° C. for 30 min before water (180 mL) was slowly added to the mixture. The precipitate was filtered, washed with water until the filtrate was pH neutral, and dried to afford the title compound. $^1$H NMR (400 MHz, DMSO-$d_6$) δ 6.75 (s, 2H), 2.49 (br., 6H), 2.17 (s, 3H).

Step C: 3-Phenylpyridin-2-amine

To a deoxygenated mixture of 3-bromopyridin-2-amine (5.00 g, 28.9 mmol), phenylboronic acid (4.23 g, 34.7 mmol) and sodium carbonate (9.19 g, 87 mmol) in 1,4-dioxane (60 mL) and water (30 mL) was added $PdCl_2(PPh_3)_2$(1.01 g, 1.44 mmol). The resulting mixture was heated at 110° C. for 4 h. The mixture was cooled and filtered. The filtrate was partitioned between water (50 mL) and EtOAc (30 mL×3). The combined organic layers were washed with brine (50 mL×3), dried over $Na_2SO_4$ and concentrated. The residue was purified by silica gel column chromatography (PE/EtOAc=4/1, 1/1) to give the title compound. $^1$H NMR (400 MHz, $CDCl_3$) δ 8.09 (d, J=3.5 Hz, 1H), 7.43-7.51 (m, 4H), 7.35-7.41 (m, 2H), 6.76 (dd, J=5.1, 7.0 Hz, 1H), 4.61 (br, 2H).

Step D: 1,2-Diamino-3-phenylpyridin-1-ium 2,4,6-trimethylbenzenesulfonate

To a solution of 3-phenylpyridin-2-amine (1.00 g, 5.88 mmol) in dichloromethane (30 mL) at 0° C. was added a solution of o-mesitylsulfonyl hydroxylamine (2.81 g, 11.8 mmol) in dichloromethane (20 mL) dropwise. The resulting mixture was warmed to 20° C. and stirred for 2 h. The mixture was concentrated, and the residue was diluted with isopropyl ether (40 mL) and stirred for 15 min. The precipitate was filtered, washed with isopropyl ether (20 mL×3), and dried to give the title compound. MS: m/z=186.0 (M+1).

Step E: Methyl 7-amino-6-phenylpyrazolo[1,5-a]pyridine-3-carboxylate

To a solution of 1,2-diamino-3-phenylpyridin-1-ium-2,4,6-trimethylbenzenesulfonate (1.40 g, 3.63 mmol) in N,N-dimethylformamide (15 mL) at 0° C. was added potassium carbonate (1.25 g, 9.08 mmol) followed by methyl propiolate (1.20 mL, 14.5 mmol). The resulting mixture was stirred at 25° C. for 16 h. The mixture was partitioned between water (50 mL) and EtOAc (30 mL×3). The combined organic layers were washed with brine (30 mL×3), dried over dried over $Na_2SO_4$ and concentrated. The residue was purified by flash silica gel chromatography (ISCO; 24 g SepaFlash® Silica Flash Column, EtOAc in petroleum ether: 0-30%, 40 mL/min, dry loaded) to give the title compound. $^1$H NMR (400 MHz, DMSO-$d_6$) δ 8.47 (s, 1H), 7.44-7.55 (m, 5H), 7.36-7.42 (m, 2H), 6.77 (br, 2H), 3.82 (s, 3H).

Reaction Scheme for Intermediate A18

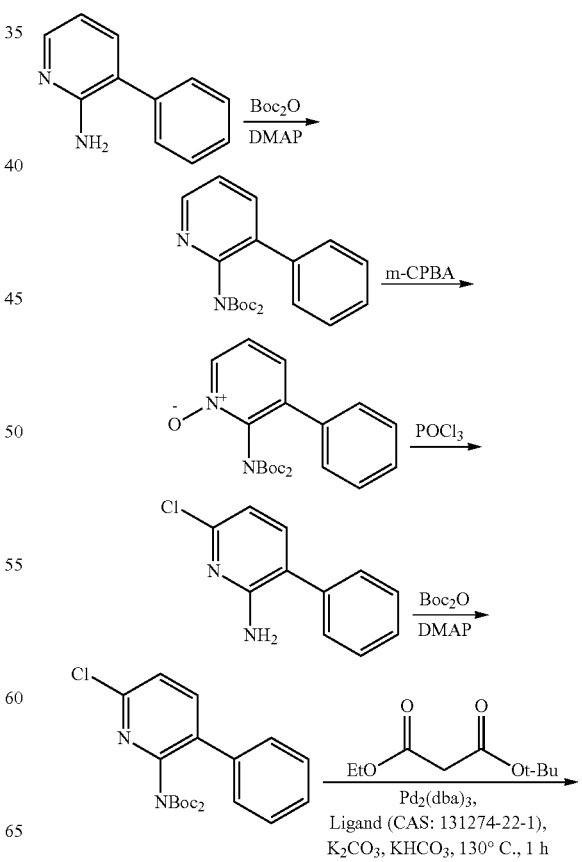

-continued

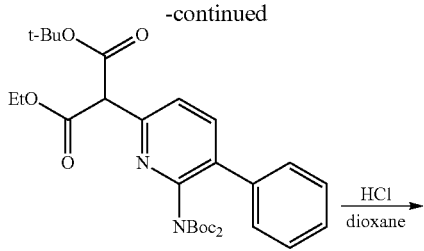

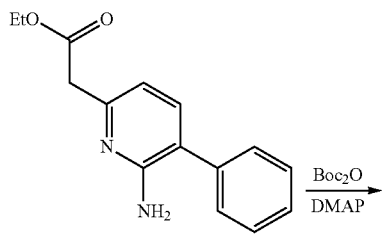

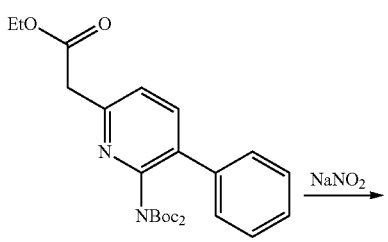

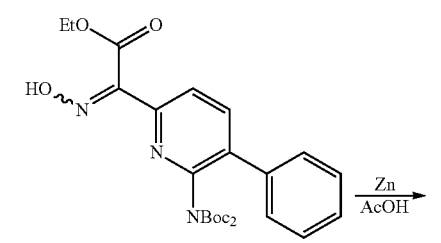

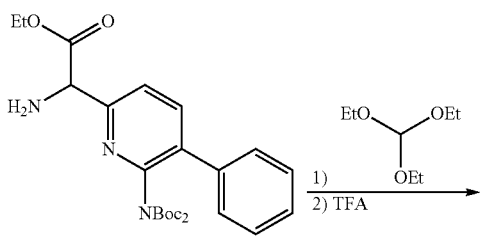

Intermediate A18

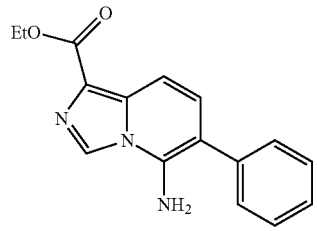 [SMILES: CCOC(=O)c1ncn2c(N)c(-c3ccccc3)ccc12]

Ethyl 5-amino-6-phenylimidazo[1,5-a]pyridine-1-carboxylate

Step A:
3-Phenylpyridin-2-(di-tert-butoxycarbonyl)amine

To a solution of 3-phenylpyridin-2-amine (10.0 g, 55.8 mmol) and di-tert-butyl dicarbonate (48.7 g, 223 mmol) in DCM (200 mL) was added DMAP (13.6 g, 112 mmol) in batches. The resulting mixture was stirred at 26° C. for 16 h, then washed with brine (100 mL×3), dried over $Na_2SO_4$ and concentrated. The residue was purified by flash silica gel chromatography (ISCO; 120 g SepaFlash® Silica Flash Column, EtOAc in petroleum ether: 0-40%, 50 mL/min, dry loaded) to give the title compound. $^1$H NMR (400 MHz, $CDCl_3$) δ 8.52 (d, J 3.1 Hz, 1H), 7.75 (dd, J=1.6, 7.4 Hz, 1H), 7.34-7.45 (m, 6H), 1.30 (s, 18H).

Step B:
2-(Di-tert-butoxycarbonyl)amino-3-phenylpyridine 1-oxide

To a solution of 3-phenylpyridin-2-(di-tert-butoxycarbonyl)amine (17.5 g, 44.9 mmol) in DCM (100 mL) was added mCPBA (48.4 g, 224 mmol), and the resulting mixture was stirred at 27° C. for 16 h. The mixture was diluted with saturated $Na_2SO_3$ (200 mL) and partitioned between saturated $NaHCO_3$ solution (300 mL) and DCM (200 mL×3). The combined organic layers were washed with brine (200 mL×3), dried over $Na_2SO_4$ and concentrated. The residue was purified by flash silica gel chromatography (ISCO; 120 g SepaFlash® Silica Flash Column, EtOAc in petroleum ether: 0-80%, 50 mL/min, dry loaded) to give the title compound. $^1$H NMR (400 MHz, $CDCl_3$) δ 8.29 (dd, J=1.4, 6.1 Hz, 1H), 7.39-7.47 (m, 5H), 7.22-7.27 (m, 2H), 1.33 (s, 18H).

Step C: 6-Chloro-3-phenylpyridin-2-amine

To a solution of 2-(di-tert-butoxycarbonyl)amino-3-phenylpyridine-1-oxide (10.0 g, 25.9 mmol) in DCM (80 mL) was added phosphoryl trichloride (20.8 mL, 223 mmol), and the resulting mixture was heated at 35° C. for 16 h. The mixture was concentrated and the residue was partitioned between saturated aqueous $NaHCO_3$ solution (300 mL) and EtOAc (100 mL×3). The combined organic layers were washed with saturated aqueous $NaHCO_3$ solution (100 mL×3), dried over dried over $Na_2SO_4$ and concentrated. The residue was purified by flash silica gel chromatography (ISCO; 40 g SepaFlash® Silica Flash Column, EtOAc in petroleum ether: 0-20%, 40 mL/min, dry loaded) to give the title compound. ¹H NMR (400 MHz, CDCl₃) δ 7.38-7.50 (m, 5H), 7.32 (d, J=7.4 Hz, 1H), 6.76 (d, J=7.8 Hz, 1H), 4.72 (br, 2H).

Step D: 6-Chloro-3-phenylpyridin-2-(di-tert-butoxycarbonyl)amine

To a solution of 6-chloro-3-phenylpyridin-2-amine (2.10 g, 9.75 mmol) and di-tert-butyl dicarbonate (8.51 g, 39.0 mmol) in DCM (30 mL) was added DMAP (2.38 g, 19.5 mmol) in batches. The resulting mixture was stirred at 26° C. for 16 h, then washed with brine, dried over Na₂SO₄ and concentrated. The residue was purified by flash silica gel chromatography (ISCO; 40 g SepaFlash® Silica Flash Column, EtOAc in petroleum ether: 0-15%, 40 mL/min, dry loaded) to give the title compound. ¹H NMR (400 MHz, CDCl₃) δ 7.71 (d, J=8.0 Hz, 1H), 7.37-7.45 (m, 6H), 1.30 (s, 18H).

Step E: 1-tert-Butyl 3-ethyl 2-(6-(di-tert-butoxycarbonyl)amino-5-phenylpyridin-2-yl)malonate A deoxygenated mixture of tri-tert-butylphosphonium tetrafluoroborate (0.34 g, 1.2 mmol), potassium hydrogen carbonate (0.88 g, 8.8 mmol), 6-chloro-3-phenylpyridin-2-(di-tert-butoxycarbonyl)amine (2.5 g, 5.9 mmol), tert-butyl ethyl malonate (3.33 mL, 17.6 mmol), Pd(dba)₂ (0.34 g, 0.59 mmol) and K₂CO₃ (1.22 g, 8.80 mmol) was heated at 130° C. for 1 h. The mixture was filtered and the filtrate was concentrated to give the title compound. MS: m/z=557.2 (M+1).

Step F: Ethyl 2-(6-amino-5-phenylpyridin-2-yl)acetate

A mixture of 1-tert-butyl 3-ethyl 2-(6-(di-tert-butoxycarbonyl)amino-5-phenylpyridin-2-yl)malonate (5.2 g, 3.69 mmol) in a solution of HCl in dioxane (12 mL, 3.69 mmol, 4 M) was stirred at 20° C. for 16 h. The mixture was partitioned between saturated aqueous NaHCO₃ solution (100 mL) and DCM (30 mL×3). The combined organic layers were washed with saturated aqueous NaHCO₃ solution and brine, dried over Na₂SO₄ and concentrated. The residue was purified by flash silica gel chromatography (ISCO; 12 g SepaFlash® Silica Flash Column, EtOAc in petroleum ether: 0-50%, 30 mL/min, dry loaded) to give the title compound. ¹H NMR (400 MHz, CDCl₃) δ 7.41-7.48 (m, 4H), 7.32-7.40 (m, 2H), 6.74 (d, J=7.4 Hz, 1H), 4.61 (s, 2H), 4.21 (q, J=7.2 Hz, 2H), 3.69 (s, 2H), 1.26-1.31 (m, 3H).

Step G: Ethyl 2-(6-(di-tert-butoxycarbonyl)amino-5-phenylpyridin-2-yl)acetate

To a solution of ethyl 2-(6-amino-5-phenylpyridin-2-yl)acetate (450 mg, 1.76 mmol) and Boc₂O (1.02 mL, 4.39 mmol) in DCM (10 mL) was added DMAP (536 mg, 4.39 mmol), and the resulting mixture was stirred at 20° C. for 16 h. The mixture was concentrated and the residue was purified by flash silica gel chromatography (ISCO; 12 g SepaFlash® Silica Flash Column, EtOAc in petroleum ether: 0-20%, 30 mL/min, dry loaded) to give the title compound. MS: m/z=457.1 (M+1).

Step H: Ethyl 2-(6-(di-tert-butoxycarbonyl)amino-5-phenylpyridin-2-yl)-2-(hydroxyimino)acetate To a solution of ethyl 2-(6-(di-tert-butoxycarbonyl)amino-5-phenylpyridin-2-yl)acetate (400 mg, 0.79 mmol) in AcOH (1 mL) was added a solution of sodium nitrite (109 mg, 1.58 mmol) in water (1 mL). The resulting mixture was stirred at 20° C. for 20 h, then partitioned between saturated aqueous NaHCO₃ solution (30 mL) and EtOAc (20 mL×3). The combined organic layers were washed with saturated aqueous NaHCO₃ solution and brine, dried over Na₂SO₄ and concentrated to give the crude title compound. MS: m/z=486.3 (M+1).

Step I: Ethyl 2-amino-2-(6-(di-tert-butoxycarbonyl)amino-5-phenylpyridin-2-yl)acetate To a solution of ethyl 2-(6-(di-tert-butoxycarbonyl)amino-5-phenylpyridin-2-yl)-2-(hydroxyimino)acetate (500 mg, 0.34 mmol) in AcOH (2 mL) was added zinc powder (112 mg, 1.71 mmol), and the resulting mixture was stirred at 15° C. for 16 h. The mixture was partitioned between saturated aqueous NaHCO₃ solution (30 mL) and EtOAc (20 mL×3). The combined organic layers were washed with brine, dried over Na₂SO₄ and concentrated. The residue was purified by flash silica gel chromatography (ISCO; 12 g SepaFlash® Silica Flash Column, EtOAc in petroleum ether: 0-60%, 30 mL/min, dry loaded) to give the title compound. MS: m/z=472.2 (M+1).

Step J: Ethyl 5-amino-6-phenylimidazo[1,5-a]pyridine-1-carboxylate

A mixture of ethyl 2-amino-2-(6-(di-tert-butoxycarbonyl)amino-5-phenylpyridin-2-yl)acetate (120 mg, 0.24 mmol) and triethoxymethane (0.41 mL, 2.4 mmol) was heated at 150° C. for 1 h, then cooled and concentrated. The residue was dissolved in TFA (2 mL, 26.0 mmol) and the resulting mixture was heated at 75° C. for 16 h. The product mixture was partitioned between saturated aqueous NaHCO₃ solution (50 mL) and DCM (50 mL×3). The combined organic layers were washed with saturated aqueous NaHCO₃ solution and brine, dried over Na₂SO₄ and concentrated to give the title compound. MS: m/z=282.0 (M+1).

Reaction Scheme for Intermediate A19

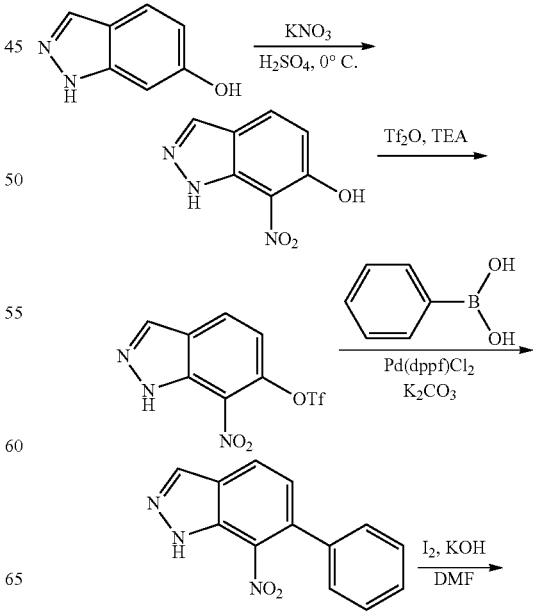

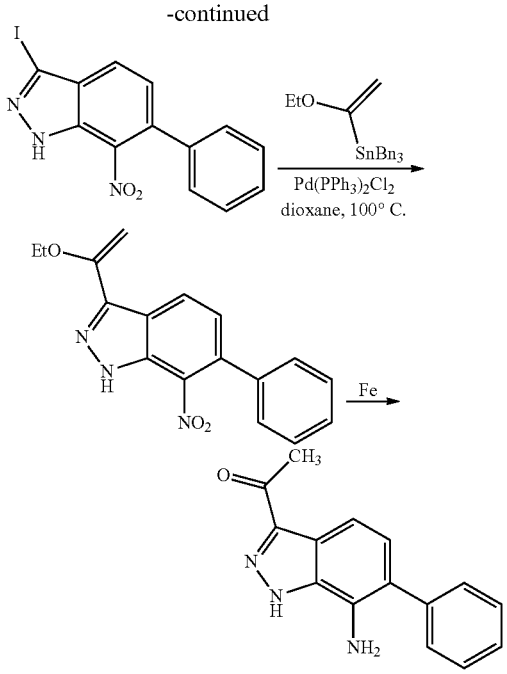

Intermediate A19

1-(7-Amino-6-phenyl-1H-indazol-3-yl)ethanone

Step A: 7-Nitro-1H-indazol-6-ol

To a solution of 1H-indazol-6-ol (500 mg, 3.7 mmol) in concentrated aqueous sulfuric acid solution (5 mL) was added potassium nitrate (380 mg, 3.7 mmol) at 0° C. in portions. The mixture was stirred at 0° C. for 30 min, then diluted with cold water (70 mL). The precipitate was filtered and dried to give the title compound. MS: m/z=180.0 (M+1).

Step B: 7-Nitro-1H-indazol-6-yl trifluoromethanesulfonate

To a solution of 7-nitro-1H-indazol-6-ol (100 mg, 0.6 mmol) in anhydrous dichloromethane (3 mL) were added triethylamine (0.20 mL, 1.7 mmol) and N, N-bis(trifluoromethylsulfonyl)aniline (300 mg, 0.8 mmol). The resulting mixture was stirred at 23° C. for 5 h. The mixture was partitioned between water (5 mL) and EtOAc (10 mL×3). The organic layer was dried over Na$_2$SO$_4$ and concentrated. The residue was purified by preparative TLC (PE/EtOAc=1/1) to give the title compound. $^1$H NMR (400 MHz, CD$_3$OD) δ 8.41 (s, 1H), 8.36 (d, J=8.5 Hz, 1H), 7.38 (d, J=8.5 Hz, 1H).

Step C: 7-Nitro-6-phenyl-1H-indazole

To a deoxygenated solution of 7-nitro-1H-indazol-6-yl trifluoromethanesulfonate (10 g, 32 mmol) in dioxane (100 mL) and water (20 mL) was added phenylboronic acid (4.7 g, 39 mmol), PdCl$_2$(dppf) (1.2 g, 1.6 mmol) and potassium carbonate (13 g, 96 mmol). The resulting mixture was heated at 90° C. for 3 h, then cooled and concentrated. The residue was partitioned between water (50 mL) and EtOAc (100 mL×3). The combined organic layers were dried over Na$_2$SO$_4$ and concentrated. The residue was purified by column chromatography on silica gel (PE/EtOAc=20/1, 15/1) to give the title compound. $^1$H NMR (400 MHz, CD$_3$OD) δ 8.29 (s, 1H), 8.14 (d, J=8.2 Hz, 1H), 7.33-7.49 (m, 5H), 7.21 (d, J=8.2 Hz, 1H).

Step D: 3-Iodo-7-nitro-6-phenyl-1H-indazole

To a solution of 7-nitro-6-phenyl-1H-indazole (2.90 g, 12.1 mmol) in DMF (40 mL) were added iodine (6.2 g, 24.2 mmol) and potassium hydroxide (2.7 g, 49 mmol). The resulting mixture was stirred at room temperature for 2 h, then diluted with aqueous sodium sulfite solution (40 mL, 5% w/w). The precipitate was filtered, washed with water (50 mL) and dried to give the title compound. MS: m/z=365.9 (M+1). $^1$H NMR (400 MHz, CDCl$_3$) δ 7.81 (d, J=8.6 Hz, 1H), 7.46 (s, 3H), 7.34 (d, J=4.3 Hz, 2H).

Step E: 3-(1-Ethoxyvinyl)-7-nitro-6-phenyl-1H-indazole

To a deoxygenated mixture of 3-iodo-7-nitro-6-phenyl-1H-indazole (3.2 g, 8.7 mmol) in dioxane (40 mL) were added tribenzyl(1-ethoxyvinyl)stannane (8.1 g, 18 mmol) and PdCl$_2$(PPh$_3$)$_2$(0.6 g, 0.9 mmol). The resulting mixture was stirred at 100° C. for 4 h, then cooled and diluted with saturated aqueous potassium fluoride solution (50 mL). The resulting mixture was filtered, and the filtrate was extracted with EtOAc (60 mL×3). The combined organic layers were dried over Na$_2$SO$_4$ and concentrated. The residue was purified by column chromatography on silica gel (PE/EtOAc=20/1, 15/1, 10/1) to give the title compound. MS: m/z=310.1 (M+1).

Step F: 1-(7-amino-6-phenyl-1H-indazol-3-yl)ethanone

To a solution of 3-(1-ethoxyvinyl)-7-nitro-6-phenyl-1H-indazole (700 mg, 2.30 mmol) in EtOH (6 mL) and water (2 mL) was added iron powder (379 mg, 6.80 mmol) and ammonium hydrochloride (363 mg, 6.80 mmol). The resulting mixture was heated at 80° C. for 1 h, then cooled and partitioned between water (10 mL) and EtOAc (10 mL×3). The combined organic layers were dried over Na$_2$SO$_4$ and concentrated to give the title compound. MS: m/z=293.2 (M+CH$_3$CN+1).

Reaction Scheme for Intermediate A20

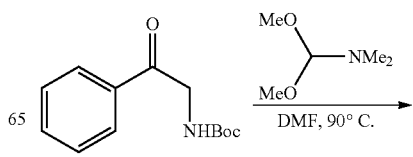

-continued

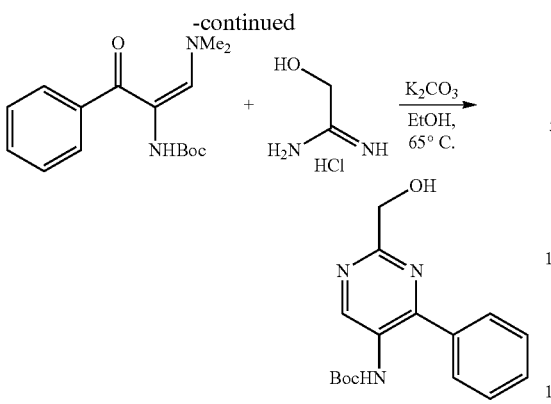

Intermediate A20

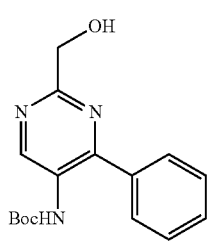 [SMILES: CC(C)(C)OC(=O)Nc1cnc(CO)nc1-c1ccccc1]

tert-Butyl (2-(hydroxymethyl)-4-phenylpyrimidin-5-yl)carbamate

Step A: (E)-tert-Butyl (1-(dimethylamino)-3-oxo-3-phenylprop-1-en-2-yl)carbamate A mixture of tert-butyl (2-oxo-2-phenylethyl)carbamate (1.00 g, 4.25 mmol) and 1,1-dimethoxy-N,N-dimethylmethanamine (0.598 mL, 4.46 mmol) in DMF (5 mL) was heated at 90° C. for 16 h. The product mixture was cooled and partitioned between EtOAc and water. The organic layer was washed with brine, dried over sodium sulfate and concentrated to give the title compound.

Step B: tert-Butyl (2-(hydroxymethyl)-4-phenylpyrimidin-5-yl)carbamate

Potassium carbonate (6.57 g, 47.5 mmol) was added to a mixture of (E)-tert-butyl (1-(dimethylamino)-3-oxo-3-phenylprop-1-en-2-yl)carbamate (4.60 g, 15.8 mmol) and 2-hydroxyacetimidamide hydrochloride (2.80 g, 25.3 mmol) in ethanol (25 mL) at 25° C. The resulting mixture was heated at 65° C. for 24 h then cooled and concentrated. The residue was partitioned between EtOAc (100 mL) and water (2×100 mL). The organic layer was washed with brine, dried over sodium sulfate and concentrated. The residue was purified by flash column chromatography on silica gel (10% EtOAc in hexanes, grading to 100% EtOAc) to provide the title compound. MS: m/z=302.6 (M+1).

Reaction Scheme for Intermediate A21

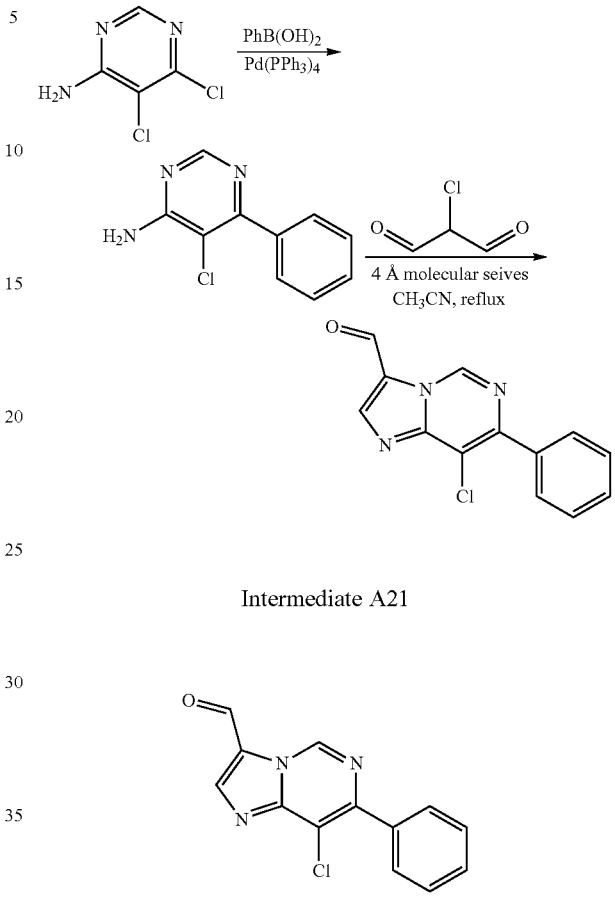

Intermediate A21

8-Chloro-7-phenylimidazo[1,2-c]pyrimidine-3-carbaldehyde

Step A: 5-Chloro-6-phenylpyrimidin-4-amine

To a deoxygenated mixture of 5,6-dichloropyrimidin-4-amine (5.00 g, 30.5 mmol) in toluene (300 mL) and EtOH (30 mL) was added aqueous $Na_2CO_3$ solution (30.5 mL, 61.0 mmol, 2M), phenylboronic acid (3.35 g, 27.4 mmol), and $Pd(PPh_3)_4$ (1.76 g, 1.52 mmol). The resulting mixture was heated at 90° C. for 16 h, then cooled and concentrated. The residue was partitioned between water (100 mL) and ethyl acetate (100 mL×3). The combined organic layers were dried over $Na_2SO_4$ and concentrated. The residue was purified by flash silica gel chromatography (ISCO, 80 g SepaFlash® Silica Flash Column, ethyl acetate in petroleum ether: 0~35%, dry loaded) to give the title compound. $^1$H NMR (400 MHz, CDCl$_3$) δ 8.53 (s, 1H), 7.73-7.81 (m, 2H), 7.43-7.53 (m, 3H), 5.50 (br., 2H).

Step B: 8-Chloro-7-phenylimidazo[1,2-c]pyrimidine-3-carbaldehyde

To a mixture of 5-chloro-6-phenylpyrimidin-4-amine (500 mg, 2.43 mmol) in acetonitrile (12 mL) were added 2-chloromalonaldehyde (388 mg, 3.65 mmol), 4 Å molecular sieves and anhydrous magnesium sulfate. The resulting mixture was heated at 100° C. for 30 h, then cooled, filtered and concentrated. The residue was purified by flash silica gel chromatography (ISCO, 24 g SepaFlash® Silica Flash Column, ethyl acetate in petroleum ether: 0-50%, dry loaded) to give the title compound. $^1$H NMR (400 MHz, CDCl$_3$) δ 10.14 (s, 1H), 10.06 (s, 1H), 8.44 (s, 1H), 7.95 (d, J=6.0 Hz, 2H), 7.52-7.58 (m, 3H).

Reaction Scheme for Intermediate B1

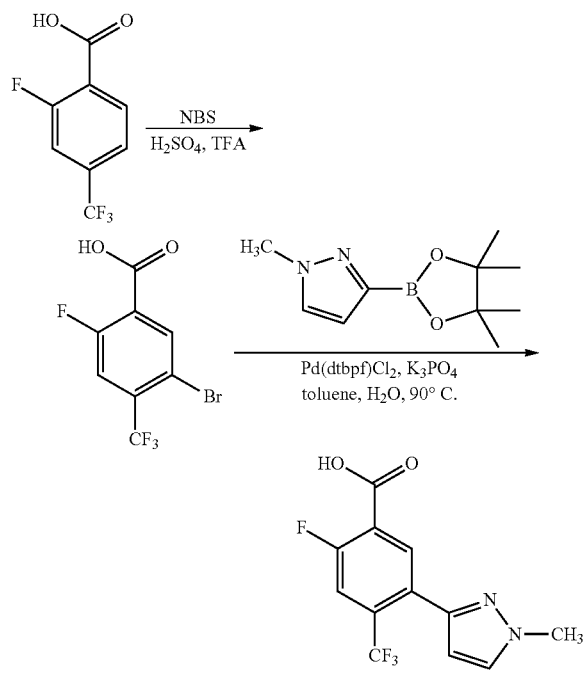

Intermediate B1

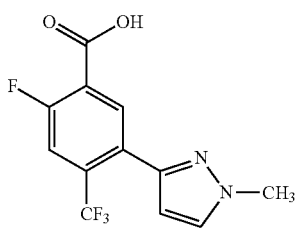 [SMILES: Cn1ccc(-c2cc(C(=O)O)c(F)cc2C(F)(F)F)n1]

2-Fluoro-5-(1-methyl-1H-pyrazol-3-yl)-4-(trifluoromethyl)benzoic acid

Step A:
5-Bromo-2-fluoro-4-(trifluoromethyl)benzoic acid

N-Bromosuccinimide (23.1 g, 130 mmol) was added portionwise to a mixture of 2-fluoro-4-(trifluoromethyl) benzoic acid (15.0 g, 72.1 mmol), sulfuric acid (9.0 mL, 170 mmol, 18 M), and TFA (50.0 mL, 650 mmol) at 50° C. and the resulting mixture was stirred at 50° C. for 18 h. Additional N-bromosuccinimide (3.0 g, 16 mmol) was added and the mixture was stirred at 50° C. for 4 h. The reaction mixture was cooled and water (150 mL) was added. The resulting precipitate was collected and dried to give the title compound. $^1$H NMR (400 MHz, CDCl$_3$) δ 9.90 (s, 1H), 8.35 (d, J=6.3 Hz, 1H), 7.55 (d, J=10.3 Hz, 1H).

Step B: 2-Fluoro-5-(1-methyl-1H-pyrazol-3-yl)-4-(trifluoromethyl)benzoic acid

To a deoxygenated mixture of 5-bromo-2-fluoro-4-(trifluoromethyl)benzoic acid (5.0 g, 17 mmol), 1-(methyl)-3-(4,4,5,5-tetramethyl-1,3,2-dioxaborolan-2-yl)-1H-pyrazole (4.35 g, 20.9 mmol) and K$_3$PO$_4$ (11.1 g, 52.3 mmol) in toluene (55 mL) and H$_2$O (7 mL) was added 1,1'-bis(di-tert-butylphosphino)ferrocene palladium dichloride (1.14 g, 1.74 mmol). The resulting mixture was heated at 90° C. for 2 h, and then stirred at 50° C. for 18 h. The mixture was cooled and filtered. The filtrate was concentrated and the residue was partitioned between water (200 mL) and EtOAc (300 mL). The aqueous layer was acidified to pH 5 with aqueous HCl solution (1 N) and the resulting precipitate was collected and dried to give the title compound. MS: m/z=289 (M+1). $^1$H NMR (400 MHz, DMSO-d$_6$) δ 13.85 (s, 1H), 8.11 (d, 1H), 7.82 (m, 2H), 6.45 (s, 1H), 3.92 (s, 3H).

The following intermediate was prepared in similar fashion to the procedure described above.

| Compound Number | Structure | Compound Name | LCMS (M + 1) |
|---|---|---|---|
| B2 | 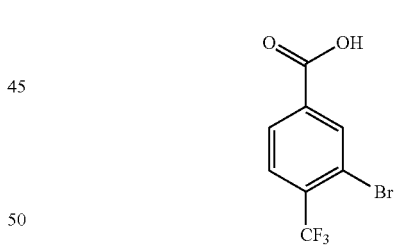 | 2-fluoro-5-(1H-pyrazol-3-yl)-4-(trifluoromethyl) benzoic acid | 275.5 |

Intermediate B3

3-Bromo-4-(trifluoromethyl)benzoic acid

Step A: Methyl 3-bromo-4-(trifluoromethyl)benzoate t-BuONO (79.0 g, 765 mmol) was added to a solution of methyl 3-amino-4-(trifluoromethyl)benzoate (67.0 g, 306 mmol) and CuBr (88.0 g, 612 mmol) in MeCN (1000 mL) at 0° C., and the resulting mixture was warmed to 25° C. and stirred for 12 h. The mixture was then poured into EtOAc (600 mL) and filtered. The filtrate was washed with an aqueous HCl solution (1 M, 200 mL×3), then brine (200 mL), dried over Na$_2$SO$_4$ and concentrated. The residue was purified by column chromatography on silica gel (PE:

EA=200:1) to give the title compound. MS: m/z=283, 285 (M+1). ¹H NMR (400 MHz, CDCl₃) δ 8.37 (s, 1H), 8.06 (d, J=8.0 Hz, 1H), 7.77 (d, J=8.0 Hz, 1H), 3.97 (s, 3H).

Step B: 3-Bromo-4-(trifluoromethyl)benzoic acid

A mixture of methyl 3-bromo-4-(trifluoromethyl)benzoate (5.0 g, 17.7 mmol) in aqueous NaOH solution (1 M, 100 mL) was stirred at 25° C. for 12 h. The mixture was acidified to pH 6 with aqueous HCl solution (1 M), and the resulting aqueous mixture was extracted with EtOAc (30 mL×3). The combined organic layers were dried over Na₂SO₄ and then concentrated to give the title compound. MS: m/z=270 (M+1). ¹H NMR (400 MHz, CDCl₃) δ 8.44 (s, 1H), 8.14 (d, J=8.0 Hz, 1H), 7.83 (d, J=8.0 Hz, 1H).

Reaction Scheme for Intermediate B4

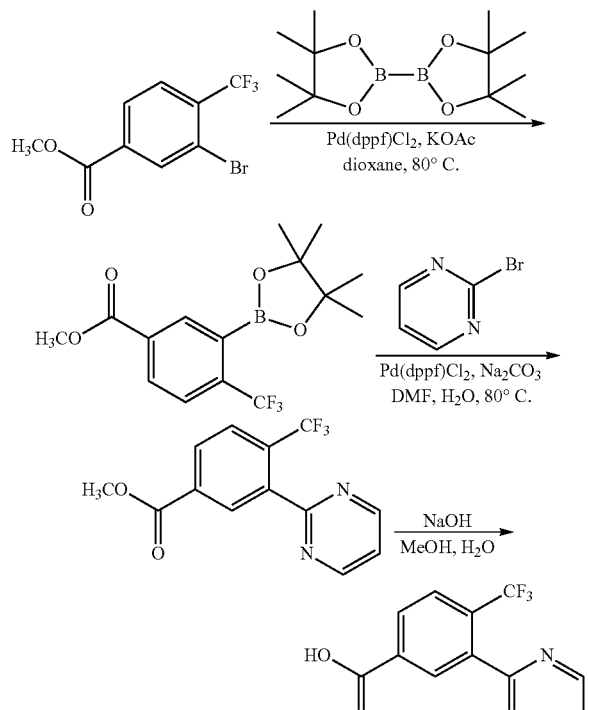

Intermediate B4

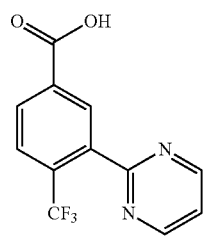 [SMILES: O=C(O)c1ccc(C(F)(F)F)c(-c2ncccn2)c1]

3-(Pyrimidin-2-yl)-4-(trifluoromethyl)benzoyl chloride

Step A: Methyl 3-(4,4,5,5-tetramethyl-1,3,2-dioxaborolan-2-yl)-4-(trifluoromethyl)benzoate To a deoxygenated mixture of methyl 3-bromo-4-(trifluoromethyl)benzoate (20.0 g, 70.7 mmol), 4,4,4',4',5,5,5',5'-octamethyl-2,2'-bi(1,3,2-dioxaborolane) (26.9 g, 106 mmol) and potassium acetate (20.8 g, 212 mmol) in dioxane (300 mL) was added PdCl₂(dppf) (2.59 g, 3.50 mmol), and the resulting mixture was heated at 80° C. for 5 h. The mixture was cooled and filtered. The filtrate was concentrated and the residue was partitioned between water (100 mL) and EtOAc (200 mL). The organic layer was washed with brine (100 mL), dried over Na₂SO₄ and concentrated. The residue was purified by column chromatography on silica gel (PE:EtOAc=15:1) to give the title compound. MS: m/z=331 (M+1).

Step B: Methyl 3-(pyrimidin-2-yl)-4-(trifluoromethyl)benzoate

To a deoxygenated mixture of methyl 3-(4,4,5,5-tetramethyl-1,3,2-dioxaborolan-2-yl)-4-(trifluoromethyl)benzoate (12.0 g, 36.4 mmol), 2-bromopyrimidine (8.67 g, 54.5 mmol) and sodium carbonate (11.6 g, 109 mmol) in DMF (450 mL) and water (60 mL) was added PdCl₂(dppf) (1.3 g, 1.8 mmol), and the resulting mixture was heated at 80° C. for 5 h. The mixture was cooled and filtered. The filtrate was concentrated and the residue was partitioned between water (100 mL) and EtOAc (200 mL). The combined organic layer was washed with brine (100 mL), dried over Na₂SO₄ and concentrated. The residue was purified by column chromatography on silica gel (PE:EtOAc=5:1) to give the title compound. MS: m/z=283 (M+1).

Step C: 3-(Pyrimidin-2-yl)-4-(trifluoromethyl)benzoic acid

A mixture of methyl 3-(pyrimidin-2-yl)-4-(trifluoromethyl)benzoate (7.0 g, 25 mmol) and NaOH (3.0 g, 74 mmol) in a 3:1 mixture of MeOH and H₂O (120 mL) was heated at 30° C. for 16 h. The reaction mixture was cooled and then partitioned between water (30 mL) and MTBE (2×60 mL). The aqueous layer was acidified to pH 4 with aqueous HCl solution (2 N). The precipitate was filtered, washed with water and dried to afford the title compound. MS: m/z=269 (M+1). ¹H NMR (400 MHz, CD₃OD) δ 8.92 (d, J=5.0 Hz, 1H), 8.30 (m, 2H), 7.97 (d, J=8.0 Hz, 1H), 7.55 (t, J=4.9 Hz, 1H).

The following intermediates were prepared in similar fashion to the procedure described above.

| Compound Number | Structure | Compound Name | LCMS (M + 1) |
|---|---|---|---|
| B5 | 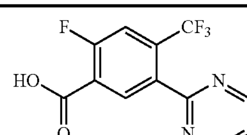 | 2-fluoro-5-(pyrimidin-2-yl)-4-(trifluoromethyl)benzoic acid | 301.1 |

-continued

| Compound Number | Structure | Compound Name | LCMS (M + 1) |
|---|---|---|---|
| B6 | 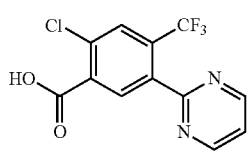 [SMILES: O=C(O)c1cc(-c2ncccn2)c(C(F)(F)F)cc1Cl] | 2-chloro-5-(pyrimidin-2-yl)-4-(trifluoromethyl)benzoic acid | 303.1 |
| B7 | 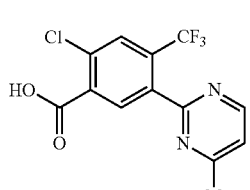 | 2-chloro-5-(4-methylpyrimidin-2-yl)-4-(trifluoromethyl)benzoic acid | 317.1 |

Reaction Scheme for Intermediate B8

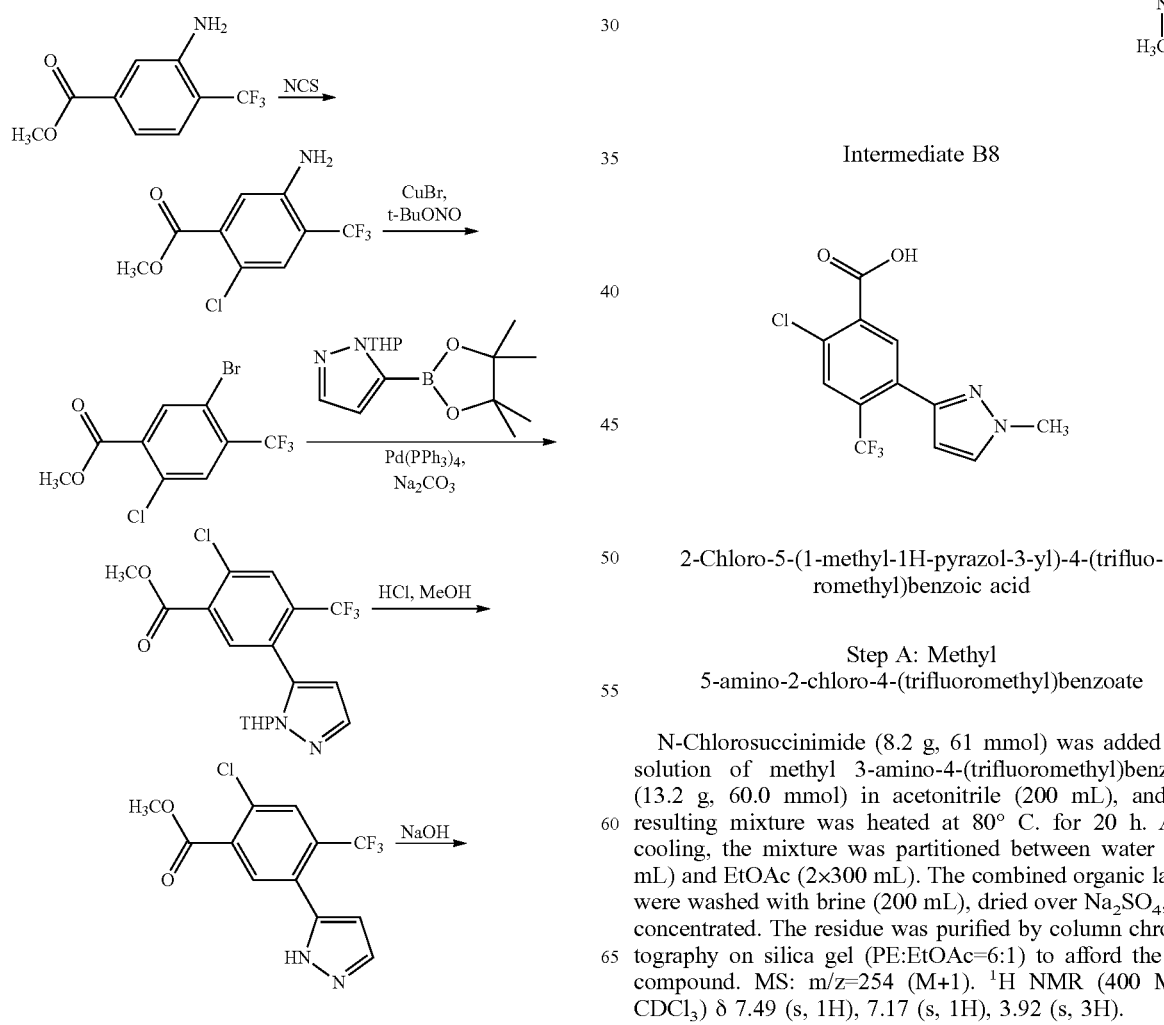

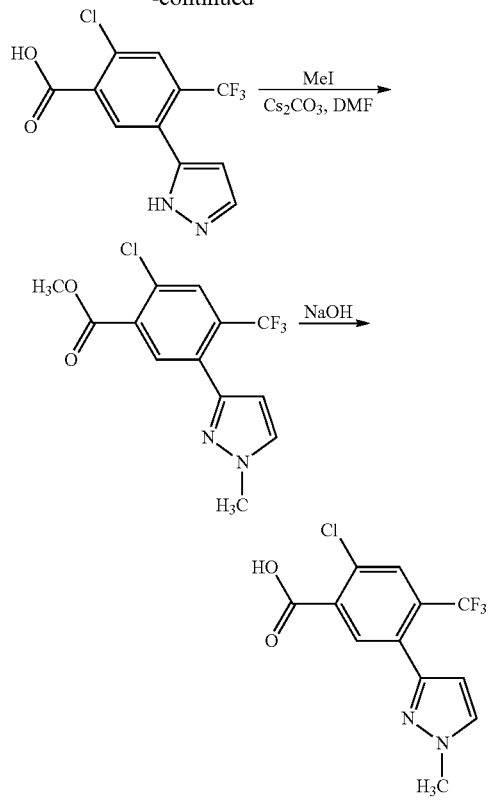

Intermediate B8

2-Chloro-5-(1-methyl-1H-pyrazol-3-yl)-4-(trifluoromethyl)benzoic acid

Step A: Methyl 5-amino-2-chloro-4-(trifluoromethyl)benzoate

N-Chlorosuccinimide (8.2 g, 61 mmol) was added to a solution of methyl 3-amino-4-(trifluoromethyl)benzoate (13.2 g, 60.0 mmol) in acetonitrile (200 mL), and the resulting mixture was heated at 80° C. for 20 h. After cooling, the mixture was partitioned between water (500 mL) and EtOAc (2×300 mL). The combined organic layers were washed with brine (200 mL), dried over $Na_2SO_4$, and concentrated. The residue was purified by column chromatography on silica gel (PE:EtOAc=6:1) to afford the title compound. MS: m/z=254 (M+1). $^1$H NMR (400 MHz, $CDCl_3$) δ 7.49 (s, 1H), 7.17 (s, 1H), 3.92 (s, 3H).

Step B: Methyl 5-bromo-2-chloro-4-(trifluoromethyl)benzoate t-Butyl nitrite (4.60 g, 44.5 mmol) and methyl 5-amino-2-chloro-4-(trifluoromethyl)benzoate (4.50 g, 17.8 mmol) were added portionwise to a suspension of copper(I) bromide (5.10 g, 35.6 mmol) in DCM (100 mL). The resulting mixture was heated at 60° C. for 2 h. After cooling, the mixture was diluted with water (50 mL) and aqueous HCl solution (2 M, 50 mL) and then extracted with EtOAc (80 mL×2). The combined organic layers were washed with water (100 mL), then brine (80 mL), dried over $Na_2SO_4$ and concentrated. The residue was purified by flash column chromatography on silica (PE:EtOAc from 50:1 to 30:1) to afford the title compound. MS: m/z=319 (M+1). $^1$H NMR (400 MHz, $CDCl_3$) δ 8.15 (s, 1H), 7.77 (s, 1H), 3.97 (s, 3H).

Step C: Methyl-2-chloro-5-(1-(tetrahydro-2H-pyran-2-yl)-1H-pyrazol-5-yl)-4-(trifluoromethyl)benzoate To a deoxygenated mixture of methyl 5-bromo-2-chloro-4-(trifluoromethyl)benzoate (4.6 g, 14 mmol), 1-(tetrahydro-2H-pyran-2-yl)-5-(4,4,5,5-tetramethyl-1,3,2-dioxaborolan-2-yl)-1H-pyrazole (4.86 g, 17.5 mmol) and $Na_2CO_3$ (4.0 g, 44 mmol) in DMF (150 mL) and $H_2O$ (24 mL) was added $Pd(PPh_3)_4$ (686 mg, 0.58 mmol). The resulting mixture was heated at 80° C. for 5 h, then cooled and filtered. The filtrate was concentrated and the residue was partitioned between water (200 mL) and EtOAc (300 mL). The organic layer was washed with brine (100 mL), dried over $Na_2SO_4$ and concentrated. The residue was purified by column chromatography on silica gel (PE/EtOAc=10/1) to give the title compound. MS: m/z=389 (M+1).

Step D: Methyl 2-chloro-5-(1H-pyrazol-5-yl)-4-(trifluoromethyl)benzoate

A solution of methyl-2-chloro-5-(1-(tetrahydro-2H-pyran-2-yl)-1H-pyrazol-5-yl)-4-(trifluoromethyl)benzoate (2.5 g, 6.4 mmol) in a solution of HCl in MeOH (4M, 50 mL) was stirred at 15° C. for 1 h and then concentrated to give the title compound. MS: m/z=305 (M+1).

Step E: 2-Chloro-5-(1H-pyrazol-5-yl)-4-(trifluoromethyl)benzoic acid

A solution of NaOH (1.2 g, 0.030 mol) in $H_2O$ (15 mL) was added to a solution of methyl 2-chloro-5-(1H-pyrazol-5-yl)-4-(trifluoromethyl)benzoate (2.3 g, 7.6 mmol) in MeOH (45 mL), and the resulting mixture was stirred at 15° C. for 16 h. The majority of the MeOH was removed under reduced pressure and the remaining aqueous mixture was partitioned between MTBE (50 mL) and water (50 mL). The aqueous layer was acidified to pH 5 with aqueous HCl solution (3 N). The precipitate was filtered, washed with water (50 mL×2) and dried to give the title compound. MS: m/z=291 (M+1).

Step F: Methyl 2-chloro-5-(1-methyl-1H-pyrazol-3-yl)-4-(trifluoromethyl)benzoate and methyl 2-chloro-5-(1-methyl-1H-pyrazol-5-yl)-4-(trifluoromethyl)benzoate A mixture of 2-chloro-5-(1H-pyrazol-5-yl)-4-(trifluoromethyl)benzoic acid (500 mg, 1.72 mmol), $Cs_2CO_3$ (1.7 g, 5.2 mmol) and iodomethane (0.54 mL, 8.6 mmol) in DMF (15 mL) was heated at 80° C. for 2 h. The reaction mixture was cooled and filtered, and the filtrate was concentrated. The residue was partitioned between water (50 mL) and EtOAc (30 mL×3). The combined organic layers were washed with $H_2O$ (50 mL×3), then brine (50 mL), dried over $Na_2SO_4$ and concentrated to give the title compound. MS: m/z=319 (M+1).

Step G: 2-Chloro-5-(1-methyl-1H-pyrazol-3-yl)-4-(trifluoromethyl)benzoic acid A solution of NaOH (414 mg, 10.4 mmol) in $H_2O$ (5 mL) was added to a mixture of methyl 2-chloro-5-(1-methyl-1H-pyrazol-3-yl)-4-(trifluoromethyl)benzoate and methyl 2-chloro-5-(1-methyl-1H-pyrazol-5-yl)-4-(trifluoromethyl)benzoate (550 mg, 3.5 mmol) in MeOH (15 mL). The resulting mixture was stirred at 15° C. for 16 h. The majority of the MeOH was removed under reduced pressure and the resulting aqueous solution was partitioned between MTBE (30 mL) and water (30 mL). The aqueous layer was acidified to pH 4 with an aqueous HCl solution (3 N). The resulting suspension was then extracted with EtOAc (50 mL×2). The combined organic layers were washed with brine (50 mL), dried over $Na_2SO_4$ and concentrated.

The residue was re-crystallized from MeOH (1 g/5 mL) to give the title compound. MS: m/z=305 (M+1). $^1$H NMR (400 MHz, $CDCl_3$) δ 8.36 (s, 1H), 7.86 (s, 1H), 7.48 (d, J=2.3 Hz, 1H), 6.59 (s, 1H), 4.15 (s, 3H).

The following intermediates were prepared in similar fashion using the corresponding tributylstannane reagent in the palladium catalyzed cross-coupling reaction.

| Compound Number | Structure | Compound Name | LCMS (M + 1) |
|---|---|---|---|
| B9 | Cl, CF3, HO, O, N (pyridine structure) | 2-chloro-5-(pyridin-2-yl)-4-(trifluoromethyl)benzoic acid | 302 |
| B10 | F, CF3, HO, O, N (pyridine structure) | 2-fluoro-5-(pyridin-2-yl)-4-(trifluoromethyl)benzoic acid | 286.0 |

Intermediate B11

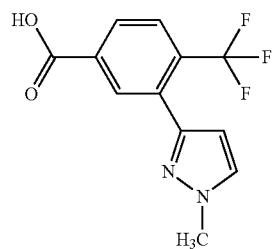 [SMILES: Cn1ccc(-c2cc(C(=O)O)ccc2C(F)(F)F)n1]

3-(1-Methyl-1H-pyrazol-3-yl)-4-(trifluoromethyl) benzoic acid

Step A: 4-Bromo-3-nitrobenzoic acid

4-Bromobenzoic acid (100 g, 0.5 mol) was added portionwise to aqueous $HNO_3$ solution (16 M, 200 mL), keeping the temperature between 0 and 25° C., followed by the dropwise addition of aqueous $H_2SO_4$ solution (18 M, 240 mL) at ambient temperature. The resulting mixture was stirred at ambient temperature for 4 h, and then carefully diluted with 1.5 L of water. The precipitate was filtered, washed with water, and dried to give the title compound. MS: m z=246.0, 248.0 (M+1). $^1$H NMR (400 MHz, DMSO) δ 8.42 (s, 1H), 8.04 (s, 2H).

Step B: Methyl 4-bromo-3-nitrobenzoate

To a solution of 4-bromo-3-nitrobenzoic acid (115 g, 47.0 mmol) in MeOH (600 mL) was added aqueous $H_2SO_4$ solution (18 M, 200 mL) at ambient temperature. The mixture was heated at reflux for 2 h, and then cooled and filtered. The filtered solid was washed with water and dried to give the title compound. MS: m z=260, 262 (M+1). $^1$H NMR (400 MHz, DMSO-$d_6$) δ 8.48 (s, 3H), 8.09 (s, 2H), 3.91 (s, 3H).

Step C: Methyl 3-nitro-4-(trifluoromethyl)benzoate

To a solution of methyl 4-bromo-3-nitrobenzoate (175 g, 0.670 mol) in anhydrous DMF (1.0 L) was added CuI (140 g, 0.73 mol) under $N_2$ atmosphere. After stirring at ambient temperature for 10 min, $FSO_2CF_2CO_2CH_3$ (185 mL, 0.730 mol) was added and the vented mixture was heated at 110° C. for 3 h until gas evolution ceased. The mixture was then cooled and filtered through Celite®, washing with EtOAc. The filtrate was concentrated and the residue was partitioned between water (400 mL) and MTBE. The organic layer was washed with water, then brine, dried over anhydrous $Na_2SO_4$ and concentrated. The residue was recrystallized from DCM/MeOH (5/1) to give the title compound. The mother liquor was concentrated and the residue purified by silica gel column chromatography (PE/EtOAc=20/1) to give additional title compound. MS: m z=250.0 (M+1). $^1$H NMR (400 MHz, DMSO-$d_6$) δ 8.55 (br s, 1H), 8.39 (d, J=7.5 Hz, 1H), 8.19 (d, J=8.0 Hz, 1H), 3.88-3.99 (m, 3H).

Step D: Methyl 3-amino-4-(trifluoromethyl)benzoate

A solution of methyl 3-nitro-4-(trifluoromethyl)benzoate (102 g, 0.410 mol) and 10% Pd/C (10 g, 10 wt %) in MeOH (1.0 L) was stirred under $H_2$ (35 psi) at 30° C. for 12 h. The suspension was filtered through Celite®, washing with MeOH (30 mL×3). The filtrate was concentrated to give the title compound. MS: m/z=220.0 (M+1). $^1$H NMR (400 MHz, DMSO-$d_6$) δ 7.40-7.50 (m, 2H), 7.09-7.15 (m, 1H), 5.92 (s, 2H), 3.82 (s, 3H).

Step E: Methyl 3-bromo-4-(trifluoromethyl)benzoate

Methyl 3-amino-4-(trifluoromethyl)benzoate (40 g, 180 mmol) was added portionwise to a suspension of CuBr (53.0 g, 365 mmol) and t-BuONO (47 g, 460 mmol) in acetonitrile (600 mL) at 0° C. The resulting mixture was stirred at 0° C. for 2 h, and then warmed to 25° C. and stirred for 16 h. The mixture was partitioned between EtOAc and aqueous HCl solution (1 M, 200 mL×4). The organic layer was washed with brine (200 mL), dried over $Na_2SO_4$ and concentrated. The residue was purified by column chromatography on silica gel (PE/EtOAc=200/1) to afford the title compound. MS: m/z=283, 285 (M+1). $^1$H NMR (400 MHz, $CDCl_3$) δ 8.37 (s, 1H), 8.06 (d, J=8.0 Hz, 1H), 7.77 (d, J=8.0 Hz, 1H), 3.97 (s, 3H).

Step F: Methyl 3-(1-(tetrahydro-2H-pyran-2-yl)-1H-pyrazol-5-yl)-4-(trifluoromethyl) benzoate A deoxygenated mixture of methyl 3-bromo-4-(trifluoromethyl)benzoate (5.0 g, 17 mmol), 1-(tetrahydro-2H-pyran-2-yl)-5-(4,4,5,5-tetramethyl-1,3,2-dioxaborolan-2-yl)-1H-pyrazole (5.9 g, 21 mmol), $Pd(PPh_3)_4$ (0.80 g, 0.69 mmol), and aqueous $Na_2CO_3$ solution (2 M, 26 mL, 53 mmol) in DMF (150 mL) was heated at 70° C. under $N_2$ for 2 h. The mixture was concentrated and the residue was partitioned between EtOAc (200 mL) and water (100 mL). The organic layer was washed with brine (100 mL), then dried over $Na_2SO_4$ and concentrated. The residue was purified by column chromatography on silica gel (PE/EtOAc=10/1) to give the title compound. MS: m/z=355.0 (M+1). $^1$H NMR (400 MHz, DMSO) δ 8.37 (s, 1H), 8.06 (d, J=8.0 Hz, 1H), 7.77 (d, J=8.0 Hz, 1H), 3.97 (s, 3H).

Step G: Methyl 3-(1H-pyrazol-5-yl)-4-(trifluoromethyl)benzoate

To a solution of methyl 3-(1-(tetrahydro-2H-pyran-2-yl)-1H-pyrazol-5-yl)-4-(trifluoromethyl)benzoate (5.0 g, 14 mmol) in MeOH (100 mL) was added a solution of HCl in MeOH (40 mL, 4 M). The mixture was stirred at 10° C. for 0.5 h then concentrated to give the title compound. MS: m/z=271.0 (M+1).

Step H: Methyl 3-(1-methyl-1H-pyrazol-3-yl)-4-(trifluoromethyl)benzoate and methyl 3-(1-methyl-1H-pyrazol-5-yl)-4-(trifluoromethyl)benzoate To a solution of methyl 3-(1H-pyrazol-5-yl)-4-(trifluoromethyl)benzoate (7.0 g, 26 mmol) in DMF (150 mL) was added $Cs_2CO_3$ (17 g, 52 mmol) and $CH_3I$ (4.8 mL, 78 mmol). The reaction mixture was heated at 80° C. for 2 h, then cooled and concentrated. The residue was partitioned between water (150 mL) and EtOAc (100 mL×3). The combined organic layers were washed with brine (150 mL), dried over $Na_2SO_4$ and concentrated to give a mixture of methyl 3-(1-methyl-1H-pyrazol-3-yl)-4-(trifluoromethyl)benzoate and methyl 3-(1-methyl-1H-pyrazol-5-yl)-4-(trifluoromethyl)benzoate. MS: m/z=285.0 (M+1).

Step I: 3-(1-Methyl-1H-pyrazol-3-yl)-4-(trifluoromethyl)benzoic acid

To a solution of methyl 3-(1-methyl-1H-pyrazol-3-yl)-4-(trifluoromethyl)benzoate and methyl 3-(1-methyl-1H-pyrazol-5-yl)-4-(trifluoromethyl)benzoate (6.5 g, 23 mmol) in MeOH (100 mL) was added aqueous NaOH solution (35 mL, 2 M). The mixture was heated at 50° C. for 50 min then cooled. The majority of the MeOH was removed under reduced pressure and the resulting aqueous solution was partitioned between EtOAc (100 mL) and water (150 mL). The aqueous layer was acidified to pH 5 with aqueous HCl solution (1 N) and then further extracted with EtOAc (150 mL×2). The combined organic layers were washed with brine (150 mL), dried over anhydrous $Na_2SO_4$ and concentrated. The residue was purified by recrystallization from MeOH (1 g/5 mL) to provide the title compound. MS: m/z=271.0 (M+1). $^1$H NMR (400 MHz, DMSO) δ 13.43-13.68 (m, 1H) 8.18-8.24 (m, 1H), 8.05-8.12 (m, 1H), 7.92-7.99 (m, 1H), 7.77-7.84 (m, 1H), 6.43-6.52 (m, 1H), 3.93 (s, 3H).

The following intermediate was prepared in similar fashion to the procedure described above.

| Compound Number | Structure | Compound Name | LCMS (M + 1) |
|---|---|---|---|
| B12 | 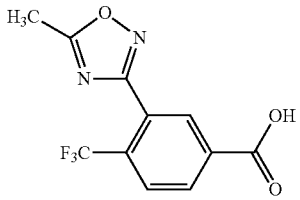 [SMILES: Cc1nc(-c2cc(C(=O)O)ccc2C(F)(F)F)no1] | 3-(1H-pyrazol-3-yl)-4-(trifluoromethyl) benzoic acid | 257.1 |

Intermediate B13

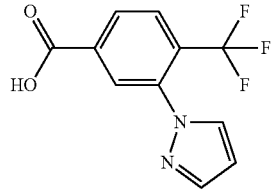 [SMILES: O=C(O)c1ccc(C(F)(F)F)c(-n2cccn2)c1]

3-(5-Methyl-1,2,4-oxadiazol-3-yl)-4-(trifluoromethyl)benzoic acid

Step A: Methyl 3-cyano-4-(trifluoromethyl)benzoate

To a mixture of methyl 3-amino-4-(trifluoromethyl)benzoate (15 g, 0.073 mol) and aqueous HCl solution (12 M, 24 mL) in $H_2O$ (100 mL) at 0° C. was added dropwise a solution of $NaNO_2$ (5.5 g, 0.080 mol) in $H_2O$ (30 mL). The reaction was stirred at 0° C. for 30 min and then added dropwise to a slurry of CuCN (7.1 g, 0.080 mol) and KCN (8.4 g, 0.13 mol) in $H_2O$ (200 mL), while maintaining the internal temperature between 5-10° C. After the addition was complete, the reaction was heated at 80° C. for 1 h. The mixture was cooled and the solution was extracted with EtOAc (200 mL×4). The combined organic layers were dried over anhydrous $Na_2SO_4$ and concentrated. The residue was purified by column chromatography on silica gel (2% EtOAc in PE) to afford the title compound. MS: m/z=230.0 (M+1). $^1$H NMR (400 MHz, $CDCl_3$) δ 8.46-8.53 (m, 1H), 8.33-8.42 (m, 1H), 7.87-7.95 (m, 1H), 4.01 (s, 3H).

Step B: Methyl 3-(N'-hydroxycarbamimidoyl)-4-(trifluoromethyl)benzoate

To a mixture of methyl 3-cyano-4-(trifluoromethyl)benzoate (1.6 g, 7.0 mmol) and hydroxylamine hydrochloride (0.98 g, 14 mmol) in MeOH (20 mL) was added $NaHCO_3$ (2.3 g, 28 mmol). The resulting mixture was heated at 85° C. for 5 h, then cooled and concentrated. The residue was purified by column chromatography on silica gel (40% EtOAc in PE) to afford the title compound. MS: m/z=263.0 (M+1). $^1$H NMR (400 MHz, $CDCl_3$) δ 8.26 (s, 1H), 8.18-8.21 (d, J=8.4 Hz, 1H), 7.80-7.83 (d, J=8.0 Hz, 1H), 7.52 (s, 1H), 4.89 (s, 2H), 3.96 (s, 3H).

Step C: Methyl 3-(N-acetyl-N'-hydroxycarbamimidoyl)-4-(trifluoromethyl) benzoate To a solution of methyl 3-(N'-hydroxycarbamimidoyl)-4-(trifluoromethyl) benzoate (282 mg, 1.07 mmol) and TEA (0.30 mL, 2.14 mmol) in anhydrous DCM (20 mL) at 25° C. was added AcCl (0.083 mL, 1.18 mmol). The resulting mixture was heated at 30° C. for 20 min, then cooled and concentrated to give the title compound. MS: m/z=305.0 (M+1).

Step D: Methyl 3-(5-methyl-1,2,4-oxadiazol-3-yl)-4-(trifluoromethyl)benzoate

A solution of methyl 3-(N-acetyl-N'-hydroxycarbamimidoyl)-4-(trifluoromethyl) benzoate (0.28 g, 0.93 mmol) in toluene (10 mL) was heated at 110° C. for 2 h, then cooled and concentrated. The residue was purified by column chromatography on silica gel (30% EtOAc in PE) to afford the title compound. MS: m/z=287.0 (M+1). $^1$H NMR (400 MHz, $CDCl_3$) δ 8.37-8.49 (m, 1H), 8.22-8.32 (m, 1H), 7.87-7.99 (m, 1H), 3.96 (s, 3H), 2.70 (s, 3H).

Step E: 3-(5-Methyl-1,2,4-oxadiazol-3-yl)-4-(trifluoromethyl)benzoic acid

To a solution of methyl 3-(5-methyl-1,2,4-oxadiazol-3-yl)-4-(trifluoromethyl) benzoate (0.13 g, 0.45 mmol) in MeOH (2.0 mL) was added aqueous NaOH solution (2.0 mL, 1 M). The resulting mixture was heated at 50° C. for 1 h, and then cooled and acidified to pH 5 with aqueous HCl solution (1 M). The aqueous mixture was extracted with EtOAc (10 mL×3). The combined organic layers were dried over anhydrous $Na_2SO_4$ and concentrated to give the title compound. MS: m/z=273.0 (M+1). $^1$H NMR (400 MHz, $CDCl_3$) δ 8.47 (s, 1H), 8.27 (d, J=8.0 Hz, 1H), 7.91 (d, J=8.8 Hz, 1H), 2.69 (s, 3H).

Intermediate B14

3-(1H-Pyrazol-1-yl)-4-(trifluoromethyl)benzoic acid

Step A: Methyl 3-(1H-pyrazol-1-yl)-4-(trifluoromethyl)benzoate

A mixture of methyl 3-bromo-4-(trifluoromethyl)benzoate (0.50 g, 1.8 mmol), pyrazole (0.18 g, 2.6 mmol), $Cs_2CO_3$ (1.4 g, 4.4 mmol), CuI (670 mg, 3.52 mmol) and 1,10-phenanthroline (0.13 g, 0.70 mmol) in anhydrous toluene (15 mL) was heated at 140° C. for 1 h under microwave irradiation. After cooling, the reaction mixture was diluted with EtOAc (50 mL) and filtered. The filtrate was concentrated and the residue was purified by preparative TLC (PE/EA=5/1) to give the title compound. MS: m/z=271.0 (M+1).

Step B:
3-(1H-Pyrazol-1-yl)-4-(trifluoromethyl)benzoic acid

To a solution of methyl 3-(1H-pyrazol-1-yl)-4-(trifluoromethyl)benzoate (0.20 g, 0.74 mmol) in MeOH (15 mL) was added aqueous NaOH solution (3.0 mL, 2 M). The mixture was heated at 50° C. for 10 min. The majority of the MeOH was removed under reduced pressure and the resulting aqueous solution was partitioned between EtOAc (30 mL) and water (20 mL). The aqueous layer was acidified to pH 5 with aqueous HCl solution (1 M) and then extracted with EtOAc (30 mL×2). The combined organic layers were washed with brine (30 mL), dried over anhydrous Na$_2$SO$_4$ and concentrated to give the title compound. MS: m/z=257.0 (M+1). $^1$H NMR (400 MHz, DMSO) δ 8.19 (m, 1H), 8.13 (m, 1H), 8.07 (m, 1H), 7.97 (m, 1H), 7.78 (m, 1H), 6.55 (m, 1H).

Intermediate B15

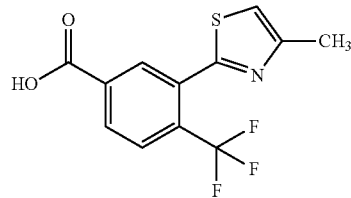 [SMILES: Cc1csc(-c2cc(C(=O)O)ccc2C(F)(F)F)n1]

3-(4-Methylthiazol-2-yl)-4-(trifluoromethyl)benzoic acid

Step A: 3-Amino-4-(trifluoromethyl)benzoic acid

A mixture of 3-nitro-4-(trifluoromethyl)benzoic acid (1.0 g, 4.3 mmol) and 10% Pd/C (0.20 g, 5% wt) in MeOH (20 mL) was stirred under H$_2$ atmosphere (15 psi) at ambient temperature for 12 h. The catalyst was filtered and the filtrate concentrated to afford the title compound. MS: m/z=206.0 (M+1). $^1$H NMR (400 MHz, DMSO) δ 7.46 (s, 1H), 7.38-7.45 (m, 1H), 7.13 (d, J=8.3 Hz, 1H), 5.84 (s, 2H).

Step B: Methyl 3-amino-4-(trifluoromethyl)benzoate

A mixture of 3-amino-4-(trifluoromethyl)benzoic acid (3.4 g, 16 mmol) and aqueous H$_2$SO$_4$ solution (18 M, 2.0 mL) in MeOH (20 mL) was heated at reflux until the starting material was consumed. The mixture was cooled then neutralized to pH 7 by the addition of aqueous NaOH solution (1N). The aqueous mixture was extracted with EtOAc (10 mL×3), and the combined organic layers were washed with brine, dried over Na$_2$SO$_4$ and concentrated to afford the title compound. MS: m/z=220.0 (M+1). $^1$H NMR (400 MHz, CDCl$_3$) δ 7.46-7.52 (m, 1H), 7.42 (s, 2H), 4.30 (br s, 2H), 3.92 (s, 3H).

Step C: Methyl 3-cyano-4-(trifluoromethyl)benzoate

To a mixture of methyl 3-amino-4-(trifluoromethyl)benzoate (3.2 g, 15 mmol) and aqueous HCl solution (12 M, 3.5 mL) in water (20 mL) was added dropwise a solution of NaNO$_2$ (1.2 g, 17 mmol) in water (7.0 mL) at 5° C. The resulting mixture was stirred for 30 min at 5° C. and then added dropwise to a slurry of CuCN (1.3 g, 15 mmol) and KCN (1.6 g, 25 mmol) in water (4 mL), while maintaining the internal temperature between 5-10° C. The mixture was stirred at 10° C. for 30 min and then heated at 80° C. for 1 h. After cooling, the mixture was extracted with DCM (30 mL×3). The combined organic layers were washed with brine, dried over Na$_2$SO$_4$ and concentrated to afford the title compound. MS: m/z=230 (M+1). $^1$H NMR (400 MHz, CDCl$_3$) δ 8.45-8.53 (m, 1H), 8.33-8.40 (m, 1H), 7.91 (d, 1H, J=8.5 Hz), 4.01 (s, 3H).

Step D: Methyl 3-carbamothioyl-4-(trifluoromethyl)benzoate

H$_2$S gas was bubbled through a solution of methyl 3-cyano-4-(trifluoromethyl)benzoate (0.10 g, 0.61 mmol) and TEA (0.20 mL, 1.4 mmol) in pyridine (10 mL) at ambient temperature for 30 min. The mixture was concentrated, and the residue was partitioned between water and EtOAc (10 mL×3). The combined organic layers were washed with brine, dried over Na$_2$SO$_4$ and concentrated. The residue was purified by column chromatography on silica gel (PE:EtOAc=5:1) to afford the title compound. MS: m/z=264.0 (M+1). $^1$H NMR (400 MHz, CDCl$_3$) δ 8.25-8.31 (m, 1H), 8.09-8.17 (m, 1H), 7.75 (d, J=8.0 Hz, 1H), 4.45-4.68 (m, 2H), 3.96 (s, 3H).

Step E: Methyl 3-(4-hydroxy-4,5-dihydrothiazol-2-yl)-4-(trifluoromethyl)benzoate A mixture of methyl 3-carbamothioyl-4-(trifluoromethyl)benzoate (100 mg, 0.38 mmol), TEA (0.20 mL, 1.4 mmol) and 1-chloropropan-2-one (0.033 mL, 0.42 mmol) in DMF (3.0 mL) was heated at 120° C. for 4 h, then concentrated. The residue was partitioned between water and EtOAc (10 mL×3). The combined organic layers were washed with brine, dried over Na$_2$SO$_4$ and concentrated. The residue was purified by column chromatography on silica gel (PE:EA=3:1) to afford the title compound. MS: m/z=320.0 (M+1).

Step F: 3-(4-Methylthiazol-2-yl)-4-(trifluoromethyl)benzoic acid

A solution of methyl 3-(4-hydroxy-4-methyl-4,5-dihydrothiazol-2-yl)-4-(trifluoromethyl)-benzoate in aqueous NaOH solution (1 M, 10 mL) was stirred at ambient temperature for 8 h. The mixture was acidified to pH 5 with aqueous HCl solution (1 M) then extracted with EtOAc (10 mL×3). The combined organic layers were washed with brine, dried over Na$_2$SO$_4$ and then concentrated to afford the title compound. MS: m/z=288.0 (M+1). $^1$H NMR (400 MHz, CDCl$_3$) δ 8.23-8.34 (m, 1H), 8.06-8.17 (m, 1H), 7.68-7.83 (m, 1H), 6.97-7.10 (m, 1H), 2.50 (s, 3H).

Intermediate B16

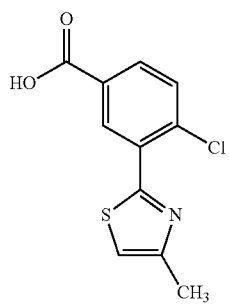

4-Chloro-3-(4-methylthiazol-2-yl)benzoic acid

Step A: Methyl 4-chloro-3-cyanobenzoate

To a mixture of methyl 3-amino-4-chlorobenzoate (10 g, 54 mmol) and aqueous HCl solution (12 M, 15 mL) in water (80 mL) at 0° C. was added dropwise a solution of NaNO$_2$ (4.5 g, 60 mmol) in water (18 mL) at 0° C. The reaction was stirred for 30 min at 0° C. and then added dropwise to a slurry of CuCN (4.9 g, 54 mmol) and KCN (6.0 g, 92 mmol) in water (40 mL), while maintaining the temperature between 5-10° C. The reaction mixture was stirred at 10° C. for 30 min and then heated at 80° C. for 1 h. After cooling, the mixture was extracted with DCM. The organic layer was washed with brine, dried over Na$_2$SO$_4$ and then concentrated to afford the title compound. MS: m/z=196.0 (M+1). $^1$H NMR (400 MHz, CDCl$_3$) δ 8.34 (d, J=2.0 Hz, 1H), 8.17-8.20 (m, 1H), 7.61 (d, J=8.4 Hz, 1H), 3.96 (s, 3H).

Step B: Methyl 3-carbamothioyl-4-chlorobenzoate

H$_2$S gas was bubbled through a solution of methyl 4-chloro-3-cyanobenzoate (3.0 g, 15 mmol) and TEA (2.13 mL, 15.3 mmol) in pyridine (15 mL) at ambient temperature for 1 h. The reaction mixture was concentrated and the residue was purified by column chromatography (PE:EtOAc=10:1) to give the title compound. MS: m/z=230.0 (M+1). $^1$H NMR (400 MHz, CDCl$_3$) δ 8.29 (d, J=1.6 Hz, 1H), 7.95-7.97 (m, 2H), 7.45 (d, J=8.4 Hz, 1H), 7.26 (s, 1H), 3.92 (s, 3H).

Step C: Methyl 4-chloro-3-(4-methylthiazol-2-yl)benzoate

A mixture of methyl 3-carbamothioyl-4-(trifluoromethyl) benzoate (1.0 g, 4.3 mmol), TEA (0.20 mL, 1.4 mmol) and 1-chloropropan-2-one (0.80 g, 8.6 mmol) in DMF (10 mL) was heated at 120° C. for 4 h, then concentrated. The residue was partitioned between water and EtOAc (10 mL×3). The combined organic layers were washed with brine, dried over Na$_2$SO$_4$ and concentrated. The residue was purified by column chromatography on silica gel (PE:EtOAc=3:1) to afford the title compound. MS: m/z=268.0 (M+1). $^1$H NMR (400 MHz, CDCl$_3$) δ 8.29 (d, J=2.0 Hz, 1H), 7.97-8.00 (m, 1H), 7.76 (d, J=8.0 Hz, 1H), 7.09 (s, 1H), 3.92 (s, 3H), 2.56 (s, 3H).

Step D: 4-Chloro-3-(4-methylthiazol-2-yl)benzoic acid

A mixture of methyl 4-chloro-3-(4-methylthiazol-2-yl) benzoate (0.40 g, 2.0 mmol) in aqueous NaOH solution (1M, 10 mL) was stirred at ambient temperature for 8 h. The mixture was acidified to pH 5 with aqueous HCl solution (2 M) and then extracted with EtOAc (10 mL×3). The combined organic layers were washed with brine, dried over Na$_2$SO$_4$ and then concentrated to afford the title compound. MS: m/z=254.0 (M+1).

Intermediate B17

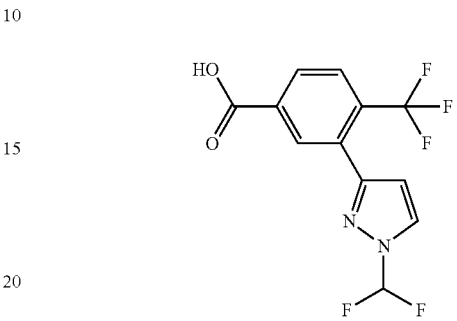

3-(1-(Difluoromethyl)-1H-pyrazol-3-yl)-4-(trifluoromethyl)benzoic acid

A solution of methyl 3-(1H-pyrazol-5-yl)-4-(trifluoromethyl)benzoate (50 mg, 0.18 mmol), sodium chlorodifluoroacetate (34 mg, 0.22 mmol), and 18-crown-6 (9.8 mg, 0.037 mmol) in acetonitrile (1 mL) was heated at reflux for 40 h. Additional sodium chlorodifluoroacetate (34 mg, 0.22 mmol) was added after 18 and 22 h. The reaction mixture was cooled to ambient temperature and aqueous NaOH solution (10M, 0.056 mL, 0.55 mmol) was added. The resulting mixture was heated at 50° C. for 2 h. The mixture was cooled and then filtered, washing with acetonitrile (1 mL) and DMF (1 mL). The filtrate was purified by reverse-phase HPLC (5-95% acetonitrile+0.1% trifluoroacetic acid in water) to provide the title compound. MS: m/z=307.0 (M+1).

Intermediate B18

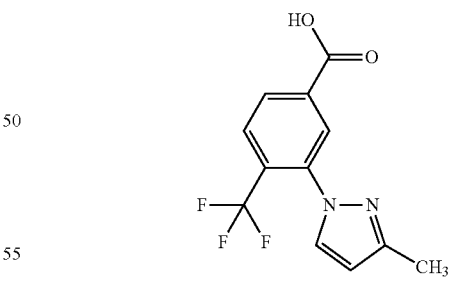

3-(3-Methyl-1H-pyrazol-1-yl)-4-(trifluoromethyl) benzoic acid

A deoxygenated solution of 3-methyl-1H-pyrazole (0.120 mL, 1.49 mmol), 3-bromo-4-(trifluoromethyl)benzoic acid (0.20 g, 0.74 mmol), copper(I) iodide (28 mg, 0.15 mmol), cesium carbonate (0.48 g, 1.5 mmol), and trans-N,N-dimethylcyclohexane-1,2-diamine (0.023 mL, 0.15 mmol) in dioxane (1.0 mL) was heated at reflux for 18 h. The mixture was cooled and filtered, washing with DMF (1.5 mL). The filtrate was purified by reverse-phase HPLC (5-95% acetonitrile+0.1% trifluoroacetic acid in water) to afford the title compound. MS: m/z=271.0 (M+1).

Intermediate B19

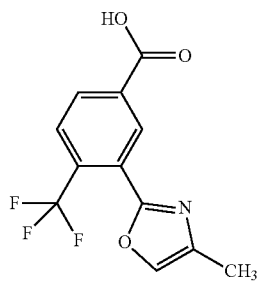 [SMILES: Cc1coc(-c2cc(C(=O)O)ccc2C(F)(F)F)n1]

3-(4-Methyloxazol-2-yl)-4-(trifluoromethyl)benzoic acid

A deoxygenated mixture of 3-bromo-4-(trifluoromethyl) benzoic acid (100 mg, 0.372 mmol), 4-methyloxazole (0.061 mL, 0.74 mmol), chloro(2-dicyclohexylphosphino-2',4',6'-tri-i-propyl-1,1'-biphenyl)[2-(2-aminoethyl)phenyl]palladium(II) methyl-t-butyl ether adduct (15.4 mg, 0.019 mmol), and sodium tert-butoxide (107 mg, 1.12 mmol) in DMA (1.5 mL) was heated under microwave irradiation at 110° C. for 18 h. The mixture was cooled and filtered, and the filtrate was purified by reverse-phase HPLC (C18 column, $H_2O$:$CH_3CN$:$CF_3CO_2H$=95:5:0.1 to 5:95:0.1) to give the title compound. MS: m/z=272.0 (M+1).

Intermediate B20

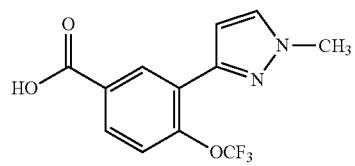 [SMILES: Cn1ccc(-c2cc(C(=O)O)ccc2OC(F)(F)F)n1]

3-(1-Methyl-1H-pyrazol-3-yl)-4-(trifluoromethoxy)benzoic acid

Step A: 3-Nitro-4-(trifluoromethoxy)benzoic acid 4-(Trifluoromethoxy)benzoic acid (37.4 g, 0.181 mol) was added portionwise to an aqueous $HNO_3$ solution (15 M, 75 mL) at 25° C. Aqueous $H_2SO_4$ solution (18 M, 90 mL) was added and the resulting mixture was stirred for 18 h. The reaction mixture was carefully diluted with water (300 mL) and the precipitate was filtered, washed with water, and dried to give the title compound. MS: m/z=252 (M+1). $^1$H NMR (400 MHz, DMSO-$d_6$) δ 8.54 (s, 1H), 8.32 (d, J=8.0 Hz, 1H), 7.82 (d, J=8.0 Hz, 1H).

Step B: Methyl 3-nitro-4-(trifluoromethoxy)benzoate

Aqueous $H_2SO_4$ solution (18 M, 60 mL) was added dropwise to a solution of 3-nitro-4-(trifluoromethoxy)benzoic acid (33.5 g, 0.135 mol) in MeOH (400 mL) at 0° C. The resulting mixture was heated at 80° C. for 2 h, then cooled and concentrated. The residue was diluted with EtOAc, and washed with water (100 mL×3), aqueous $NaHCO_3$ solution (100 mL×3), and brine. The organic layer was dried over $Na_2SO_4$ and concentrated to give the title compound. MS: m/z: 266 (M+1). $^1$H NMR (400 MHz, DMSO-$d_6$) δ 8.54 (s, 1H), 8.32 (d, J=8.0 Hz, 1H), 7.82 (d, J=8.0 Hz, 1H), 3.90 (s, 3H).

Step C: Methyl 3-amino-4-(trifluoromethoxy)benzoate

A mixture of methyl 3-nitro-4-(trifluoromethoxy)benzoate (14 g, 0.053 mol) and 10% Pd/C (1.0 g, 10 wt %) in MeOH (200 mL) was stirred under $H_2$ (50 psi) at 15° C. for 24 h. The suspension was filtered and the filtrate was concentrated. The residue was purified by column chromatography on silica gel (PE:EtOAc=5:1) to give the title compound. MS: m/z 236 (M+1). $^1$H NMR (400 MHz, DMSO-$d_6$) δ 7.47 (d, J=2.0 Hz, 1H), 7.19-7.25 (m, 1H), 7.11-7.17 (m, 1H), 5.71 (s, 2H), 3.82 (s, 3H).

Step D: Methyl 3-bromo-4-(trifluoromethoxy)benzoate

A mixture of CuBr (5.0 g, 34 mmol) and t-BuONO (5.0 g, 43 mmol) in MeCN (60 mL) was stirred at 0° C. for 15 min, and then methyl 3-amino-4-(trifluoromethoxy)benzoate (4.0 g, 17 mmol) was added. The resulting mixture was stirred at 0° C. for 2 h, and then stirred at 15° C. for 16 h. The mixture was filtered and the filter cake was washed with EtOAc. The filtrate was washed with aqueous HCl solution (1N), water, and then brine. The organic layer was dried over $Na_2SO_4$ and concentrated. The residue was purified by column chromatography on silica gel (PE:EtOAc=20:1) to give the title compound. MS: m/z=298/300 (M+1). $^1$H NMR (400 MHz, DMSO-$d_6$) δ 8.14 (d, J=2.0 Hz, 1H), 7.96 (dd, J=8.7, 1.9 Hz, 1H), 7.55 (dd, J=8.7, 1.1 Hz, 1H), 3.84 (s, 3H).

Step E: Methyl 3-(1-(tetrahydro-2H-pyran-2-yl)-1H-pyrazol-5-yl)-4-(trifluoro-methoxy)benzoate A deoxygenated mixture of methyl 3-bromo-4-(trifluoromethoxy)benzoate (500 mg, 1.67 mmol), 1-(tetrahydro-2H-pyran-2-yl)-5-(4,4,5,5-tetramethyl-1,3,2-dioxaborolan-2-yl)-1H-pyrazole (510 mg, 1.84 mmol), Pd(PPh$_3$)$_4$(50 mg, 0.05 mmol), and $Na_2CO_3$ (530 mg, 5.0 mmol) in DMF (5 mL) was heated at 100° C. under $N_2$ atmosphere for 16 h. The reaction mixture was cooled and then partitioned between water (15 mL) and EtOAc (15 mL×3). The combined organic layers were dried over $Na_2SO_4$ and concentrated. The residue was purified by preparative TLC (PE:EtOAc=3:1) to give the title compound. MS: m/z=371 (M+1).

Step F: Methyl 3-(1H-pyrazol-5-yl)-4-(trifluoromethoxy)benzoate

A solution of HCl in EtOAc (4 M, 10 mL, 40 mmol) was added to a solution of methyl 3-(1-(tetrahydro-2H-pyran-2-yl)-1H-pyrazol-5-yl)-4-(trifluoromethoxy)benzoate (300 mg, 1.1 mmol) in EtOAc (2 mL). The resulting mixture was stirred at 15° C. for 1 h and then concentrated to give the title compound. MS: m/z=287 (M+1).

Step G: Methyl 3-(1-methyl-1H-pyrazol-3-yl)-4-(trifluoromethoxy)benzoate

A mixture of methyl 3-(1H-pyrazol-5-yl)-4-(trifluoromethoxy)benzoate (220 mg, 0.81 mmol), CH$_3$I (0.292 mL, 4.00 mmol), and Cs$_2$CO$_3$ (780 mg, 2.4 mmol) in DMF (5 mL) was heated at 70° C. for 1 h. The mixture was cooled and then partitioned between water (10 mL) and EtOAc (10 mL×2). The combined organic layers were dried over Na$_2$SO$_4$ and concentrated. The residue was purified by preparative TLC (PE:EtOAc=2:1) to give the title compound. MS: m/z=301 (M+1).

Step H: 3-(1-Methyl-1H-pyrazol-3-yl)-4-(trifluoromethoxy)benzoic acid

A mixture of methyl 3-(1-methyl-1H-pyrazol-3-yl)-4-(trifluoromethoxy)benzoate (120 mg, 0.4 mmol) and aqueous NaOH solution (2M, 10 mmol, 5 mL) was heated at 50° C. for 30 min. The reaction mixture was cooled, acidified to pH 5 with aqueous HCl solution (1M), and then extracted with EtOAc (10 mL×2). The combined organic layers were dried over Na$_2$SO$_4$ and concentrated to give the title compound. MS: m/z=287 (M+1).

Example 1

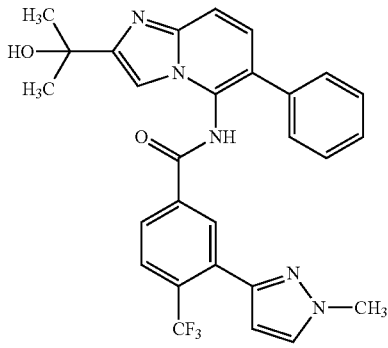 [SMILES: Cn1ccc(-c2cc(C(=O)Nc3c(-c4ccccc4)ccc4nc(C(C)(C)O)cn34)ccc2C(F)(F)F)n1]

N-(2-(2-Hydroxypropan-2-yl)-6-phenylimidazo[1,2-a]pyridin-5-yl)-3-(1-methyl-1H-pyrazol-3-yl)-4-(trifluoromethyl)benzamide

Step A: Ethyl 5-(3-(1-methyl-1H-pyrazol-3-yl)-4-(trifluoromethyl)benzamido)-6-phenylimidazo[1,2-a]pyridine-2-carboxylate To a solution of 3-(1-methyl-1H-pyrazol-3-yl)-4-(trifluoromethyl)benzoic acid (230 mg, 0.85 mmol) and ethyl 5-amino-6-phenylimidazo[1,2-a]pyridine-2-carboxylate (265 mg, 0.94 mmol) in pyridine (15 mL) at 20° C. was added POCl$_3$ (0.24 mL, 2.61 mmol), and the resulting mixture was stirred for 2 h. The product mixture was partitioned between saturated aqueous NaHCO$_3$ solution (10 mL) and EtOAc (30 mL×3). The combined organic phases were dried over Na$_2$SO$_4$ and concentrated. The residue was purified by preparative TLC (PE/EtOAc=1/3) to give the title compound. MS: m/z=534.2 (M+1). $^1$H NMR (400 MHz, CDCl$_3$) δ 9.15 (br., 1H), 8.17 (s, 1H), 7.82-7.92 (m, 2H), 7.57-7.75 (m, 2H), 7.22-7.35 (m, 7H), 6.36-6.44 (m, 1H), 4.34 (q, J=7.0 Hz, 2H), 3.64 (s, 3H), 1.31 (t, J=7.0 Hz, 3H).

Step B: N-(2-(2-Hydroxypropan-2-yl)-6-phenylimidazo[1,2-a]pyridin-5-yl)-3-(1-methyl-1H-pyrazol-3-yl)-4-(trifluoromethyl)benzamide To a solution of ethyl 5-(3-(1-methyl-1H-pyrazol-3-yl)-4-(trifluoromethyl)benzamido)-6-phenylimidazo[1,2-a]pyridine-2-carboxylate (60 mg, 0.11 mmol) in THF (4 mL) at 0° C. was added a solution of methyl magnesium bromide in diethyl ether (1.5 mL, 4.5 mmol, 3M). The resulting mixture was warmed to 23° C. and stirred for 30 min. The mixture was diluted with saturated aqueous NH$_4$Cl solution (5 mL) and EtOAc (5 mL×3). The combined organic layers were dried over Na$_2$SO$_4$ and concentrated. The residue was purified by reverse-phase HPLC under acidic conditions (H$_2$O/CH$_3$CN gradient with 0.1% NH$_4$OH present) to give the title compound. MS: m/z=520.2 (M+1). $^1$H NMR (400 MHz, CD$_3$OD) δ 8.13 (s, 2H), 8.04 (t, J 9.8 Hz, 2H), 7.93 (d, J=9.0 Hz, 2H), 7.67 (d, J=2.0 Hz, 1H), 7.39-7.50 (m, 5H), 6.47 (s, 1H), 3.95 (s, 3H), 1.67 (s, 6H).

Example 2

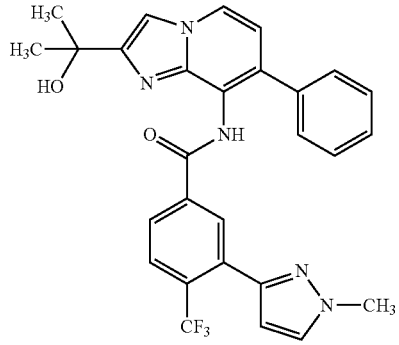 [SMILES: Cn1ccc(-c2cc(C(=O)Nc3c(-c4ccccc4)ccn4cc(C(C)(C)O)nc34)ccc2C(F)(F)F)n1]

N-(2-(2-Hydroxypropan-2-yl)-7-phenylimidazo[1,2-a]pyridin-8-yl)-3-(1-methyl-1H-pyrazol-3-yl)-4-(trifluoromethyl)benzamide

Step A: Ethyl 8-(3-(1-methyl-1H-pyrazol-3-yl)-4-(trifluoromethyl)-benzamido)-7-phenylimidazo[1,2-a]pyridine-2-carboxylate To a solution of 3-(1-methyl-1H-pyrazol-3-yl)-4-(trifluoromethyl)benzoic acid (192 mg, 0.71 mmol) and ethyl 8-amino-7-phenylimidazo[1,2-a]pyridine-2-carboxylate (200 mg, 0.71 mmol) in pyridine (4 mL) at 20° C. was added phosphoryl trichloride (0.66 mL, 0.71 mmol). The resulting mixture was stirred at 20° C. for 10 min, then partitioned between water (10 mL) and EtOAc (20 mL×3). The organic layer was dried over Na$_2$SO$_4$ and concentrated. The residue was purified by preparative TLC (PE/EtOAc=3/1) to give the title compound. MS: m/z=534.2 (M+1). $^1$H NMR (400 MHz, CD$_3$OD) δ 8.47 (s, 1H), 8.12 (d, J=6.3 Hz, 1H), 8.01 (d, J=7.4 Hz, 1H), 7.83 (d, J=8.2 Hz, 1H), 7.60-7.67 (m, 2H), 7.53 (d, J=7.0 Hz, 2H), 7.34-7.42 (m, 3H), 7.09 (d, J=7.0 Hz, 1H), 6.43 (s, 1H), 4.37 (q, J=7.0 Hz, 2H), 3.93 (s, 3H), 1.37 (t, J=7.0 Hz, 3H).

Step B: N-(2-(2-Hydroxypropan-2-yl)-7-phenylimidazo[1,2-a]pyridin-8-yl)-3-(1-methyl-1H-pyrazol-3-yl)-4-(trifluoromethyl)benzamide To a solution of ethyl 8-(3-(1-methyl-1H-pyrazol-3-yl)-4-(trifluoromethyl) benzamide)-7-phenylimidazo[1,2-a]

pyridine-2-carboxylate (100 mg, 0.19 mmol) in tetrahydrofuran (5 mL) at 0° C. was added a solution of methylmagnesium bromide in diethyl ether (0.16 mL, 0.47 mmol, 3M) under nitrogen atmosphere. The resulting mixture was stirred at 20° C. for 10 min, then partitioned between water (10 mL) and EtOAc (20 mL×3). The combined organic layers were dried over $Na_2SO_4$ and concentrated. The residue was purified by reverse-phase HPLC to give the title compound. MS: m/z=520.2 (M+1). $^1$H NMR (400 MHz, $CD_3OD$) δ 8.41 (d, J=7.0 Hz, 1H), 8.09 (s, 1H), 7.99 (d, J=7.8 Hz, 1H), 7.86 (d, J=7.8 Hz, 1H), 7.80 (s, 1H), 7.63 (d, J=2.0 Hz, 1H), 7.50 (d, J=7.4 Hz, 2H), 7.36 (t, J=7.2 Hz, 2H), 7.26-7.31 (m, 1H), 6.95 (d, J=7.0 Hz, 1H), 6.44 (s, 1H), 3.93 (s, 3H), 1.60 (s, 6H).

Example 3

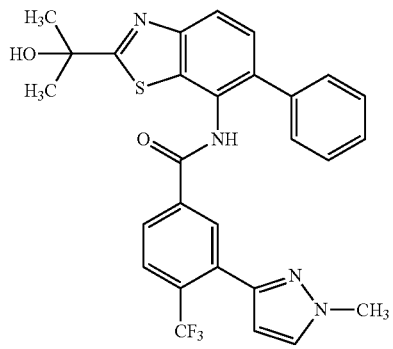 [SMILES: Cn1ccc(-c2cc(C(=O)Nc3c(-c4ccccc4)ccc4nc(C(C)(C)O)sc34)ccc2C(F)(F)F)n1]

N-(2-(2-Hydroxypropan-2-yl)-6-phenylbenzo[d]thiazol-7-yl)-3-(1-methyl-1H-pyrazol-3-yl)-4-(trifluoromethyl)benzamide Step A: N-(2-(1-Ethoxyvinyl)-6-phenylbenzo[d]thiazol-7-yl)-3-(1-methyl-1H-pyrazol-3-yl)-4-(trifluoromethyl)benzamide To a stirred solution of 2-(1-ethoxyvinyl)-6-phenylbenzo[d]thiazol-7-amine (35 mg, 0.12 mmol) and 3-(1-methyl-1H-pyrazol-3-yl)-4-(trifluoromethyl)benzoic acid (32 mg, 0.12 mmol) in pyridine (2 mL) at 15° C. was added phosphoryl trichloride (0.011 mL, 0.12 mmol). The resulting mixture was stirred for 5 min, then partitioned between water (8 mL) and EtOAc (10 mL×3). The combined organic layers were dried over $Na_2SO_4$ and concentrated. The residue was purified by preparative TLC (PE:EtOAc=1:1) to give the title compound. MS: m/z=549.2 (M+1). $^1$H NMR (400 MHz, $CDCl_3$) δ 8.11 (d, J=8.5 Hz, 2H), 7.98 (s, 1H), 7.89 (s, 2H), 7.57 (d, J=8.5 Hz, 1H), 7.39-7.54 (m, 5H), 6.56 (s, 1H), 5.57 (d, J=2.5 Hz, 1H), 4.58 (d, J=2.5 Hz, 1H), 4.10 (q, J=6.9 Hz, 2H), 4.03 (s, 3H), 1.52 (t, J=7.0 Hz, 3H).

Step B: N-(2-Acetyl-6-phenylbenzo[d]thiazol-7-yl)-3-(1-methyl-1H-pyrazol-3-yl)-4-(trifluoromethyl)benzamide To a stirred solution of N-(2-(1-ethoxyvinyl)-6-phenylbenzo[d]thiazol-7-yl)-3-(1-methyl-1H-pyrazol-3-yl)-4-(trifluoromethyl)benzamide (53 mg, 0.097 mmol) in tetrahydrofuran (3 mL) was added concentrated aqueous hydrochloric acid solution (0.2 mL, 2.4 mmol), and the resulting mixture was stirred at 15° C. for 1 h. The mixture was basified to pH 8 with saturated aqueous sodium dicarbonate solution and extracted with EtOAc (10 mL×3). The combined organic layers were dried over $Na_2SO_4$ and concentrated to give the title compound. MS: m/z=521.2 (M+1). $^1$H NMR (400 MHz, $CDCl_3$) δ 8.13 (d, J=8.6 Hz, 1H), 7.97 (s, 1H), 7.88 (s, 1H), 7.76 (s, 2H), 7.55 (d, J=8.2 Hz, 1H), 7.29-7.46 (m, 6H), 6.43 (s, 1H), 3.90 (s, 3H), 2.77 (s, 3H).

Step C: N-(2-(2-hydroxypropan-2-yl)-6-phenylbenzo[d]thiazol-7-yl)-3-(1-methyl-1H-pyrazol-3-yl)-4-(trifluoromethyl)benzamide To a stirred solution of N-(2-acetyl-6-phenylbenzo[d]thiazol-7-yl)-3-(1-methyl-1H-pyrazol-3-yl)-4-(trifluoromethyl)benzamide (60 mg, 0.12 mmol) in anhydrous tetrahydrofuran (2 mL) was added dropwise a solution of methylmagnesium bromide in diethyl ether (0.2 mL, 0.6 mmol, 3M) at 0° C. The resulting mixture was stirred at 0° C. for 1 h, then partitioned between saturated aqueous ammonium chloride (5 mL) and EtOAc (10 mL×3). The combined organic layers were dried over $Na_2SO_4$ and concentrated. The residue was purified by reverse-phase HPLC under acidic conditions ($H_2O/CH_3CN$ gradient with 0.1% TFA present) to afford the title compound. MS: m/z=537.1 (M+1). $^1$H NMR (400 MHz, $CD_3OD$) δ 8.01 (s, 1H), 7.97 (d, J=8.4 Hz, 1H), 7.89-7.91 (m, 2H), 7.65 (d, J=2.0 Hz, 1H), 7.58 (d, J=8.4 Hz, 1H), 7.46 (d, J=7.2 Hz, 2H), 7.38 (t, J=7.6 Hz, 2H) 7.28-7.33 (m, 1H), 6.45 (s, 1H), 3.94 (s, 3H), 1.68 (s, 6H).

Example 4

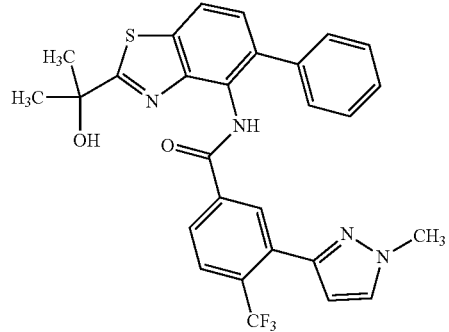 [SMILES: Cn1ccc(-c2cc(C(=O)Nc3c(-c4ccccc4)ccc4sc(C(C)(C)O)nc34)ccc2C(F)(F)F)n1]

N-(2-(2-Hydroxypropan-2-yl)-5-phenylbenzo[d]thiazol-4-yl)-3-(1-methyl-1H-pyrazol-3-yl)-4-(trifluoromethyl)benzamide To a solution of 3-(1-methyl-1H-pyrazol-3-yl)-4-(trifluoromethyl)benzoic acid (170 mg, 0.63 mmol) and 2-(4-amino-5-phenylbenzo[d]thiazol-2-yl)propan-2-ol (90 mg, 0.32 mmol) in pyridine (5 mL) at 20° C. was added phosphoryl trichloride (0.024 mL, 0.32 mmol) under nitrogen atmosphere. The resulting mixture was stirred at 20° C. for 10 min, then partitioned between water (10 mL) and EtOAc (20 mL×3). The combined organic layers were dried over $Na_2SO_4$ and concentrated. The residue was purified by reverse-phase HPLC to give the title compound. MS: m/z=537.1 (M+1). $^1$H NMR (400 MHz, $CD_3OD$) δ 7.97-8.09 (m, 2H), 7.92 (s, 1H), 7.85 (d, J=7.8 Hz, 1H), 7.64 (d, J=2.0 Hz, 1H), 7.41-7.53 (m, 3H), 7.35 (t, J=7.6 Hz, 2H), 7.23-7.30 (m, 1H), 6.44 (s, 1H), 3.94 (s, 3H), 1.64 (s, 6H).

Examples 5 and 6

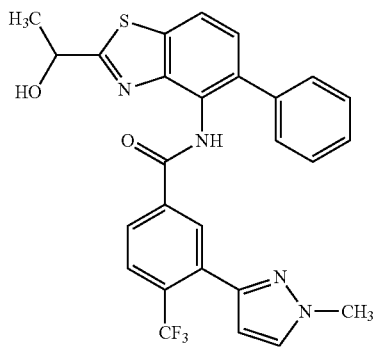 [SMILES: CC(O)c1nc2c(NC(=O)c3ccc(C(F)(F)F)c(-c4ccn(C)n4)c3)c(-c3ccccc3)ccc2s1]

(R and S)—N-(2-(1-Hydroxyethyl)-5-phenylbenzo[d]thiazol-4-yl)-3-(1-methyl-1H-pyrazol-3-yl)-4-(trifluoromethyl)benzamide Step A: N-(2-(1-((tert-Butyldimethylsilyl)oxy)ethyl)-5-phenylbenzo[d]thiazol-4-yl)-3-(1-methyl-1H-pyrazol-3-yl)-4-(trifluoromethyl)benzamide To a solution of 3-(1-methyl-1H-pyrazol-3-yl)-4-(trifluoromethyl)benzoic acid (84 mg, 0.31 mmol) and 2-(1-((tert-butyldimethylsilyl)oxy)ethyl)-5-phenylbenzo[d]thiazol-4-amine (120 mg, 0.31 mmol) in pyridine (5 mL) at 20° C. was added phosphoryl trichloride (0.06 mL, 0.62 mmol). The resulting mixture was stirred for 10 min, then partitioned between water (20 mL) and EtOAc (20 mL×3). The combined organic layers were dried over Na$_2$SO$_4$ and concentrated. The residue was purified by preparative TLC (PE/EtOAc=1/1) to give the title compound. MS: m/z=637.2 (M+1). $^1$H NMR (400 MHz, CD$_3$OD) δ 8.40 (d, J=4.3 Hz, 1H), 7.91 (d, J=8.2 Hz, 2H), 7.60-7.80 (m, 2H), 7.48-7.56 (m, 1H), 7.36 (d, J=8.2 Hz, 2H), 7.28-7.33 (m, 1H), 7.22-7.26 (m, 1H), 7.10-7.19 (m, 1H), 6.27-6.37 (m, 1H), 5.15 (q, J=6.3 Hz, 1H), 3.75-3.87 (m, 3H), 1.46 (d, J=6.3 Hz, 3H), 0.62-1.10 (m, 9H), 0.02 (d, J=14.9 Hz, 6H).

Step B: (R and S)—N-(2-(1-Hydroxyethyl)-5-phenylbenzo[d]thiazol-4-yl)-3-(1-methyl-1H-pyrazol-3-yl)-4-(trifluoromethyl)benzamide To a solution of N-(2-(1-((tert-butyldimethylsilyl)oxy)ethyl)-5-phenylbenzo[d]-thiazol-4-yl)-3-(1-methyl-1H-pyrazol-3-yl)-4-(trifluoromethyl)benzamide (80 mg, 0.13 mmol) in dioxane (5 mL) was added a solution of HCl in dioxane (4 M, 5 mL). The resulting mixture was stirred at 20° C. for 30 min, then concentrated. The residue was purified by reverse-phase HPLC, followed by SFC (250 mm×30 mm, 5 um, AD column) eluting with 40% EtOH (0.1% NH$_3$.H$_2$O), at 50 mL/min to give the title compounds. Enantiomer 1, Example 5: MS: m/z=523.2 (M+1). $^1$H NMR (400 MHz, CD$_3$OD) δ 8.06 (s, 1H), 7.89-8.01 (m, 2H), 7.83 (d, J=8.2 Hz, 1H), 7.61 (d, J=2.0 Hz, 1H), 7.39-7.51 (m, 3H), 7.33 (t, J=7.2 Hz, 2H), 7.20-7.29 (m, 1H), 6.42 (s, 1H), 5.13 (q, J=6.7 Hz, 1H), 3.90 (s, 3H), 1.58 (d, J=6.3 Hz, 3H). Enantiomer 2, Example 6: MS: m/z=523.2 (M+1). $^1$H NMR (400 MHz, CD$_3$OD) δ 8.05 (s, 1H), 7.89-8.02 (m, 2H), 7.83 (d, J=7.8 Hz, 1H), 7.62 (d, J=2.0 Hz, 1H), 7.39-7.52 (m, 3H), 7.34 (t, J=7.4 Hz, 2H), 7.21-7.30 (m, 1H), 6.43 (s, 1H), 5.13 (q, J=6.5 Hz, 1H), 3.91 (s, 3H), 1.58 (d, J=6.7 Hz, 3H).

Example 7

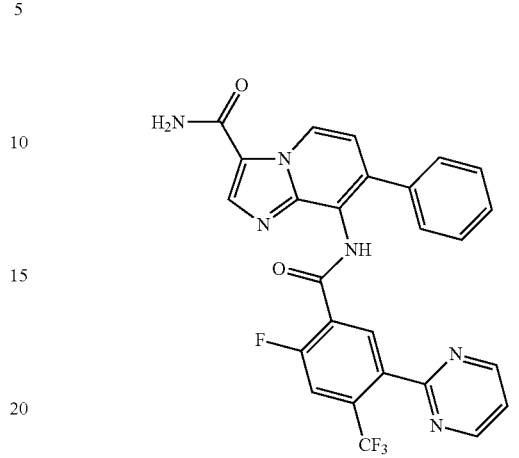

8-(2-Fluoro-5-(pyrimidin-2-yl)-4-(trifluoromethyl)benzamido)-7-phenylimidazo[1,2-a]pyridine-3-carboxamide Step A: Ethyl 8-(2-fluoro-5-(pyrimidin-2-yl)-4-(trifluoromethyl)benzamido)-7-phenylimidazo[1,2-a]pyridine-3-carboxylate To a solution of 2-fluoro-5-(pyrimidin-2-yl)-4-(trifluoromethyl)benzoic acid (112 mg, 0.39 mmol) in pyridine (5 mL) at 20° C. was added POCl$_3$ (0.04 mL, 0.43 mmol). The mixture was stirred for 5 min before ethyl 8-amino-7-phenylimidazo[1,2-a]pyridine-3-carboxylate (100 mg, 0.36 mmol) was added. The resulting mixture was stirred at 20° C. for 20 min, then partitioned between water (5 mL) and EtOAc (10 mL×3). The combined organic layers were washed with brine (10 mL), dried over Na$_2$SO$_4$ and concentrated to give the title compound. MS: m/z=550.1 (M+1).

Step B: 8-(2-Fluoro-5-(pyrimidin-2-yl)-4-(trifluoromethyl)benzamido)-7-phenlimidazo[1,2-a]pyridine-3-carboxylic acid To a solution of ethyl 8-(2-fluoro-5-(pyrimidin-2-yl)-4-(trifluoromethyl)benzamido)-7-phenylimidazo[1,2-a]pyridine-3-carboxylate (100 mg, 0.18 mmol) in THF (5 mL) and water (1 mL) was added LiOH (13 mg, 0.55 mmol), and the resulting mixture was stirred at 20° C. for 12 h. The mixture was acidified to pH 6 by the addition of aqueous HCl solution (2M). The precipitate was filtered and dried to give the title compound. MS: m/z=522.1 (M+1).

Step C: 8-(2-Fluoro-5-(pyrimidin-2-yl)-4-(trifluoromethyl)benzamido)-7-phenylimidazo[1,2-a]pyridine-3-carboxamide To a solution of 8-(2-fluoro-5-(pyrimidin-2-yl)-4-(trifluoromethyl)benzamido)-7-phenylimidazo[1,2-a]pyridine-3-carboxylic acid (80 mg, 0.15 mmol) in DMF (2 mL) at 25° C. were added Et$_3$N (0.060 mL, 0.46 mmol) and HATU (58 mg, 0.15 mmol). The mixture was stirred for 10 min before NH$_4$Cl (82 mg, 1.5 mmol) was added. The resulting mixture was stirred at 25° C. for 1 h, then concentrated. The residue was purified by reverse-phase HPLC under basic conditions (H$_2$O/CH$_3$CN gradient with 0.05% NH$_4$OH present) to give the title compound. MS: m/z=521.1 (M+1). $^1$H NMR (400 MHz, CD$_3$OD) δ 9.56 (d, J=7.4 Hz, 1H), 8.80-9.01 (m, 2H), 8.30 (s, 1H), 8.20 (d, J=6.7 Hz, 1H), 7.74 (d, J=10.6 Hz, 1H), 7.48-7.62 (m, 3H), 7.34-7.47 (m, 3H), 7.24 (d, J=7.0 Hz, 1H).

Example 8

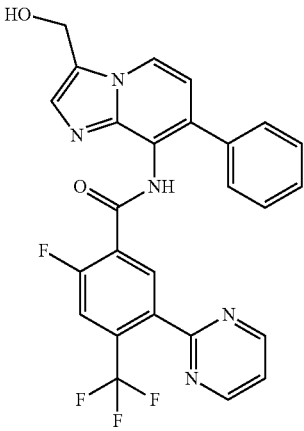 [SMILES: O=C(Nc1c(-c2ccccc2)ccn2c(CO)cnc12)c1cc(-c2ncccn2)c(C(F)(F)F)cc1F]

2-Fluoro-N-(3-(1-hydroxyethyl)-7-phenylimidazo[1,2-a]pyridin-8-yl)-5-(pyrimidin-2-yl)-4-(trifluoromethyl)benzamide Step A: Ethyl 8-(2-fluoro-5-(pyrimidin-2-yl)-4-(trifluoromethyl)benzamido)-7-phenylimidazo[1,2-a]pyridine-3-carboxylate To a stirred solution of ethyl 8-amino-7-phenylimidazo[1,2-a]pyridine-3-carboxylate (1.00 g, 3.55 mmol) and 2-fluoro-5-(pyrimidin-2-yl)-4-(trifluoromethyl)benzoic acid (1.02 g, 3.55 mmol) in pyridine (15 mL) at 20° C. was added dropwise POCl$_3$ (0.50 mL, 5.33 mmol). The resulting mixture was stirred for 15 min, then partitioned between saturated aqueous NaHCO$_3$ solution (20 mL) and EtOAc (30 mL×3). The combined organic layers were dried over Na$_2$SO$_4$ and concentrated. The residue was purified by column chromatography on silica gel (PE/EA=5/1 to 1/1) to give the title compound. MS: m/z=550.2 (M+1).

Step B: 2-Fluoro-N-(3-(hydroxymethyl)-7-phenylimidazo[1,2-a]pyridin-8-yl)-5-(pyrimidin-2-yl)-4-(trifluoromethyl)benzamide To a stirred solution of ethyl 8-(2-fluoro-5-(pyrimidin-2-yl)-4-(trifluoromethyl)benzamido)-7-phenylimidazo[1,2-a]pyridine-3-carboxylate (1.5 g, 2.73 mmol) in THF (20 mL) at 0° C. was added LAH (0.31 g, 8.19 mmol) in portions under nitrogen atmosphere. The resulting mixture was stirred at 0° C. for 30 min. Excess LAH was quenched by the successive dropwise addition of water (0.3 mL), aqueous 15% NaOH solution (0.3 mL) and water (0.9 mL). MgSO$_4$ (1 g) was added and the resulting mixture was stirred at 23° C. for 10 min. The mixture was filtered and the filtrate was concentrated. The residue was purified by reverse-phase HPLC to give the title compound. MS: m/z=508.1 (M+1).

$^1$H NMR (400 MHz, CD$_3$OD) δ 8.93 (d, J=4.8 Hz, 2H), 8.54 (d, J=7.0 Hz, 1H), 8.24 (d, J=6.5 Hz, 1H), 7.75 (d, J=10.5 Hz, 1H), 7.52-7.62 (m, 4H), 7.44-7.50 (m, 2H), 7.37-7.43 (m, 1H), 7.15 (d, J=7.0 Hz, 1H), 5.01 (s, 2H).

Examples 9 and 10

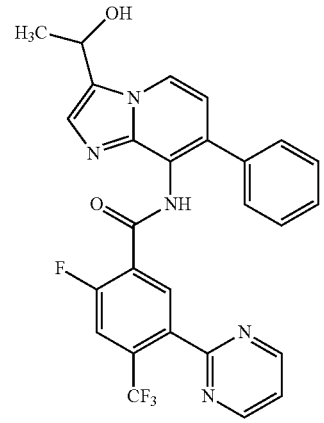 [SMILES: CC(O)c1cnc2c(NC(=O)c3cc(-c4ncccn4)c(C(F)(F)F)cc3F)c(-c3ccccc3)ccn12]

(R) or (S)-2-Fluoro-N-(3-(1-hydroxyethyl)-7-phenylimidazo[1,2-a]pyridin-8-yl)-5-(pyrimidin-2-yl)-4-(trifluoromethyl)benzamide Step A: 2-Fluoro-N-(3-formyl-7-phenylimidazo[1,2-a]pyridin-8-yl)-5-(pyrimidin-2-yl)-4-(trifluoromethyl)benzamide To a stirred solution of 2-fluoro-N-(3-(hydroxymethyl)-7-phenylimidazo[1,2-a]pyridin-8-yl)-5-(pyrimidin-2-yl)-4-(trifluoromethyl)benzamide (1.20 g, 2.37 mmol) in dioxane (10 mL) was added MnO$_2$ (1.23 g, 14.19 mmol), and the resulting mixture was heated at 70° C. for 12 h. The mixture was filtered and the filtrate was concentrated to give the title compound. MS: m/z=506.1 (M+1).

Step B: (R or S)-2-Fluoro-N-(3-(1-hydroxyethyl)-7-phenylimidazo[1,2-a]pyridin-8-yl)-5-(pyrimidin-2-yl)-4-(trifluoromethyl)benzamide To a stirred solution of 2-fluoro-N-(3-formyl-7-phenylimidazo[1,2-a]pyridin-8-yl)-5-(pyrimidin-2-yl)-4-(trifluoromethyl)benzamide (1.00 g, 1.98 mmol) in THF (15 mL) at 0° C. was added a solution of methylmagnesium bromide in diethyl ether (1.98 mL, 5.94 mmol, 3M) dropwise under nitrogen atmosphere. The resulting mixture was stirred at 20° C. for 1 h, then diluted with water (10 mL) and extracted with EtOAc (15 mL×3). The combined organic layers were dried over Na$_2$SO$_4$ and concentrated. The residue was purified by column chromatography on silica gel (PE/EA=5/1 to 1/1) followed by SFC (Column: AD 250×30 mm I.D., 10 um. Mobile phase: A: Supercritical CO$_2$, B: EtOH with 0.1% NH$_3$.H$_2$O; A:B=45:55 at 80 mL/min. Column Temp: 38° C. Nozzle Pressure: 100 Bar. Nozzle Temp: 60° C. Evaporator Temp: 20° C.) to give the title compounds. Enantiomer 1, Example 9: MS: m/z=522.1 (M+1). $^1$H NMR (400 MHz, CD$_3$OD) δ 8.89 (d, J=5.1 Hz, 2H), 8.55 (d, J=7.0 Hz, 1H), 8.21 (d, J=6.7 Hz, 1H), 7.72 (d, J=10.6 Hz, 1H), 7.49-7.56 (m, 4H), 7.42 (t, J=7.2 Hz, 2H), 7.33-7.38 (m, 1H), 7.08 (d, J=7.0 Hz, 1H), 5.24 (q, J=6.3 Hz, 1H), 1.73 (d, J=6.7 Hz, 3H). Enantiomer 2, Example 10: MS: m/z=522.1 (M+1). ¹H NMR (400 MHz, CD₃OD) δ 8.88 (d, J=5.1 Hz, 2H), 8.52 (d, J=7.0 Hz, 1H), 8.22 (d, J=6.7 Hz, 1H), 7.71 (d, J=10.6 Hz, 1H), 7.46-7.54 (m, 4H), 7.41 (t, J=7.4 Hz, 2H), 7.32-7.37 (m, 1H), 7.04 (d, J=7.0 Hz, 1H), 5.22 (q, J=6.3 Hz, 1H), 1.71 (d, J=6.3 Hz, 3H).

Example 11

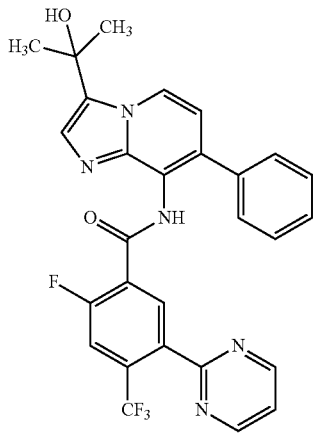 [SMILES: CC(C)(O)c1cnc2c(NC(=O)c3cc(-c4ncccn4)c(C(F)(F)F)cc3F)c(-c3ccccc3)ccn12]

2-Fluoro-N-(3-(2-hydroxypropan-2-yl)-7-phenylimidazo[1,2-a]pyridin-8-yl)-5-(pyrimidin-2-yl)-4-(trifluoromethyl)benzamide Step A: Ethyl 8-(2-fluoro-5-(pyrimidin-2-yl)-4-(trifluoromethyl)benzamido)-7-phenylimidazo[1,2-a]pyridine-3-carboxylate To a solution of 2-fluoro-5-(pyrimidin-2-yl)-4-(trifluoromethyl)benzoic acid (183 mg, 0.63 mmol) in pyridine (3 mL) at 20° C. was added phosphorus oxychloride (0.060 mL, 0.65 mmol). The mixture was stirred for 5 min before ethyl 8-amino-7-phenylimidazo-[1,2-a]pyridine-3-carboxylate (150 mg, 0.53 mmol) was added. The resulting mixture was stirred for 20 min, then partitioned between water (10 mL) and EtOAc (30 mL×3). The combined organic layers were washed with brine (10 mL), dried over Na₂SO₄ and concentrated. The residue was purified by preparative TLC (PE/EtOAc=1/2) to give the title compound. MS: m/z=550.1 (M+1).

Step B: 2-Fluoro-N-(3-(2-hydroxypropan-2-yl)-7-phenylimidazo[1,2-a]pyridin-8-yl)-5-(pyrimidin-2-yl)-4-(trifluoromethyl)benzamide To a solution of ethyl 8-(2-fluoro-5-(pyrimidin-2-yl)-4-(trifluoromethyl)benzamido)-7-phenylimidazo[1,2-a]pyridine-3-carboxylate (90 mg, 0.16 mmol) in anhydrous tetrahydrofuran (2 mL) at 20° C. was added a solution of methylmagnesium bromide in diethyl ether (1.5 mL, 4.50 mmol, 3M). The resulting mixture was stirred for 1 h, then diluted with saturated aqueous ammonium chloride solution (10 mL) and extracted with EtOAc (10 mL×3). The combined organic layers were dried over Na₂SO₄ and concentrated. The residue was purified by reverse-phase HPLC under acidic conditions (H₂O/CH₃CN gradient with 0.1% TFA present) to give the title compound. MS: m/z=536.1 (M+1). ¹H NMR (400 MHz, CD₃OD) δ 9.34 (d, J=7.3 Hz, 1H), 8.96 (d, J=5.0 Hz, 2H), 8.29 (d, J=7.0 Hz, 1H), 8.06 (s, 1H), 7.85 (d, J=10.8 Hz, 1H), 7.51-7.67 (m, 7H), 1.84 (s, 6H).

The following examples were prepared in similar fashion to the procedures described above.

| Compound Number | Structure | Compound Name | LCMS (M + 1) |
|---|---|---|---|
| 12 | ![structure] | 8-({[3-(1-methyl-1H-pyrazol-3-yl)-4-(trifluoromethyl)phenyl]carbonyl}amino)-7-phenylimidazo[1,2-a]pyridine-3-carboxamide | 505.1 |

-continued

| Compound Number | Structure | Compound Name | LCMS (M + 1) |
|---|---|---|---|
| 13 | 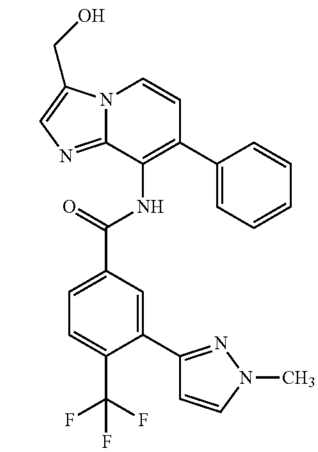 [SMILES: Cn1ccc(-c2cc(C(=O)Nc3c(-c4ccccc4)ccn4c(CO)cnc34)ccc2C(F)(F)F)n1] | N-[3-(hydroxymethyl)-7-phenylimidazo[1,2-a]pyridin-8-yl]-3-(1-methyl-1H-pyrazol-3-yl)-4-(trifluoromethyl)benzamide | 492.1 |
| 14 | 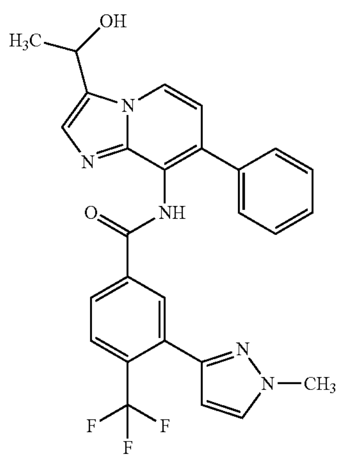 [SMILES: CC(O)c1cnc2c(NC(=O)c3ccc(C(F)(F)F)c(-c4ccn(C)n4)c3)c(-c3ccccc3)ccn12] | (R) or (S)-N-[3-(1-hydroxyethyl)-7-phenylimidazo[1,2-a]pyridin-8-yl]-3-(1-methyl-1H-pyrazol-3-yl)-4-(trifluoromethyl)benzamide | 506.1 |
| 15 | 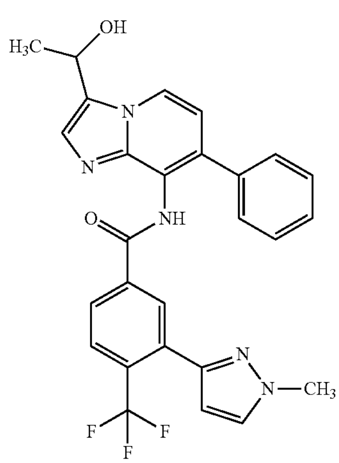 [SMILES: CC(O)c1cnc2c(NC(=O)c3ccc(C(F)(F)F)c(-c4ccn(C)n4)c3)c(-c3ccccc3)ccn12] | (R) or (S)-N-[3-(1-hydroxyethyl)-7-phenylimidazo[1,2-a]pyridin-8-yl]-3-(1-methyl-1H-pyrazol-3-yl)-4-(trifluoromethyl)benzamide | 506.1 |

-continued

| Compound Number | Structure | Compound Name | LCMS (M + 1) |
|---|---|---|---|
| 16 | 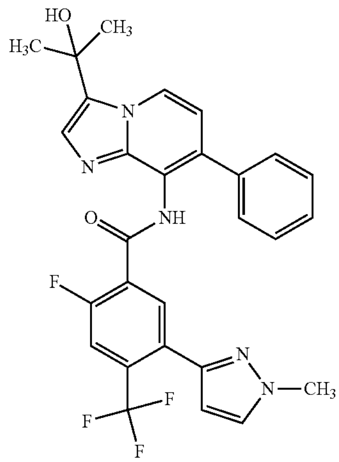 [SMILES: Cn1ccc(-c2cc(C(=O)Nc3c(-c4ccccc4)ccn4c(C(C)(C)O)cnc34)c(F)cc2C(F)(F)F)n1] | 2-fluoro-N-[3-(1-hydroxy-1-methylethyl)-7-phenylimidazo[1,2-a]pyridin-8-yl]-5-(1-methyl-1H-pyrazol-3-yl)-4-(trifluoromethyl)benzamide | 538.1 |
| 17 | 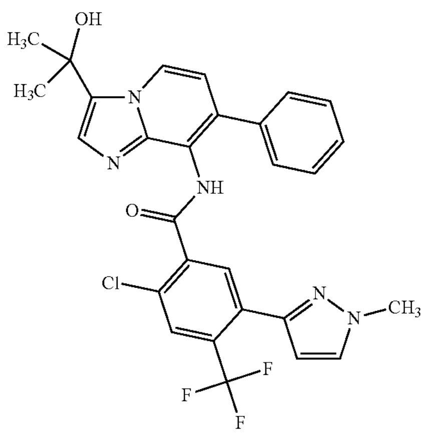 [SMILES: Cn1ccc(-c2cc(C(=O)Nc3c(-c4ccccc4)ccn4c(C(C)(C)O)cnc34)c(Cl)cc2C(F)(F)F)n1] | 2-chloro-N-[3-(1-hydroxy-1-methylethyl)-7-phenylimidazo[1,2-a]pyridin-8-yl]-5-(1-methyl-1H-pyrazol-3-yl)-4-(trifluoromethyl)benzamide | 554.1 |
| 18 | 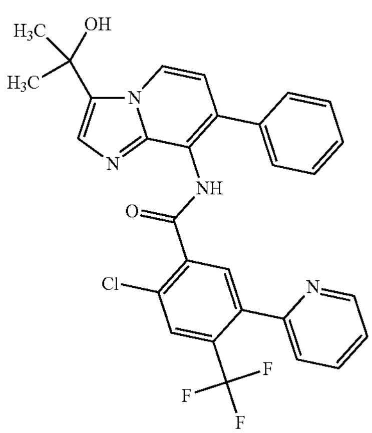 [SMILES: CC(C)(O)c1cnc2c(NC(=O)c3cc(-c4ccccn4)c(C(F)(F)F)cc3Cl)c(-c3ccccc3)ccn12] | 2-chloro-N-[3-(1-hydroxy-1-methylethyl)-7-phenylimidazo[1,2-a]pyridin-8-yl]-5-pyridin-2-yl-4-(trifluoromethyl)benzamide | 551.1 |

-continued

| Compound Number | Structure | Compound Name | LCMS (M + 1) |
|---|---|---|---|
| 19 | 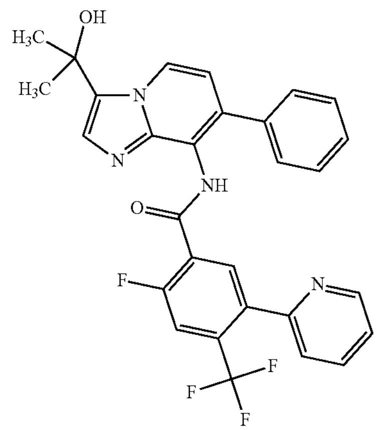 [SMILES: CC(C)(O)c1cnc2c(NC(=O)c3cc(-c4ccccn4)c(C(F)(F)F)cc3F)c(-c3ccccc3)ccn12] | 2-fluoro-N-[3-(1-hydroxy-1-methylethyl)-7-phenylimidazo[1,2-a]pyridin-8-yl]-5-pyridin-2-yl-4-(trifluoromethyl)benzamide | 535.1 |
| 20 | 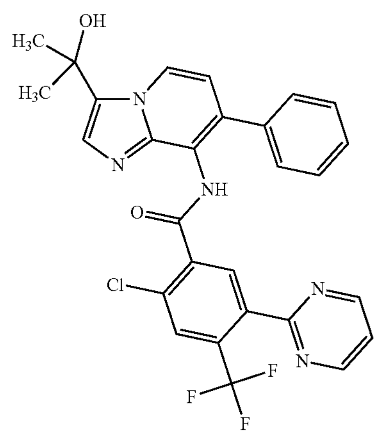 [SMILES: CC(C)(O)c1cnc2c(NC(=O)c3cc(-c4ncccn4)c(C(F)(F)F)cc3Cl)c(-c3ccccc3)ccn12] | 2-chloro-N-[3-(1-hydroxy-1-methylethyl)-7-phenylimidazo[1,2-a]pyridin-8-yl]-5-pyrimidin-2-yl-4-(trifluoromethyl)benzamide | 552.1 |
| 21 | 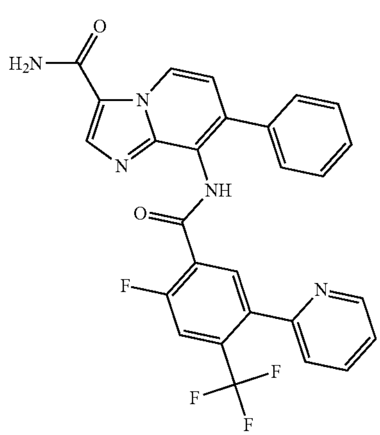 [SMILES: NC(=O)c1cnc2c(NC(=O)c3cc(-c4ccccn4)c(C(F)(F)F)cc3F)c(-c3ccccc3)ccn12] | 8-({[2-fluoro-5-pyridin-2-yl-4-(trifluoromethyl)phenyl]carbonyl}amino)-7-phenylimidazo[1,2-a]pyridine-3-carboxamide | 520.1 |

-continued

| Compound Number | Structure | Compound Name | LCMS (M + 1) |
|---|---|---|---|
| 22 | 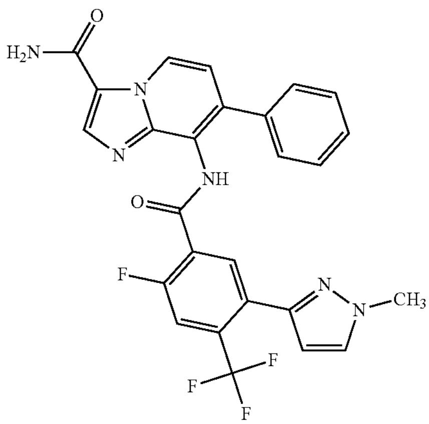 [SMILES: Cn1ccc(-c2cc(C(=O)Nc3c(-c4ccccc4)ccn4c(C(N)=O)cnc34)c(F)cc2C(F)(F)F)n1] | 8-({[2-fluoro-5-(1-methyl-1H-pyrazol-3-yl)-4-(trifluoromethyl)phenyl]carbonyl}amino)-7-phenylimidazo[1,2-a]pyridine-3-carboxamide | 523.1 |
| 23 | 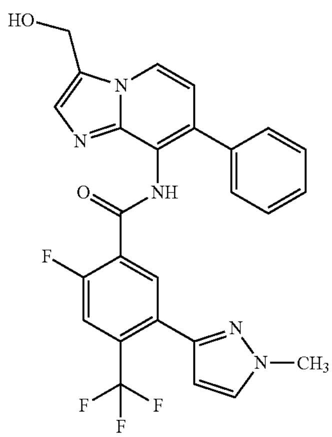 [SMILES: Cn1ccc(-c2cc(C(=O)Nc3c(-c4ccccc4)ccn4c(CO)cnc34)c(F)cc2C(F)(F)F)n1] | 2-fluoro-N-[3-(hydroxymethyl)-7-phenylimidazo[1,2-a]pyridin-8-yl]-5-(1-methyl-1H-pyrazol-3-yl)-4-(trifluoromethyl)benzamide | 510.1 |
| 24 | 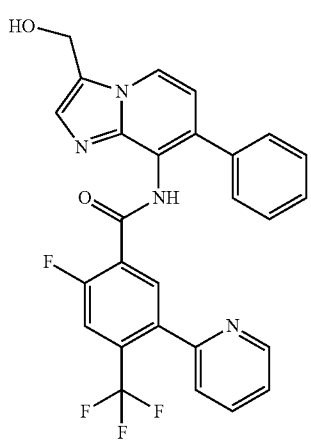 [SMILES: O=C(Nc1c(-c2ccccc2)ccn2c(CO)cnc12)c1cc(-c2ccccn2)c(C(F)(F)F)cc1F] | 2-fluoro-N-[3-(hydroxymethyl)-7-phenylimidazo[1,2-a]pyridin-8-yl]-5-pyridin-2-yl-4-(trifluoromethyl)benzamide | 507.1 |

-continued

| Compound Number | Structure | Compound Name | LCMS (M + 1) |
|---|---|---|---|
| 25 | 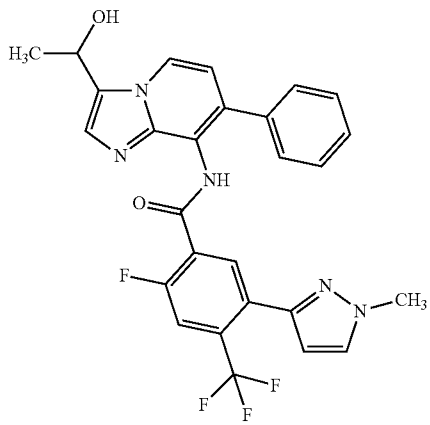 [SMILES: CC(O)c1cnc2c(NC(=O)c3cc(-c4ccn(C)n4)c(C(F)(F)F)cc3F)c(-c3ccccc3)ccn12] | (R) or (S)-2-fluoro-N-[3-(1-hydroxyethyl)-7-phenylimidazo[1,2-a]pyridin-8-yl]-5-(1-methyl-1H-pyrazol-3-yl)-4-(trifluoromethyl)benzamide | 524.2 |
| 26 | 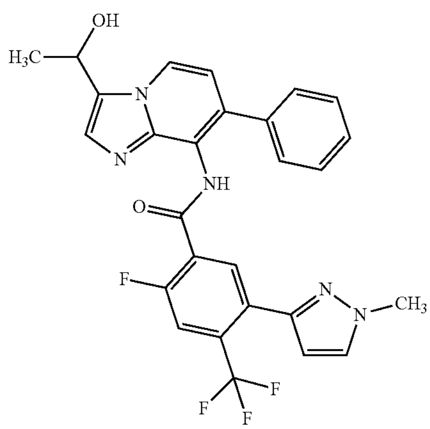 [SMILES: CC(O)c1cnc2c(NC(=O)c3cc(-c4ccn(C)n4)c(C(F)(F)F)cc3F)c(-c3ccccc3)ccn12] | (R) or (S)-2-fluoro-N-[3-(1-hydroxyethyl)-7-phenylimidazo[1,2-a]pyridin-8-yl]-5-(1-methyl-1H-pyrazol-3-yl)-4-(trifluoromethyl)benzamide | 524.1 |
| 27 | 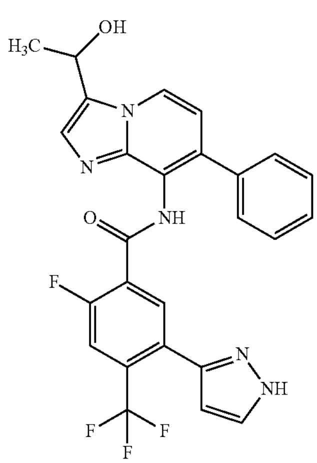 [SMILES: CC(O)c1cnc2c(NC(=O)c3cc(-c4cc[nH]n4)c(C(F)(F)F)cc3F)c(-c3ccccc3)ccn12] | (R) or (S)-2-fluoro-N-[3-(1-hydroxyethyl)-7-phenylimidazo[1,2-a]pyridin-8-yl]-5-(1H-pyrazol-3-yl)-4-(trifluoromethyl)benzamide | 510.1 |

| Compound Number | Structure | Compound Name | LCMS (M + 1) |
|---|---|---|---|
| 28 | 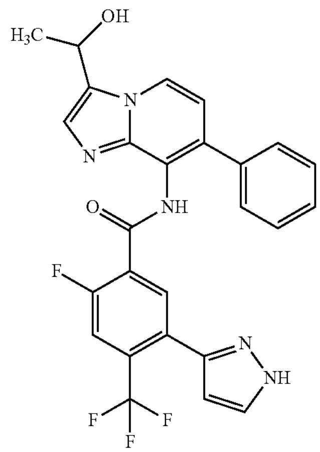 [SMILES: CC(O)c1cnc2c(NC(=O)c3cc(-c4cc[nH]n4)c(C(F)(F)F)cc3F)c(-c3ccccc3)ccn12] | (R) or (S)-2-fluoro-N-[3-(1-hydroxyethyl)-7-phenylimidazo[1,2-a]pyridin-8-yl]-5-(1H-pyrazol-3-yl)-4-(trifluoromethyl)benzamide | 510.1 |
| 29 | 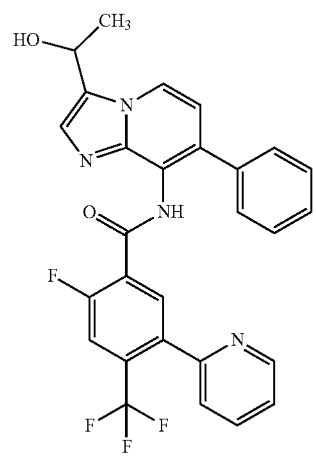 [SMILES: CC(O)c1cnc2c(NC(=O)c3cc(-c4ccccn4)c(C(F)(F)F)cc3F)c(-c3ccccc3)ccn12] | (R) or (S)-2-fluoro-N-[3-(1-hydroxyethyl)-7-phenylimidazo[1,2-a]pyridin-8-yl]-5-pyridin-2-yl-4-(trifluoromethyl)benzamide | 521.1 |
| 30 | 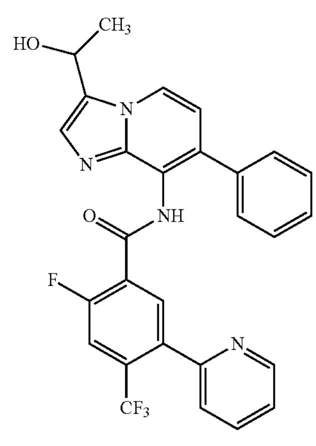 [SMILES: CC(O)c1cnc2c(NC(=O)c3cc(-c4ccccn4)c(C(F)(F)F)cc3F)c(-c3ccccc3)ccn12] | (R) or (S)-2-fluoro-N-[3-(1-hydroxyethyl)-7-phenylimidazo[1,2-a]pyridin-8-yl]-5-pyridin-2-yl-4-(trifluoromethyl)benzamide | 521.1 |

-continued

| Compound Number | Structure | Compound Name | LCMS (M + 1) |
|---|---|---|---|
| 31 | 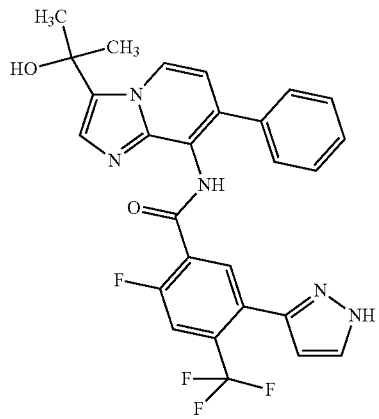 [SMILES: CC(C)(O)c1cnc2c(NC(=O)c3cc(-c4cc[nH]n4)c(C(F)(F)F)cc3F)c(-c3ccccc3)ccn12] | 2-fluoro-N-[3-(1-hydroxy-1-methylethyl)-7-phenylimidazo[1,2-a]pyridin-8-yl]-5-(1H-pyrazol-3-yl)-4-(trifluoromethyl)benzamide | 524.1 |
| 32 | 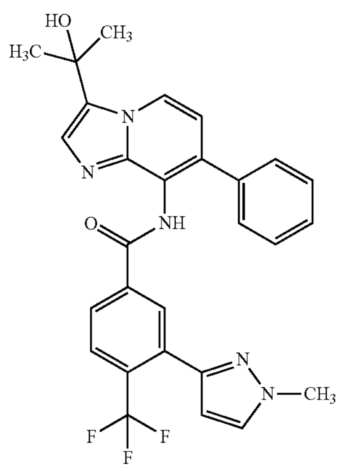 [SMILES: Cn1ccc(-c2cc(C(=O)Nc3c(-c4ccccc4)ccn4c(C(C)(C)O)cnc34)ccc2C(F)(F)F)n1] | N-[3-(1-hydroxy-1-methylethyl)-7-phenylimidazo[1,2-a]pyridin-8-yl]-3-(1-methyl-1H-pyrazol-3-yl)-4-(trifluoromethyl)benzamide | 520.1 |
| 33 | 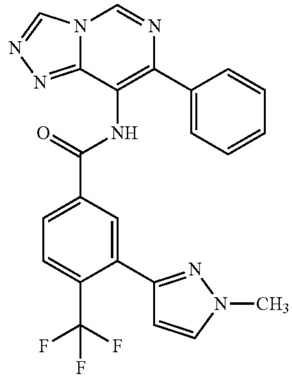 [SMILES: Cn1ccc(-c2cc(C(=O)Nc3c(-c4ccccc4)ncn4cnnc34)ccc2C(F)(F)F)n1] | 3-(1-methyl-1H-pyrazol-3-yl)-N-(7-phenyl[1,2,4]triazolo[4,3-c]pyrimidin-8-yl)-4-(trifluoromethyl)benzamide | 464.3 |

Reaction Scheme for Example 34

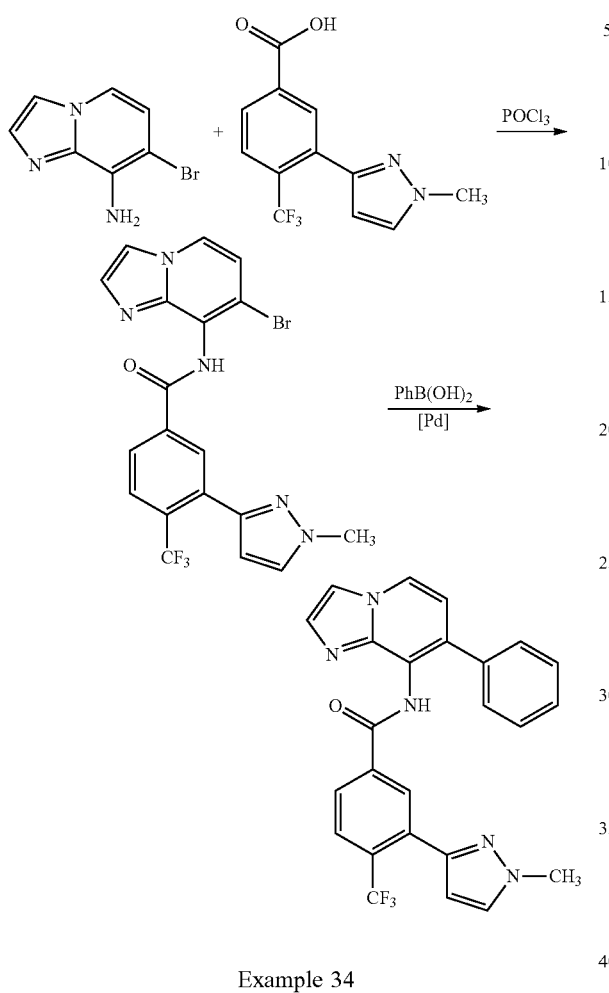

Example 34

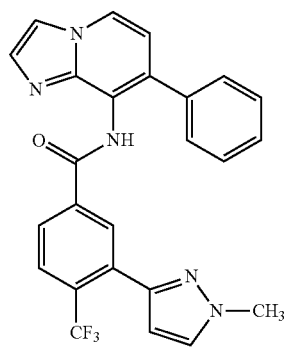 [SMILES: Cn1ccc(-c2cc(C(=O)Nc3c(-c4ccccc4)ccn4ccnc34)ccc2C(F)(F)F)n1]

3-(1-Methyl-1H-pyrazol-3-yl)-N-(7-phenylimidazo[1,2-a]pyridin-8-yl)-4-(trifluoromethyl)benzamide Step A: N-(7-Bromoimidazo[1,2-a]pyridin-8-yl)-3-(1-methyl-1H-pyrazol-3-yl)-4-(trifluoromethyl)benzamide POCl₃ (0.066 mL, 0.707 mmol) was added to a solution of 7-bromoimidazo[1,2-a]pyridin-8-amine (100 mg, 0.472 mmol) and 3-(1-methyl-1H-pyrazol-3-yl)-4-(trifluoromethyl)benzoic acid in pyridine (1 mL) at 23° C., and the resulting mixture was stirred for 2 h. The product mixture was diluted with DMF (2 mL) and purified by reverse-phase HPLC (5-95% ACN/H₂O w/0.1% TFA, YMC Pro C18 column) to provide the title compound. MS: m/z=464.1 (M+1).

Step B: 3-(1-Methyl-1H-pyrazol-3-yl)-N-(7-phenylimidazo[1,2-a]pyridin-8-yl)-4-(trifluoromethyl)benzamide Bis(tri-tert-butylphosphine)palladium(0) (8.3 mg, 0.016 mmol) was added to a deoxygenated solution of N-(7-bromoimidazo[1,2-a]pyridin-8-yl)-3-(1-methyl-1H-pyrazol-3-yl)-4-(trifluoromethyl)benzamide (150 mg, 0.323 mmol), phenylboronic acid (118 mg, 0.969 mmol), and cesium carbonate (0.323 mL, 0.646 mmol) in dioxane (1 mL). The resulting mixture was heated at 100° C. for 1 h in a microwave reactor, then cooled, diluted with DMF (1 mL), filtered, and purified by reverse-phase HPLC (5-95% CH₃CN/H₂O w/0.1% TFA, YMC Pro C18 column) to afford the title compound. MS: m/z=462.2 (M+1). ¹H NMR (500 MHz, CDCl₃) δ 11.20 (br s, 1H), 8.29 (d, 1H), 8.05 (s, 1H), 7.84 (d, 1H), 7.78 (m, 3H), 7.68 (d, 2H), 7.38 (m, 4H), 6.42 (s, 1H), 3.91 (s, 3H).

Example 35

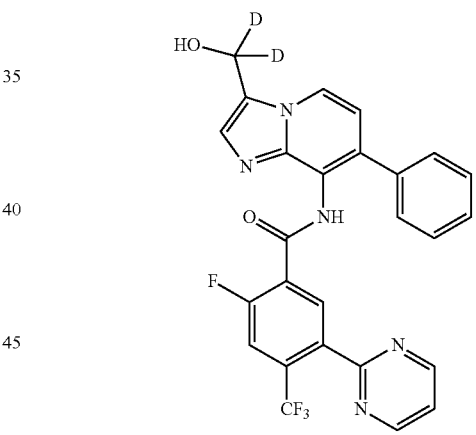

2-Fluoro-N-(3-(hydroxymethyl-d2)-7-phenylimidazo[r 12-a]pyridin-8-yl)-5-(pyrimidin-2-yl)-4-(trifluoromethyl)benzamide To a solution of ethyl 8-(2-fluoro-5-(pyrimidin-2-yl)-4-(trifluoromethyl)benzamido)-7-phenylimidazo[1,2-a]pyridine-3-carboxylate (53 mg, 0.096 mmol) in THF (1 mL) at 0° C. was added LiAlD₄ (10.1 mg, 0.241 mmol). The mixture was stirred for 15 min before 10 uL of water, 10 uL of 15% NaOH solution, and 10×3 uL of water were added in succession. The resulting precipitate was filtered and rinsed with 25 mL of EtOAc. The filtrate was concentrated, and the residue purified by flash column chromatography, eluting with 3:1 v/v EtOAc/EtOH (product Rf=0.55), to provide the title compound. MS: m/z=510.0 (M+1). ¹H NMR (500 MHz, CD₃OD) δ 8.94 (d, 2H), 8.51 (d, 1H), 8.23

(d, 1H), 7.73 (d, 1H), 7.30-7.58 (m, 4H), 7.42-7.48 (m, 2H), 7.35-7.39 (m, 1H), 7.14 (d, 1H).

Example 36

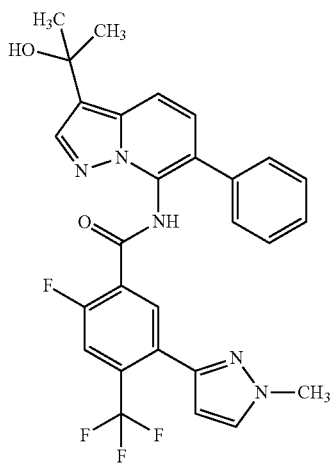 [SMILES: Cn1ccc(-c2cc(C(=O)Nc3c(-c4ccccc4)ccc4c(C(C)(C)O)cnn34)c(F)cc2C(F)(F)F)n1]

2-Fluoro-N-(3-(2-hydroxypropan-2-yl)-6-phenlpyrazolo[1,5-a]pyridin-7-yl)-5-(1-methyl-1H-pyrazol-3-yl)-4-(trifluoromethyl)benzamide Step A: Methyl 7-(2-fluoro-5-(1-methyl-1H-pyrazol-3-yl)-4-(trifluoromethyl)benzamido)-6-phenylpyrazolo[1,5-a]pyridine-3-carboxylate To a solution of methyl 7-amino-6-phenylpyrazolo[1,5-a]pyridine-3-carboxylate (50 mg, 0.18 mmol) and 2-fluoro-5-(1-methyl-1H-pyrazol-3-yl)-4-(trifluoromethyl)benzoic acid (56 mg, 0.20 mmol) in pyridine (3 mL) at 30° C. was added phosphoryl trichloride (0.020 mL, 0.23 mmol). The resulting mixture was stirred for 16 h, then partitioned between saturated aqueous NaHCO$_3$ solution (20 mL) and EtOAc (15 mL×3). The combined organic layers were dried over Na$_2$SO$_4$ and concentrated. The residue was diluted with THF (5 mL) and lithium hydroxide in H$_2$O (16 mg, 0.37 mmol) was added. The resulting mixture was stirred at 30° C. for 3 h, then partitioned between water (20 mL) and EtOAc (15 mL×3). The combined organic layers were dried over Na$_2$SO$_4$ and concentrated. The residue was purified by preparative TLC (PE/EtOAc=1/1) to give the title compound. MS: m/z=538.2 (M+1).

Step B: 2-Fluoro-N-(3-(2-hydroxypropan-2-yl)-6-phenylpyrazolo[1,5-a]pyridin-7-yl)-5-(1-methyl-1H-pyrazol-3-yl)-4-(trifluoromethyl)benzamide To a solution of methyl 7-(2-fluoro-5-(1-methyl-1H-pyrazol-3-yl)-4-(trifluoromethyl)benzamido)-6-phenylpyrazolo[1,5-a]pyridine-3-carboxylate (20 mg, 0.035 mmol) in THF (3 mL) at 0° C. was added a solution of MeMgBr in diethyl ether (0.35 mL, 1.0 mmol, 3M), and the resulting mixture was stirred at 0° C. for 1.5 h. The product mixture was diluted with saturated aqueous NH$_4$Cl solution (20 mL) and extracted with EtOAc (10 mL×3). The combined organic layers were dried over Na$_2$SO$_4$ and concentrated. The residue was purified by reverse-phase HPLC under basic conditions (H$_2$O/CH$_3$CN gradient with 0.05% NH$_4$OH present) to give the title compound. MS: m/z=538.2 (M+1). $^1$H NMR (400 MHz, CD$_3$OD) δ 7.96-8.07 (m, 2H), 7.93 (s, 1H), 7.64-7.72 (m, 2H), 7.54 (br, 2H), 7.43 (t, J=7.2 Hz, 2H), 7.35 (dd, J=8.2, 14.5 Hz, 2H), 6.45 (br, 1H), 3.96 (s, 3H), 1.72 (s, 6H).

The following examples were prepared in similar fashion to the procedures described above.

| Compound Number | Structure | Compound Name | LCMS (M + 1) |
|---|---|---|---|
| 37 | ![structure] | N-[3-(1-hydroxy-1-methylethyl)-6-phenylpyrazolo[1,5-a]pyridin-7-yl]-3-(1-methyl-1H-pyrazol-3-yl)-4-(trifluoromethyl)benzamide | 520.1 [M − H$_2$O + 1] observed |

-continued

| Compound Number | Structure | Compound Name | LCMS (M + 1) |
|---|---|---|---|
| 38 | 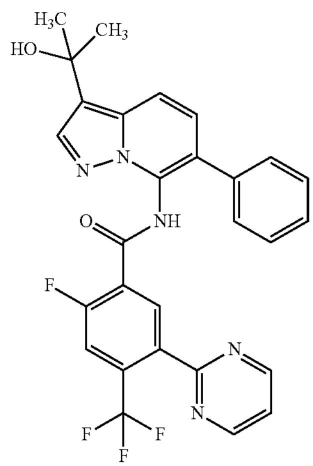 [SMILES: CC(C)(O)c1cnn2c(NC(=O)c3cc(-c4ncccn4)c(C(F)(F)F)cc3F)c(-c3ccccc3)ccc12] | 2-fluoro-N-[3-(1-hydroxy-1-methylethyl)-6-phenylpyrazolo[1,5-a]pyridin-7-yl]-5-pyrimidin-2-yl-4-(trifluoromethyl)benzamide | 536.2 |
| 39 | 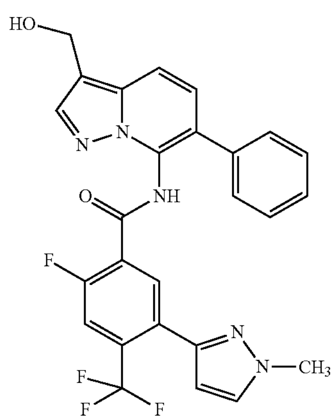 [SMILES: Cn1ccc(-c2cc(C(=O)Nc3c(-c4ccccc4)ccc4c(CO)cnn34)c(F)cc2C(F)(F)F)n1] | 2-fluoro-N-[3-(hydroxymethyl)-6-phenylpyrazolo[1,5-a]pyridin-7-yl]-5-(1-methyl-1H-pyrazol-3-yl)-4-(trifluoromethyl)benzamide | 510.1 |
| 40 | 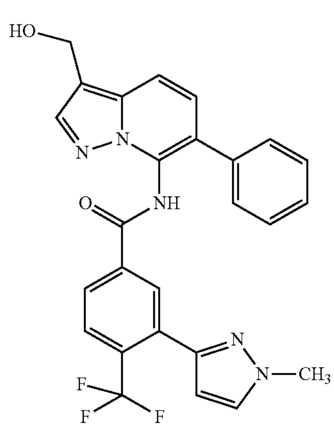 [SMILES: Cn1ccc(-c2cc(C(=O)Nc3c(-c4ccccc4)ccc4c(CO)cnn34)ccc2C(F)(F)F)n1] | N-[3-(hydroxymethyl)-6-phenylpyrazolo[1,5-a]pyridin-7-yl]-3-(1-methyl-1H-pyrazol-3-yl)-4-(trifluoromethyl)benzamide | 492.2 |

| Compound Number | Structure | Compound Name | LCMS (M + 1) |
|---|---|---|---|
| 41 | 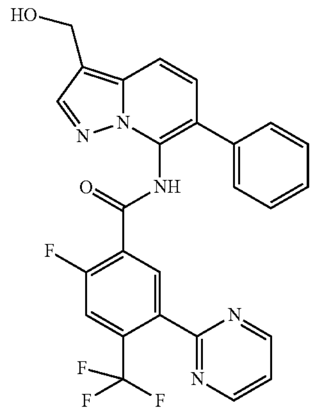 [SMILES: O=C(Nc1c(-c2ccccc2)ccc2c(CO)cnn12)c1cc(-c2ncccn2)c(C(F)(F)F)cc1F] | 2-fluoro-N-[3-(hydroxymethyl)-6-phenylpyrazolo[1,5-a]pyridin-7-yl]-5-pyrimidin-2-yl-4-(trifluoromethyl)benzamide | 508.1 |

Example 42

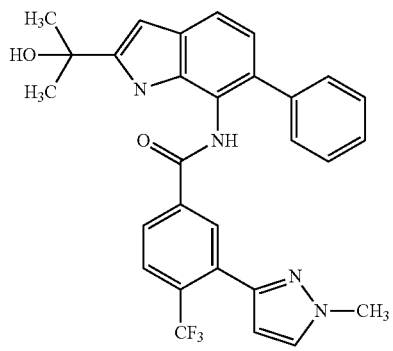 [SMILES: Cn1ccc(-c2cc(C(=O)Nc3c(-c4ccccc4)ccc4cc(C(C)(C)O)[nH]c34)ccc2C(F)(F)F)n1]

N-(2-(2-Hydroxypropan-2-yl)-6-phenyl-1H-indol-7-yl)-3-(1-methyl-1H-pyrazol-3-yl)-4-(trifluoromethyl) benzamide

Step A: Ethyl 7-(3-(1-methyl-1H-pyrazol-3-yl)-4-(trifluoromethyl)benzamido)-6-phenyl-1H-indole-2-carboxylate To a stirred solution of ethyl 7-amino-6-phenyl-1H-indole-2-carboxylate (80 mg, 0.29 mmol) and 3-(1-methyl-1H-pyrazol-3-yl)-4-(trifluoromethyl)benzoic acid (85 mg, 0.31 mmol) in pyridine (2 mL) at 25° C. was added phosphoryl trichloride (0.032 mL, 0.34 mmol). The resulting mixture was stirred for 5 min, then partitioned between water (5 mL) and EtOAc (10 mL×3). The combined organic layers were dried over Na₂SO₄ and concentrated. The residue was purified by preparative TLC (PE/EtOAc=1/1) to give the title compound. MS: m/z=533.2 (M+1). ¹H NMR (400 MHz, CD₃OD) δ 8.07 (s, 1H), 7.96 (d, J=8.2 Hz, 1H), 7.85 (d, J 8.2 Hz, 1H), 7.71 (d, J=8.2 Hz, 1H), 7.65 (d, J=2.0 Hz, 1H), 7.45 (d, J=7.0 Hz, 2H), 7.34 (t, J=7.6 Hz, 2H), 7.23-7.30 (m, 2H), 7.17 (d, J=8.2 Hz, 1H), 6.44 (s, 1H), 4.37 (q, J=7.0 Hz, 2H), 3.95 (s, 3H), 1.38 (t, J=7.2 Hz, 3H).

Step B: N-(2-(2-Hydroxypropan-2-yl)-6-phenyl-1H-indol-7-yl)-3-(1-methyl-1H-pyrazol-3-yl)-4-(trifluoromethyl)benzamide To a stirred solution of ethyl 7-(3-(1-methyl-1H-pyrazol-3-yl)-4-(trifluoromethyl)benzamido)-6-phenyl-1H-indole-2-carboxylate (60 mg, 0.11 mmol) in THF (5 mL) at 80° C. was added dropwise a solution of methyl magnesium bromide in ethyl ether (1.13 mL, 3.38 mmol). The resulting mixture was stirred for 30 min, then cooled and diluted with saturated aqueous ammonium chloride solution (5 mL). The aqueous layer was extracted with EtOAc (5 mL×3). The combined organic layers were dried over Na₂SO₄ and concentrated. The residue was purified by reverse-phase HPLC under basic conditions (H₂O/CH₃CN gradient with 0.05% NH₄OH present) to give the title compound. MS: m/z=501.2 (M-H₂O+1). ¹H NMR (400 MHz, CD₃OD) δ 8.12 (s, 1H), 8.01 (d, J=8.5 Hz, 1H), 7.90 (d, J=8.5 Hz, 1H), 7.68 (d, J 2.0 Hz, 1H), 7.55 (d, J=8.0 Hz, 1H), 7.48 (d, J=7.5 Hz, 2H), 7.36 (t, J=7.5 Hz, 2H), 7.23-7.30 (m, 1H), 7.09 (d, J=8.0 Hz, 1H), 6.48 (s, 1H), 6.41 (s, 1H), 3.99 (s, 3H), 1.67 (s, 6H).

Example 43

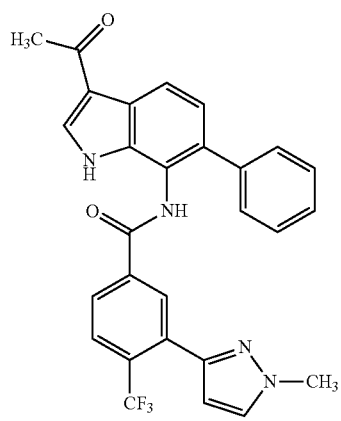 [SMILES: CC(=O)c1c[nH]c2c(NC(=O)c3ccc(C(F)(F)F)c(-c4ccn(C)n4)c3)c(-c3ccccc3)ccc12]

N-(3-Acetyl-6-phenyl-1H-indol-7-yl)-3-(1-methyl-1H-pyrazol-3-yl)-4-(trifluoromethyl)benzamide Step A: 3-(1-Methyl-1H-pyrazol-3-yl)-N-(6-phenyl-1H-indol-7-yl)-4-(trifluoromethyl)benzamide To a stirred solution of 6-phenyl-1H-indol-7-amine (100 mg, 0.48 mmol) and 3-(1-methyl-1H-pyrazol-3-yl)-4-(trifluoromethyl)benzoic acid (130 mg, 0.48 mmol) in pyridine (3 mL) at 25° C. was added phosphoryl trichloride (0.045 mL, 0.48 mmol). The resulting mixture was stirred for 5 min then partitioned between water (5 mL) and EtOAc (10 mL×3). The combined organic layers were dried over $Na_2SO_4$ and concentrated. The residue was purified by preparative TLC (PE/EtOAc=1/1) to give the title compound. MS: m/z=461.2 (M+1). $^1$H NMR (400 MHz, CDCl$_3$) δ 9.87 (br, 1H), 8.68 (s, 1H), 8.22 (s, 1H), 7.93 (s, 1H), 7.73 (d, J=8.2 Hz, 1H), 7.65 (d, J=7.4 Hz, 1H), 7.54 (d, J=7.8 Hz, 1H), 7.35-7.45 (m, 3H), 7.25-7.33 (m, 2H), 7.03 (d, J=8.2 Hz, 1H), 6.54 (s, 1H), 6.41 (s, 1H), 3.92 (s, 3H).

Step B: N-(3-Acetyl-6-phenyl-1H-indol-7-yl)-3-(1-methyl-1H-pyrazol-3-yl)-4-(trifluoromethyl)benzamide To a solution of 3-(1-methyl-1H-pyrazol-3-yl)-N-(6-phenyl-1H-indol-7-yl)-4-(trifluoromethyl)benzamide (50 mg, 0.11 mmol) in toluene (2 mL) at 0° C. was added acetyl chloride (8.5 mg, 0.11 mmol). After stirring for 15 min, a solution of perchlorostannane (28 mg, 0.11 mmol) in toluene (0.5 mL) was added. The resulting solution was stirred at 0° C. for 2 h before aqueous sodium bicarbonate solution (3 mL, 8% w/w) was added dropwise. The product mixture was extracted with EtOAc (5 mL×2), and the combined organic layers were dried over $Na_2SO_4$ and concentrated. The residue was purified by HPLC under neutral conditions (H$_2$O/CH$_3$CN gradient with 0.01 M NH$_4$HCO$_3$ present) to afford the title compound. MS: m/z=503.2 (M+1). $^1$H NMR (400 MHz, CD$_3$OD) δ 10.90 (br, 1H), 8.33-8.43 (m, 2H), 7.96 (s, 1H), 7.92 (d, J=2.7 Hz, 1H), 7.76 (d, J=8.2 Hz, 1H), 7.64 (d, J=8.2 Hz, 1H), 7.48 (d, J=4.3 Hz, 4H), 7.35-7.43 (m, 2H), 6.45 (s, 1H), 3.96 (s, 3H), 2.57 (s, 3H).

2-Fluoro-N-(2-(2-hydroxypropan-2-yl)-5-phenyl-1H-indol-6-yl)-5-(pyrimidin-2-yl)-4-(trifluoromethyl)benzamide Step A: Ethyl 6-(2-fluoro-5-(pyrimidin-2-yl)-4-(trifluoromethyl)benzamido)-5-phenyl-1H-indole-2-carboxylate To a solution of 2-fluoro-5-(pyrimidin-2-yl)-4-(trifluoromethyl)benzoic acid (153 mg, 0.453 mmol) in pyridine (2 mL) at 25° C. was added phosphorus oxychloride (0.1 mL, 0.6 mmol). The mixture was stirred at for 5 min before ethyl 6-amino-5-phenyl-1H-indole-2-carboxylate (150 mg, 0.45 mmol) was added. The resulting mixture was stirred for 20 min, then partitioned between water (10 mL) and EtOAc (10 mL×3). The combined organic layers were dried over $Na_2SO_4$ and concentrated. The residue was purified by preparative TLC (PE/EtOAc=2/1) to give the title compound. MS: m/z=549.1 (M+1).

Step B: 2-Fluoro-N-(2-(2-hydroxypropan-2-yl)-5-phenyl-1H-indol-6-yl)-5-(pyrimidin-2-yl)-4-(trifluoromethyl)benzamide To a solution of ethyl 4-(2-fluoro-5-(pyrimidin-2-yl)-4-(trifluoromethyl)benzamido)-5-phenyl-1H-indole-2-carboxylate (150 mg, 0.30 mmol) in tetrahydrofuran (3 mL) at 0° C. was added a solution of methylmagnesium bromide in diethyl ether (0.5 mL, 1.4 mmol, 3 M) dropwise under nitrogen atmosphere. The resulting mixture was stirred at 25° C. for 12 h, then diluted with saturated aqueous ammonium chloride solution (10 mL) and extracted with EtOAc (10 mL×3). The combined organic layers were dried over $Na_2SO_4$ and concentrated. The residue was purified by reverse-phase HPLC under basic conditions (H$_2$O/CH$_3$CN gradient with 0.05% NH$_4$OH present) to give the title compound. MS: m/z=535.2 (M+1). $^1$H NMR (400 MHz, CD$_3$OD) δ 8.92 (d, J=5.1 Hz, 2H), 7.93 (d, J=6.7 Hz, 1H), 7.80 (s, 1H), 7.70 (d, J 10.6 Hz, 1H), 7.54 (t, J=4.9 Hz, 1H), 7.44 (d, J=8.6 Hz, 3H), 7.35-7.39 (m, 2H), 7.24-7.29 (m, 1H), 6.34 (s, 1H), 1.66 (s, 6H).

Example 44

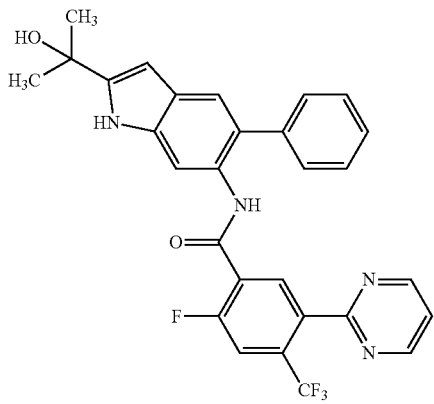 [SMILES: CC(C)(O)c1cc2cc(-c3ccccc3)c(NC(=O)c3cc(-c4ncccn4)c(C(F)(F)F)cc3F)cc2[nH]1]

Example 45

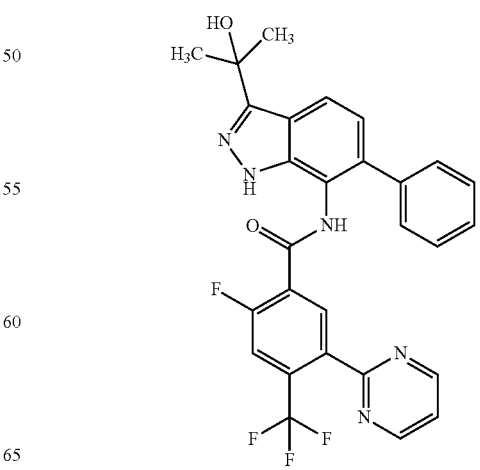

2-Fluoro-N-(3-(2-hydroxypropan-2-yl)-6-phenyl-1H-indazol-7-yl)-5-(pyrimidin-2-yl)-4-(trifluoromethyl)benzamide

Step A: N-(3-Acetyl-6-phenyl-1H-indazol-7-yl)-2-fluoro-5-(pyrimidin-2-yl)-4-(trifluoromethyl)benzamide To a solution of 2-fluoro-5-(pyrimidin-2-yl)-4-(trifluoromethyl)benzoic acid (96 mg, 0.30 mmol) in pyridine (2 mL) at 26° C. was added POCl$_3$ (103 mg, 0.7 mmol). The mixture was stirred at for 5 min before 1-(7-amino-6-phenyl-1H-indazol-3-yl)ethanone (100 mg, 0.40 mmol) was added. The resulting mixture was stirred for another 30 min, then partitioned between water (10 mL) and EtOAc (10 mL×3). The combined organic layers were dried over Na$_2$SO$_4$ and concentrated. The residue was purified by preparative TLC (PE/EtOAc=1/1) to give the title compound. MS: m/z=520.1 (M+1).

Step B: 2-Fluoro-N-(3-(2-hydroxypropan-2-yl)-6-phenyl-1H-indazol-7-yl)-5-(pyrimidin-2-yl)-4-(trifluoromethyl)benzamide To a solution of N-(3-acetyl-6-phenyl-1H-indazol-7-yl)-2-fluoro-5-(pyrimidin-2-yl)-4-(trifluoromethyl)benzamide (80 mg, 0.10 mmol) in THF (2 mL) at 0° C. was added dropwise a solution of methylmagnesium bromide in diethyl ether (0.5 mL, 1.40 mmol, 3M). The resulting mixture was stirred at 26° C. for 1 h, then partitioned between saturated aqueous ammonium chloride solution (10 mL) and EtOAc (10 mL×3). The combined organic layers were dried over Na$_2$SO$_4$ and concentrated. The residue was purified by reverse-phase HPLC under basic conditions (H$_2$O/CH$_3$CN gradient with 0.05% NH$_4$OH present) to give the title compound. MS: m/z=536.1 (M+1). $^1$H NMR (400 MHz, CD$_3$OD) δ 8.95 (d, J=5.0 Hz, 2H), 8.21 (d, J=6.5 Hz, 1H), 8.13 (d, J=8.5 Hz, 1H), 7.76 (d, J=10.5 Hz, 1H), 7.57 (t, J=4.8 Hz, 1H), 7.49-7.54 (m, 2H), 7.43 (t, J=7.5 Hz, 2H), 7.33-7.38 (m, 1H), 7.20 (d, J=8.5 Hz, 1H), 1.77 (s, 6H).

Examples 46 and 47

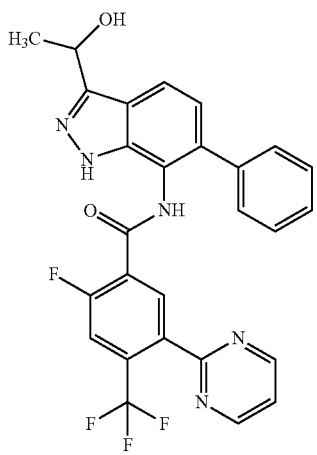 [SMILES: CC(O)c1n[nH]c2c(NC(=O)c3cc(-c4ncccn4)c(C(F)(F)F)cc3F)c(-c3ccccc3)ccc12]

(R) and (S)-2-Fluoro-N-(3-(1-hydroxyethyl)-6-phenyl-1H-indazol-7-yl)-5-(pyrimidin-2-yl)-4-(trifluoromethyl)benzamide To a solution of N-(3-acetyl-6-phenyl-1H-indazol-7-yl)-2-fluoro-5-(pyrimidin-2-yl)-4-(trifluoromethyl)benzamide (100 mg, 0.185 mmol) in MeOH (2 ml) at 26° C. was added sodium tetrahydroborate (21 mg, 0.55 mmol). The resulting mixture was stirred for 1 h, then diluted with water (0.5 ml) and concentrated. The residue was purified by reverse-phase HPLC under basic conditions (H$_2$O/CH$_3$CN gradient with 0.05% NH$_4$OH present) followed by SFC (column: AD (250 mm*30 mm, 10 um); Mobile phase: A: Supercritical CO$_2$, B: EtOH(base), A:B=50:50 at 80 mL/min; Wavelength: 220 nm) to give the title compounds. Enantiomer 1, Example 46: MS: m/z=522.2 (M+1). $^1$H NMR (400 MHz, CD$_3$OD) δ 8.92 (d, 2H), 8.44 (d, 1H), 8.20 (d, 1H), 7.78 (d, 1H), 7.56 (t, 1H), 7.49-7.54 (m, 2H), 7.43 (t, 2H), 7.33-7.38 (m, 1H), 7.24 (d, 1H), 5.76 (m, 1H), 1.73 (d, 3H). Enantiomer 2, Example 47: MS: m/z=522.0 (M+1). $^1$H NMR (400 MHz, CD$_3$OD) δ 8.92 (d, 2H), 8.44 (d, 1H), 8.20 (d, 1H), 7.78 (d, 1H), 7.56 (t, 1H), 7.49-7.54 (m, 2H), 7.43 (t, 2H), 7.33-7.38 (m, 1H), 7.24 (d, 1H), 5.76 (m, 1H), 1.73 (d, 3H).

The following examples were prepared in similar fashion to the procedures described above.

| Compound Number | Structure | Compound Name | LCMS (M + 1) |
|---|---|---|---|
| 48 | 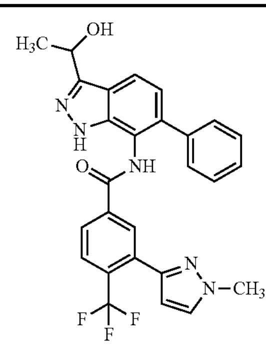 | (R) or (S)-N-[3-(1-hydroxyethyl)-6-phenyl-1H-indazol-7-yl]-3-(1-methyl-1H-pyrazol-3-yl)-4-(trifluoromethyl)benzamide | 506.1 |
| 49 | 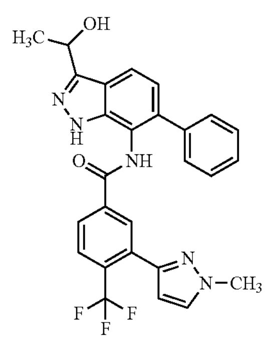 [SMILES: CC(O)c1n[nH]c2c(NC(=O)c3ccc(C(F)(F)F)c(-c4ccn(C)n4)c3)c(-c3ccccc3)ccc12] | (R) or (S)-N-[3-(1-hydroxyethyl)-6-phenyl-1H-indazol-7-yl]-3-(1-methyl-1H-pyrazol-3-yl)-4-(trifluoromethyl)benzamide | 506.1 |

Example 50

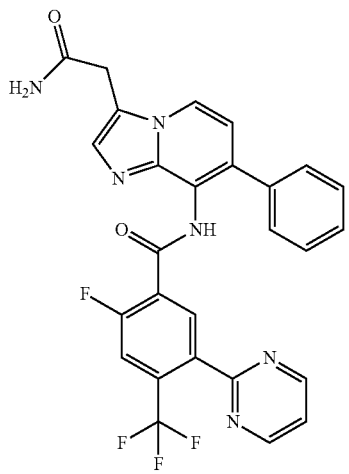 [SMILES: NC(=O)Cc1cnc2c(NC(=O)c3cc(-c4ncccn4)c(C(F)(F)F)cc3F)c(-c3ccccc3)ccn12]

N-(3-(2-Amino-2-oxoethyl)-7-phenylimidazo[1,2-a]pyridin-8-yl)-2-fluoro-5-(pyrimidin-2-yl)-4-(trifluoromethyl)benzamide

Step A: N-(3-(Cyanomethyl)-7-phenylimidazo[1,2-a]pyridin-8-yl)-2-fluoro-5-(pyrimidin-2-yl)-4-(trifluoromethyl)benzamide To a solution of 2-(8-amino-7-phenylimidazo[1,2-a]pyridin-3-yl)acetonitrile (9 mg, 0.04 mmol) and 2-fluoro-5-(pyrimidin-2-yl)-4-(trifluoromethyl)benzoic acid (12 mg, 0.039 mmol) in pyridine (0.3 mL) at 20° C. was added POCl$_3$ (0.0067 mL, 0.072 mmol). The resulting mixture was stirred for 20 min, thn partitioned between saturated aqueous sodium carbonate solution (5 mL) and EtOAc (10 mL×3). The combined organic layers were dried over Na$_2$SO$_4$ and concentrated to afford the title compound. MS: m/z=517.1 (M+1).

Step B: N-(3-(2-Amino-2-oxoethyl)-7-phenylimidazo[1,2-a]pyridin-8-yl)-2-fluoro-5-(pyrimidin-2-yl)-4-(trifluoromethyl)benzamide To a solution of N-(3-(cyanomethyl)-7-phenylimidazo[1,2-a]pyridin-8-yl)-2-fluoro-5-(pyrimidin-2-yl)-4-(trifluoromethyl)benzamide (9 mg, 0.02 mmol) in DMSO (0.5 mL) at 0° C. was added K$_2$CO$_3$ (2.4 mg, 0.017 mmol) and aqueous 35% H$_2$O$_2$ solution (0.003 mL, 0.03 mmol). The resulting mixture was stirred at 0° C. for 15 min, then partitioned between EtOAc (10 mL) and brine (5 mL). The organic layer was dried over Na$_2$SO$_4$ and concentrated. The residue was purified by column chromatography on silica gel (PE/EtOAc=4/5) to afford the title compound. MS: m/z=535.1 (M+1). $^1$H NMR (400 MHz, CDCl$_3$) δ 8.84 (d, J=4.70 Hz, 2H), 8.71 (d, J=11.35 Hz, 1H), 8.40 (d, J=6.65 Hz, 1H), 8.08 (d, J=7.04 Hz, 1H), 7.56-7.64 (m, 2H), 7.52 (d, J=7.43 Hz, 2H), 7.42 (t, J=7.43 Hz, 2H), 7.30-7.37 (m, 2H), 7.03 (d, J=7.04 Hz, 1H), 5.66 (br s, 1H), 5.41 (br s, 1H), 3.93 (s, 2H).

Example 51

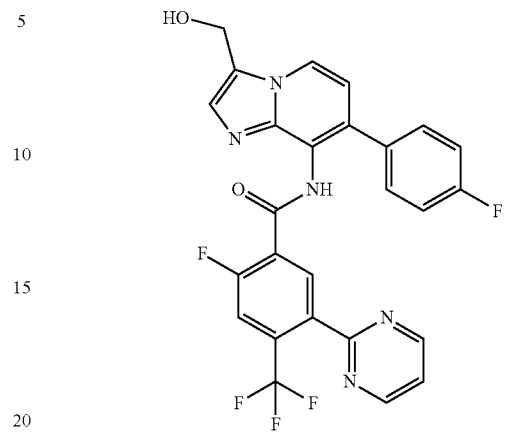

2-Fluoro-N-(7-(4-fluorophenyl)-3-(hydroxymethyl)imidazo[1,2-a]pyridin-8-yl)-5-(pyrimidin-2-yl)-4-(trifluoromethyl)benzamide

Step A: Ethyl 8-(2-fluoro-5-(pyrimidin-2-yl)-4-(trifluoromethyl)benzamido)-7-(4-fluorophenyl) imidazo[1,2-a]pyridine-3-carboxylate To a solution of 2-fluoro-5-(pyrimidin-2-yl)-4-(trifluoromethyl)benzoic acid (406 mg, 1.4 mmol)) and ethyl 8-amino-7-(4-fluorophenyl)imidazo[1,2-a]pyridine-3-carboxylate (500 mg, 1.4 mmol) in pyridine (8.0 mL) at 26° C. was added phosphorus oxychloride (0.30 mL, 2.8 mmol). The resulting mixture was stirred for 5 min, then partitioned between water (20 mL) and EtOAc (20 mL×3). The combined organic layers were dried over Na$_2$SO$_4$ and concentrated to give the title compound. MS: m/z=568.2 (M+1).

Step B: 2-Fluoro-N-(7-(4-fluorophenyl)-3-(hydroxymethyl)imidazo[1,2-a]pyridin-8-yl)-5-(pyrimidin-2-yl)-4-(trifluoromethyl)benzamide To a solution of ethyl 8-(2-fluoro-5-(pyrimidin-2-yl)-4-(trifluoromethyl)benzamido)-7-(4-fluorophenyl)imidazo[1,2-a]pyridine-3-carboxylate (410 mg, 0.722 mmol) in tetrahydrofuran (10 mL) at 0° C. was added LAH (55 mg, 1.4 mmol). The resulting mixture was stirred for 10 min, then partitioned between water (10 mL) and EtOAc (10 mL×3). The combined organic layers were dried over Na$_2$SO$_4$ and concentrated. The residue was purified by reverse-phase HPLC under basic conditions (H$_2$O/CH$_3$CN gradient with 0.05% NH$_4$OH present) to give the title compound. MS: m/z=526.1 (M+1). $^1$H NMR (400 MHz, CD$_3$OD) δ 8.90 (d, J=5.1 Hz, 2H), 8.50 (d, J=7.0 Hz, 1H), 8.21 (d, J=6.7 Hz, 1H), 7.73 (d, J=10.6 Hz, 1H), 7.55 (br, 3H), 7.50-7.53 (m, 1H), 7.17 (t, J=8.4 Hz, 2H), 7.10 (d, J=6.7 Hz, 1H), 4.96 (br, 2H).

The following examples were prepared in similar fashion to the procedures described above, as well as the procedures for Examples 9-11.

| Compound Number | Structure | Compound Name | LCMS (M + 1) |
|---|---|---|---|
| 52 | 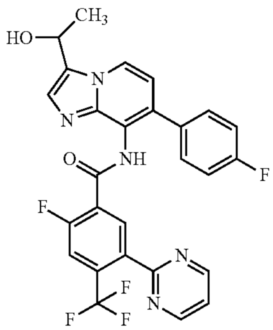 [SMILES: CC(O)c1cnc2c(NC(=O)c3cc(-c4ncccn4)c(C(F)(F)F)cc3F)c(-c3ccc(F)cc3)ccn12] | (R) or (S)-2-fluoro-N-[7-(4-fluorophenyl)-3-(1-hydroxyethyl)imidazo[1,2-a]pyridin-8-yl]-5-pyrimidin-2-yl-4-(trifluoromethyl)benzamide | 540.1 |
| 53 | 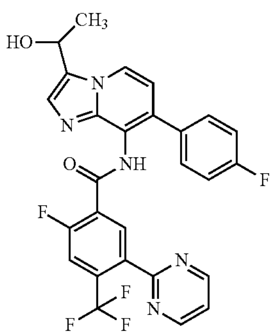 [SMILES: CC(O)c1cnc2c(NC(=O)c3cc(-c4ncccn4)c(C(F)(F)F)cc3F)c(-c3ccc(F)cc3)ccn12] | (R) or (S)-2-fluoro-N-[7-(4-fluorophenyl)-3-(1-hydroxyethyl)imidazo[1,2-a]pyridin-8-yl]-5-pyrimidin-2-yl-4-(trifluoromethyl)benzamide | 540.1 |
| 54 | 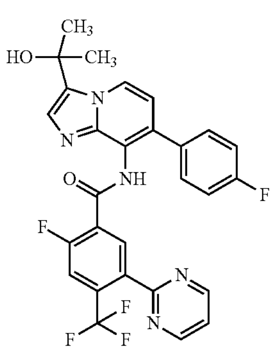 [SMILES: CC(C)(O)c1cnc2c(NC(=O)c3cc(-c4ncccn4)c(C(F)(F)F)cc3F)c(-c3ccc(F)cc3)ccn12] | 2-fluoro-N-[7-(4-fluorophenyl)-3-(1-hydroxy-1-methylethyl)imidazo[1,2-a]pyridin-8-yl]-5-pyrimidin-2-yl-4-(trifluoromethyl)benzamide | 554.1 |

Example 55

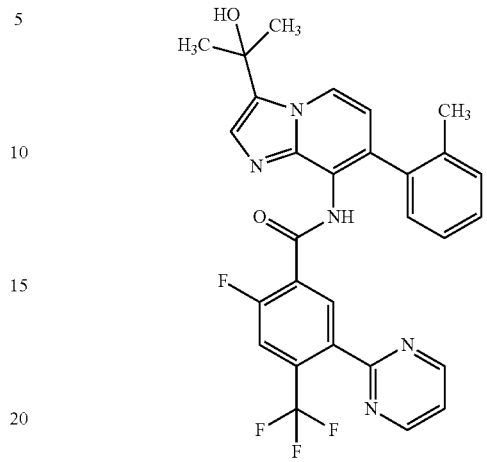

2-Fluoro-N-(3-(2-hydroxypropan-2-yl)-7-(o-tolyl)imidazo[1,2-a]pyridin-8-yl)-5-(pyrimidin-2-yl)-4-(trifluoromethyl)benzamide Step A: Ethyl 8-(2-fluoro-5-(pyrimidin-2-yl)-4-(trifluoromethyl)benzamido)-7-(o-tolyl)-imidazo[1,2-a]pyridine-3-carboxylate To a solution of 2-fluoro-5-(pyrimidin-2-yl)-4-(trifluoromethyl)benzoic acid (0.26 g, 0.91 mmol) and ethyl 8-amino-7-(o-tolyl)imidazo[1,2-a]pyridine-3-carboxylate (0.30 g, 0.91 mmol) in pyridine (6 mL) at 26° C. was added POCl$_3$ (0.17 mL, 1.83 mmol). The resulting mixture was stirred for 10 min, then partitioned between water (20 mL) and EtOAc (20 mL×2). The combined organic layers were dried over Na$_2$SO$_4$ and concentrated. The residue was dissolved in a mixture of THF (5 mL) and water (5 mL), and lithium hydroxide (34 mg, 1.4 mmol) was added. The resulting mixture was stirred at 26° C. for 1 h, then partitioned between water (10 mL) and EtOAc (20 mL×2). The combined organic layers were dried over Na$_2$SO$_4$ and concentrated. The residue was purified by preparative TLC (PE/EtOAc=1/1) to give the title compound. $^1$H NMR (400 MHz, CD$_3$OD) δ 9.37 (d, J=7.0 Hz, 1H), 8.89 (d, J=5.1 Hz, 2H), 8.27 (s, 1H), 7.98 (d, J=5.5 Hz, 1H), 7.66 (d, J=10.2 Hz, 1H), 7.51 (t, J=4.9 Hz, 1H), 7.15-7.28 (m, 5H), 4.44 (q, J=7.0 Hz, 2H), 1.42 (t, J=7.2 Hz, 3H).

Step B: 2-Fluoro-N-(3-(2-hydroxypropan-2-yl)-7-(o-tolyl)imidazo[1,2-a]pyridin-8-yl)-5-(pyrimidin-2-yl)-4-(trifluoromethyl)benzamide To a solution of ethyl 8-(2-fluoro-5-(pyrimidin-2-yl)-4-(trifluoromethyl)benzamido)-7-(o-tolyl)imidazo[1,2-a]pyridine-3-carboxylate (50 mg, 0.06 mmol) in THF (10 mL) at 0° C. was added a solution of methylmagnesium bromide in diethyl ether (0.41 mL, 1.24 mmol, 3M). The resulting mixture was stirred at 0° C. for 10 min, then partitioned between saturated aqueous ammonia chloride solution (10 mL) and EtOAc (20 mL×3). The combined organic layers were dried over Na$_2$SO$_4$ and concentrated. The residue was purified by reverse-phase HPLC under basic conditions (H$_2$O/CH$_3$CN gradient with 0.05% NH$_4$OH present) to give the title compound. MS: m/z=550.1 (M+1). ¹H NMR (400 MHz, CD₃OD) δ 8.87-8.96 (m, 3H), 8.04 (d, J=6.3 Hz, 1H), 7.68 (d, J=9.8 Hz, 1H), 7.54 (t, J=4.9 Hz, 1H), 7.48 (s, 1H), 7.20-7.32 (m, 4H), 6.94 (d, J=7.0 Hz, 1H), 2.27 (s, 3H), 1.79 (s, 6H).

Example 56

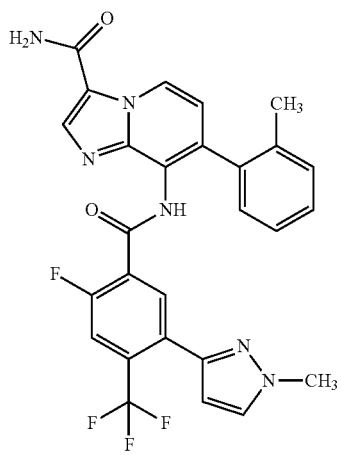 [SMILES: Cc1ccccc1-c1ccn2c(C(N)=O)cnc2c1NC(=O)c1cc(-c2ccn(C)n2)c(C(F)(F)F)cc1F]

8-(2-Fluoro-5-(1-methyl-1H-pyrazol-3-yl)-4-(trifluoromethyl)benzamido)-7-(o-tolyl)imidazo[1,2-a]pyridine-3-carboxamide Step A: Ethyl 8-(2-fluoro-5-(1-methyl-1H-pyrazol-3-yl)-4-(trifluoromethyl)benzamido)-7-(o-tolyl)imidazo[1,2-a]pyridine-3-carboxylate To a solution of 2-fluoro-5-(1-methyl-1H-pyrazol-3-yl)-4-(trifluoromethyl)benzoic acid (146 mg, 0.51 mmol) and ethyl 8-amino-7-(o-tolyl)imidazo[1,2-a]pyridine-3-carboxylate (150 mg, 0.51 mmol) in pyridine (8 mL) at 15° C. was added phosphoryl trichloride (0.046 mL, 0.51 mmol). The resulting mixture was stirred for 20 min, then partitioned between water (20 mL) and EtOAc (20 mL×2). The combined organic layers were dried over Na₂SO₄ and concentrated to give the title compound. MS: m/z=566.2 (M+1). ¹H NMR (400 MHz, CD₃OD) δ 9.42 (d, J 7.0 Hz, 1H), 8.32 (s, 1H), 7.85 (s, 1H), 7.68 (s, 1H), 7.63 (d, J=10.5 Hz, 1H), 7.18-7.35 (m, 5H), 6.44 (s, 1H), 4.49 (q, J=7.0 Hz, 2H), 3.98 (s, 3H), 2.27 (s, 3H), 1.46 (t, J=7.0 Hz, 3H).

Step B: 8-(2-Fluoro-5-(1-methyl-1H-pyrazol-3-yl)-4-(trifluoromethyl)benzamido)-7-(o-tolyl)imidazo[1,2-a]pyridine-3-carboxylic acid To a solution of ethyl 8-(2-fluoro-5-(1-methyl-1H-pyrazol-3-yl)-4-(trifluoromethyl)benzamido)-7-(o-tolyl)imidazo[1,2-a]pyridine-3-carboxylate (126 mg, 0.22 mmol) in a mixture of THF (3 mL) and water (3 mL) was added sodium hydroxide (27 mg, 0.67 mmol). The resulting mixture was stirred at 15° C. for 1 h, then diluted with water (10 mL) and acidified with aqueous hydrochloric acid solution (1 M) to pH 4. The aqueous layer was extracted with EtOAc (20 mL×2). The combined organic layers were dried over Na₂SO₄ and concentrated to give the title compound. MS: m/z=538.1 (M+1).

Step C: 8-(2-Fluoro-5-(1-methyl-1H-pyrazol-3-yl)-4-(trifluoromethyl)benzamido)-7-(o-tolyl)imidazo[1,2-a]pyridine-3-carboxamide To a solution of 8-(2-fluoro-5-(1-methyl-1H-pyrazol-3-yl)-4-(trifluoromethyl)benzamido)-7-(o-tolyl)imidazo[1,2-a]pyridine-3-carboxylic acid (90 mg, 0.17 mmol) in dichloromethane (5 mL) at 15° C. were added ammonium chloride (18 mg, 0.34 mmol), TEA (0.070 mL, 0.50 mmol) and HATU (127 mg, 0.34 mmol). The resulting mixture was stirred for 1.5 h, then partitioned between water (10 mL) and EtOAc (20 mL×3). The combined organic layers were dried over Na₂SO₄ and concentrated. The residue was purified by reverse-phase HPLC under basic conditions (H₂O/CH₃CN gradient with 0.05% NH₄OH present) to give the title compound. MS: m/z=537.1 (M+1). ¹H NMR (400 MHz, CD₃OD) δ 9.53 (d, J=7.0 Hz, 1H), 8.32 (s, 1H), 7.83 (d, J=6.3 Hz, 1H), 7.62 (s, 1H), 7.57 (d, J=10.6 Hz, 1H), 7.16-7.32 (m, 4H), 7.09 (d, J=7.0 Hz, 1H), 6.39 (s, 1H), 3.93 (s, 3H), 2.22 (s, 3H).

Example 57

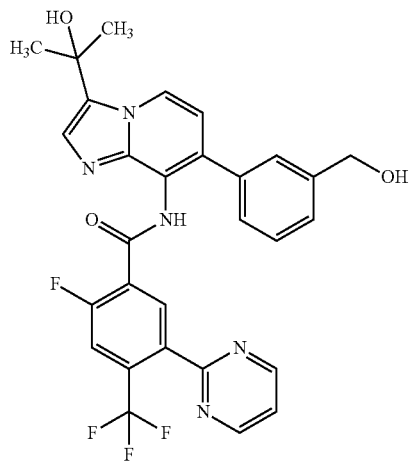 [SMILES: CC(C)(O)c1cnc2c(NC(=O)c3cc(-c4ncccn4)c(C(F)(F)F)cc3F)c(-c3cccc(CO)c3)ccn12]

2-Fluoro-N-(7-(3-(hydroxymethyl)phenyl)-3-(2-hydroxypropan-2-yl)imidazo[1,2-a]pyridin-8-yl)-5-(pyrimidin-2-yl)-4-(trifluoromethyl)benzamide Step A: 8-Ethyl 7-(3-(((tert-butyldimethylsilyl)oxy)methyl)phenyl)-8-(2-fluoro-5-(pyrimidin-2-yl)-4-(trifluoromethyl)benzamido)imidazo[1,2-a]pyridine-3-carboxylate To a solution of 2-fluoro-5-(pyrimidin-2-yl)-4-(trifluoromethyl)benzoic acid (200 mg, 0.69 mmol) and ethyl 8-amino-7-(3-(((tert-butyldimethylsilyl)oxy)methyl)phenyl)imidazo[1,2-a]pyridine-3-carboxylate (390 mg, 0.69 mmol) in pyridine (8 mL) at 26° C. was added POCl₃ (0.13 mL, 1.4 mmol). The resulting mixture was stirred for 10 min, then partitioned between water (20 mL) and EtOAc (20 mL×3). The combined organic layers were dried over Na₂SO₄ and concentrated. The residue was dissolved in a mixture of THF (10 mL) and water (10 mL), and lithium hydroxide (23 mg, 0.95 mmol) was added. The mixture was stirred at 26° C. for 1 h, then partitioned between water (10 mL) and EtOAc (20 mL×3). The combined organic layers were dried over Na₂SO₄ and concentrated. The residue was purified by preparative TLC (PE/EtOAc=1/1) to give the title compound. ¹H NMR (400 MHz, CD₃OD) δ 9.35 (d, J=7.0 Hz, 1H), 8.81-8.91 (m, 2H), 8.23 (s, 1H), 8.15 (d, J=6.3 Hz, 1H), 7.69 (d, J=10.2 Hz, 1H), 7.45-7.52 (m, 2H), 7.34-7.43 (m, 3H), 7.27 (d, J=7.0 Hz, 1H), 4.72 (s, 2H), 4.41 (q, J=7.3 Hz, 2H), 1.39 (t, J=7.0 Hz, 3H), 0.82-0.85 (m, 9H), 0.00 (s, 6H).

Step B: N-(7-(3-(((tert-butyldimethylsilyl)oxy) methyl)phenyl)-3-(2-hydroxypropan-2-yl) imidazo [1,2-a]pyridin-8-yl)-2-fluoro-5-(pyrimidin-2-yl)-4-(trifluoromethyl)benzamide To a solution of ethyl 7-(3-(((tert-butyldimethylsilyl)oxy) methyl)phenyl)-8-(2-fluoro-5-(pyrimidin-2-yl)-4-(trifluoromethyl)benzamido)imidazo[1,2-a]pyridine-3-carboxylate (40 mg, 0.043 mmol) in THF (10 mL) at 0° C. was added a solution of methylmagnesium bromide in ethyl ether (0.29 mL, 0.87 mmol, 3M). The resulting mixture was stirred at 0° C. for 30 min, then partitioned between saturated aqueous ammonia chloride solution (10 mL) and EtOAc (20 mL×3). The combined organic layers were dried over Na₂SO₄ and concentrated. The residue was purified by preparative TLC (PE/EtOAc=1/1) to give the title compound. MS: m/z=680.2 (M+1).

Step C: 2-Fluoro-N-(7-(3-(hydroxymethyl)phenyl)-3-(2-hydroxypropan-2-yl)imidazo-[1,2-a]pyridin-8-yl)-5-(pyrimidin-2-yl)-4-(trifluoromethyl)benzamide To a solution of N-(7-(3-(((tert-butyldimethylsilyl)oxy) methyl)phenyl)-3-(2-hydroxypropan-2-yl)imidazo[1,2-a] pyridin-8-yl)-2-fluoro-5-(pyrimidin-2-yl)-4-(trifluoromethyl)benzamide (32 mg, 0.039 mmol) in THF (5 mL) at 26° C. was added a solution of TBAF in THF (0.12 mL, 0.12 mmol, 1M). The resulting mixture was stirred for 3 h, then purified by prep-TLC (100% EtOAc) followed by reverse-phase HPLC under basic conditions (H₂O/CH₃CN gradient with 0.05% NH₄OH present) to give the title compound. MS: m/z=566.2 (M+1). ¹H NMR (400 MHz, CD₃OD) δ 8.88-8.97 (m, 3H), 8.22 (d, J=6.8 Hz, 1H), 7.76 (d, J=10.5 Hz, 1H), 7.53-7.60 (m, 2H), 7.44-7.52 (m, 3H), 7.39-7.43 (m, 1H), 7.10 (d, J=7.0 Hz, 1H), 4.66 (s, 2H), 1.78 (s, 6H).

Example 58

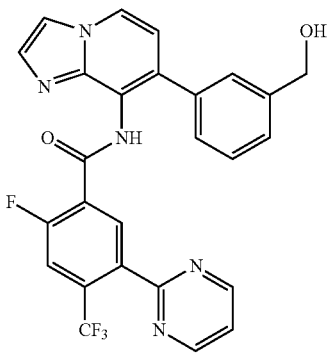 [SMILES: O=C(Nc1c(-c2cccc(CO)c2)ccn2ccnc12)c1cc(-c2ncccn2)c(C(F)(F)F)cc1F]

2-Fluoro-N-(7-(3-(hydroxymethyl)phenyl)imidazo [1,2-a]pyridin-8-yl)-5-(pyrimidin-2-yl)-4-(trifluoromethyl)benzamide Step A: Methyl 3-(8-(2-fluoro-5-(pyrimidin-2-yl)-4-(trifluoromethyl)-benzamido)imidazo[1,2-a]pyridin-7-yl)benzoate To a solution of 2-fluoro-5-(pyrimidin-2-yl)-4-(trifluoromethyl)benzoic acid (160 mg, 0.56 mmol) and methyl 3-(8-aminoimidazo[1,2-a]pyridin-7-yl)benzoate (150 mg, 0.56 mmol) in pyridine (5 mL) at 15° C. was added phosphoryl trichloride (0.10 mL, 1.12 mmol). The resulting mixture was stirred for 20 min, then partitioned between water (20 mL) and EtOAc (20 mL×3). The combined organic layers were dried over Na₂SO₄ and concentrated. The residue was dissolved in a mixture of THF (5 mL) and water (2 mL), and lithium hydroxide (5.7 mg, 0.24 mmol) was added. The resulting mixture was stirred at 15° C. for 1 h, then partitioned between water (10 mL) and EtOAc (20 mL×2). The combined organic layers were dried over Na₂SO₄ and concentrated. The residue was purified by preparative TLC (PE/EtOAc=1/1) to give the title compound. MS: m/z=536.2 (M+1).

Step B: 2-Fluoro-N-(7-(3-(hydroxymethyl)phenyl) imidazo[1,2-a]pyridin-8-yl)-5-(pyrimidin-2-yl)-4-(trifluoromethyl)benzamide To a solution of methyl 3-(8-(2-fluoro-5-(pyrimidin-2-yl)-4-(trifluoromethyl)benzamido)imidazo[1,2-a]pyridin-7-yl) benzoate (80 mg, 0.15 mmol) in THF (5 mL) at 0° C. was added LAH (17 mg, 0.45 mmol). The resulting mixture was stirred at 0° C. for 10 min, then partitioned between water (10 mL) and EtOAc (10 mL×3). The combined organic layers were dried over Na₂SO₄ and concentrated. The residue was purified by reverse-phase HPLC under basic conditions (H₂O/CH₃CN gradient with 0.05% NH₄OH present) to give the title compound. MS: m/z=508.1 (M+1). ¹H NMR (400 MHz, CD₃OD) δ 8.89 (d, J=5.1 Hz, 2H), 8.50 (d, J=7.0 Hz, 1H), 8.18 (d, J=6.7 Hz, 1H), 7.92 (s, 1H), 7.72 (d, J=10.2 Hz, 1H), 7.58 (s, 1H), 7.48-7.55 (m, 2H), 7.34-7.47 (m, 3H), 7.02 (d, J=6.7 Hz, 1H), 4.61 (s, 2H).

Example 59

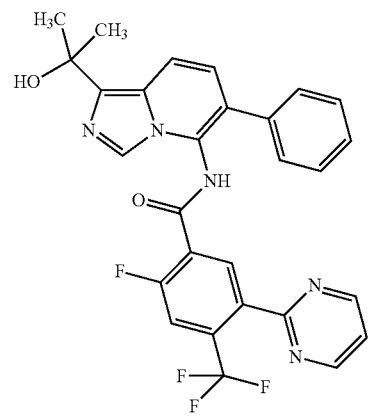 [SMILES: CC(C)(O)c1ncn2c(NC(=O)c3cc(-c4ncccn4)c(C(F)(F)F)cc3F)c(-c3ccccc3)ccc12]

2-Fluoro-N-(1-(2-hydroxypropan-2-yl)-6-phenylimidazo[1,5-a]pyridin-5-yl)-5-(pyridin-2-yl)-4-(trifluoromethyl)benzamide

Step A: Ethyl 5-(2-fluoro-5-(pyrimidin-2-yl)-4-(trifluoromethyl)benzamido)-6-phenylimidazo[1,5-a]pyridine-1-carboxylate To a solution of ethyl 5-amino-6-phenylimidazo[1,5-a]pyridine-1-carboxylate (97 mg, 0.35 mmol) and 2-fluoro-5-(pyrimidin-2-yl)-4-(trifluoromethyl)benzoic acid (109 mg, 0.38 mmol) in pyridine (5 mL) at 20° C. was added $POCl_3$ (0.032 mL, 0.35 mmol). The resulting mixture was stirred for 30 min, then partitioned between saturated aqueous $NaHCO_3$ solution (30 mL) and ethyl acetate (20 mL×3). The combined organic layers were washed with saturated aqueous $NaHCO_3$ solution and brine, dried over $Na_2SO_4$ and concentrated. The residue was purified by preparative TLC (PE/EA=1/1) to give the title compound. MS: m/z=550.1 (M+1).

Step B: 2-Fluoro-N-(1-(2-hydroxypropan-2-yl)-6-phenylimidazo[1,5-a]pyridin-5-yl)-5-(pyridin-2-yl)-4-(trifluoromethyl)benzamide To a solution of ethyl 5-(2-fluoro-5-(pyrimidin-2-yl)-4-(trifluoromethyl)benzamido)-6-phenylimidazo[1,5-a]pyridine-1-carboxylate (100 mg, 0.18 mmol) in THF (3 mL) at 0° C. was added a solution of methylmagnesium bromide in diethyl ether (1.82 mL, 5.46 mmol, 3M) dropwise under $N_2$ atmosphere. The resulting mixture was stirred at 0° C. for 1.5 h, then partitioned between saturated aqueous $NH_4Cl$ solution (20 mL) and ethyl acetate (10 mL×3).

The combined organic layers were washed with brine, dried over $Na_2SO_4$ and concentrated. The residue was purified by preparative TLC (PE/EA=1/3) to give the title compound. MS: m/z=536.1 (M+1). $^1H$ NMR (400 MHz, $CD_3OD$) δ 8.93 (d, J=4.9 Hz, 2H), 8.18-8.24 (m, 1H), 8.05 (d, J=9.4 Hz, 1H), 7.99 (d, J=6.5 Hz, 1H), 7.83 (br, 1H), 7.55 (t, J=5.0 Hz, 1H), 7.50 (d, J=7.0 Hz, 2H), 7.43 (t, J=7.3 Hz, 2H), 7.36 (d, J=7.2 Hz, 1H), 6.89-6.99 (m, 1H), 1.70 (s, 6H).

Reaction Scheme for Example 60

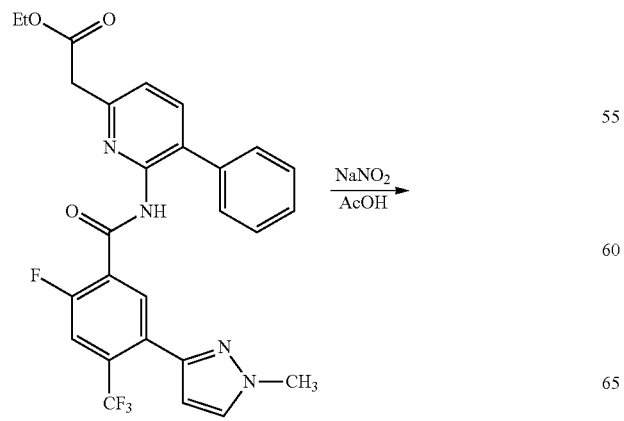

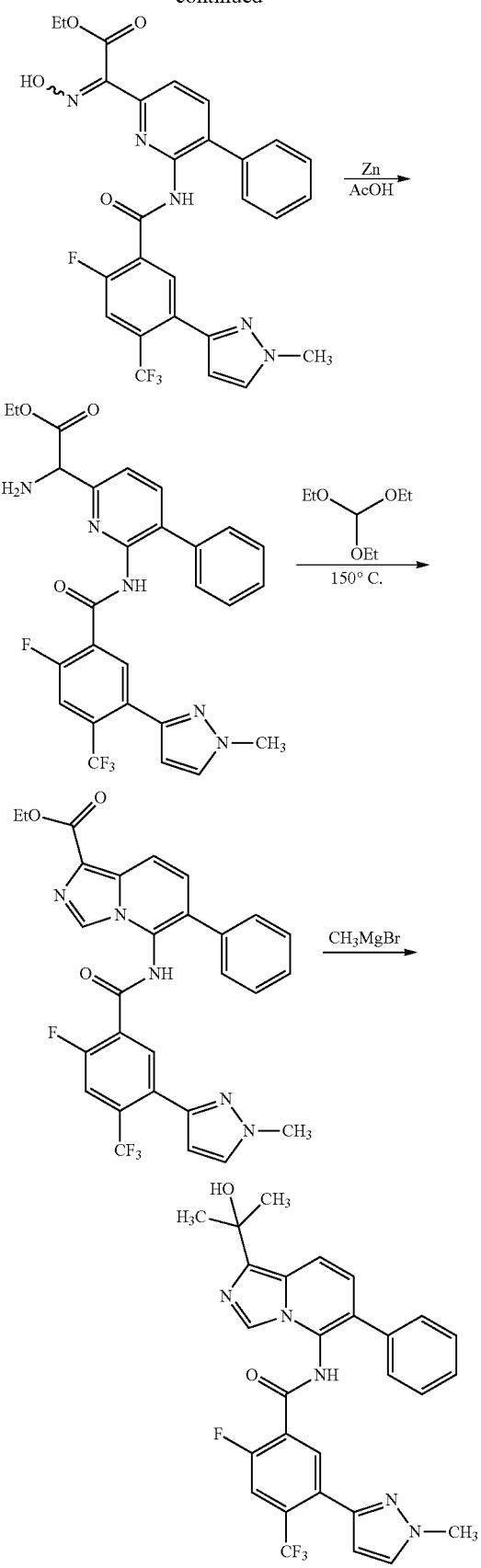

Example 60

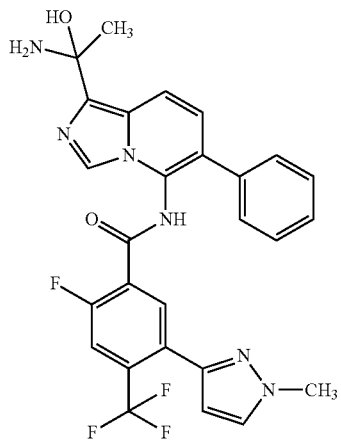 [SMILES: Cn1ccc(-c2cc(C(=O)Nc3c(-c4ccccc4)ccc4c(C(C)(N)O)ncn34)c(F)cc2C(F)(F)F)n1]

2-Fluoro-N-(1-(2-hydroxypropan-2-yl)-6-phenylimidazo[1,5-a]pyridin-5-yl)-5-(1-methyl-1H-pyrazol-3-yl)-4-(trifluoromethyl)benzamide

Step A: Ethyl 2-(6-(2-fluoro-5-(1-methyl-1H-pyrazol-3-yl)-4-(trifluoromethyl)benzamido)-5-phenylpyridin-2-yl)acetate To a solution of ethyl 2-(6-amino-5-phenylpyridin-2-yl)acetate (400 mg, 1.56 mmol) and 2-fluoro-5-(1-methyl-1H-pyrazol-3-yl)-4-(trifluoromethyl)benzoic acid (495 mg, 1.72 mmol) in pyridine (5 mL) at 20° C. was added $POCl_3$ (0.15 mL, 1.6 mmol). The resulting mixture was stirred for 30 min, then carefully diluted with saturated aqueous $NaHCO_3$ solution (30 mL) and extracted with EtOAc (20 mL×3). The combined organic layers were washed with saturated aqueous $NaHCO_3$ solution and brine, dried over $Na_2SO_4$ and concentrated. The residue was purified by flash silica gel chromatography (ISCO; 12 g SepaFlash® Silica Flash Column, EtOAc in petroleum ether: 0-50%, 30 mL/min, dry loaded) to give the title compound. MS: m/z=527.2 (M+1). $^1$H NMR (400 MHz, CDCl$_3$) δ 8.42 (br, 1H), 8.16 (br, 1H), 7.75 (d, J=6.0 Hz, 1H), 7.69 (d, J=7.0 Hz, 1H), 7.42-7.52 (m, 4H), 7.36-7.41 (m, 2H), 6.43 (d, J=18.6 Hz, 2H), 3.91-3.98 (m, 4H), 1.25 (q, J=7.0 Hz, 3H).

Step B: Ethyl 2-(6-(2-fluoro-5-(1-methyl-1H-pyrazol-3-yl)-4-(trifluoromethyl)benzamido)-5-phenylpyridin-2-yl)-2-(hydroxyimino)acetate To a solution of ethyl 2-(6-(2-fluoro-5-(1-methyl-1H-pyrazol-3-yl)-4-(trifluoromethyl)benzamido)-5-phenylpyridin-2-yl)acetate (150 mg, 0.19 mmol) in AcOH (1 mL) was added a solution of sodium nitrite (26 mg, 0.38 mmol) in water (1 mL). The resulting mixture was stirred at 20° C. for 2 h, then partitioned between saturated aqueous $NaHCO_3$ solution (30 mL) and EtOAc (20 mL×3). The combined organic layers were washed with saturated aqueous $NaHCO_3$ solution and brine, dried over $Na_2SO_4$ and concentrated to give the title compound. MS: m/z=556.1 (M+1).

Step C: Ethyl 2-amino-2-(6-(2-fluoro-5-(1-methyl-1H-pyrazol-3-yl)-4-(trifluoromethyl)benzamido)-5-phenylpyridin-2-yl)acetate To a solution of ethyl 2-(6-(2-fluoro-5-(1-methyl-1H-pyrazol-3-yl)-4-(trifluoromethyl)benzamido)-5-phenylpyridin-2-yl)-2-(hydroxyiminso)acetate (120 mg, 0.14 mmol) in AcOH (2 mL) at 15° C. was added zinc powder (44.5 mg, 0.68 mmol). The resulting mixture was stirred for 3 h, then partitioned between saturated aqueous $NaHCO_3$ solution (30 mL) and EtOAc (20 mL×3). The combined organic layers were washed with brine, dried over $Na_2SO_4$ and concentrated to give the title compound. MS: m/z=542.1 (M+1).

Step D: Ethyl 2-amino-2-(6-(2-fluoro-5-(1-methyl-1H-pyrazol-3-yl)-4-(trifluoromethyl)benzamido)-5-phenylpyridin-2-yl)acetate The mixture of ethyl 2-amino-2-(6-(2-fluoro-5-(1-methyl-1H-pyrazol-3-yl)-4-(trifluoromethyl)benzamido)-5-phenylpyridin-2-yl)acetate (85 mg, 0.13 mmol) and triethoxymethane (0.22 mL, 1.29 mmol) was heated at 150° C. for 1 h. The product mixture was concentrated and the residue was purified by flash silica gel chromatography (ISCO; 12 g SepaFlash® Silica Flash Column, EtOAc in petroleum ether: 0-60%, 30 mL/min, dry loaded) to give the title compound. $^1$H NMR (400 MHz, CDCl$_3$) δ 8.39-8.51 (m, 2H), 8.29 (d, J=9.0 Hz, 1H), 8.03 (s, 1H), 7.55 (d, J=12.1 Hz, 1H), 7.40-7.46 (m, 5H), 7.23 (br, 1H), 6.47 (br, 1H), 4.50 (q, J=6.9 Hz, 2H), 3.98 (s, 3H), 1.26 (d, J=6.3 Hz, 3H).

Step E: 2-Fluoro-N-(1-(2-hydroxypropan-2-yl)-6-phenylimidazo[1,5-a]pyridin-5-yl)-5-(1-methyl-1H-pyrazol-3-yl)-4-(trifluoromethyl)benzamide To a solution of ethyl 5-(2-fluoro-5-(1-methyl-1H-pyrazol-3-yl)-4-(trifluoromethyl)benzamido)-6-phenylimidazo[1,5-a]pyridine-1-carboxylate (40 mg, 0.073 mmol) in THF (3 mL) at 0° C. was added a solution of methylmagnesium bromide in diethyl ether (0.73 mL, 2.18 mmol, 3M) dropwise. The resulting mixture was stirred at 0° C. for 1.5 h, then partitioned between saturated aqueous $NH_4Cl$ solution (20 mL) and EtOAc (10 mL×3). The combined organic layers were washed with brine (15 mL×3), dried over $Na_2SO_4$ and concentrated. The residue was purified by reverse-phase HPLC under basic conditions ($H_2O/CH_3CN$ gradient with 0.05% $NH_4OH$ present) to give the title compound. MS: m/z=538.2 (M+1). $^1$H NMR (400 MHz, CD$_3$OD) δ 8.18 (s, 1H), 8.05 (d, J=9.5 Hz, 1H), 7.83 (d, J=6.5 Hz, 1H), 7.73 (d, J=10.5 Hz, 1H), 7.67 (d, J=2.5 Hz, 1H), 7.48-7.52 (m, 2H), 7.44 (t, J=7.3 Hz, 2H), 7.37 (d, J=7.5 Hz, 1H), 6.90 (d, J=9.5 Hz, 1H), 6.45 (s, 1H), 3.97 (s, 3H), 1.70 (s, 6H).

Reaction Scheme for Example 61

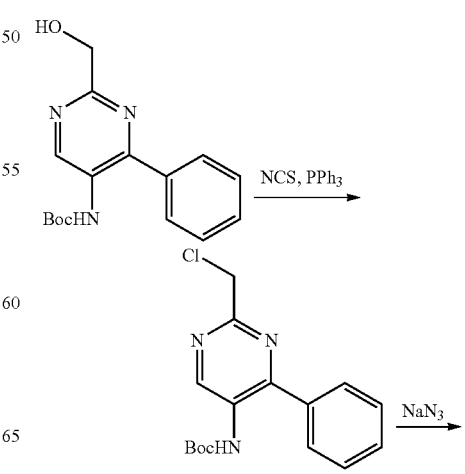

-continued
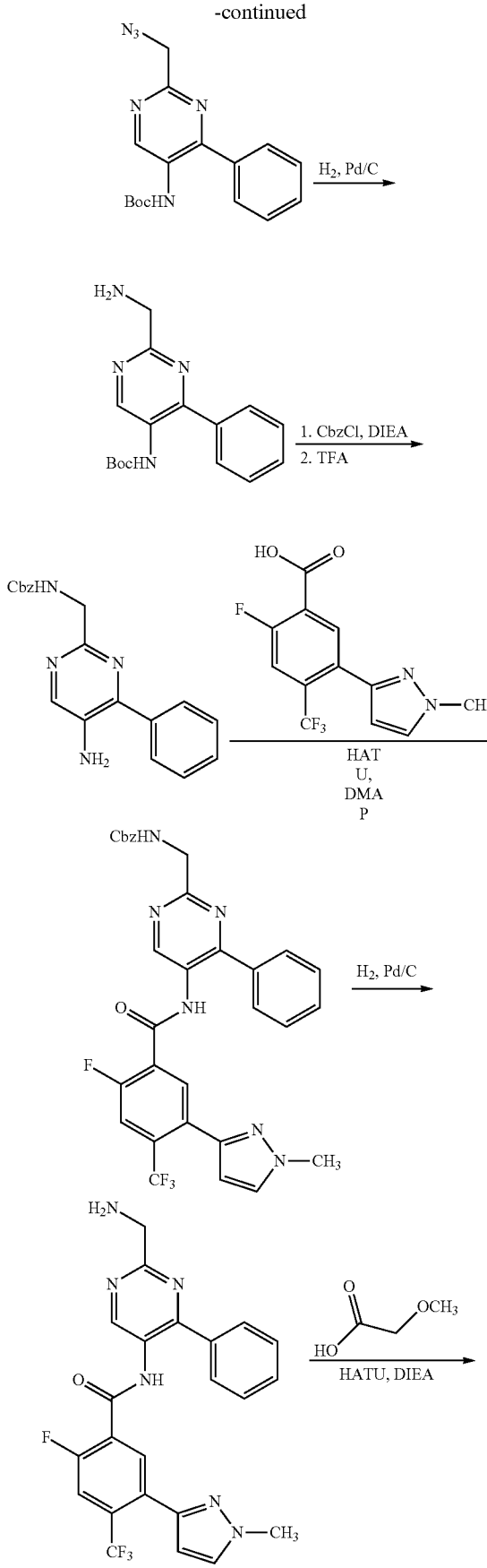
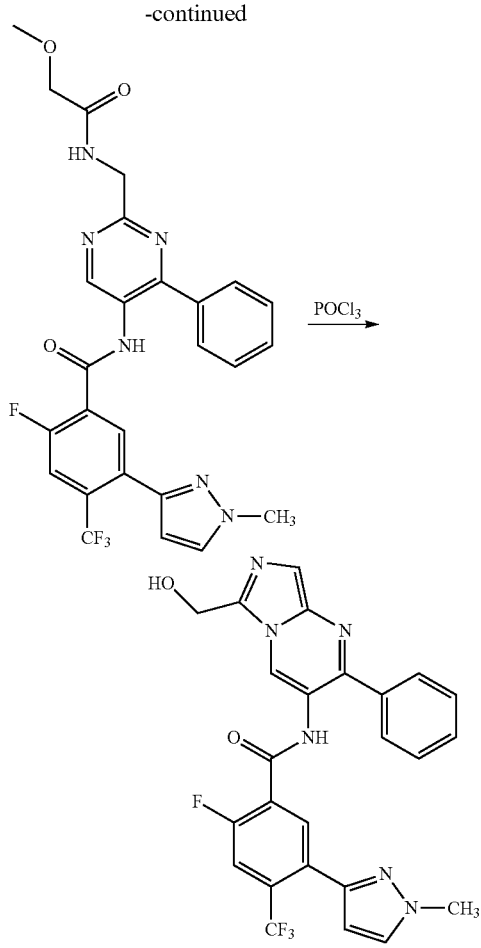
Example 61
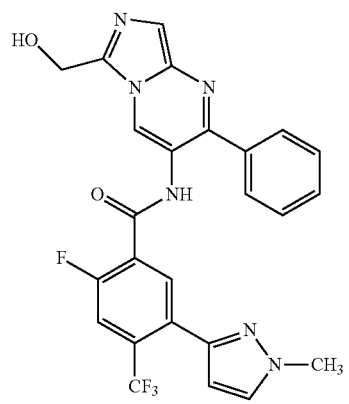 [SMILES: Cn1ccc(-c2cc(C(=O)Nc3cn4c(CO)ncc4nc3-c3ccccc3)c(F)cc2C(F)(F)F)n1]
2-Fluoro-N-(6-(hydroxymethyl)-2-phenylimidazo[1,5-a]pyrimidin-3-yl)-5-(1-methyl-1H-pyrazol-3-yl)-4-(trifluoromethyl)benzamide
Step A: tert-Butyl (2-(chloromethyl)-4-phenylpyrimidin-5-yl)carbamate
A solution of tert-butyl (2-(hydroxymethyl)-4-phenylpyrimidin-5-yl)carbamate (1.50 g, 4.98 mmol), N-chlorosuccinimide (0.798 g, 5.97 mmol), and triphenylphosphane (1.70 g, 6.47 mmol) in DCM (40 mL) was stirred at 23° C. for 16 h. The product mixture was partitioned between water and dichloromethane (3×). The combined organic layers were dried over $Na_2SO_4$, and concentrated. The residue was purified by flash column chromatography ($SiO_2$, 120 g cartridge), eluting with EtOAc/hexanes (0% to 50%) to afford the title compound. MS: m/z=320 (M+1).

Step B: tert-Butyl (2-(azidomethyl)-4-phenylpyrimidin-5-yl)carbamate

A solution of tert-butyl (2-(chloromethyl)-4-phenylpyrimidin-5-yl)carbamate (564 mg, 1.76 mmol), sodium azide (229 mg, 3.53 mmol) in a mixture of acetonitrile (12 mL) and water (4.8 mL) was heated at 80° C. for 1 h. The product mixture was concentrated and the residue partitioned between water and ethyl acetate (3×). The combined organic layers were dried over $Na_2SO_4$, filtered and concentrated to afford the title compound. MS: m/z=327 (M+1).

Step C: tert-Butyl (2-(aminomethyl)-4-phenylpyrimidin-5-yl)carbamate

A mixture of tert-butyl (2-(azidomethyl)-4-phenylpyrimidin-5-yl)carbamate (365 mg, 1.12 mmol) and 10% Pd/C (120 mg, 0.113 mmol) in ethanol (10 mL) was stirred under a hydrogen balloon at 23° C. for 16 h. The product mixture was filtered and the filtrate concentrated to afford the title compound. MS: m/z=301 (M+1).

Step D: Benzyl ((5-amino-4-phenylpyrimidin-2-yl)methyl)carbamate

A solution of tert-butyl (2-(aminomethyl)-4-phenylpyrimidin-5-yl)carbamate (1.31 g, 4.36 mmol), N,N-diisopropylethylamine (0.913 mL, 5.23 mmol) and benzyl chloroformate (0.653 ml, 4.57 mmol) in DCM (30 mL) was stirred at 23° C. for 2 h. The product mixture was partitioned between aqueous sodium bicarbonate solution and dichloromethane (3×). The combined organic layers were dried over $Na_2SO_4$, filtered and concentrated. The residue was dissolved in a mixture of TFA and DCM (30 mL), and the resulting solution was stirred at 23° C. for 1 h, then concentrated. The residue was partitioned between aqueous sodium bicarbonate solution and dichloromethane (3×). The combined organic layers were dried over $Na_2SO_4$, filtered and concentrated. The residue was purified by flash chromatography ($SiO_2$, 80 g cartridge), eluting with MeOH/$CH_2Cl_2$ (0% to 15%) to afford the title compound. MS: m/z=335 (M+1).

Step E: Benzyl ((5-(2-fluoro-5-(1-methyl-1H-pyrazol-3-yl)-4-(trifluoromethyl)benzamido)-4-phenylpyrimidin-2-yl)methyl)carbamate A mixture of benzyl ((5-amino-4-phenylpyrimidin-2-yl)methyl)carbamate (700 mg, 2.09 mmol), 2-fluoro-5-(1-methyl-1H-pyrazol-3-yl)-4-(trifluoromethyl)benzoic acid (664 mg, 2.30 mmol), HATU (876 mg, 2.30 mmol) and 2,6-lutidine (0.362 mL, 3.14 mmol) in acetonitrile (12 mL) was heated at 80° C. for 16 h. The product mixture was concentrated and the residue was purified by flash chromatography ($SiO_2$, 120 g cartridge), eluting with MeOH/$CH_2Cl_2$ (0% to 15%) to provide the title compound. MS: m/z=605 (M+1).

Step F: N-(2-(Aminomethyl)-4-phenylpyrimidin-5-yl)-2-fluoro-5-(1-methyl-1H-pyrazol-3-yl)-4-(trifluoromethyl)benzamide A mixture of benzyl ((5-(2-fluoro-5-(1-methyl-1H-pyrazol-3-yl)-4-(trifluoromethyl)benzamido)-4-phenylpyrimidin-2-yl)methyl)carbamate 2,2,2-trifluoroacetate (1.09 g, 1.51 mmol) and 10% Pd/C (0.161 g, 0.151 mmol) in EtOH (10 mL) was stirred under a hydrogen balloon at 23° C. for 16 h. The product mixture was filtered and the filtrate concentrated to give the title compound. MS: m/z=471 (M+1).

Step G: 2-Fluoro-N-(2-((2-methoxyacetamido)methyl)-4-phenylpyrimidin-5-yl)-5-(1-methyl-1H-pyrazol-3-yl)-4-(trifluoromethyl)benzamide A mixture of N-(2-(aminomethyl)-4-phenylpyrimidin-5-yl)-2-fluoro-5-(1-methyl-1H-pyrazol-3-yl)-4-(trifluoromethyl)benzamide (252 mg, 0.431 mmol), methoxyacetic acid (0.066 ml, 0.862 mmol), HATU (197 mg, 0.517 mmol) and DIEA (0.226 mL, 1.29 mmol) DMF (3 mL) was stirred at 23° C. for 16 h. The product mixture was partitioned between water and ethyl acetate (3×). The combined organic layers were dried over $Na_2SO_4$, filtered and concentrated. The residue was purified by preparative HPLC (reverse phase, C-18, 150 g) eluting with acetonitrile/water/w 0.05% TFA (10% to 100% organic, 85 mL/min) to provide the title compound. MS: m/z=543 (M+1).

Step H: 2-Fluoro-N-(6-(hydroxymethyl)-2-phenylimidazo[1,5-a]pyrimidin-3-yl)-5-(1-methyl-1H-pyrazol-3-yl)-4-(trifluoromethyl)benzamide A mixture of 2-fluoro-N-(2-((2-methoxyacetamido)methyl)-4-phenylpyrimidin-5-yl)-5-(1-methyl-1H-pyrazol-3-yl)-4-(trifluoromethyl)benzamide 2,2,2-trifluoroacetate (159 mg, 0.242 mmol) and phosphorus oxychloride (0.113 mL, 1.21 mmol) in DCE (5 mL) was heated at 90° C. for 4 h. The product mixture was cooled and partitioned between water and ethyl acetate (3×). The combined organic layers were dried over $Na_2SO_4$, filtered and concentrated. The residue was purified by reverse-phase HPLC ($CH_3CN$/water gradient with 0.05% TFA) to provide the title compound. MS: m/z=511 (M+1). $^1$H NMR (500 MHz, DMSO-$d_6$): δ 10.46 (s, 1H); 8.97 (s, 1H); 7.80-7.86 (m, 3H); 7.72 (d, J=5.5 Hz, 2H); 7.56 (s, 1H); 7.46 (t, J=3.3 Hz, 3H); 6.43 (s, 1H); 4.88 (s, 2H); 3.92 (s, 3H).

Example 62

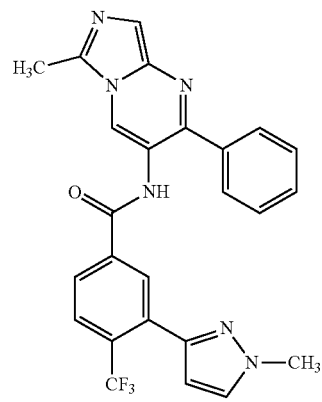 [SMILES: Cc1ncc2nc(-c3ccccc3)c(NC(=O)c3ccc(C(F)(F)F)c(-c4ccn(C)n4)c3)cn12]

3-(1-Methyl-1H-pyrazol-3-yl)-N-(6-methyl-2-phenylimidazo[1,5-a]pyrimidin-3-yl)-4-(trifluoromethyl)benzamide The title compound was prepared according to the procedure described for Example 61 with two modifications: 1) Step E-5-(1-methyl-1H-pyrazol-3-yl)-4-(trifluoromethyl)benzoic acid was used in place of 2-fluoro-5-(1-methyl-1H-pyrazol-3-yl)-4-(trifluoromethyl)benzoic acid; 2) Step G—acetic acid was used in place of methoxyacetic acid. MS: m/z=477 (M+1). $^1$H NMR (500 MHz, CD$_3$OD): δ 9.15 (s, 1H); 8.04 (s, 1H); 7.90-7.98 (m, 3H); 7.78 (d, J=6.3 Hz, 2H); 7.67 (s, 1H); 7.50 (s, 3H); 6.47 (s, 1H); 3.97 (s, 3H); 2.90 (s, 3H).

Reaction Scheme for Examples 63 and 64

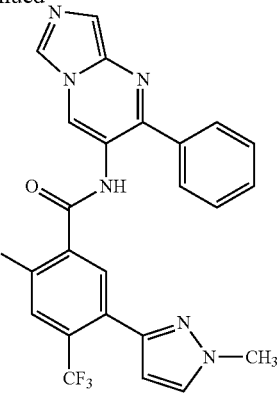

EXAMPLE 64

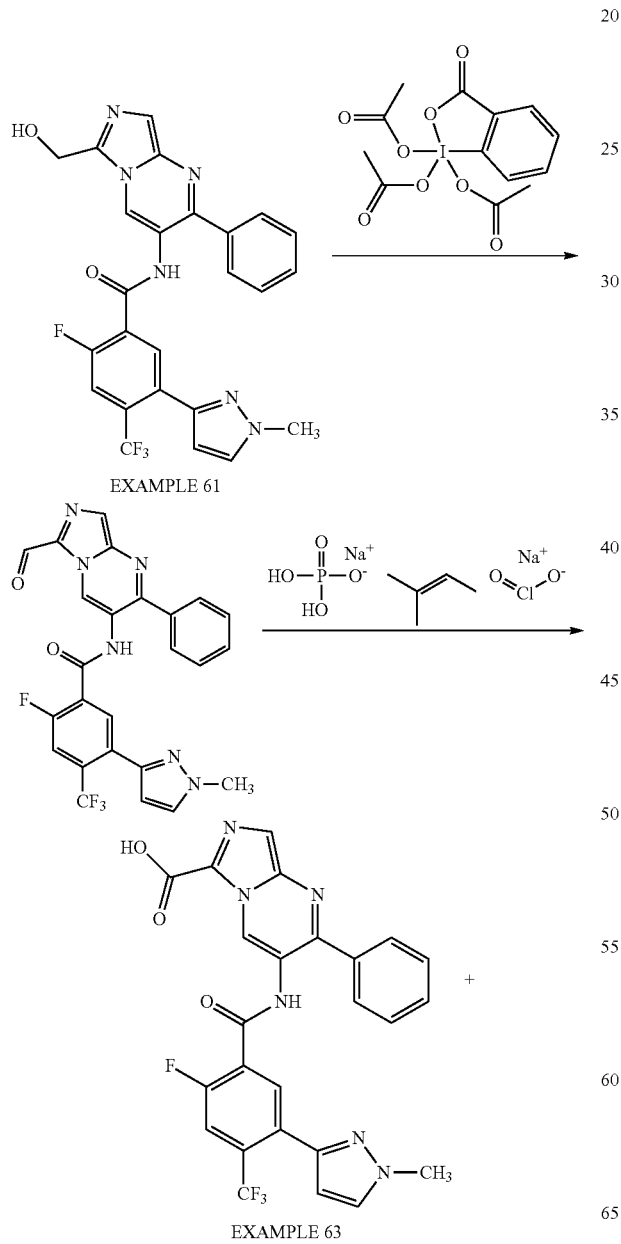

Example 63

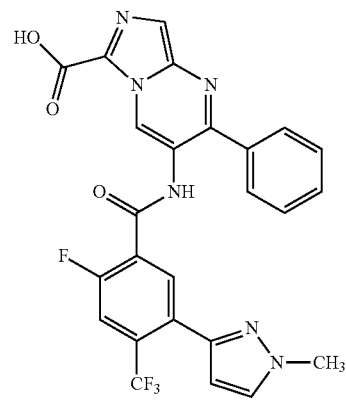 [SMILES: Cn1ccc(-c2cc(C(=O)Nc3cn4c(C(=O)O)ncc4nc3-c3ccccc3)c(F)cc2C(F)(F)F)n1]

3-(2-Fluoro-5-(1-methyl-1H-pyrazol-3-yl)-4-(trifluoromethyl)benzamido)-2-phenylimidazo[1,5-a]pyrimidine-6-carboxylic acid Example 64

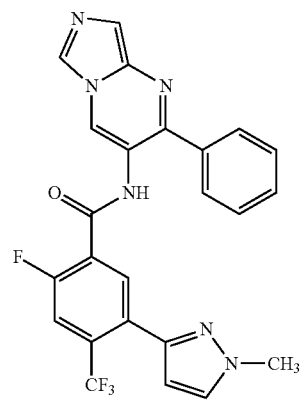 [SMILES: Cn1ccc(-c2cc(C(=O)Nc3cn4cncc4nc3-c3ccccc3)c(F)cc2C(F)(F)F)n1]

2-Fluoro-5-(1-methyl-1H-pyrazol-3-yl)-N-(2-phenylimidazo[1,5-a]pyrimidin-3-yl)-4-(trifluoromethyl)benzamide

Step A: 2-Fluoro-N-(6-formyl-2-phenylimidazo[1,5-a]pyrimidin-3-yl)-5-(1-methyl-1H-pyrazol-3-yl)-4-(trifluoromethyl)benzamide Dess-Martin periodinane (43.2 mg, 0.102 mmol) was added to a mixture of 2-fluoro-N-(6-(hydroxymethyl)-2-phenylimidazo[1,5-a]pyrimidin-3-yl)-5-(1-methyl-1H-pyrazol-3-yl)-4-(trifluoromethyl)benzamide (26 mg, 0.051 mmol) in CH$_2$Cl$_2$ (1 mL) at 0° C. The resulting mixture was stirred at 0° C. for 10 min then allowed to warm to 23° C. After 2 h, the product mixture was partitioned between aqueous sodium hydrogen carbonate solution and ethyl acetate (3×). The combined organic extracts were dried over Na$_2$SO$_4$, filtered and concentrated to afford the title compound. MS: m/z=509 (M+1).

Step B: 2-Fluoro-N-(6-formyl-2-phenylimidazo[1,5-a]pyrimidin-3-yl)-5-(1-methyl-1H-pyrazol-3-yl)-4-(trifluoromethyl)benzamide (EXAMPLE 63) and 2-fluoro-N-(6-formyl-2-phenylimidazo[1,5-a]pyrimidin-3-yl)-5-(1-methyl-1H-pyrazol-3-yl)-4-(trifluoromethyl)benzamide (EXAMPLE 64)

Sodium dihydrogen phosphate (17.7 mg, 0.148 mmol), 2-methyl-2-butene (0.026 mL, 0.25 mmol) and sodium chlorite (6.7 mg, 0.074 mmol) were successively added to a solution of 2-fluoro-N-(6-formyl-2-phenylimidazo[1,5-a]pyrimidin-3-yl)-5-(1-methyl-1H-pyrazol-3-yl)-4-(trifluoromethyl)benzamide (25 mg, 0.049 mmol) in a 5:1 mixture of t-BuOH and water (1 mL) at 23° C. The resulting mixture was stirred for 20 min, then partitioned between water and EtOAc (3×). The combined organic layers were dried over Na$_2$SO$_4$, filtered and concentrated. The residue was purified by reversed-phase HPLC to afford the title compounds. EXAMPLE 63: MS: m/z=525 (M+1). $^1$H NMR (500 MHz, DMSO-d$_6$): δ 10.47 (s, 1H); 9.98 (s, 1H); 7.87-7.78 (m, 3H); 7.75-7.71 (m, 2H); 7.56-7.51 (m, 2H); 7.47-7.42 (m, 2H); 6.44 (s, 1H); 3.92 (s, 3H). EXAMPLE 64: MS: m/z=481 (M+1). $^1$H NMR (500 MHz, CD$_3$OD): δ 9.19 (s, 1H); 8.35 (s, 1H); 7.91-7.88 (m, 1H); 7.70-7.73 (m, 2H); 7.68 (s, 1H); 7.66 (t, J=2.5 Hz, 2H); 7.57 (s, 1H); 7.49-7.51 (m, 3H); 6.43 (s, 1H); 3.97 (s, 3H).

Reaction Scheme for Example 65

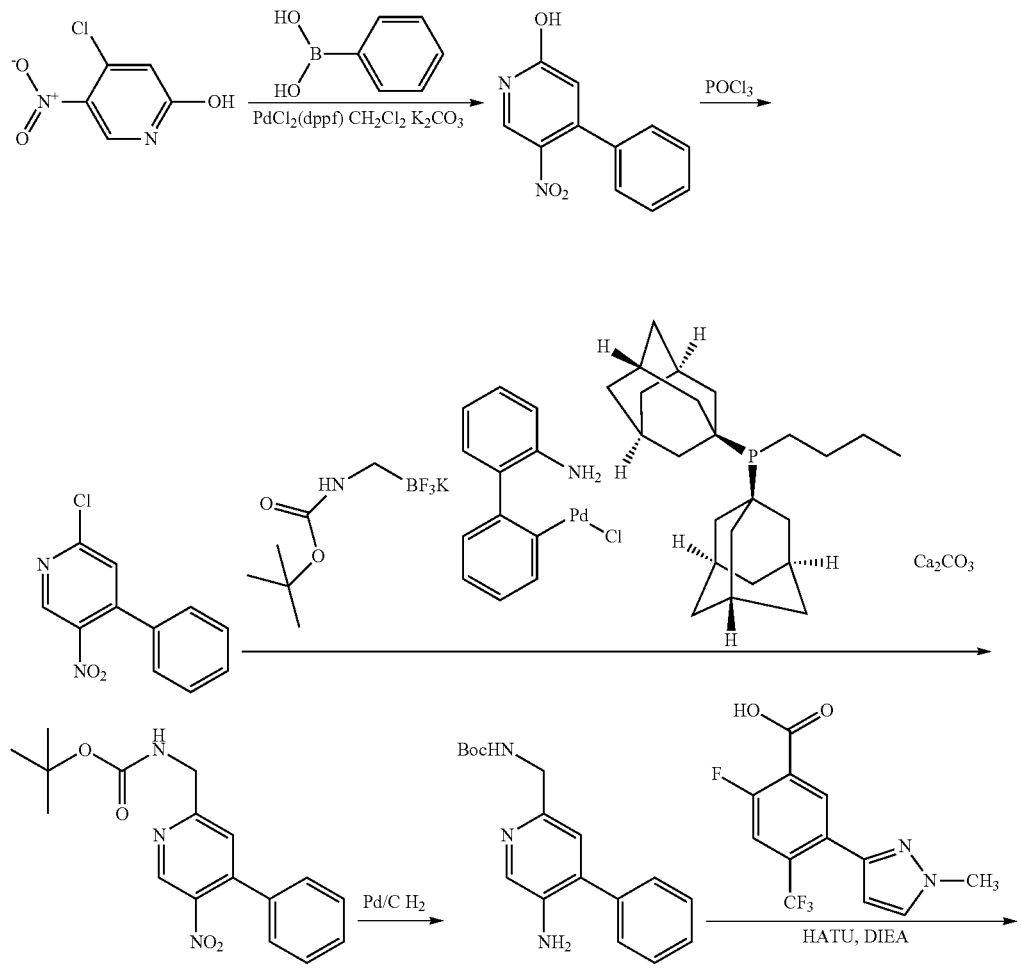

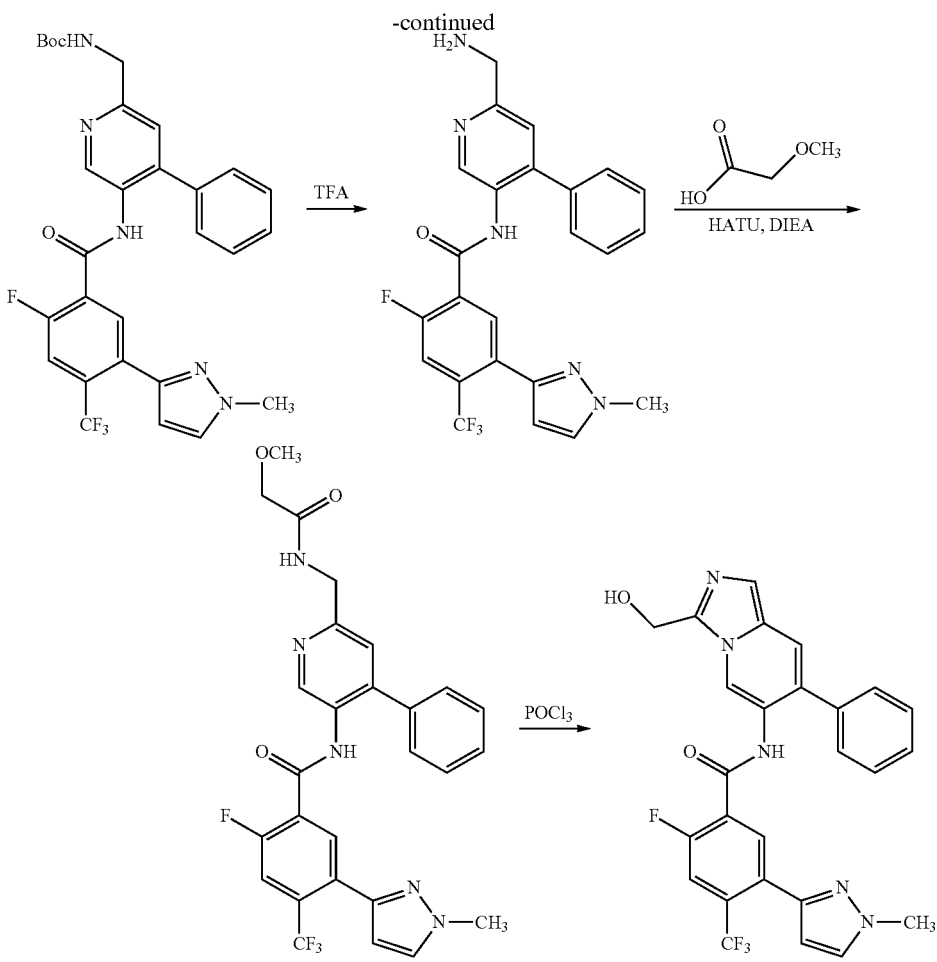

Example 65

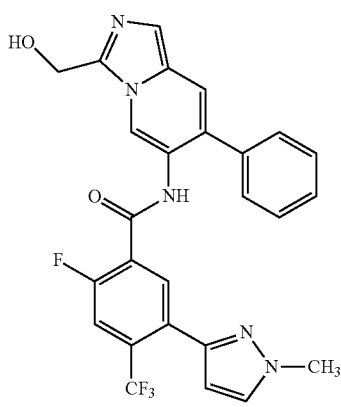 [SMILES: Cn1ccc(-c2cc(C(=O)Nc3cn4c(CO)ncc4cc3-c3ccccc3)c(F)cc2C(F)(F)F)n1]

2-Fluoro-N-(3-(hydroxymethyl)-7-phenylimidazo[1,5-a]pyridin-6-yl)-5-(1-methyl-1H-pyrazol-3-yl)-4-(trifluoromethyl)benzamide Step A: 5-Nitro-4-phenylpyridin-2-ol A mixture of 4-chloro-2-hydroxy-5-nitropyridine (3.00 g, 17.2 mmol), phenylboronic acid (2.51 g, 20.6 mmol), PdCl₂(dppf)-CH₂Cl₂ adduct (1.40 g, 1.72 mmol), and potassium carbonate (4.75 g, 34.4 mmol) in THF (100 mL) was heated at 85° C. for 16 h. The product mixture was cooled and partitioned between water and ethyl acetate (3×). The combined organic layers were dried over Na₂SO₄, filtered and concentrated. The residue was purified by flash column chromatography (SiO₂ cartridge), eluting with MeOH/CH₂Cl₂ (0-10%) to afford the title compound. MS: m/z=217 (M+1).

Step B: 2-Chloro-5-nitro-4-phenylpyridine

A mixture of 5-nitro-4-phenylpyridin-2-ol (50 mg, 0.23 mmol) and POCl₃ (1.0 mL, 11 mmol) in acetonitrile (5 mL) was heated at 100° C. for 6 h. The product mixture was cooled and partitioned between saturated aqueous NaHCO₃ solution and EtOAc (3×). The combined organic layers were dried over Na₂SO₄, filtered and concentrated. The residue was purified by flash chromatography (SiO₂, 40 g cartridge), eluting with EtOAc/hexanes (0% to 50%) to give the title compound. MS: m/z=235 (M+1).

Step C: tert-Butyl ((5-nitro-4-phenylpyridin-2-yl)methyl)carbamate

Chloro[(di(1-adamantyl)-n-butylphosphine)-2-(2-aminobiphenyl)]palladium(II) (114 mg, 0.170 mmol) was added to a stirred, degassed mixture of 2-chloro-5-nitro-4-phenylpyridine (400 mg, 1.70 mmol), Cs$_2$CO$_3$ (1666 mg, 5.11 mmol), tert-butyl ((trifluoro-14-boranyl)methyl)carbamate and potassium salt (525 mg, 2.22 mmol) in toluene (13 mL)/water (1.3 mL). The resulting mixture was heated at 100° C. for 12 h, then partitioned between water and ethyl acetate (3×). The combined organic layers were washed with brine, dried over Na$_2$SO$_4$, filtered and concentrated. The residue was purified by flash chromatography (SiO$_2$, 120 g cartridge), eluting with EtOAc/hexanes (0% to 40%) to provide the title compound. MS: m/z=330 (M+1).

Step D: tert-Butyl ((5-amino-4-phenylpyridin-2-yl)methyl)carbamate

A mixture of tert-butyl ((5-nitro-4-phenylpyridin-2-yl)methyl)carbamate (148 mg, 0.451 mmol) and 10% Pd/C (48 mg, 0.045 mmol) in EtOH (3 mL) was stirred under a H$_2$ balloon at 23° C. for 16 h. The product mixture was filtered and concentrated to afford the title compound.
MS: m/z=300 (M+1).

Step E: tert-Butyl ((5-(2-fluoro-5-(1-methyl-1H-pyrazol-3-yl)-4-(trifluoromethyl)benzamido)-4-phenylpyridin-2-yl)methyl)carbamate A mixture of tert-butyl ((5-amino-4-phenylpyridin-2-yl)methyl)carbamate (77 mg, 0.26 mmol), 2-fluoro-5-(1-methyl-1H-pyrazol-3-yl)-4-(trifluoromethyl)benzoic acid (81 mg, 0.28 mmol), HATU (117 mg, 0.308 mmol) and DIEA (0.112 mL, 0.642 mmol) in DMF (1.5 mL) was stirred at 23° C. for 16 h. The product mixture was purified by preparative HPLC (reverse-phase, YMC-Pack Pro C-18 100×20 mm) eluting with acetonitrile/water+0.05% TFA (20% to 78% organic in 10 min, then to 100% for 2 min, 20 mL/min) to afford the title compound. MS: m/z=570 (M+1).

Step F: N-(6-(Aminomethyl)-4-phenylpyridin-3-yl)-2-fluoro-5-(1-methyl-1H-pyrazol-3-yl)-4-(trifluoromethyl)benzamide A solution of tert-butyl ((5-(2-fluoro-5-(1-methyl-1H-pyrazol-3-yl)-4-(trifluoromethyl)benzamido)-4-phenylpyridin-2-yl)methyl)carbamate 2,2,2-trifluoroacetate (94 mg, 0.14 mmol) in a mixture of TFA (1 mL) and DCM (2 mL) was stirred at 23° C. for 2 h. The product mixture was concentrated to afford the title compound. MS: m/z=470 (M+1).

Step G: 2-Fluoro-N-(6-((2-methoxyacetamido)methyl)-4-phenylpyridin-3-yl)-5-(1-methyl-H-pyrazol-3-yl)-4-(trifluoromethyl)benzamide A mixture of N-(6-(aminomethyl)-4-phenylpyridin-3-yl)-2-fluoro-5-(1-methyl-1H-pyrazol-3-yl)-4-(trifluoromethyl)benzamide (64 mg, 0.14 mmol), methoxyacetic acid (25 mg, 0.27 mmol), HATU (52 mg, 0.14 mmol) and DIEA (0.048 mL, 0.27 mmol) in DMF (1 mL) was stirred at 23° C. for 16 h. The product mixture was purified by preparative HPLC (reverse-phase, YMC-Pack Pro C-18 100×20 mm) eluting with acetonitrile/water w/0.05% TFA (20% to 80% organic in 10 min, then to 100% for 2 min, 20 mL/min) to provide the title compound. MS: m/z=542 (M+1).

Step H: 2-Fluoro-N-(3-(hydroxymethyl)-7-phenylimidazo[1,5-a]pyridin-6-yl)-5-(1-methyl-1H-pyrazol-3-yl)-4-(trifluoromethyl)benzamide A mixture of 2-fluoro-N-(6-((2-methoxyacetamido)methyl)-4-phenylpyridin-3-yl)-5-(1-methyl-1H-pyrazol-3-yl)-4-(trifluoromethyl)benzamide 2,2,2-trifluoroacetate (37 mg, 0.056 mmol) and phosphorus oxychloride (0.026 mL, 0.28 mmol) in dichloroethane (1 mL) was heated at 90° C. for 2 h. The product mixture was cooled and partitioned between water and ethyl acetate (3×). The combined organic layers were dried over Na$_2$SO$_4$, filtered and concentrated.

The residue was purified by preparative HPLC (reverse phase, YMC-Pack Pro C-18 100×20 mm) eluting with acetonitrile/water (20% to 53% organic in 10 min, then to 100% for 2 min, 20 mL/min) to give the title compound. MS: m/z=510 (M+1). $^1$H NMR (500 MHz, CD$_3$OD): δ 8.90 (s, 1H); 7.85 (d, J=7.0 Hz, 1H); 7.62-7.66 (m, 2H); 7.56 (s, 1H); 7.39-7.49 (m, 6H); 6.42 (s, 1H); 5.02 (s, 3H); 3.97 (s, 3H).

Reaction Scheme for Example 66

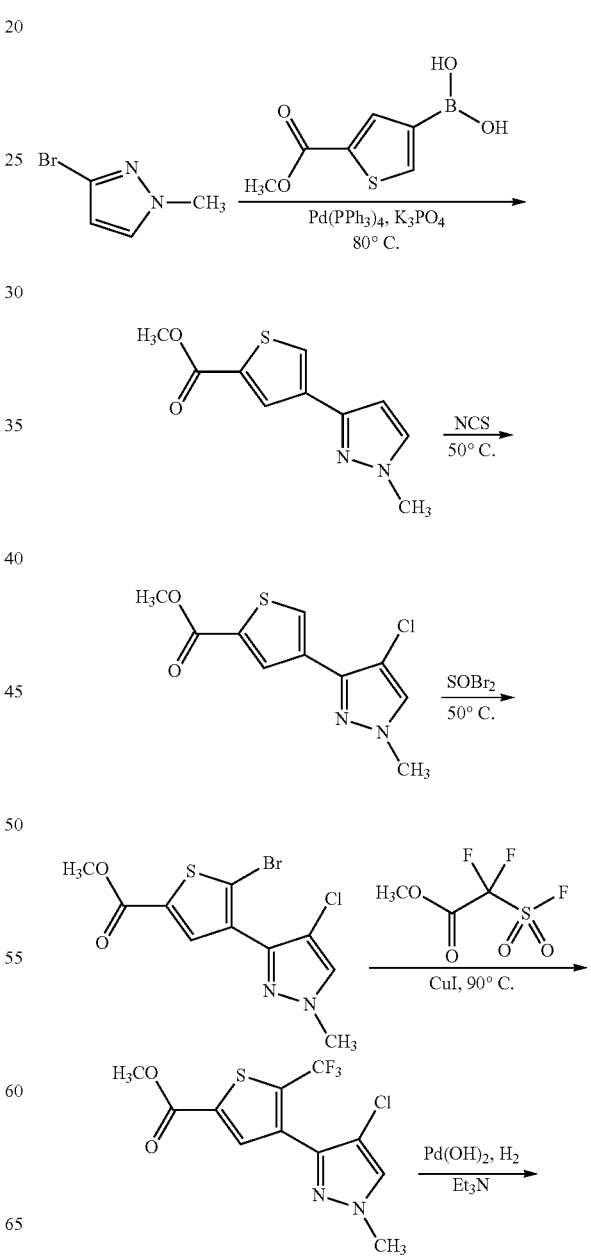

147

-continued

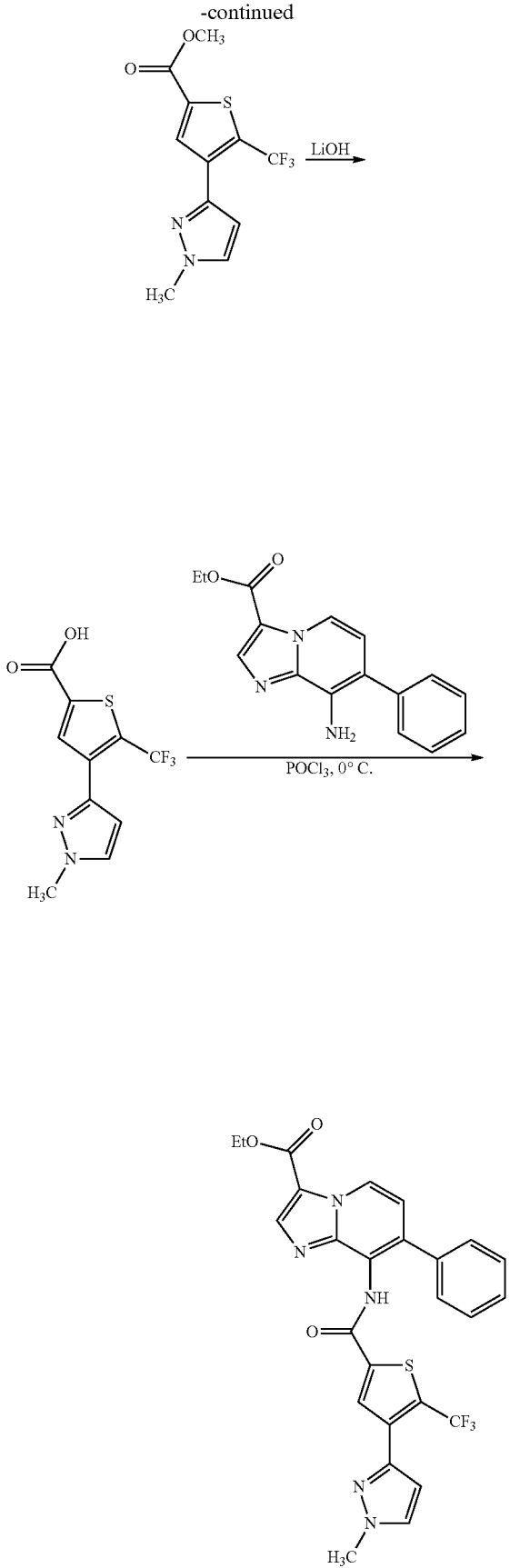

148

Example 66

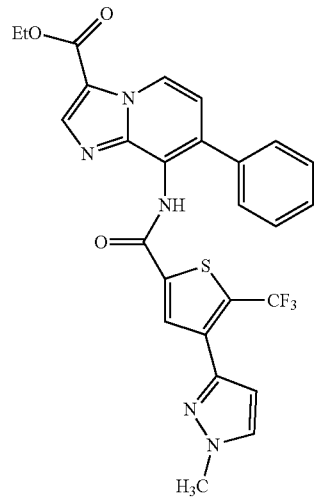 [SMILES: CCOC(=O)c1cnc2c(NC(=O)c3cc(-c4ccn(C)n4)c(C(F)(F)F)s3)c(-c3ccccc3)ccn12]

Ethyl 8-(4-(1-methyl-1H-pyrazol-3-yl)-5-(trifluoromethyl)thiophene-2-carboxamido)-7-phenylimidazo[1,2-a]pyridine-3-carboxylate Step A: Methyl 4-(1-methyl-1H-pyrazol-3-yl)thiophene-2-carboxylate To a solution of (5-(methoxycarbonyl)thiophen-3-yl)boronic acid (5.30 g, 28.5 mmol) and 3-bromo-1-methyl-1H-pyrazole (4.59 g, 28.5 mmol) in dioxane (108 mL) were added Pd(PPh$_3$)$_4$ (1.04 g, 1.42 mmol) and 1.5 M aqueous K$_3$PO$_4$ solution (57 mL, 85 mmol). The resulting mixture was heated at 80° C. for 1 h, then cooled, diluted with CH$_2$Cl$_2$, dried over Na$_2$SO$_4$, filtered through a pad of silic, and concentrated. The residue was purified by column chromatography on silica gel, eluting with EtOAc/hexanes, to give the title compound. MS: m/z=223 (M+1). $^1$H NMR (400 MHz, CDCl$_3$) δ 8.18 (s, 1H), 7.80 (s, 1H), 7.40 (s, 1H), 6.44 (s, 1H), 3.96 (s, 3H), 3.94 (s, 3H).

Step B: Methyl 4-(4-chloro-1-methyl-1H-pyrazol-3-yl)thiophene-2-carboxylate

To the mixture of methyl 4-(1-methyl-1H-pyrazol-3-yl)thiophene-2-carboxylate (4.57 g, 20.6 mmol) in DCE (60 mL) was added N-chlorosuccinimide (2.75 g, 20.6 mmol). The resulting mixture was heated at 50° C. for 24 h, then cooled and concentrated. The residue was purified by column chromatography on silica gel, eluting with EtOAc/hexanes, to give the title compound. MS: m/z=257.0 (M+1). $^1$H NMR (400 MHz, CDCl$_3$) δ 8.36 (s, 1H), 8.08 (s, 1H), 7.42 (s, 1H), 3.92 (s, 3H).

Step C: Methyl 5-bromo-4-(4-chloro-1-methyl-1H-pyrazol-3-yl)thiophene-2-carboxylate To a solution of methyl 4-(4-chloro-1-methyl-11H-pyrazol-3-yl)thiophene-2-carboxylate (2.98 g, 11.6 mmol) in a sealed tube was added thionyl bromide (9.00 mL, 116 mmol) dropwise. The resulting mixture was heated at 50° C. for 16 h, then cooled and partitioned between water and EtOAc. The organic layer was washed with brine, dried over MgSO4, filtered and concentrated. The residue was purified by column chromatography on silica gel, eluting with EtOAc/hexanes, to give the title compound. MS: m/z=336.9 (M+1). $^1$H NMR (400 MHz, CDCl$_3$) δ 7.85 (s, 1H), 7.50 (s, 1H), 3.95 (s, 3H), 3.90 (s, 3H).

Step D: Methyl 4-(4-chloro-1-methyl-1H-pyrazol-3-yl)-5-(trifluoromethyl)thiophene-2-carboxylate To a solution of methyl 5-bromo-4-(4-chloro-1-methyl-1H-pyrazol-3-yl)thiophene-2-carboxylate (1.20 g, 3.58 mmol) in N-methyl-2-pyrrolidinone (10 mL) were added methyl 2,2-difluoro-2-(fluorosulfonyl)acetate (2.06 g, 10.7 mmol) and copper(I) iodide (0.204 g, 1.07 mmol). The resulting mixture was heated at 90° C. for 16 h, then cooled and diluted with ethyl acetate. The organic layer was washed with H$_2$O and brine, dried over MgSO4 and concentrated. The residue was purified by column chromatography on silica gel, eluting with EtOAc/hexanes to give the title compound. MS: m/z=325 (M+1). $^1$H NMR (400 MHz, CDCl$_3$) δ 7.98 (s, 1H), 7.48 (s, 1H), 3.96 (s, 3H), 3.94 (s, 3H).

Step E: Methyl 4-(1-methyl-1H-pyrazol-3-yl)-5-(trifluoromethyl)thiophene-2-carboxylate A mixture of methyl 4-(4-chloro-1-methyl-1H-pyrazol-3-yl)-5-(trifluoromethyl) thiophene-2-carboxylate (1.00 g, 3.08 mmol), 20% palladium hydroxide on carbon (0.216 g, 0.308 mmol) and triethylamine (0.215 mL, 1.540 mmol) in DMF (15 mL) was heated under a H$_2$ balloon at 100° C. for 16 h. The product mixture was filtered and the filtrate was concentrated. The residue was purified by column chromatography on silica gel, eluting with EtOAc/hexanes to give the title compound. MS: m/z=291 (M+1). $^1$H NMR (400 MHz, CDCl$_3$) δ 8.38 (s, 1H), 7.42 (s, 1H), 6.6 (s, 1H), 3.96 (s, 3H), 3.94 (s, 3H).

Step F: 4-(1-Methyl-1H-pyrazol-3-yl)-5-(trifluoromethyl)thiophene-2-carboxylic acid To a solution of methyl 4-(1-methyl-1H-pyrazol-3-yl)-5-(trifluoromethyl)thiophene-2-carboxylate (243 mg, 0.837 mmol) in a mixture of MeOH (1 mL) and THF (1 mL) was added 1M aqueous lithium hydroxide solution (1.674 mL, 1.674 mmol). The resulting mixture was stirred at 23° C. for 16 h, then cooled and concentrated. The residue was purified by preparative reverse phase HPLC (C-18), eluting with acetonitrile/water+0.1% TFA, to give the title compound. MS: m/z=277.0 (M+1). $^1$H NMR (400 MHz, CD$_3$OD) δ 8.20 (s, 1H), 7.62 (s, 1H), 6.58 (s, 1H), 3.96 (s, 3H).

Step G: Ethyl 8-(4-(1-methyl-1H-pyrazol-3-yl)-5-(trifluoromethyl)thiophene-2-carboxamido)-7-phenylimidazo[1,2-a]pyridine-3-carboxylate To a solution of 4-(1-methyl-1H-pyrazol-3-yl)-5-(trifluoromethyl)thiophene-2-carboxylic acid hydrochloride (89 mg, 0.28 mmol) in pyridine (2 mL) at 0° C. were added ethyl 8-amino-7-phenylimidazo[1,2-a]pyridine-3-carboxylate (80 mg, 0.28 mmol) and phosphoryl trichloride (0.034 mL, 0.37 mmol). The resulting mixture was stirred 1 h, then partition between aqueous CuSO$_4$ solution and EtOAc. The organic layer was washed with brine, dried over MgSO$_4$, and concentrated. The residue was purified by column chromatography on silica gel, eluting with EtOAc/hexanes, to give the title compound. MS: m/z=540.0 (M+1). $^1$H NMR (400 MHz, CDCl$_3$) δ 9.08 (d, 1H), 8.32 (m, 1H), 8.15 (m, 1H), 7.78 (m, 2H), 7.48 (m, 2H), 7.40 (m, 1H), 7.30 (s, 1H), 7.10 (m, 1H), 6.50 (s, 1H), 4.40 (q, 2H), 3.80 (s, 3H), 1.42 (t, 3H).

Reaction Scheme for Example 67

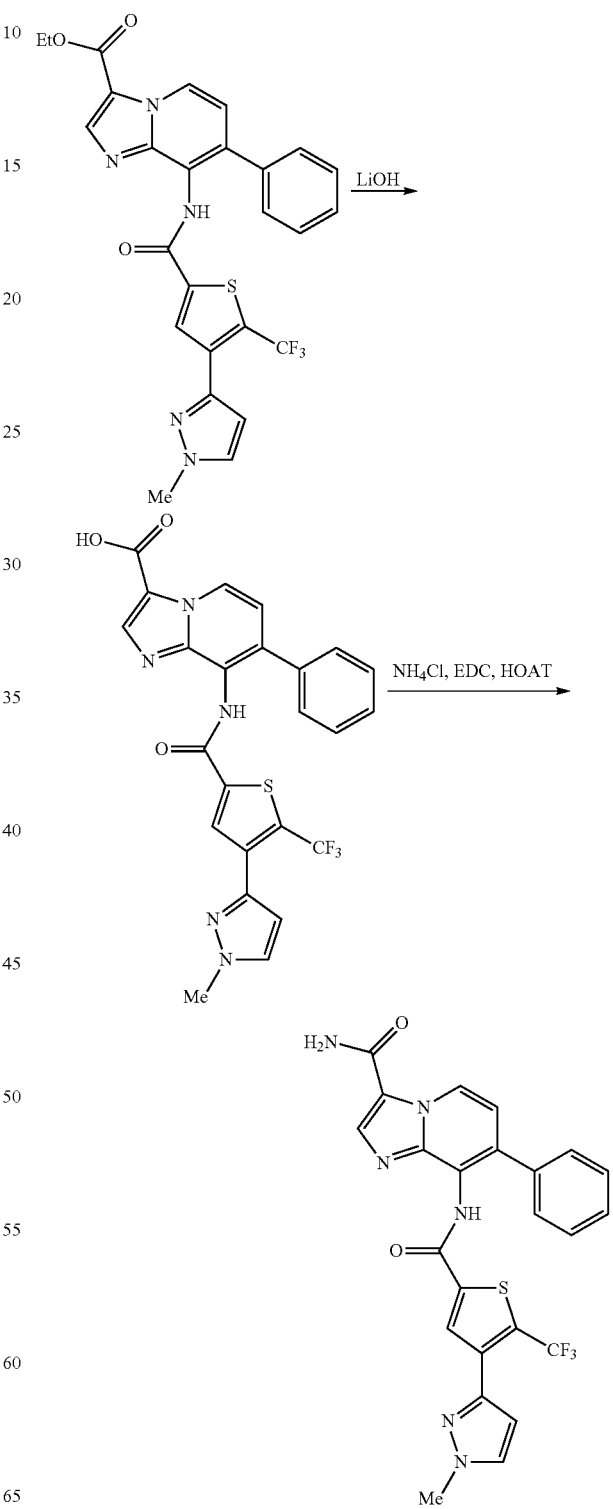

EXAMPLE 67

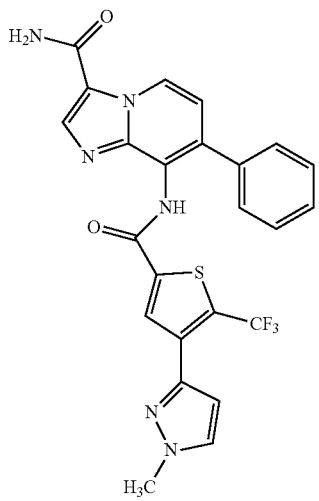 [SMILES: Cn1ccc(-c2cc(C(=O)Nc3c(-c4ccccc4)ccn4c(C(N)=O)cnc34)sc2C(F)(F)F)n1]

8-(4-(1-Methyl-1H-pyrazol-3-yl)-5-(trifluoromethyl) thiophene-2-carboxamido)-7-phenylimidazo[1,2-a]pyridine-3-carboxamide Step A: 8-(4-(1-Methyl-1H-pyrazol-3-yl)-5-(trifluoromethyl)thiophene-2-carboxamido)-7-phenylimidazo[1,2-a]pyridine-3-carboxylic acid To a solution of ethyl 8-(4-(1-methyl-1H-pyrazol-3-yl)-5-(trifluoromethyl)thiophene-2-carboxamido)-7-phenylimidazo[1,2-a]pyridine-3-carboxylate (Example 66, 30 mg, 0.056 mmol) in a mixture of MeOH (0.5 mL) and THF (0.5 mL) was added 1 M aqueous lithium hydroxide solution (0.056 mL, 0.056 mmol). The resulting mixture was stirred at 23° C. for 16 h. The product mixture was purified by preparative reverse-phase HPLC (C-18), eluting with acetonitrile/water+0.1% TFA, to give the title compound. MS: m/z=511.9 (M+1). $^1$H NMR (400 MHz, CD$_3$OD) δ 9.60 (d, 1H), 8.60 (s, 1H), 8.08 (s, 1H), 7.65 (s, 1H), 7.60 (m, 3H), 7.50 (m, 3H), 6.60 (s, 1H), 3.90 (s, 3H).

Step B: 8-(4-(1-Methyl-1H-pyrazol-3-yl)-5-(trifluoromethyl)thiophene-2-carboxamido)-7-phenylimidazo[1,2-a]pyridine-3-carboxamide A solution of 8-(4-(1-methyl-1H-pyrazol-3-yl)-5-(trifluoromethyl)thiophene-2-carboxamido)-7-phenylimidazo[1,2-a]pyridine-3-carboxylic acid (20 mg, 0.037 mmol) in DMF (0.5 mL) at 23° C. were added EDC (10 mg, 0.055 mmol) and HOAT (7.4 mg, 0.055 mmol). The mixture was stirred for 10 min before a solution of ammonium hydrochloride 121 mg, 0.22 mmol) and DIEA (25 mg, 0.22 mmol) in DMF (0.5 mL) was added. The resulting mixture was stirred at 23° C. for 16 h, then purified by preparative reverse-phase HPLC (C-18), eluting with acetonitrile/water+0.1% TFA, to give the title compound. MS: m/z=510.97 (M+1). $^1$H NMR (400 MHz, CD$_3$OD) δ 9.70 (d, 1H), 8.45 (s, 1H), 8.12 (s, 1H), 7.64 (s, 1H), 7.60 (m, 2H), 7.50-7.40 (m, 4H), 6.60 (s, 1H), 3.92 (s, 3H).

Reaction Scheme for Example 68

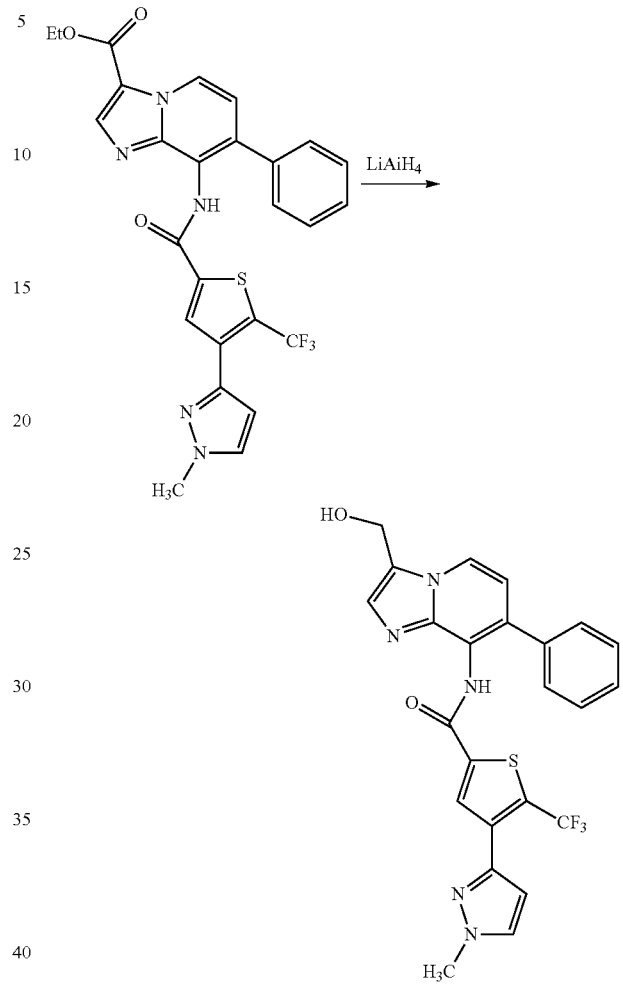

Example 68

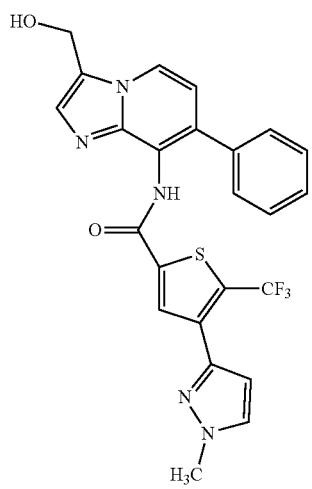 [SMILES: Cn1ccc(-c2cc(C(=O)Nc3c(-c4ccccc4)ccn4c(CO)cnc34)sc2C(F)(F)F)n1]

N-(3-(Hydroxymethyl)-7-phenylimidazo[1,2-a]pyridin-8-yl)-4-(1-methyl-1H-pyrazol-3-yl)-5-(trifluoromethyl)thiophene-2-carboxamide To a solution of ethyl 8-(4-(1-methyl-1H-pyrazol-3-yl)-5-(trifluoromethyl)thiophene-2-carboxamido)-7-phenylimidazo[1,2-a]pyridine-3-carboxylate (Example 66, 60 mg, 0.11 mmol) in THF (1 mL) at 0° C. was added LiAlH$_4$ (5.5 mg, 0.14 mmol). The resulting mixture was stirred at 0° C. for 1 h. H$_2$O (1 mL) was added and the precipitate was filtered and washed with DMF. The filtrate was purified by preparative reverse-phase HPLC (C-18), eluting with acetonitrile/water+0.1% TFA, followed by preparative TLC on silica (5% MeOH in CH$_2$Cl$_2$) to give the title compound. MS: m/z=498.0 (M+1). $^1$H NMR (400 MHz, CD$_3$OD) δ 8.90 (d, 1H), 8.15 (d, 1H), 8.10 (s, 1H), 7.68 (m, 2H), 7.50-7.60 (m, 5H), 6.58 (s, 1H), 5.10 (s, 2H), 3.96 (s, 3H).

Example 69

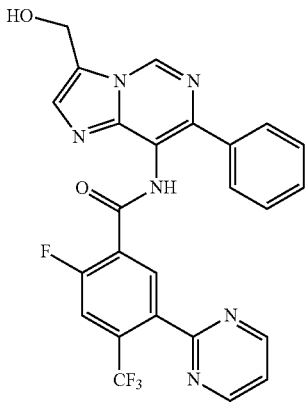 [SMILES: O=C(Nc1c(-c2ccccc2)ncn2c(CO)cnc12)c1cc(-c2ncccn2)c(C(F)(F)F)cc1F]

2-Fluoro-N-(3-(hydroxymethyl)-7-phenylimidazo[1,2-c]pyrimidin-8-yl)-5-(pyrimidin-2-yl)-4-(trifluoromethyl)benzamide Step A: 2-Fluoro-5-(pyrimidin-2-yl)-4-(trifluoromethyl)benzamide To a solution of 2-fluoro-5-(pyrimidin-2-yl)-4-(trifluoromethyl)benzoic acid (1.00 g, 3.49 mmol) in dichloromethane (10 mL) were added SOCl$_2$ (2.00 mL, 27.4 mmol) and DMF (0.05 mL, 0.65 mmol). The resulting mixture was heated at 55° C. for 16 h, then cooled and concentrated. The residue was dissolved in a mixture of aqueous NH$_4$OH solution (20 mL, 144 mmol) and THF (5 mL). The resulting mixture was stirred at 15° C. for 5 min, then extracted with ethyl acetate (30 mL×3). The combined organic layers were washed with brine, dried over Na$_2$SO$_4$ and concentrated to give the title compound. MS: m/z=285.9 (M+1).

Step B: 2-Fluoro-N-(3-formyl-7-phenylimidazo[1,2-c]pyrimidin-8-yl)-5-(pyrimidin-2-yl)-4-(trifluoromethyl)benzamide To a deoxygenated mixture of 8-chloro-7-phenylimidazo[1,2-a]pyridine-3-carbaldehyde (100 mg, 0.39 mmol), 2-fluoro-5-(pyrimidin-2-yl)-4-(trifluoromethyl)benzamide (144 mg, 0.51 mmol) and Cs$_2$CO$_3$ (381 mg, 1.17 mmol) in toluene (2 mL) was added Pd(OAc)$_2$ (8.75 mg, 0.039 mmol) and XantPhos (45 mg, 0.078 mmol). The resulting mixture was heated at 110° C. for 16 h, then cooled and concentrated. The residue was purified by preparative TLC (100% ethyl acetate) to give the title compound. $^1$H NMR (400 MHz, CDCl$_3$) δ 10.16 (s, 1H), 10.04 (s, 1H), 8.86 (d, J=4.9 Hz, 2H), 8.67 (d, J=13.0 Hz, 1H), 8.51 (d, J=7.5 Hz, 1H), 8.37 (s, 1H), 7.84 (d, J=6.6 Hz, 2H), 7.67 (d, J=11.7 Hz, 1H), 7.42-7.52 (m, 3H), 7.34 (t, J=4.9 Hz, 1H).

Step C: 2-Fluoro-N-(3-(hydroxymethyl)-7-phenylimidazo[1,2-c]pyrimidin-8-yl)-5-(pyrimidin-2-yl)-4-(trifluoromethyl)benzamide To a solution of 2-fluoro-N-(3-formyl-7-phenylimidazo[1,2-a]pyridin-8-yl)-5-(pyrimidin-2-yl)-4-(trifluoromethyl)benzamide (55 mg, 0.11 mmol) in ethanol (1 mL) was added sodium borohydride (21 mg, 0.54 mmol). The resulting mixture was stirred at 15° C. for 1 h, then partitioned between water (10 mL) and ethyl acetate (5 mL×3). The combined organic layers were dried over Na$_2$SO$_4$ and concentrated. The residue was purified by reverse-phase HPLC under basic conditions (H$_2$O/CH$_3$CN gradient with 0.05% NH$_4$OH present) to give the title compound. MS: m/z=509.1 (M+1). $^1$H NMR (400 MHz, CDCl$_3$) δ 9.21 (s, 1H), 8.75-8.87 (m, 3H), 8.46 (d, J=7.1 Hz, 1H), 7.78 (d, J=7.3 Hz, 2H), 7.62 (d, J=11.7 Hz, 1H), 7.52 (s, 1H), 7.36-7.47 (m, 3H), 7.33 (t, J=4.9 Hz, 1H), 5.06 (s, 2H).

Example 70

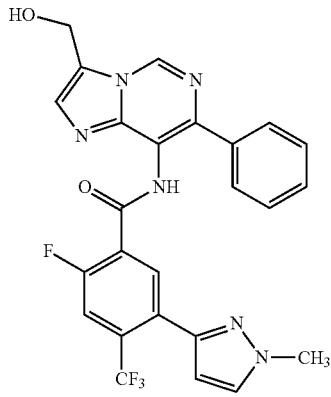 [SMILES: Cn1ccc(-c2cc(C(=O)Nc3c(-c4ccccc4)ncn4c(CO)cnc34)c(F)cc2C(F)(F)F)n1]

2-Fluoro-N-(3-(hydroxymethyl)-7-phenylimidazo[1,2-c]pyrimidin-8-yl)-5-(1-methyl-1H-pyrazol-3-yl)-4-(trifluoromethyl)benzamide The title compound was prepared in similar fashion to the procedures described in Examples 69. MS: m/z=511.1

(M+1). ¹H NMR (400 MHz, CDCl₃) δ 9.21 (s, 1H), 8.63 (d, J=12.1 Hz, 1H), 8.33 (d, J=7.3 Hz, 1H), 7.80 (d, J=7.1 Hz, 2H), 7.53-7.59 (m, 2H), 7.37-7.47 (m, 4H), 6.42 (s, 1H), 5.09 (s, 2H), 3.95 (s, 3H).

Examples 71 and 72

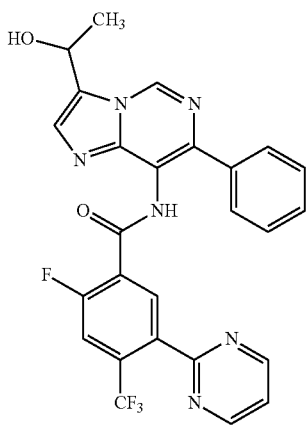 [SMILES: CC(O)c1cnc2c(NC(=O)c3cc(-c4ncccn4)c(C(F)(F)F)cc3F)c(-c3ccccc3)ncn12]

(R and S)-2-Fluoro-N-(3-(1-hydroxyethyl)-7-phenylimidazo[1,2-c]pyrimidin-8-yl)-5-(pyrimidin-2-yl)-4-(trifluoromethyl)benzamide To a solution of 2-fluoro-N-(3-formyl-7-phenylimidazo[1,2-a]pyridin-8-yl)-5-(pyrimidin-2-yl)-4-(trifluoromethyl)benzamide (360 mg, 0.71 mmol) in THF (10 mL) at 0° C. was added a solution of methylmagnesium bromide in diethyl ether (1.19 mL, 3.56 mmol, 3 M). The resulting mixture was stirred at 0° C. for 1 h, then partitioned between saturated aqueous NH₄Cl solution (30 mL) and ethyl acetate (20 mL×3). The combined organic layers were dried over Na₂SO₄ and concentrated. The residue was purified by reverse-phase HPLC under basic conditions (H₂O/CH₃CN gradient with 0.05% NH₄OH present), followed by SFC (Column: AD (250 mm*30 mm, 10 um); Mobile phase: A: Supercritical CO₂, B: EtOH(base), A:B=50:50 at 80 mL/min; Wavelength: 220 nm) to give the title compounds. Enantiomer 1, Example 72: MS: m/z=523.1 (M+1). ¹H NMR (400 MHz, CDCl₃) δ 9.31 (s, 1H), 8.84 (d, J=4.9 Hz, 2H), 8.72 (d, J=12.6 Hz, 1H), 8.46 (d, J=7.3 Hz, 1H), 7.78 (d, J=7.1 Hz, 2H), 7.62 (d, J=11.7 Hz, 1H), 7.36-7.48 (m, 4H), 7.33 (t, J=4.9 Hz, 1H), 5.32 (d, J=6.0 Hz, 1H), 1.80 (d, J=6.4 Hz, 3H). Enantiomer 2, Example 73: MS: m/z=523.1 (M+1). ¹H NMR (400 MHz, CDCl₃) δ 9.29 (s, 1H), 8.83 (d, J=4.9 Hz, 3H), 8.45 (d, J=7.1 Hz, 1H), 7.76 (d, J=7.1 Hz, 2H), 7.60 (d, J=11.5 Hz, 1H), 7.36-7.47 (m, 4H), 7.33 (t, J=5.0 Hz, 1H), 5.24-5.33 (m, 1H), 1.77 (d, J=6.4 Hz, 3H).

Example 73

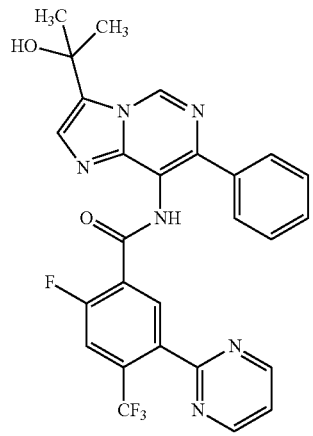 [SMILES: CC(C)(O)c1cnc2c(NC(=O)c3cc(-c4ncccn4)c(C(F)(F)F)cc3F)c(-c3ccccc3)ncn12]

2-Fluoro-N-(3-(2-hydroxypropan-2-yl)-7-phenylimidazo[1,2-c]pyrimidin-8-yl)-5-(pyrimidin-2-yl)-4-(trifluoromethyl)benzamide Step A: N-(3-Acetyl-7-phenylimidazo[1,2-c]pyrimidin-8-yl)-2-fluoro-5-(pyrimidin-2-yl)-4-(trifluoromethyl)benzamide To a solution of 2-fluoro-N-(3-(1-hydroxyethyl)-7-phenylimidazo[1,2-a]pyridin-8-yl)-5-(pyrimidin-2-yl)-4-(trifluoromethyl)benzamide (70 mg, 0.13 mmol) in dichloromethane (5 mL) was added manganese dioxide (117 mg, 1.34 mmol), and the resulting mixture was heated at 40° C. for 60 h. The product mixture was filtered and the filtrate was concentrated to give the title compound. MS: m/z=521.2 (M+1).

Step B: 2-Fluoro-N-(3-(2-hydroxypropan-2-yl)-7-phenylimidazo[1,2-c]pyrimidin-8-yl)-5-(pyrimidin-2-yl)-4-(trifluoromethyl)benzamide To a solution of N-(3-acetyl-7-phenylimidazo[1,2-a]pyridin-8-yl)-2-fluoro-5-(pyrimidin-2-yl)-4-(trifluoromethyl)benzamide (80 mg, 0.096 mmol) in THF (10 mL) at 0° C. was added a solution of methylmagnesium bromide in diethyl ether (0.16 mL, 0.48 mmol, 3 M). The resulting mixture was stirred at 0° C. for 1 h, then partitioned between saturated aqueous NH₄Cl solution (30 mL) and ethyl acetate (15 mL×3). The combined organic layers were dried over Na₂SO₄ and concentrated. The residue was purified by reverse-phase under basic conditions (H₂O/CH₃CN gradient with 0.05% NH₄OH present) to give the title compound. MS: m/z=537.1 (M+1). ¹H NMR (400 MHz, CDCl₃) δ 9.56 (s, 1H), 8.85 (d, J=4.9 Hz, 2H), 8.69 (d, J=11.7 Hz, 1H), 8.48 (d, J=7.1 Hz, 1H), 7.78 (d, J=7.1 Hz, 2H), 7.62 (d, J=11.5 Hz, 1H), 7.32-7.46 (m, 5H), 1.78 (s, 6H).

Examples 74 and 75

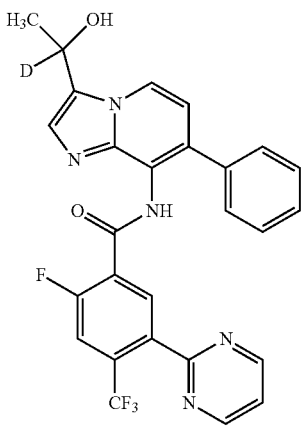 [SMILES: [2H]C(C)(O)c1cnc2c(NC(=O)c3cc(-c4ncccn4)c(C(F)(F)F)cc3F)c(-c3ccccc3)ccn12]

(R and S)-2-Fluoro-N-(3-(1-hydroxyethyl-1-d)-7-phenylimidazo[1,2-a]pyridin-8-yl)-5-(pyrimidin-2-yl)-4-(trifluoromethyl)benzamide Step A: N-(3-Acetyl-7-phenylimidazo[1,2-a]pyridin-8-yl)-2-fluoro-5-(pyrimidin-2-yl)-4-(trifluoromethyl) benzamide To a solution of (R or S)-2-fluoro-N-(3-(1-hydroxyethyl)-7-phenylimidazo[1,2-a]pyridin-8-yl)-5-(pyrimidin-2-yl)-4-(trifluoromethyl)benzamide (Example 9, 50 mg, 0.096 mmol) in 1,4-dioxane (2 mL) was added manganese dioxide (67 mg, 0.77 mmol)). The resulting mixture was heated at 70° C. for 30 min, then cooled and concentrated to give the title compound. MS: m/z=520.0 (M+1).

Step B: (R and S)-2-Fluoro-N-(3-(1-hydroxyethyl-1-d)-7-phenylimidazo[1,2-a]pyridin-8-yl)-5-(pyrimidin-2-yl)-4-(trifluoromethyl)benzamide To a solution of N-(3-acetyl-7-phenylimidazo[1,2-a]pyridin-8-yl)-2-fluoro-5-(pyrimidin-2-yl)-4-(trifluoromethyl)benzamide (from Step A) in THF (2 mL) at 0° C. was added LiAlD$_4$ (10 mg, 0.24 mmol). After 5 min at 0° C., 10 uL of water, 10 uL of 15% NaOH solution, and 10×3 uL of water, were added in succession. The precipitate was filtered and washed with 25 mL of EtOAc. The filtrate was concentrated and the residue was purified by flash column chromatography on silica, eluting with 3:1 v/v EtOAc/EtOH (product Rf=0.65), followed by SFC (preparative method: AD-H (2×25 cm), 50% EtOH (0.1% NH$_4$OH)/CO$_2$, 100 bar, 55 mL/min, 220 nM, inj vol: 1 mL, 2 mg/mL, methanol; analytical method: AD-H (0.46×25 cm), 50% EtOH (DEA)/CO$_2$, 100 bar, 3 mL/min, 220 and 250 nM) to give the title compounds. Enantiomer 1, Example 74: MS: m/z=523.0 (M+1). $^1$H NMR (500 MHz, CD$_3$OD) δ 8.92 (d, 2H), 8.75 (d, 1H), 8.22 (d, 1H), 7.73 (d, 1H), 7.52-7.58 (m, 4H), 7.41-7.45 (m, 2H), 7.37-7.39 (m, 1H), 7.08 (d, 1H), 1.76 (s, 3H). Enantiomer 2, Example 75: MS and $^1$H NMR were identical to Enantiomer 1.

Biological Utility

TrkA functional activity was measured using a DiscoverX PathHunter assay. In this assay, U2OS cells express the human TrkA receptor as a fusion with the weakly complementing fragment of B-galactosidase, which DiscoverX calls "Prolink (PK)"; additionally, Shc1 is fused with a larger fragment, which is called "Enzyme Acceptor (EA)". Activation of the TrkA receptor, upon NGF addition, results in the kinase domain being phosphorylated, resulting in subsequent recruitment of Shc1-EA protein. That recruitment results in an active B-galactosidase enzyme that is detected by addition of a chemiluminescent substrate. The human p75$^{NTR}$ protein was also expressed as a co-receptor for NGF.

All reagents were purchased from DiscoverX, except for the receptor agonists (NGF, BDNF, NT3) which were purchased from Peprotech. Cells were expanded and frozen into cryovials, and stored in the vapor phase of liquid nitrogen, and thawed immediately before use. Thawed cells were added to a 384-well plate at 7500 cells/well, and allowed to incubate overnight. Compound at various concentrations was added the following morning and allowed to incubate on cells for 1 h. Then, NGF was added at a concentration sufficient to elicit ~80% of a maximal response and allowed to incubate for 3 h at ambient temperature. DiscoverX PathHunter detection reagent was then added and the plate was further incubated for 1 h in the dark. The plate was then read via luminescence on the Perkin Elmer Envision.

The percent inhibition was calculated for each compound concentration, and the IC$_{50}$ was determined using Equation 1 below.

$$\% \text{ Inhibition} = \left( \text{Max} + \frac{(\text{Max} - \text{Min})}{1 + \left( \frac{\text{Conc}}{\text{IC}_{50}} \right)^{\text{Hill}}} \right) \quad \text{Equation 1}$$

IC$_{50}$ values from the aforementioned assay for the compounds of this invention range between 0.1 nM to 1000 nM. IC$_{50}$ values for particular compounds of this invention are provided in the table below.

TABLE

| Compound Number | TrkA IC$_{50}$ (nM) |
| --- | --- |
| 1 | 17 |
| 2 | 139 |
| 3 | 323 |
| 4 | 67 |
| 5 | 13 |
| 6 | 11 |
| 7 | 2.1 |
| 8 | 6.2 |
| 9 | 3.3 |
| 10 | 1.1 |
| 11 | 4.0 |
| 12 | 5.7 |
| 13 | 2.4 |
| 14 | 5.1 |
| 15 | 2.2 |
| 16 | 0.2 |
| 17 | 1.1 |
| 18 | 6.7 |
| 19 | 1.9 |
| 20 | 16 |
| 21 | 3.7 |
| 22 | 0.51 |
| 23 | 0.52 |
| 24 | 2.5 |
| 25 | 0.81 |
| 26 | 0.31 |
| 27 | 3.5 |
| 28 | 1.8 |
| 29 | 1.7 |
| 30 | 0.74 |
| 31 | 0.94 |

TABLE-continued

| Compound Number | TrkA IC$_{50}$ (nM) |
|---|---|
| 32 | 6.2 |
| 33 | 6.3 |
| 34 | 53 |
| 35 | 4.4 |
| 36 | 0.40 |
| 37 | 4.5 |
| 38 | 1.8 |
| 39 | 0.33 |
| 40 | 1.4 |
| 41 | 2.1 |
| 42 | 0.66 |
| 43 | 5.0 |
| 44 | 96 |
| 45 | 4.3 |
| 46 | 2.9 |
| 47 | 4.5 |
| 48 | 0.90 |
| 49 | 2.0 |
| 50 | 28 |
| 51 | 60 |
| 52 | 4.9 |
| 53 | 29 |
| 54 | 58 |
| 55 | 82 |
| 56 | 29 |
| 57 | 201 |
| 58 | 232 |
| 59 | 25 |
| 60 | 50 |
| 61 | 4.0 |
| 62 | 47 |
| 63 | 32 |
| 64 | 5.5 |
| 65 | 4.4 |
| 66 | 204 |
| 67 | 56 |
| 68 | 48 |
| 69 | 6.5 |
| 70 | 1.2 |
| 71 | 6.6 |
| 72 | 5.1 |
| 73 | 4.8 |
| 74 | 4.2 |
| 75 | 2.0 |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. It is intended, therefore, that the invention be defined by the scope of the claims that follow and that such claims be interpreted as broadly as is reasonable.

What is claimed is:

1. A compound of formula I:

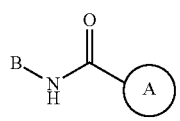

or a pharmaceutically acceptable salt thereof, wherein:

A is phenyl, said phenyl optionally substituted with 1 to 3 groups of R$^a$;

B is represented by structural formula:

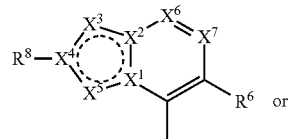

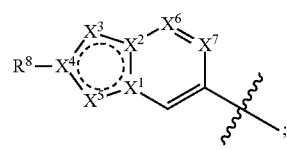

---- represents a double bond between $X^1$-$X^2$, $X^2$-$X^3$, $X^3$-$X^4$, and/or $X^4$-$X^5$, wherein no more than two double bonds are present at $X^1$-$X^2$, $X^3$-$X^4$, and/$X^4$-$X^5$ at the same time;

$X^1$, $X^2$, $X^3$, $X^4$ and $X^5$ are represented as follows: $X^1$=C, $X^2$=N, $X^3$=CR$^c$, $X^4$=C, and $X^5$=N;

$X^6$ is CH;

X7 is CR7, wherein R7 is H;

R6 is independently selected from the group consisting of hydrogen, OH, C$_{1-6}$alkyl, C$_{6-10}$aryl, and halogen, said alkyl and aryl optionally substituted with 1 to 3 groups of R$^a$;

R8 is selected from the group consisting of C(CH3)2OH, CH(CH3)OH, methyl, ethyl and propyl;

R is selected from the group consisting of hydrogen, OH, or —C$_{1-6}$alkyl;

R$^a$ is selected from the group consisting of —CN, NO$_2$, —O—C$_{1-6}$alkyl, OH, —C$_{1-4}$haloalkyl, —OC$_{1-4}$haloalkyl, —C$_{1-6}$alkyl, —C$_{2-6}$alkenyl, —C$_{2-6}$alkynyl, —(CHR)$_n$C$_{6-10}$ aryl, —(CHR)$_n$C$_{4-10}$ heterocycle, C$_{3-6}$cycloalkyl, —O—, —(CH$_2$)$_n$N(R)$_2$, —C(O)CF$_3$, COR, C(O)OR, —(CH$_2$)$_n$halo, —(CH$_2$)$_n$NHC(O)R—(CHR)$_n$C(O)N(R)$_2$, said alkyl, cycloalkyl, aryl and heterocycle optionally substituted with 1 to 3 groups of R$^b$, R$^b$ is selected from the group consisting of —C$_{1-6}$alkyl, —C$_{1-6}$alkylOR, —C$_{1-4}$haloalkyl, —(CH$_2$)$_n$N(R)$_2$, —(CH$_2$)$_n$OR, —O—, halogen, —CN, —(CH$_2$)$_n$C$_{6-10}$ aryl, —(CH$_2$)$_n$C$_{4-10}$ heterocycle, —(CH$_2$)$_n$C(O)N(R)$_2$, —(CH$_2$)$_n$NHC(O)R, Rc is selected from the group consisting of —C1-6alkyl, —C$_{1-6}$alkylOR, —C$_{1-4}$haloalkyl, C(O)R, C(O)OR, —(CH$_2$)$_n$C(O)N(R)$_2$, and —(CH$_2$)$_n$N(R)$_2$, said alkyl optionally substituted with 1 to 3 groups of OH, CH$_3$, and halogen, and n represents 0-4, with the proviso that the n in —(CH2)nN(R)2 of Rc is 0.

2. The compound according to claim 1 or a pharmaceutically acceptable salt thereof wherein A is substituted phenyl represented by structural formula (i):

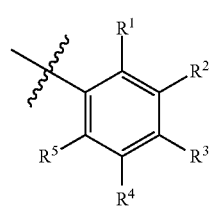

wherein:
R¹ and R⁵ are independently selected from the group consisting of hydrogen, CN, OH, $C_{1-6}$alkyl, and halogen;
R² and R⁴ are independently selected from the group consisting of hydrogen, halogen, $C_{1-4}$ haloalkyl, $C_{1-6}$ alkyl, $(CHR)_nC_{6-10}$ aryl and $(CHR)_nC_{5-10}$ heterocycle, said alkyl, aryl, and heterocycle optionally substituted with 1 to 3 groups of Rb, and
R³ is selected from the group consisting of hydrogen, $C_{1-6}$ alkyl, $C_{1-4}$ haloalkyl, $—OC_{1-4}$ haloalkyl, and halogen, wherein at least one of $R^1$-$R^5$ is other than hydrogen.

3. The compound according to claim 1 or a pharmaceutically acceptable salt thereof, wherein B is B1.

4. The compound according to claim 1 or a pharmaceutically acceptable salt thereof, wherein B is B2.

5. The compound according to claim 1 or a pharmaceutically acceptable salt thereof wherein, R⁶ is $C_{6-10}$aryl.

6. The compound according to claim 5 or a pharmaceutically acceptable salt thereof, wherein B is linked to —NHC₇(O)-A, wherein A is phenyl substituted with 1 to 3 groups of R$^a$.

7. The compound according to claim 1 or a pharmaceutically acceptable salt thereof, represented by structural formulas (B'):

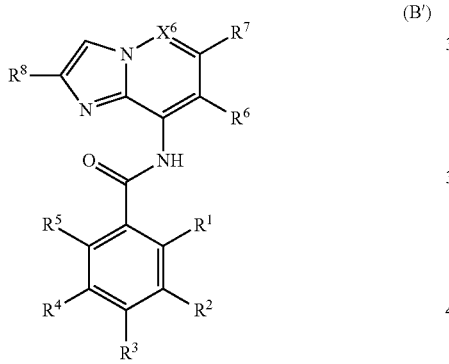

wherein X⁶ is CH R⁶ is $C_{6-10}$aryl, R¹ and R⁵ are both hydrogen, or one of R¹ and R⁵ is hydrogen and the other is halogen, R³ is selected from the group consisting of hydrogen, CF₃, OCF₃, CH₃, CF₂CH₂F, chlorine, and fluorine, one of R² and R⁴ is hydrogen and the other is $(CHR)_nC_{5-10}$ heterocycle, and the n in the heterocycle of R² and R⁴ is zero.

8. The compound according to claim 7 or a pharmaceutically acceptable salt thereof wherein the heterocycle of R² and R⁴ is selected from optionally substituted pyrazolyl, pyridyl, thiazolyl, oxazolyl, pyrimidinyl, pyridazinyl, pyrazinyl, thiadiazolyl, oxadiazolyl, and triazolyl, and R³ is selected from the group consisting of hydrogen, CF₃, OCF₃, CH₃, CF₂CH₂F, chlorine, and fluorine.

9. A compound which is selected from the group consisting of
N-(2-(2-Hydroxypropan-2-yl)-6-phenylimidazo[1,2-a]pyridin-5-yl)-3-(1-methyl-1H-pyrazol-3-yl)-4-(trifluoromethyl)benzamide,
N-(2-(2-Hydroxypropan-2-yl)-7-phenylimidazo[1,2-a]pyridin-8-yl)-3-(1-methyl-1H-pyrazol-3-yl)-4-(trifluoromethyl)benzamide,
8-(2-Fluoro-5-(pyrimidin-2-yl)-4-(trifluoromethyl)benzamido)-7-phenylimidazo[1,2-a]pyridine-3-carboxamide,
2-Fluoro-N-(3-(1-hydroxyethyl)-7-phenylimidazo[1,2-a]pyridin-8-yl)-5-(pyrimidin-2-yl)-4-(trifluoromethyl)benzamide,
2-Fluoro-N-(3-(2-hydroxypropan-2-yl)-7-phenylimidazo[1,2-a]pyridin-8-yl)-5-(pyrimidin-2-yl)-4-(trifluoromethyl)benzamide,
8-({[3-(1-methyl-1H-pyrazol-3-yl)-4-(trifluoromethyl)phenyl]carbonyl}amino)-7-phenylimidazo[1,2-a]pyridine-3-carboxamide,
N-[3-(hydroxymethyl)-7-phenylimidazo[1,2-a]pyridin-8-yl]-3-(1-methyl-1H-pyrazol-3-yl)-4-(trifluoromethyl)benzamide,
2-fluoro-N-[3-(1-hydroxy-1-methylethyl)-7-phenylimidazo[1,2-a]pyridin-8-yl]-5-(1-methyl-1H-pyrazol-3-yl)-4-(trifluoromethyl)benzamide,
2-chloro-N-[3-(1-hydroxy-1-methylethyl)-7-phenylimidazo[1,2-a]pyridin-8-yl]-5-(1-methyl-1H-pyrazol-3-yl)-4-(trifluoromethyl)benzamide,
2-chloro-N-[3-(1-hydroxy-1-methylethyl)-7-phenylimidazo[1,2-a]pyridin-8-yl]-5-pyridin-2-yl-4-(trifluoromethyl)benzamide,
2-fluoro-N-[3-(1-hydroxy-1-methylethyl)-7-phenylimidazo[1,2-a]pyridin-8-yl]-5-pyri din-2-yl-4-(trifluoromethyl)benzamide,
2-chloro-N-[3-(1-hydroxy-1-methylethyl)-7-phenylimidazo[1,2-a]pyridin-8-yl]-5-pyrimidin-2-yl-4-(trifluoromethyl)benzamide,
8-({[2-fluoro-5-pyridin-2-yl-4-(trifluoromethyl)phenyl]carbonyl}amino)-7-phenylimidazo[1,2-a]pyridine-3-carboxamide,
8-({[2-fluoro-5-(1-methyl-1H-pyrazol-3-yl)-4-(trifluoromethyl)phenyl]carbonyl}amino)-7-phenylimidazo[1,2-a]pyridine-3-carboxamide,
2-fluoro-N-[3-(hydroxymethyl)-7-phenylimidazo[1,2-a]pyridin-8-yl]-5-(1-methyl-1H-pyrazol-3-yl)-4-(trifluoromethyl)benzamide,
2-fluoro-N-[3-(hydroxymethyl)-7-phenylimidazo[1,2-a]pyridin-8-yl]-5-pyridin-2-yl-4-(trifluoromethyl)benzamide,
2-fluoro-N-[3-(1-hydroxy-1-methylethyl)-7-phenylimidazo[1,2-a]pyridin-8-yl]-5-(1H-pyrazol-3-yl)-4-(trifluoromethyl)benzamide,
N-[3-(1-hydroxy-1-methylethyl)-7-phenylimidazo[1,2-a]pyridin-8-yl]-3-(1-methyl-1H-pyrazol-3-yl)-4-(trifluoromethyl)benzamide,
3-(1-Methyl-1H-pyrazol-3-yl)-N-(7-phenylimidazo[1,2-a]pyridin-8-yl)-4-(trifluoromethyl)benzamide,
2-Fluoro-N-(3-(hydroxymethyl-d2)-7-phenylimidazo[1,2-a]pyridin-8-yl)-5-(pyrimidin-2-yl)-4-(trifluoromethyl)benzamide,
N-(3-(2-Amino-2-oxoethyl)-7-phenylimidazo[1,2-a]pyridin-8-yl)-2-fluoro-5-(pyrimidin-2-yl)-4-(trifluoromethyl)benzamide,
2-Fluoro-N-(7-(4-fluorophenyl)-3-(hydroxymethyl)imidazo[1,2-a]pyridin-8-yl)-5-(pyrimidin-2-yl)-4-(trifluoromethyl)benzamide
2-fluoro-N-[7-(4-fluorophenyl)-3-(1-hydroxy-1-methylethyl)imidazo[1,2-a]pyridin-8-yl]-5-pyrimidin-2-yl-4-(trifluoromethyl)benzamide,
2-Fluoro-N-(3-(2-hydroxypropan-2-yl)-7-(o-tolyl)imidazo[1,2-a]pyridin-8-yl)-5-(pyrimidin-2-yl)-4-(trifluoromethyl)benzamide 8-(2-Fluoro-5-(1-methyl-1H-pyrazol-3-yl)-4-(trifluoromethyl)benzamido)-7-(o-tolyl)imidazo[1,2-a]pyridine-3-carboxamide 2-Fluoro-N-(7-(3-(hydroxymethyl)phenyl)-3-(2-hydroxypropan-2-yl)imidazo[1,2-a]pyridin-8-yl)-5-(pyrimidin-2-yl)-4-(trifluoromethyl)benzamide 2-Fluoro-N-(7-(3-(hydroxymethyl)phenyl)imidazo[1,2-a]pyridin-8-yl)-5-(pyrimidin-2-yl)-4-(trifluoromethyl)benzamide Ethyl 8-(4-(1-methyl-1H-pyrazol-3-yl)-5-(trifluoromethyl)thiophene-2-carboxamido)-7-phenylimidazo[1,2-a]pyridine-3-carboxylate, 8-(4-(1-Methyl-1H-pyrazol-3-yl)-5-(trifluoromethyl)thiophene-2-carboxamido)-7-phenylimidazo[1,2-a]pyridine-3-carboxamide, N-(3-(Hydroxymethyl)-7-phenylimidazo[1,2-a]pyridin-8-yl)-4-(1-methyl-1H-pyrazol-3-yl)-5-(trifluoromethyl)thiophene-2-carboxamide, or a pharmaceutically acceptable salt thereof.

10. A pharmaceutical composition comprising a therapeutically effective amount of a compound of claim 1 or a pharmaceutically acceptable salt thereof, and a pharmaceutically acceptable carrier.

11. A compound which is:
- (R) or (S)-2-Fluoro-N-(3-(1-hydroxyethyl)-7-phenylimidazo[1,2-a]pyridin-8-yl)-5-(pyrimidin-2-yl)-4-(trifluoromethyl)benzamide
- (R) or (S)—N-[3-(1-hydroxyethyl)-7-phenylimidazo[1,2-a]pyridin-8-yl]-3-(1-methyl-1H-pyrazol-3-yl)-4-(trifluoromethyl)benzamide,
- (R) or (S)-2-fluoro-N-[3-(1-hydroxyethyl)-7-phenylimidazo[1,2-a]pyridin-8-yl]-5-(1-methyl-1H-pyrazol-3-yl)-4-(trifluoromethyl)benzamide,
- (R) or (S)-2-fluoro-N-[3-(1-hydroxyethyl)-7-phenylimidazo[1,2-a]pyridin-8-yl]-5-(1H-pyrazol-3-yl)-4-(trifluoromethyl)benzamide,
- (R) or (S)-2-fluoro-N-[3-(1-hydroxyethyl)-7-phenylimidazo[1,2-a]pyridin-8-yl]-5-pyridin-2-yl-4-(trifluoromethyl)benzamide,
- (R) or (S)-2-fluoro-N-[7-(4-fluorophenyl)-3-(1-hydroxyethyl)imidazo[1,2-a]pyridin-8-yl]-5-pyrimidin-2-yl-4-(trifluoromethyl)benzamide,
- (R or S)-2-Fluoro-N-(3-(1-hydroxyethyl-1-d)-7-phenylimidazo[1,2-a]pyridin-8-yl)-5-(pyrimidin-2-yl)-4-(trifluoromethyl)benzamide, or a pharmaceutically acceptable salt thereof.

* * * * *